US012178174B2

(12) United States Patent
Yu et al.

(10) Patent No.: US 12,178,174 B2
(45) Date of Patent: Dec. 31, 2024

(54) RICE GRAIN WITH REDUCED ROS1a ACTIVITY

(71) Applicants: Commonwealth Scientific and Industrial Research Organisation, Acton (AU); Institute of Botany, Chinese Academy of Sciences, Beijing (CN)

(72) Inventors: Ronald Chun Wai Yu, Gungahlin (AU); Crispin Alexander Howitt, Evatt (AU); Philip John Larkin, Weston (AU); Chun-Ming Liu, Beijing (CN); Xiao-Ba Wu, Florey (AU); Jinxin Liu, Beijing (CN)

(73) Assignees: COMMONWEALTH SCIENTIFIC AND INDUSTRIAL RESEARCH ORGANISATION, Acton (AU); INSTITUTE OF BOTANY, CHINESE ACADEMY OF SCIENCES, Beijing (CN)

( * ) Notice: Subject to any disclaimer, the term of this patent is extended or adjusted under 35 U.S.C. 154(b) by 65 days.

(21) Appl. No.: 17/842,998

(22) Filed: Jun. 17, 2022

(65) Prior Publication Data

US 2023/0018861 A1 Jan. 19, 2023

Related U.S. Application Data

(62) Division of application No. 15/777,059, filed as application No. PCT/AU2016/051106 on Nov. 17, 2016, now Pat. No. 11,452,272.

(30) Foreign Application Priority Data

Nov. 18, 2015 (AU) ................................ 2015904754

(51) Int. Cl.

| | |
|---|---|
| ***A01H 6/46*** | (2018.01) |
| ***A01H 1/00*** | (2006.01) |
| ***A01H 1/06*** | (2006.01) |
| ***A01H 5/10*** | (2018.01) |
| ***C12N 9/24*** | (2006.01) |

(52) U.S. Cl.

CPC ............. *A01H 6/4636* (2018.05); *A01H 1/06* (2013.01); *A01H 1/102* (2021.01); *A01H 1/12* (2021.01); *A01H 1/121* (2021.01); *A01H 5/10* (2013.01); *C12N 9/2497* (2013.01)

(58) Field of Classification Search

None

See application file for complete search history.

(56) References Cited

U.S. PATENT DOCUMENTS

| | | | | |
|---|---|---|---|---|
| 11,452,272 B2 * | 9/2022 | Yu | ............................ | A01H 5/10 |
| 2003/0135890 A1 * | 7/2003 | Fischer | .............. | C12N 15/8233 536/23.6 |
| 2018/0332812 A1 | 11/2018 | Yu et al. | | |

FOREIGN PATENT DOCUMENTS

| | | |
|---|---|---|
| CN | 102177778 | 4/2011 |
| CN | 102177778 A | 9/2011 |
| WO | WO2001/080626 | 11/2001 |
| WO | WO 2003/011015 A2 | 2/2003 |
| WO | WO 2005/038040 A2 | 4/2005 |
| WO | WO2017/083920 | 5/2017 |

OTHER PUBLICATIONS

Chen et al. Heat stress yields a unique MADS box transcription factor in determining seed size and thermal sensitivity. (2016) Plant Physiology; vol. 171, pp. 606-622 (Year: 2016).*

Li et al. Transcriptome and DNA methylome analysis of two contrasting rice genotypes under salt stress during germination. (2023) Int. J. Mol. Sci.; vol. 24; pp. 1-16 (Year: 2023).*

Walia et al. Comparative transcriptional profiling of two contrasting rice genotypes under salinity stress during the vegetative growth stage. (2005) Plant Physiology; vol. 139; pp. 822-835 (Year: 2005).*

Bulatao et al. Phytochemical and functional properties of Philippine sprouted brown rice (Oryza sativa L.) and its potential as base ingredient for functional beverages. (2012) Philipp. Agric. Scientist; vol. 95; pp. 225-235 (Year: 2012).*

Wang et al. Mutant resources for the functional analysis of the rice genome. (2013) Molecular Plant; vol. 6; pp. 596-604 (Year: 2013).*

Aug. 26, 2021 Rejection Decision issued in connection with corresponding Taiwanese Patent Application 105137863.

Aug. 6, 2021 Office Action issued in connection with counterpart Chinese Patent Application No. 201680072090 and English language translation thereof.

Dec. 9, 2021 Response filed to the examination report in connection with corresponding Philippine Patent Application 1-2018-501071.

Extended European Search Report issued Mar. 12, 2019 in connection with European Application No. EP 16 86 5304.

First Examination Report issued Sep. 14, 2017 by the Bangladesh Department of Patents, Designs & Trademarks in connection with related Bangladesh Patent Application No. 286/2016.

International Preliminary Report on Patentability completed Sep. 27, 2017 in connection with PCT International Application No. PCT/AU2016/051106.

International Search Report and Written Opinion of the International Searching Authority issued Feb. 2, 2017 in connection with PCT International Application No. PCT/AU2016/051106.

Jan. 31, 2022 Communication Pursuant to Article 94 (3) EPC issued in connection with corresponding European patent application 16865304.6.

(Continued)

*Primary Examiner* — Cathy Kingdon Worley

(74) *Attorney, Agent, or Firm* — Gary J. Gershik

(57) ABSTRACT

The present invention relates to rice grain with thickened aleurone. Also provided is a rice plant comprising at least one genetic variation which reduces the activity of at least one ROS1a gene in the plant. Grain of the invention, or aleurone therefrom, has improved nutritional properties, and hence is particularly useful for human and animal feed products.

20 Claims, 11 Drawing Sheets

Figure 1:
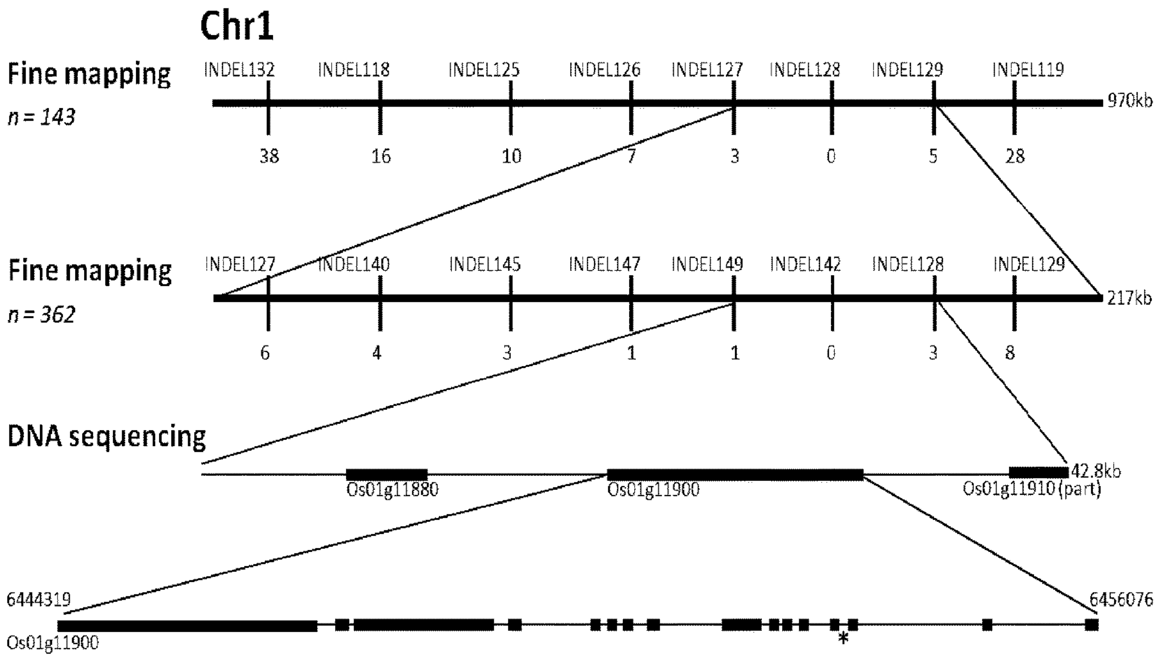

Specification includes a Sequence Listing.

(56) References Cited

OTHER PUBLICATIONS

Jan. 28, 2021 Office Action issued in connection with the corresponding Colombian patent application No. NC2018/0006215, including English translation thereof.

Jun. 24, 2021 Communication pursuant to Article 94 (3) EPC issued in connection with corresponding European Patent Application No. 16 865 304.6.

Kawakatsu, T., et al."Compensation and interaction between RISBZ1 and RPBF during grain filling in rice", The Plant Journal, 2009, vol. 59, pp. 908-920.

Nov. 17, 2021 Response filed to the Jun. 24, 2021 Examination Report issued in connection with corresponding European patent application 16865304.6.

Nov. 2, 2021 Second Office Action issued in connection with corresponding Japanese patent application 2018-526629 and English translation thereof.

Oct. 21, 2020 Response to the First Examination Report filed in connection with the corresponding Australian patent application No. 201655920.

Oct. 27, 2020 Second Examination Report issued in connection with the corresponding Australian patent application No. 201655920.

Oct. 29, 2020 Response to the Second Examination Report filed in connection with the corresponding Australian patent application No. 201655920.

Ono, A. et al."A null mutation of ROS1a for DNA demethylation rice is not transmittable to progeny" The Plant Journal, 2012, vol. 71, pp. 564-574.

Response to First Examination Report filed May 19, 2018 in connection with related Bangladesh Patent Application No. 286/2016.

Nov. 9, 2020 Office Action issued in connection with the corresponding Thai patent application No. 1801002923, including English translation thereof.

Nov. 19, 2020 Examination and Search Report issued in connection with the corresponding Taiwanese patent application No. 105137863, including English translation thereof.

Nov. 10, 2020 Office Action issued in connection with the corresponding Japanese patent application No. 2018-526629, including English translation thereof.

Sep. 10, 2021 Office Action issued in connection with counterpart Colombian Patent Application NC2018/0006215 and English language translation thereof.

Sep. 15, 2017 Amendment in Response to the Feb. 2, 2017 Written Opinion.

Second Examination Report issued Jun. 11, 2018 by the Bangladesh Department of Patents, Designs & Trademarks in connection with related Bangladesh Patent Application No. 286/2016.

Yu, C. W., et al "Small Change in Seed, Big Benefits to Nutrition: Nutritional Enhancement of Rice by Thick Aleurone Phenotype", ComBio2014 Symposia SYM-40-05, Oct. 2014, accessed from the internet on Jan. 13, 2017 from https://www.asbmb.org.au/combio2014/abstracts/edited/Symposium%20Abstracts.pdf, Abstract.

Yu, R. C. W., "PhD Exit Seminar—Studies on multi-layer aleurone mutants in cereals and their nutritional significance", Jun. 3, 2016, accessed from the internet on Dec. 7, 2016 from http://biology.anu.edu.au/news-events/phd-exit-seminar-studies-multi-layer-aleurone-mutants-cereals-and-their-nutritional, Abstract.

Agius, F., et al., "Role of the Arabidopsis DNA glycosylase/lyase ROS1 in active DNA demethylation", Aug. 1, 2006, Proc. Nat'l. Acad. Sci. USA 103(31) : 11796-11801.

Becraft, P. W. and Yi, G. "Regulation of aleurone development in cereal grains", Nov. 25, 2010, Journal of Experimental Botany 62(5) : 1669-1675.

Becraft, P.W. and Asuncion-Crabb, Y. "Positional cues specify and maintain aleurone cell fate in maize endosperm development", Aug. 22, 2000, Development 127: 4039-4048.

Becraft, P.W., et al., "The maize dekl gene functions in embryonic pattern formation and cell fate specification", Aug. 23, 2002, Development 129: 5217-5225.

Becraft, P.W., et al., "Endosperm Development", Current Trends in the Embryology of Angiosperms 353-374 (S. S. Bhojwani and W. Y. Soh eds., 2001).

Buri, R.C., et al., "Description and Characterization of Wheat Aleurone", Sep.-Oct. 2004, Cereal Foods World 49 (5) : 274-282.

Buttrose, M.S. "Ultrastructure of the Developing Aleurone Cells of Wheat Grain", 1963, Aust. J. Biol. Sci. 16, 768-774.

Chan, S. W.-L., et al., "Gardening the Genome: DNA Methylation in Arabidopsis Thaliana", May 2005, Nat. Rev. Genet. 6: 351-360.

Choi, Y., et al., "Demeter, a DNA Glycosylase Domain Protein, Is Required for Endosperm Gene Imprinting and Seed Viability in Arabidopsis", Jul. 12, 2002, Cell 110: 33-42.

Choi, Y., et al., "An invariant aspartic acide in the DNA glycosylase domain of Demeter is necessary for transcriptional activation of the imprinted Medea gene", Apr. 1, 2004, Proc. Nat'l. Acad. Sci. USA 101: 7481-7486.

First Examination Report issued Mar. 20, 2020 in connection with Australian patent application 2016355920.

First Office Action issued Apr. 20, 2020 in connection with Colombian patent application NC2018/0006215, including English language translation.

Gehring, M., et al., "Demeter DNA Glycosylase Establishes MEDEA Polycomb Gene Self-Imprinting by Allele-Specific Demethylation", Feb. 10, 2006, Cell 124: 495-506.

Gong, Z., et al., "ROS1, a Repressor of Transcriptional Gene Silencing in Arabidopsis, Encodes a DNA Glycosylase/Lyase", Dec. 13, 2002, Cell 111: 803-814.

Hoshikawa, K. "Anthesis, Fertilization and Development of Caryopsis", Science of the Rice Plant: Morphology 339-376 (Matsuo and Hoshikawa eds., 1993).

Jones, R. L., "The Fine Structure of Barley Aleurone Cells", 1969, Planta 85: 359-375.

Kawakatsu, T., et al., "Compensation and interaction between RISBZ1 and RPBF during grain filling in rice", Jun. 22, 2009, the Plant Journal 59: 908-920.

Kessler, S., et al., "Xcl1 causes delayed oblique periclinal cell divisions in developing maize leaves, leading to cellular differentiation by lineage instead of position", 2002, Development 129: 1859-1869.

Law, J.A. and Jacobsen, S.E. "Establishing, maintaining and modifying DNA methylation patterns in plants and animals", Mar. 2010, Nat. Rev. Genet. 11(3) : 204-220.

Lewis, D., et al., "Aberrant Cell Expansion in the elongation Mutants of Barley", 2009, Plant Cell Physiol. 50 (3) : 554-571.

Lid, S.E., et al. "The maize disorganized aleurone layer 1 and 2 (dil1, dil2) mutants lack control of the mitotic division plane in the aleurone layer of developing endosperm", 2004, Planta 2018: 370-378.

Lin, X., et al., NCIB Nucleotide Database Accession No. GenBank NM_129207.5, Arabidopsis thaliana demeter-like 1 (DML1) , mRNA, complete cds. Published May 17, 2016.

Mathieu, O., et al., "Transgenerational Stability of the Arabidopsis Epigenome is Coordinated by CG Methylation", Sep. 7, 2007, Cell 130: 851-862.

Mayer, K., et al., NCBI Nucleotide Database Accession No. GenBank NM_119567.4, Arabidopsis thaliana demeter-like 2 (DML2) , mRNA, complete cds. Published May 17, 2016.

Morales-Ruiz, T., et al., "Demeter and Repressor of Silencing 1 encode 5-methylcytosine DNA glycosylases", May 2, 2006, Proc. Nat'l. Acad. Sci. USA 103 (18) : 6853-6858.

Ono, A., et al., "A null mutation of ROS1a for DNA demethylation in rice is not transmittable to progeny", Jun. 19, 2012, The Plant Journal 71: 564-574.

Ortega-Galisteo, A. P., et al. "Arabidopsis Demeter-Like proteins DML2 and DML3 are required for appropriate distribution of DNA methylation marks", May 21, 2008, Plant Mol. Biol. 67: 671-681.

Penterman, J., et al., "DNA demethylation in the Arabidopsis genome", Apr. 17, 2007, Proc. Nat'l. Acad. Sci. USA 104 (16) : 6752-6757.

Preliminary Office Action issued Nov. 17, 2016, in connection with Brazilian patent application BR112018010101-0, filed Nov. 18, 2015, including English language translation.

(56) References Cited

OTHER PUBLICATIONS

Rice Genome Annotation Project Locus LOC Os01g11900.1, hhH-GPD superfamily base excision DNA repair protein, expressed, complete cds. Retrieved Jan. 11, 2020 from rice.plantbiology.msu.edu/cgi-bin/ORF_infopage.cgi?orf=LOC_Os01g11900.

Rice Genome Annotation Project Locus LOC_Os02g29230.1, expressed protein, complete cds. Retrieved Jan. 11, 2020 from rice.plantbiology.msu.edu/cgi-bin/ORF_infopage.cgi?orf=LOC_Os02g29230.

Rice Genome Annotation Project Locus LOC_Os02g29380.1, expressed protein, complete cds. Retrieved Jan. 11, 2020 from rice.plantbiology.msu.edu/cgi-bin/ORF_infopage.cgi?orf=LOC_Os02g29380.

Rice Genome Annotation Project Locus LOC_Os04g28860.1, expressed protein, complete cds. Retrieves Jan. 11, 2002 from rice.plantbiology.msu.edu/cgi-bin/ORF_infopage.cgi?orf=LOC_Os04g28860.

Rice Genome Annotation Project Locus LOC_Os05g37350.1, hhH-GPD superfamily base excision DNA repair protein, expressed, complete cds. Retrieved Jan. 11, 2020 from rice.plantbiology.msu.edu/cgi-bin/ORF_infopage.cgi?orf=LOC_Os05g37350.

Rice Genome Annotation Project Locus LOC_Os05g37410.1, hhH-GPD superfamily base excision DNA repair protein, expressed, complete cds. Retrieved Jan. 11, 2020 from rice.plantbiology.msu.edu/cgi-bin/ORF_infopage.cgi?orf=LOC_Os05g37410.

Salanoubat, M., et al., NCBI Nucleotide Database Accession No. GenBank NM 111836.5, Arabidopsis thaliana demeter-like 2 (DML2), partial mRNA, incomplete on the 5' end. Published May 17, 2016.

Shen, B., et al., "sal1 determines the number of aleurone cell layers in maize endosperm and encodes a class E vacuolar sorting protein", May 27, 2003, Proc. Nat'l. Acad. Sci. USA 100 (11) : 6552-6557.

Tabata, S., et al., NCBI Nucleotide Database Accession No. GenBank NM_001085058.2, Arabidopsis thaliana HhH-GPD base excision DNA repair family protein (DME), mRNA, complete cds. Published Feb. 18, 2011.

Walbot, V. "Overview of Key Steps in Aleurone Development", The Maize Handbook 78-80 (M. Freeling and V. Walbot eds., 1994).

Wen, S., et al., "Structural genes of wheat and barley 5-methylcytosine DNA glycosylases and their potential applications for human health", Dec. 11, 2012, Proc. Nat'l. Acad. Sci. USA 109 (50) : 20543-20548.

Zemach, A. et al., "Local DNA hypomethylation activates genes in rice endosperm", Oct. 26, 2010, Proc. Nat'l. Acad. Sci. USA 107 (43) : 18729-18734.

Zhu, J., et al., "The DNA Glycosylase/Lyase ROS1 Functions in Pruning DNA Methylation Patterns in Arabidopsis", Jan. 9, 2007, Current Biology 17: 54-59.

Apr. 5, 2021 Office Action issued in connection with U.S. Appl. No. 15/777,059.

Aug. 17, 2020 Office Action issued in connection with U.S. Appl. No. 15/777,059.

Dec. 20, 2019 Office Action issued in connection with U.S. Appl. No. 15/777,059.

Feb. 18, 2022 Amendment filed in Response to Oct. 28, 2021 Office Action & Feb. 18, 2022 Advisory Action issued in connection with U.S. Appl. No. 15/777,059.

Feb. 18, 2022 Advisory Action issued in connection with U.S. Appl. No. 15/777,059.

Jan. 28, 2022 Amendment filed in Response to Oct. 28, 2021 Office Action issued in connection with U.S. Appl. No. 15/777,059.

Jul. 30, 2019 Office Action issued in connection with U.S. Appl. No. 15/777,059.

Mar. 4, 2022 Notice of Allowance issued in connection with U.S. Appl. No. 15/777,059.

May 27, 2020 Amendment filed in Response to Dec. 20, 2019 Office Action issued in connection with U.S. Appl. No. 15/777,059.

Nov. 17, 2020 Amendment filed in Response to Aug. 17, 2020 Office Action issued in connection with U.S. Appl. No. 15/777,059.

Oct. 28, 2021 Office Action issued in connection with U.S. Appl. No. 15/777,059.

Oct. 30, 2019 Amendment filed in Response to Jul. 30, 2019 Office Action issued in connection with U.S. Appl. No. 15/777,059.

Sep. 13, 2021 Amendment filed in Response to Apr. 5, 2021 Office Action issued in connection with U.S. Appl. No. 15/777,059.

May 5, 2023 Written Opinion issued in connection with Brazilian Patent Application No. BR112018010101-0 including English language translation thereof.

Dec. 23, 2022 Office Action issued in connection with Canadian Patent Application No. 3,005,466.

English translation of Jun. 16, 2022 Resolution of Denial issued in connection with Colombian Patent Application No. NC2018/0006215.

Oct. 28, 2022 Response to First Examination Report filed in connection with Indian Patent Application No. 201817022280.

Sep. 6, 2022 Office Action issued in connection with Japanese Patent Application No. 2018-526629 including English language translation thereof.

Apr. 22, 2022 Office Action issued in connection with Mexican Patent Application No. MX/a/2018/006192 including English language translation thereof.

Aug. 16, 2022 Office Action issued in connection with Mexican Patent Application No. MX/a/2018/006192 including English language translation thereof.

Apr. 5, 2023 Examination Report issued in connection with New Zealand Patent Applcation No. 742693.

Aug. 12, 2022 Response to Office Action filed in connection with Philippines Patent Application No. PH/1/2018/501071.

Jan. 6, 2023 Subsequent Substantive Examination Report issued in connection with Philippines Patent Application No. PH/1/2018/501071.

Mar. 6, 2023 Response to Office Action filed in connection with Philippines Patent Application No. PH/1/2018/501071.

Sep. 28, 2022 Reexamination Report issued in connection with Taiwanese Patent Application No. 105137863 including English language translation thereof.

Aug. 10, 2022 Response to Office Action filed in connection with European Patent Application No. 16865304.6.

Dec. 12, 2023 Office Action issued in connection with Japanese Patent Application No. 2023-001127 including English language translation thereof.

* cited by examiner

EXHIBIT A

```
CNSQENGELCASNTCGSCNSIREAQAQKVRGTLLIPCRTAMRGSFPLNGTYFQVNE----
CNSQENGELCASNTCGSCNSIREAQAQKVRGTLLIPCRTAMRGSFPLNGTYFQVNECSNV
********************************************************

---VFADHDSSRNPIDVPRSWIWNLPRRTVYFGTSIPTIFKGLTTEEIQHCFWRGFVCVR
MRQVFADHDSSRNPIDVPRSWIWNLPRRTVYFGTSIPTIFKGLTTEEIQHCFWRGFVCVR
   *********************************************************

GFDRTSRAPRPLYARLHFPASKITRNKKSAGSAPGRDDE
GFDRTSRAPRPLYARLHFPASKITRNKKSAGSAPGRDDE
***************************************
```

Figure 3

```
AtDME      MNSRADPGDRYFRVPLENQTQQEFMGSWIPFTPKKPRSSLMVDERVINQDLNGFPGGEFV
AtROS1a    ------------------------------------------------------------
OsROS1a    ------------------------------------------------------------

AtDME      DRGFCNTGVDHNGVFDHGAHQGVTNLSMMINSLAGSHAQAWSNSERDLLGRSEVTSPLAP
AtROS1a    ------------------------------------------------------------
OsROS1a    ------------------------------------------------------------

AtDME      VIRNTTGNVEPVNGNFTSDVGMVNGPFTQSGTSQAGYNEFELDDLLNPDQMPFSFTSLLS
AtROS1a    -------------------------------------------------------MEKQR
OsROS1a    ------------------------------------------------------------

AtDME      GGDSLFKVRQYGPPACNKPL-YNLNSPIRRE-------------AVGSVCESSFQY----
AtROS1a    REESSFQQPPWIPQTPMKPFSPICPYTVEDQYHSSQLEERR---FVGNKDMSGLDHLSFG
OsROS1a    ----MQDFGQWLPQSQTTADLYFSSIPIPSQFDTSIETQTRTSAVVSSEKE---------
                 .   : * :  .         :  :              *..

AtDME      ----VPSTPS------LFRTGEKTGFLEQIVTTTGHEIPEPKSDKSMQSIMDSSAVNATE
AtROS1a    DLLALANTASLIFSGQTPIPTRNTEVMQ-----KGT------------------------
OsROS1a    -------------SANSFVPHNGTGLVERISNDAGL------------------------
                                . * .::      *

AtDME      ATEQNDGSRQDVLEFDLNKTPQQKPSKRKRKFMPKVVVEGKPKRKPRKPAELPKVVVEGK
AtROS1a    -EEVESLSSVSNNVAEQILKTPEKPKR--KKHRPKVRREAKPKREPKPRAPRKSVVTDGQ
OsROS1a    -TEVVGSSAGPTECIDLNKTPARKPKK--KKHRPKVLKDDKPSKTPKSATPIPST--EKV
             *    *       :   .  .**.:  :*. ***  : **.: *:  :   ..  :

AtDME      PKRKPRKAATQEKVKSKETGSAKKKNLKESATKKPANVGDMSNKSPEVTLKSCRKALNFD
AtROS1a    ESKTPKRKYVRKKVEVS---------------KDQ-------------------------
OsROS1a    EKPSGKRKYVRKKTSPG---------------QPPAEQAA--SSHCRSELKSVKRSLDFG
            . . ::  .::*..                 :

AtDME      LENPGDARQGDSESEIVQNSSGANSF-----------SEIR-------------------
AtROS1a    ------------------------------------------------------------
OsROS1a    GEVLQESTQSGSQVPVAEICTGPKRQSIPSTIQRDSQSQLACHVVSSTSSIHTSASQMVN

AtDME      ---------------------DAIGGTNGSFLDSVSQ-----IDKTNGLGAMNQPLEVSM
AtROS1a    ------------------------------------------------------------
OsROS1a    AHLFPPDNMPNGVLLDLNNSTSQLQNEHAKFVDSPARLFGSRIRQTSGKN---SLLEIYA

AtDME      G----NQPDK---LSTGAKLARDQQPDLLTR--------------------------NQQ
AtROS1a    ------------------------------------------------------------
OsROS1a    GMSDRNVPDLNSSISQTHSMSTDFAQYLLSSSQASVRETQMANQMLNGHRMPENPITPSH

AtDME      CQF-----------------------PVA---TQNTQFPM---------ENQQAWLQMKN
AtROS1a    ------------------------------------------------------------
OsROS1a    CIERAALKEHLNHVPHAKAAVMNGQMPHSYRLAQNPILPPNHIEGYQVMENLSELVTTND

AtDME      QLIGFPFGNQQPRMTIRNQQPCLAMGNQQPMYLIGTPRPAL----VSGNQQ---------
AtROS1a    --DATPVESSAAVET-----------STRPKR--------LCRRVLDFEAENGE------
OsROS1a    YLTASPFSQTGAANRQHNIGDSMHIHALDPRRESNASSGSWISLGVNFNQQNNGWASAGA
              . *. .                    *               :. : :

AtDME      ----------LGGPQGNKRPIFLNHQTCLPAGNQLYGSPTDMHQLVMSTGGQQHGLLIKN
AtROS1a    -----------------------NQTNGDIREA---------------------GEMESA
OsROS1a    ADAASSHAPYFSEPHKRMRTAYLNNYPNGVVGHFS-TSSTDLS---NN----ENENVASA
                                   .       .                       : .
```

Figure 4

```
AtDME          QQPGSLIRGQQPCVPLIDQQPATPKGFTHLNQMVATS-MSSPGLRPHSQSQVPTTYLHVE
AtROS1a        LQEKQLDSGN---------------------QELKDCLLSAPSTPKRKRSQGKR------
OsROS1a        INSNVF--------------------------TLADA----QRLIAREKSRASQ------
                :   :                           :  .         :.:*:

AtDME          SVSRILNGTTGTCQRSRAPAYDSLQQDIHQGNKYILS--HEISNGNGCKKALPQNSS---
AtROS1a        ----------------KGVQPKKNGSN-LEEVDISMAQAAKRRQGPTCCDM-NLS----G
OsROS1a        ----------------RMISFRSSKNDMVNRSEMVHQHGRPAPHGSACRESIEVPDKQFG
                               :     .  .:  :  .          .*  * .

AtDME          LPTPIMAKLEEA--RGSKRQYHRAMGQTEK-----------------HDL----NLA---
AtROS1a        ---------------------IQYDEQCDYQKMHWLYSPNLQQGGMRYDAICSKVFSGQQ
OsROS1a        LMTEELTQLPSMPNNPQREKYIPQTGSCQLQSLE-------------HDMVKGHNLAGEL
                                         . :                  :*      ::

AtDME          -QQIAQSQDVERHNSSTCVEYLDAAKKTKIQKV--------------VQENLHGM-----
AtROS1a        HNYVSAF-------HATCYSSTSQLSANRVLTVEERREGIFQ---GRQE-------SELN
OsROS1a        HKQVTSPQVV--IQSNFCVTPPDVLGR-R-TSGEHLRTLIAPTHASTCKDTLKALSCQLE
                : ::            *    .     :  .                :

AtDME          ------PPEVIEIEDDPTDGARKGKNTASISKGASKGNSSPVKKTAEKEKCIVPKTPAKK
AtROS1a        VLSDKIDTPIKKKTTGHA---RFRN----LSSM------NKLVEVPEH---------LTS
OsROS1a        SSRDIIRPPVNPIGPSSADVPRTDNHQVKVSEE------TVTAKLPEKRKVGRPRKELKP
                        :       :   *  :    :*.       .   :  *:          .

AtDME          GRAGRKKSVPPP--AHASEIQLWQPTPPKTPLSRSKPK-----------GKGRKSIQD--
AtROS1a        GYCSKPQQNNK--ILVDTRVTVSKKKPTKSEKSQTKQKNLLPNLCRFPPSFTGLSPDEL-
OsROS1a        GEKPKPRGRPRKGKVVGGEL--------ASKDSHTNPLQNESTSCSYGPYAGEASVGRAV
               *   : :           .:         :  *:::                  *

AtDME          --SGKARGPSGELL-CQDSIAEIIYRMQNLYLGDKEREQEQNAMVLYKG----------D
AtROS1a        -------------WKRRNSIETISEL---LRLLDINREHSETALVPYTMNSQIVLFGGGA
OsROS1a        KANRVGENISGAMVSLLDSLDIVIQK---IKVLDINKSEDPV---TAEPHGALVPYNGEF
                                :*:  :      : : * ::...

AtDME          GALVPYES--KKRKPRPKVDIDDETTRIWNLLMGKGDEKEGDEEKDKKKEKWWEEERRVF
AtROS1a        GAIVPVT-PVKKPRPRPKVDLDDETDRVWKLLLENIN-SEGVDGSDEQKAKWWEEERNVF
OsROS1a        GPIVPFEGKVKRKRSRAKVDLDPVTALMWKLLMGPDM-SDCAEGMDKDKEKWLNEERKIF
               * :**     *: : * ***:*  *  :*:**:     .:  :  *:.* ** :***.:*

AtDME          RGRADSFIARMHLVQGDRRFSPWKGSVVDSVIGVFLTQNVSDHLSSSAFMSLAARFPPKL
AtROS1a        RGRADSFIARMHLVQGDRRFTPWKGSVVDSVVGVFLTQNVSDHLSSSAFMSLASQFPVPF
OsROS1a        QGRVDSFIARMHLVQGDRRFSPWKGSVVDSVVGVFLTQNVSDHLSSSAFMALAAKFPVKP
               :**.****************:**********:******************:**::**

AtDME          SSSREDERNVRSVVVEDPEGCILNLNEIPSWQEK--VQHPSDMEVSGVDSGSK------E
AtROS1a        VPSSNFDA----------GTS-SMP----SI------------QITYLDSEETMSS----
OsROS1a        EASEKPANVMFHTISEN-GDCSGLFGNSVKLQGEILVQEASNTAASFITTEDKEGSNSVE
                 * :               .        .               : : : ..

AtDME          QLRDCSNSGIERF---------------NFLEKSIQNL-----------------EEEVL
AtROS1a        -----------------------PPDHNHS---SV-TLKNTQPDEE--KDYVPSNETS--
OsROS1a        LLGSSFGDGVDGAAGVYSNIYENLPARLHATRRPVVQTGNAVEAEDGSLEGVVSSENSTI
                                           .     :                    * .

AtDME          SSQDSFDPAIFQSC------------GRVGSCSCSKSDAEFPTTRCETKT----VSGTS-
AtROS1a        --RSSSEIA--ISAH-----------ES--------------------------VDKTTD
OsROS1a        SSQNSSDYLFHMSDHMFSSMLLNFTAEDIGSRNMPKATRTTYTELLRMQELKNKSNETIE
                 :.* :     *                                          . *

AtDME          QSVQTGSPNL-SD------EICLQGNER-----PHLYEGSGDVQKQETTNVAQKKPDLEK
AtROS1a        SKEYVDSDR--------------KGS-------SVEVD----------------------
OsROS1a        SSEYHGVPVSCSNNIQVLNGIQNIGSKHQPLHSSISYHQTGQVH----------LPDIVH
               ..                      *.           .
```

Figure 4 (Cont.)

```
AtDME       TMNWKDSVCFGQPRN------DTNWQTTPSSSYEQCATRQPHVLDIEDFGMQGEGLGYSW
AtROS1a     --------------KTDEKCRVLNLFPSEDSAL-TCQ-----------------------
OsROS1a     ASDLEQSVYTGLNRVLDSNVTQTSYYPSPHPGI-ACN-----------------------
                                   .   :   .   *

AtDME       MSISPRVDRVKNKNVPRRFFRQGGSVPREFTGQIIPSTPHELPGMGLSGSSSAVQEHQDD
AtROS1a     --------HSMVSDAPQNTERAGSSSEIDLEGEYRTSFMKLLQGVQVSLEDSNQVSPNMS
OsROS1a     --------NETQK---------------------ADSLSNMLYGIDRSDKTTSLSEPTPR
                    .   .                       *  . * *:  * . :   .

AtDME       TQHNQQDEMNKASHLQKTFLDLLNSSEECLTRQ---------------------------
AtROS1a     PG----DCSS--------------------------------------------------
OsROS1a     ID----NCFQPLSSEKMSFAREQSSSENYLSRNEAEAAFVKQHGTSNVQGDNTVRTEQNG
                  :  .

AtDME       ---------------------S---STKQNITDGCLPRDRTAEDVVDPLSNNSSLQNILV
AtROS1a     ------------EIKGFQSMKEPTKSSVDSSEPGCCSQQD--GDVLSCQ-----------
OsROS1a     GENSQSGYSQQDDNVGFQTATT---SNL--YSSNLCQNQKANSEVLHGVSS-----NLIE
                                     *.          .:    :*:

AtDME       ESNSSNKEQTAVEYKETNATILREMKGTLADGKKPTSQWDSLRKDVEGNEGRQERNKNNM
AtROS1a     --------KP----------TLKEKGKKVLKEEKKAFDWDCLRREAQARAGIREKTRSTM
OsROS1a     NSKDDKKTSP-----KVPVDGSKAKRPRVGAGKKKTYDWDMLRKEVLYSHGNKERSQNAK
                    .             :     :   :* : :** **::.    * :*:.:.

AtDME       DSIDYEAIRRASISEISEAIKERGMNNMLAVRIKDFLERIVKDHGGIDLEWLRESPPDKA
AtROS1a     DTVDWKAIRAADVKEVAETIKSRGMNHKLAERIQGFLDRLVNDHGSIDLEWLRDVPPDKA
OsROS1a     DSIDWETIRQAEVKEISDTIRERGMNNMLAERIKDFLNRLVRDHGSIDLEWLRYVDSDKA
            *::*:::** *.:.*::::*:.****. ** **: **:*:*.***.*******    ***

AtDME       KDYLLSIRGLGLKSVECVRLLTLHNLAFPVDTNVGRIAVRMGWVPLQPLPESLQLHLLEL
AtROS1a     KEYLLSFNGLGLKSVECVRLLTLHHLAFPVDTNVGRIAVRLGWVPLQPLPESLQLHLLEM
OsROS1a     KDYLLSIRGLGLKSVECVRLLTLHHMAFPVDTNVGRICVRLGWVPLQPLPESLQLHLLEM
            *:****:.****************.:***********.**:******************:

AtDME       YPVLESIQKFLWPRLCKLDQRTLYELHYQLITFGKVFCTKSRPNCNACPMRGECRHFASA
AtROS1a     YPMLESIQKYLWPRLCKLDQKTLYELHYQMITFGKVFCTKSKPNCNACPMKGECRHFASA
OsROS1a     YPMLENIQKYLWPRLCKLDQRTLYELHYQMITFGKVFCTKSKPNCNACPMRAECKHFASA
            **:**.***:**********:********:***********:********:.**:*****

AtDME       YASARLALPAPEERSLTSATIPVPPESYPPVAIPMIELPLPLEKSLASGAPSNRENCEPI
AtROS1a     FASARLALPSTEKGMGTPDKNPLPLHLP-EPFQR--EQGSEVV--QHSEPAKKVTCCEPI
OsROS1a     FASARLALPGPEEKSLVTSGTPIAAETFHQTYISSRPVVSQLEW-NSNTCHHGMNNRQPI
            :********. *:   .    *:  .               :     .         :**

AtDME       IEEPASPGQEC--TEITESDIEDAYYNEDPDEIPTIKLNIEQFGMTLREHMER-NMELQE
AtROS1a     IEEPASPEPET--AEVSIADIEEAFF-EDPEEIPTIRLNMDAFTSNLKKIMEH-NKELQD
OsROS1a     IEEPASPEPEHETEEMKECAIEDSFV-DDPEEIPTIKLNFEEFTQNLKSYMQANNIEIED
            *******  *    *:. . **:::  :**:*****:**:: *  .*:. *:  * *:::

AtDME       GDMSKALVALHPTTTSIPTPKLKNISRLRTEHQVYELPDSHRLLDGMDKREPDDPSPYLL
AtROS1a     GNMSSALVALTAETASLPMPKLKNISQLRTEHRVYELPDEHPLLAQLEKREPDDPCSYLL
OsROS1a     ADMSKALVAITPEVASIPTPKLKNVSRLRTEHQVYELPDSHPLLEGFNQREPDDPCPYLL
            .:**.****:   .:*:* *****:*:*****:******.* **  :::******. ***

AtDME       AIWTPGETANSAQPPEQKCGGKASGKMCFDETCSECNSLREANSQTVRGTLLIPCRTAMR
AtROS1a     AIWTPGETADSIQPSVSTCIFQANGMLCDEETCFSCNSIKETRSQIVRGTILIPCRTAMR
OsROS1a     SIWTPGETAQSTDAPKSVCNSQENGELCASNTCFSCNSIREAQAQKVRGTLLIPCRTAMR
            :********:* :   . *  : .* :* .:** .***::*:.:* ****:*********

AtDME       GSFPLNGTYFQVNELFADHESSLKPIDVPRDWIWDLPRRTVYFGTSVTSIFRGLSTEQIQ
AtROS1a     GSFPLNGTYFQVNEVFADHASSLNPINVPRELIWELPRRTVYFGTSVPTIFKGLSTEKIQ
OsROS1a     GSFPLNGTYFQVNEVFADHDSSRNPIDVPRSWIWNLPRRTVYFGTSIPTIFKGLTTEEIQ
            **************:**** ** :**:***. **:***********: :**:**:**:**
```

Figure 4 (Cont.)

```
AtDME         FCFWKGFVCVRGFEQKTRAPRPLMARLHFPASKLKNNKT-----------
AtROS1a       ACFWKGYVCVRGFDRKTRGPKPLIARLHFPASKLKGQQANLA--------
OsROS1a       HCFWRGFVCVRGFDRTSRAPRPLYARLHFPASKITRNKKSAGSAPGRDDE
               ***:*:******::.:*.*:** *********:. ::
```

Figure 4 (Cont.)

```
AtROS1a    MEKQRREESSFQQPPWIPQTPMKPFSPICPYTVEDQYHSSQLEERR---FVGNKDMSGLD
OsROS1a    ---------MQDFGQWLPQSQTTADLYFSSIPIPSQFDTSIETQTRTSAVVSSEKE----
                       :    *:**:   .     :.    :  .*:.:*    :  *    .*..:.

AtROS1a    HLSFGDLLALANTASLIFSGQTPIPTRNTEVMQ-----KGTEEVESLSSVSNNVAEQILK
OsROS1a    ------------------SANSFVPHNGTGLVERISNDAGLTEVVGSSAGPTECIDLNKT
                             *.:: :* . * :::       *   ** . *:   .:  :    .

AtROS1a    TPEKPKRKKHRPKVRREAKPKREPKPRAPRKSVVTDGQESKTPKRKYVRKKVEVSKDQ--
OsROS1a    PARKPKKKKHRPKVLKDDKPSKTPKSATPIPST--EKVEKPSGKRKYVRKKTSPGQPPAE
             .***:******* :: **.: **   :*   *.   :   *. : ********..  .:

AtROS1a    ------------------------------------------------------------
OsROS1a    QAASSHCRSELKSVKRSLDFGGEVLQESTQSGSQVPVAEICTGPKRQSIPSTIQRDSQSQ

AtROS1a    ------------------------------------------------------------
OsROS1a    LACHVVSSTSSIHTSASQMVNAHLFPPDNMPNGVLLDLNNSTSQLQNEHAKFVDSPARLF

AtROS1a    ------------------------------------------------------------
OsROS1a    GSRIRQTSGKNSLLEIYAGMSDRNVPDLNSSISQTHSMSTDFAQYLLSSSQASVRETQMA

AtROS1a    ------------------------------------------------------------
OsROS1a    NQMLNGHRMPENPITPSHCIERAALKEHLNHVPHAKAAVMNGQMPHSYRLAQNPILPPNH

AtROS1a    --------------------DATPVESSAAVET-----------STRPKR--------LC
OsROS1a    IEGYQVMENLSELVTTNDYLTASPFSQTGAANRQHNIGDSMHIHALDPRRESNASSGSWI
                               *:*...:.*.:                :   *:*

AtROS1a    RRVLDFEAENGE------------------------------NQTNGDIREA--------
OsROS1a    SLGVNFNQQNNGWASAGAADAASSHAPYFSEPHKRMRTAYLNNYPNGVVGHFSTSSTDLS
               ::*: :*                                *   ** :  .

AtROS1a    ----GEMESALQEKQLDSGNQELKDCLLSAPSTPKRKRSQGKRKGVQPKKNGSN-LEEVD
OsROS1a    NNENENVASAINSNVF-----TLADA----QRLIAREKSRASQRMISFRSSKNDMVNRSE
                 :: **::.: :      * *.           *::*:..:: :. :.. .: ::. :

AtROS1a    ISMAQAAKRRQGPTCCDM-NLS----G--------------------IQYDEQCDYQKM
OsROS1a    MVHQHGRPAPHGSACRESIEVPDKQFGLMTEELTQLPSMPNNPQREKYIPQTGSCQLQSL
           :    :.     :*  :*  :   ::      *                    *     .*: *.:

AtROS1a    HWLYSPNLQQGGMRYDAICSKVFSGQQHNYVSAF-----HATCYSSTSQLSANRVLTVEE
OsROS1a    E-------------HDMVKGHNLAGELHKQVTSPQVVIQSNFCVTPPDVLGR-R-TSGEH
           .              :*  :  .:  ::*:  *:  *::           *  :   . *.   *   : *.

AtROS1a    RREGIFQ---GRQE-------SELNVLSDKIDTPIKKKTTGHA---RFRN----LSSMNK
OsROS1a    LRTLIAPTHASTCKDTLKALSCQLESSRDIIRPPVNPIGPSSADVPRTDNHQVKVSEETV
            *  *      .   :          .:*:    * *   *::     .  *    *   *     :*. .

AtROS1a    LVEVPEH---------LTSGYCSKPQQNNK--ILVDTRVTVSKKKPTKSEKSQTKQKNLL
OsROS1a    TAKLPEKRKVGRPRKELKPGEKPKPRGRPRKGKVVGGEL--------ASKDSHTNPLQNE
             .::**:             *. *    **:  .  :    :*   .:          *:.*:*:   :

AtROS1a    PNLCRFPPSFTGLSPDEL--------------WKRRNSIETISELLRLLDINREHSETAL
OsROS1a    STSCSYGPYAGEASVGRAVKANRVGENISGAMVSLLDSLDIVIQKIKVLDINKSEDPV--
             .  *  :  *       *    .                  .   :*:: :  :  :::****:...  .

AtROS1a    VPYTMNSQIVLFGGGAGAIVPVT-PVKKPRPRPKVDLDDETDRVWKLLLENINSEGVDGS
OsROS1a    -TAEPHGALVPYNGEFGPIVPFEGKVKRKRSRAKVDLDPVTALMWKLLMGPDMSDCAEGM
                 .. :*  :  *   *  ***.    **:  *  *  *****  *   :****:     *:  .:*
```

Figure 5

```
AtROS1a            DEQKAKWWEEERNVFRGRADSFIARMHLVQGDRRFTPWKGSVVDSVVGVFLTQNVSDHLS
OsROS1a            DKDKEKWLNEERKIFQGRVDSFIARMHLVQGDRRFSPWKGSVVDSVVGVFLTQNVSDHLS
                   *::* ** :***::*:**.****************:************************

AtROS1a            SSAFMSLASQFPVPFVPSSNFDA---------GTS-SMP----SI------------QIT
OsROS1a            SSAFMALAAKFPVKPEASEKPANVMFHTISENGDCSGLFGNSVKLQGEILVQEASNTAAS
                   *****:**::***    *.:            * . .:     .:              :

AtROS1a            YLDSEETMSS---------------------------PPDHNHS---SV-TLKNTQPDEE
OsROS1a            FITTEDKEGSNSVELLGSSFGDGVDGAAGVYSNIYENLPARLHATRRPVVQTGNAVEAED
                   :: :*:. .*                            * : *:    *    *:   *:

AtROS1a            --KDYVPSNETS----RSSSEIA--ISAH-----------ES------------------
OsROS1a            GSLEGVVSSENSTISSQNSSDYLFHMSDHMFSSMLLNFTAEDIGSRNMPKATRTTYTELL
                      : * *.*.*    :.**:    :* *           *.

AtROS1a            --------VDKTTDSKEYVDSDR--------------KGS-------SVEVD--------
OsROS1a            RMQELKNKSNETIESSEYHGVPVSCSNNIQVLNGIQNIGSKHQPLHSSISYHQTGQVHLP
                            ::* :*.**                    **       *:. .

AtROS1a            ------------------KTDEKCRVLNLFPSEDSALTCQHSMVSDAPQNTERAGSSSEI
OsROS1a            DIVHASDLEQSVYTGLNRVLDSNVTQTSYYPSPHPGIACNNETQK---------------
                                       *.:    . :** . .::*:..  .

AtROS1a            DLEGEYRTSFMKLLQGVQVSLEDSNQVSPNMSPGDCSS----------------------
OsROS1a            ------ADSLSNMLYGIDRSDKTTSLSEPTPRIDNCFQPLSSEKMSFAREQSSSENYLSR
                           *: ::* *:: * : :.  .*.    :* .

AtROS1a            ----------------------------------------EIKGFQSMKEPTKSSVDSSE
OsROS1a            NEAEAAFVKQHGTSNVQGDNTVRTEQNGGENSQSGYSQQDDNVGFQTATT---SNL--YS
                                                           :  ***: .    *.:   .

AtROS1a            PGCCSQQD--GDVLSCQ--------------KP-----TLKEKGKKVLKEEKKAFDWDCL
OsROS1a            SNLCQNQKANSEVLHGVSSNLIENSKDDKKTSPKVPVDGSKAKRPRVGAGKKKTYDWDML
                      *.:*.  .:**                 .*       * *  :*   :**::*** *

AtROS1a            RREAQARAGIREKTRSTMDTVDWKAIRAADVKEVAETIKSRGMNHKLAERIQGFLDRLVN
OsROS1a            RKEVLYSHGNKERSQNAKDSIDWETIRQAEVKEISDTIRERGMNNMLAERIKDFLNRLVR
                   *:*.    * :*:::.: *::**::** *:***:::**:.****. *****: **:***.

AtROS1a            DHGSIDLEWLRDVPPDKAKEYLLSFNGLGLKSVECVRLLTLHHLAFPVDTNVGRIAVRLG
OsROS1a            DHGSIDLEWLRYVDSDKAKDYLLSIRGLGLKSVECVRLLTLHHMAFPVDTNVGRICVRLG
                   *********** *  ****:****:.*****************:***********.****

AtROS1a            WVPLQPLPESLQLHLLEMYPMLESIQKYLWPRLCKLDQKTLYELHYQMITFGKVFCTKSK
OsROS1a            WVPLQPLPESLQLHLLEMYPMLENIQKYLWPRLCKLDQRTLYELHYQMITFGKVFCTKSK
                   ***********************.**************:*********************

AtROS1a            PNCNACPMKGECRHFASAFASARLALPSTEKGMGTPDKNPLPLHLP-EPFQR--EQGSEV
OsROS1a            PNCNACPMRAECKHFASAFASARLALPGPEEKSLVTSGTPIAAETFHQTYISSRPVVSQL
                   ********:.**:**************. *:   . . .*:  .   : :       *::

AtROS1a            V-QHSEPAKKVTCCEPIIEEPASPEPET--AEVSIADIEEAFFEDPEEIPTIRLNMDAFT
OsROS1a            EWNSNTCHHGMNNRQPIIEEPASPEPEHETEEMKECAIEDSFVDDPEEIPTIKLNFEEFT
                     : .   : :.  :************    *:. . **::*.:********:**:: **

AtROS1a            SNLKKIMEH-NKELQDGNMSSALVALTAETASLPMPKLKNISQLRTEHRVYELPDEHPLL
OsROS1a            QNLKSYMQANNIEIEDADMSKALVAITPEVASIPTPKLKNVSRLRTEHQVYELPDSHPLL
                   .***. *:  * *::*.:**.****:* *.**:* *****:*:*****:******.****

AtROS1a            AQLEKREPDDPCSYLLAIWTPGETADSIQPSVSTCIFQANGMLCDEETCFSCNSIKETRS
OsROS1a            EGFNQREPDDPCPYLLSIWTPGETAQSTDAPKSVCNSQENGELCASNTCFSCNSIREAQA
                     :::******* ***:********:* :   *.*  * ** ** .:********:*:::
```

Figure 5 (Cont.)

```
AtROS1a      QIVRGTILIPCRTAMRGSFPLNGTYFQVNEVFADHASSLNPINVPRELIWELPRRTVYFG
OsROS1a      QKVRGTLLIPCRTAMRGSFPLNGTYFQVNEVFADHDSSRNPIDVPRSWIWNLPRRTVYFG
             * ****:**************************** ** ***:***. **:*********

AtROS1a      TSVPTIFKGLSTEKIQACFWKGYVCVRGFDRKTRGPKPLIARLHFPASKLKGQQANLA--
OsROS1a      TSIPTIFKGLTTEEIQHCFWRGFVCVRGFDRTSRAPRPLYARLHFPASKITRNKKSAGSA
             **:*******:**:** ***:*:********.:*.*:** *********:.  :: . .

AtROS1a      ------
OsROS1a      PGRDDE
```

Figure 5 (Cont.)

SEQUENCE LISTING

<160> NUMBER OF SEQ ID NOS: 50

<210> SEQ ID NO 1
<211> LENGTH: 1959
<212> TYPE: PRT
<213> ORGANISM: Artificial Sequence
<220> FEATURE:
<223> OTHER INFORMATION: Rice ROS1a mutant (Ta2) polypeptide

<400> SEQUENCE: 1

```
Met Gln Asp Phe Gly Gln Trp Leu Pro Gln Ser Gln Thr Thr Ala Asp
1               5                   10                  15

Leu Tyr Phe Ser Ser Ile Pro Ile Pro Ser Gln Phe Asp Thr Ser Ile
            20                  25                  30

Glu Thr Gln Thr Arg Thr Ser Ala Val Val Ser Ser Glu Lys Glu Ser
        35                  40                  45

Ala Asn Ser Phe Val Pro His Asn Gly Thr Gly Leu Val Glu Arg Ile
    50                  55                  60

Ser Asn Asp Ala Gly Leu Thr Glu Val Val Gly Ser Ser Ala Gly Pro
65                  70                  75                  80

Thr Glu Cys Ile Asp Leu Asn Lys Thr Pro Ala Arg Lys Pro Lys Lys
                85                  90                  95

Lys Lys His Arg Pro Lys Val Leu Lys Asp Asp Lys Pro Ser Lys Thr
            100                 105                 110

Pro Lys Ser Ala Thr Pro Ile Pro Ser Thr Glu Lys Val Glu Lys Pro
        115                 120                 125

Ser Gly Lys Arg Lys Tyr Val Arg Lys Lys Thr Ser Pro Gly Gln Pro
    130                 135                 140

Pro Ala Glu Gln Ala Ala Ser Ser His Cys Arg Ser Glu Leu Lys Ser
145                 150                 155                 160

Val Lys Arg Ser Leu Asp Phe Gly Gly Glu Val Leu Gln Glu Ser Thr
                165                 170                 175

Gln Ser Gly Ser Gln Val Pro Val Ala Glu Ile Cys Thr Gly Pro Lys
            180                 185                 190

Arg Gln Ser Ile Pro Ser Thr Ile Gln Arg Asp Ser Gln Ser Gln Leu
        195                 200                 205

Ala Cys His Val Val Ser Ser Thr Ser Ser Ile His Thr Ser Ala Ser
    210                 215                 220

Gln Met Val Asn Ala His Leu Phe Pro Pro Asp Asn Met Pro Asn Gly
225                 230                 235                 240

Val Leu Leu Asp Leu Asn Asn Ser Thr Ser Gln Leu Gln Asn Glu His
                245                 250                 255

Ala Lys Phe Val Asp Ser Pro Ala Arg Leu Phe Gly Ser Arg Ile Arg
            260                 265                 270

Gln Thr Ser Gly Lys Asn Ser Leu Leu Glu Ile Tyr Ala Gly Met Ser
        275                 280                 285

Asp Arg Asn Val Pro Asp Leu Asn Ser Ser Ile Ser Gln Thr His Ser
    290                 295                 300

Met Ser Thr Asp Phe Ala Gln Tyr Leu Leu Ser Ser Ser Gln Ala Ser
305                 310                 315                 320

Val Arg Glu Thr Gln Met Ala Asn Gln Met Leu Asn Gly His Arg Met
                325                 330                 335

Pro Glu Asn Pro Ile Thr Pro Ser His Cys Ile Glu Arg Ala Ala Leu
            340                 345                 350

Lys Glu His Leu Asn His Val Pro His Ala Lys Ala Ala Val Met Asn
```

-continued

```
        355                 360                 365

Gly Gln Met Pro His Ser Tyr Arg Leu Ala Gln Asn Pro Ile Leu Pro
    370                 375                 380

Pro Asn His Ile Glu Gly Tyr Gln Val Met Glu Asn Leu Ser Glu Leu
385                 390                 395                 400

Val Thr Thr Asn Asp Tyr Leu Thr Ala Ser Pro Phe Ser Gln Thr Gly
                405                 410                 415

Ala Ala Asn Arg Gln His Asn Ile Gly Asp Ser Met His Ile His Ala
            420                 425                 430

Leu Asp Pro Arg Arg Glu Ser Asn Ala Ser Ser Gly Ser Trp Ile Ser
        435                 440                 445

Leu Gly Val Asn Phe Asn Gln Gln Asn Asn Gly Trp Ala Ser Ala Gly
    450                 455                 460

Ala Ala Asp Ala Ala Ser Ser His Ala Pro Tyr Phe Ser Glu Pro His
465                 470                 475                 480

Lys Arg Met Arg Thr Ala Tyr Leu Asn Asn Tyr Pro Asn Gly Val Val
                485                 490                 495

Gly His Phe Ser Thr Ser Ser Thr Asp Leu Ser Asn Asn Glu Asn Glu
            500                 505                 510

Asn Val Ala Ser Ala Ile Asn Ser Asn Val Phe Thr Leu Ala Asp Ala
        515                 520                 525

Gln Arg Leu Ile Ala Arg Glu Lys Ser Arg Ala Ser Gln Arg Met Ile
    530                 535                 540

Ser Phe Arg Ser Ser Lys Asn Asp Met Val Asn Arg Ser Glu Met Val
545                 550                 555                 560

His Gln His Gly Arg Pro Ala Pro His Gly Ser Ala Cys Arg Glu Ser
                565                 570                 575

Ile Glu Val Pro Asp Lys Gln Phe Gly Leu Met Thr Glu Glu Leu Thr
            580                 585                 590

Gln Leu Pro Ser Met Pro Asn Asn Pro Gln Arg Glu Lys Tyr Ile Pro
        595                 600                 605

Gln Thr Gly Ser Cys Gln Leu Gln Ser Leu Glu His Asp Met Val Lys
    610                 615                 620

Gly His Asn Leu Ala Gly Glu Leu His Lys Gln Val Thr Ser Pro Gln
625                 630                 635                 640

Val Val Ile Gln Ser Asn Phe Cys Val Thr Pro Pro Asp Val Leu Gly
                645                 650                 655

Arg Arg Thr Ser Gly Glu His Leu Arg Thr Leu Ile Ala Pro Thr His
            660                 665                 670

Ala Ser Thr Cys Lys Asp Thr Leu Lys Ala Leu Ser Cys Gln Leu Glu
        675                 680                 685

Ser Ser Arg Asp Ile Ile Arg Pro Pro Val Asn Pro Ile Gly Pro Ser
    690                 695                 700

Ser Ala Asp Val Pro Arg Thr Asp Asn His Gln Val Lys Val Ser Glu
705                 710                 715                 720

Glu Thr Val Thr Ala Lys Leu Pro Glu Lys Arg Lys Val Gly Arg Pro
                725                 730                 735

Arg Lys Glu Leu Lys Pro Gly Glu Lys Pro Lys Pro Arg Gly Arg Pro
            740                 745                 750

Arg Lys Gly Lys Val Val Gly Gly Glu Leu Ala Ser Lys Asp Ser His
        755                 760                 765

Thr Asn Pro Leu Gln Asn Glu Ser Thr Ser Cys Ser Tyr Gly Pro Tyr
    770                 775                 780
```

-continued

```
Ala Gly Glu Ala Ser Val Gly Arg Ala Val Lys Ala Asn Arg Val Gly
785                 790                 795                 800

Glu Asn Ile Ser Gly Ala Met Val Ser Leu Leu Asp Ser Leu Asp Ile
                805                 810                 815

Val Ile Gln Lys Ile Lys Val Leu Asp Ile Asn Lys Ser Glu Asp Pro
            820                 825                 830

Val Thr Ala Glu Pro His Gly Ala Leu Val Pro Tyr Asn Gly Glu Phe
        835                 840                 845

Gly Pro Ile Val Pro Phe Glu Gly Lys Val Lys Arg Lys Arg Ser Arg
    850                 855                 860

Ala Lys Val Asp Leu Asp Pro Val Thr Ala Leu Met Trp Lys Leu Leu
865                 870                 875                 880

Met Gly Pro Asp Met Ser Asp Cys Ala Glu Gly Met Asp Lys Asp Lys
                885                 890                 895

Glu Lys Trp Leu Asn Glu Glu Arg Lys Ile Phe Gln Gly Arg Val Asp
            900                 905                 910

Ser Phe Ile Ala Arg Met His Leu Val Gln Gly Asp Arg Arg Phe Ser
        915                 920                 925

Pro Trp Lys Gly Ser Val Val Asp Ser Val Val Gly Val Phe Leu Thr
    930                 935                 940

Gln Asn Val Ser Asp His Leu Ser Ser Ser Ala Phe Met Ala Leu Ala
945                 950                 955                 960

Ala Lys Phe Pro Val Lys Pro Glu Ala Ser Glu Lys Pro Ala Asn Val
                965                 970                 975

Met Phe His Thr Ile Ser Glu Asn Gly Asp Cys Ser Gly Leu Phe Gly
            980                 985                 990

Asn Ser Val Lys Leu Gln Gly Glu  Ile Leu Val Gln Glu  Ala Ser Asn
        995                 1000                1005

Thr Ala  Ala Ser Phe Ile Thr  Thr Glu Asp Lys Glu  Gly Ser Asn
    1010                1015                1020

Ser Val  Glu Leu Leu Gly Ser  Ser Phe Gly Asp Gly  Val Asp Gly
    1025                1030                1035

Ala Ala  Gly Val Tyr Ser Asn  Ile Tyr Glu Asn Leu  Pro Ala Arg
    1040                1045                1050

Leu His  Ala Thr Arg Arg Pro  Val Val Gln Thr Gly  Asn Ala Val
    1055                1060                1065

Glu Ala  Glu Asp Gly Ser Leu  Glu Gly Val Val Ser  Ser Glu Asn
    1070                1075                1080

Ser Thr  Ile Ser Ser Gln Asn  Ser Ser Asp Tyr Leu  Phe His Met
    1085                1090                1095

Ser Asp  His Met Phe Ser Ser  Met Leu Leu Asn Phe  Thr Ala Glu
    1100                1105                1110

Asp Ile  Gly Ser Arg Asn Met  Pro Lys Ala Thr Arg  Thr Thr Tyr
    1115                1120                1125

Thr Glu  Leu Leu Arg Met Gln  Glu Leu Lys Asn Lys  Ser Asn Glu
    1130                1135                1140

Thr Ile  Glu Ser Ser Glu Tyr  His Gly Val Pro Val  Ser Cys Ser
    1145                1150                1155

Asn Asn  Ile Gln Val Leu Asn  Gly Ile Gln Asn Ile  Gly Ser Lys
    1160                1165                1170

His Gln  Pro Leu His Ser Ser  Ile Ser Tyr His Gln  Thr Gly Gln
    1175                1180                1185
```

-continued

```
Val His Leu Pro Asp Ile Val His Ala Ser Asp Leu Glu Gln Ser
    1190                1195                1200

Val Tyr Thr Gly Leu Asn Arg Val Leu Asp Ser Asn Val Thr Gln
    1205                1210                1215

Thr Ser Tyr Tyr Pro Ser Pro His Pro Gly Ile Ala Cys Asn Asn
    1220                1225                1230

Glu Thr Gln Lys Ala Asp Ser Leu Ser Asn Met Leu Tyr Gly Ile
    1235                1240                1245

Asp Arg Ser Asp Lys Thr Thr Ser Leu Ser Glu Pro Thr Pro Arg
    1250                1255                1260

Ile Asp Asn Cys Phe Gln Pro Leu Ser Ser Glu Lys Met Ser Phe
    1265                1270                1275

Ala Arg Glu Gln Ser Ser Ser Glu Asn Tyr Leu Ser Arg Asn Glu
    1280                1285                1290

Ala Glu Ala Ala Phe Val Lys Gln His Gly Thr Ser Asn Val Gln
    1295                1300                1305

Gly Asp Asn Thr Val Arg Thr Glu Gln Asn Gly Gly Glu Asn Ser
    1310                1315                1320

Gln Ser Gly Tyr Ser Gln Gln Asp Asp Asn Val Gly Phe Gln Thr
    1325                1330                1335

Ala Thr Thr Ser Asn Leu Tyr Ser Ser Asn Leu Cys Gln Asn Gln
    1340                1345                1350

Lys Ala Asn Ser Glu Val Leu His Gly Val Ser Ser Asn Leu Ile
    1355                1360                1365

Glu Asn Ser Lys Asp Asp Lys Lys Thr Ser Pro Lys Val Pro Val
    1370                1375                1380

Asp Gly Ser Lys Ala Lys Arg Pro Arg Val Gly Ala Gly Lys Lys
    1385                1390                1395

Lys Thr Tyr Asp Trp Asp Met Leu Arg Lys Glu Val Leu Tyr Ser
    1400                1405                1410

His Gly Asn Lys Glu Arg Ser Gln Asn Ala Lys Asp Ser Ile Asp
    1415                1420                1425

Trp Glu Thr Ile Arg Gln Ala Glu Val Lys Glu Ile Ser Asp Thr
    1430                1435                1440

Ile Arg Glu Arg Gly Met Asn Asn Met Leu Ala Glu Arg Ile Lys
    1445                1450                1455

Asp Phe Leu Asn Arg Leu Val Arg Asp His Gly Ser Ile Asp Leu
    1460                1465                1470

Glu Trp Leu Arg Tyr Val Asp Ser Asp Lys Ala Lys Asp Tyr Leu
    1475                1480                1485

Leu Ser Ile Arg Gly Leu Gly Leu Lys Ser Val Glu Cys Val Arg
    1490                1495                1500

Leu Leu Thr Leu His His Met Ala Phe Pro Val Asp Thr Asn Val
    1505                1510                1515

Gly Arg Ile Cys Val Arg Leu Gly Trp Val Pro Leu Gln Pro Leu
    1520                1525                1530

Pro Glu Ser Leu Gln Leu His Leu Leu Glu Met Tyr Pro Met Leu
    1535                1540                1545

Glu Asn Ile Gln Lys Tyr Leu Trp Pro Arg Leu Cys Lys Leu Asp
    1550                1555                1560

Gln Arg Thr Leu Tyr Glu Leu His Tyr Gln Met Ile Thr Phe Gly
    1565                1570                1575

Lys Val Phe Cys Thr Lys Ser Lys Pro Asn Cys Asn Ala Cys Pro
```

```
    1580                1585                1590

Met Arg  Ala Glu Cys Lys His  Phe Ala Ser Ala Phe  Ala Ser Ala
    1595                1600                1605

Arg Leu  Ala Leu Pro Gly Pro  Glu Glu Lys Ser Leu  Val Thr Ser
    1610                1615                1620

Gly Thr  Pro Ile Ala Ala Glu  Thr Phe His Gln Thr  Tyr Ile Ser
    1625                1630                1635

Ser Arg  Pro Val Val Ser Gln  Leu Glu Trp Asn Ser  Asn Thr Cys
    1640                1645                1650

His His  Gly Met Asn Asn Arg  Gln Pro Ile Ile Glu  Glu Pro Ala
    1655                1660                1665

Ser Pro  Glu Pro Glu His Glu  Thr Glu Glu Met Lys  Glu Cys Ala
    1670                1675                1680

Ile Glu  Asp Ser Phe Val Asp  Asp Pro Glu Glu Ile  Pro Thr Ile
    1685                1690                1695

Lys Leu  Asn Phe Glu Glu Phe  Thr Gln Asn Leu Lys  Ser Tyr Met
    1700                1705                1710

Gln Ala  Asn Asn Ile Glu Ile  Glu Asp Ala Asp Met  Ser Lys Ala
    1715                1720                1725

Leu Val  Ala Ile Thr Pro Glu  Val Ala Ser Ile Pro  Thr Pro Lys
    1730                1735                1740

Leu Lys  Asn Val Ser Arg Leu  Arg Thr Glu His Gln  Val Tyr Glu
    1745                1750                1755

Leu Pro  Asp Ser His Pro Leu  Leu Glu Gly Phe Asn  Gln Arg Glu
    1760                1765                1770

Pro Asp  Asp Pro Cys Pro Tyr  Leu Leu Ser Ile Trp  Thr Pro Gly
    1775                1780                1785

Glu Thr  Ala Gln Ser Thr Asp  Ala Pro Lys Ser Val  Cys Asn Ser
    1790                1795                1800

Gln Glu  Asn Gly Glu Leu Cys  Ala Ser Asn Thr Cys  Phe Ser Cys
    1805                1810                1815

Asn Ser  Ile Arg Glu Ala Gln  Ala Gln Lys Val Arg  Gly Thr Leu
    1820                1825                1830

Leu Ile  Pro Cys Arg Thr Ala  Met Arg Gly Ser Phe  Pro Leu Asn
    1835                1840                1845

Gly Thr  Tyr Phe Gln Val Asn  Glu Cys Ser Asn Val  Met Arg Gln
    1850                1855                1860

Val Phe  Ala Asp His Asp Ser  Ser Arg Asn Pro Ile  Asp Val Pro
    1865                1870                1875

Arg Ser  Trp Ile Trp Asn Leu  Pro Arg Arg Thr Val  Tyr Phe Gly
    1880                1885                1890

Thr Ser  Ile Pro Thr Ile Phe  Lys Gly Leu Thr Thr  Glu Glu Ile
    1895                1900                1905

Gln His  Cys Phe Trp Arg Gly  Phe Val Cys Val Arg  Gly Phe Asp
    1910                1915                1920

Arg Thr  Ser Arg Ala Pro Arg  Pro Leu Tyr Ala Arg  Leu His Phe
    1925                1930                1935

Pro Ala  Ser Lys Ile Thr Arg  Asn Lys Lys Ser Ala  Gly Ser Ala
    1940                1945                1950

Pro Gly  Arg Asp Asp Glu
    1955
```

<210> SEQ ID NO 2

```
<211> LENGTH: 1952
<212> TYPE: PRT
<213> ORGANISM: Oryza sativa

<400> SEQUENCE: 2

Met Gln Asp Phe Gly Gln Trp Leu Pro Gln Ser Gln Thr Thr Ala Asp
1               5                   10                  15

Leu Tyr Phe Ser Ser Ile Pro Ile Pro Ser Gln Phe Asp Thr Ser Ile
            20                  25                  30

Glu Thr Gln Thr Arg Thr Ser Ala Val Val Ser Ser Glu Lys Glu Ser
        35                  40                  45

Ala Asn Ser Phe Val Pro His Asn Gly Thr Gly Leu Val Glu Arg Ile
    50                  55                  60

Ser Asn Asp Ala Gly Leu Thr Glu Val Val Gly Ser Ser Ala Gly Pro
65                  70                  75                  80

Thr Glu Cys Ile Asp Leu Asn Lys Thr Pro Ala Arg Lys Pro Lys Lys
                85                  90                  95

Lys Lys His Arg Pro Lys Val Leu Lys Asp Asp Lys Pro Ser Lys Thr
            100                 105                 110

Pro Lys Ser Ala Thr Pro Ile Pro Ser Thr Glu Lys Val Glu Lys Pro
        115                 120                 125

Ser Gly Lys Arg Lys Tyr Val Arg Lys Lys Thr Ser Pro Gly Gln Pro
    130                 135                 140

Pro Ala Glu Gln Ala Ala Ser Ser His Cys Arg Ser Glu Leu Lys Ser
145                 150                 155                 160

Val Lys Arg Ser Leu Asp Phe Gly Gly Glu Val Leu Gln Glu Ser Thr
                165                 170                 175

Gln Ser Gly Ser Gln Val Pro Val Ala Glu Ile Cys Thr Gly Pro Lys
            180                 185                 190

Arg Gln Ser Ile Pro Ser Thr Ile Gln Arg Asp Ser Gln Ser Gln Leu
        195                 200                 205

Ala Cys His Val Val Ser Ser Thr Ser Ser Ile His Thr Ser Ala Ser
    210                 215                 220

Gln Met Val Asn Ala His Leu Phe Pro Pro Asp Asn Met Pro Asn Gly
225                 230                 235                 240

Val Leu Leu Asp Leu Asn Asn Ser Thr Ser Gln Leu Gln Asn Glu His
                245                 250                 255

Ala Lys Phe Val Asp Ser Pro Ala Arg Leu Phe Gly Ser Arg Ile Arg
            260                 265                 270

Gln Thr Ser Gly Lys Asn Ser Leu Leu Glu Ile Tyr Ala Gly Met Ser
        275                 280                 285

Asp Arg Asn Val Pro Asp Leu Asn Ser Ser Ile Ser Gln Thr His Ser
    290                 295                 300

Met Ser Thr Asp Phe Ala Gln Tyr Leu Leu Ser Ser Ser Gln Ala Ser
305                 310                 315                 320

Val Arg Glu Thr Gln Met Ala Asn Gln Met Leu Asn Gly His Arg Met
                325                 330                 335

Pro Glu Asn Pro Ile Thr Pro Ser His Cys Ile Glu Arg Ala Ala Leu
            340                 345                 350

Lys Glu His Leu Asn His Val Pro His Ala Lys Ala Ala Val Met Asn
        355                 360                 365

Gly Gln Met Pro His Ser Tyr Arg Leu Ala Gln Asn Pro Ile Leu Pro
    370                 375                 380

Pro Asn His Ile Glu Gly Tyr Gln Val Met Glu Asn Leu Ser Glu Leu
```

385 390 395 400

Val Thr Thr Asn Asp Tyr Leu Thr Ala Ser Pro Phe Ser Gln Thr Gly
405 410 415

Ala Ala Asn Arg Gln His Asn Ile Gly Asp Ser Met His Ile His Ala
420 425 430

Leu Asp Pro Arg Arg Glu Ser Asn Ala Ser Ser Gly Ser Trp Ile Ser
435 440 445

Leu Gly Val Asn Phe Asn Gln Gln Asn Asn Gly Trp Ala Ser Ala Gly
450 455 460

Ala Ala Asp Ala Ala Ser Ser His Ala Pro Tyr Phe Ser Glu Pro His
465 470 475 480

Lys Arg Met Arg Thr Ala Tyr Leu Asn Asn Tyr Pro Asn Gly Val Val
485 490 495

Gly His Phe Ser Thr Ser Ser Thr Asp Leu Ser Asn Asn Glu Asn Glu
500 505 510

Asn Val Ala Ser Ala Ile Asn Ser Asn Val Phe Thr Leu Ala Asp Ala
515 520 525

Gln Arg Leu Ile Ala Arg Glu Lys Ser Arg Ala Ser Gln Arg Met Ile
530 535 540

Ser Phe Arg Ser Ser Lys Asn Asp Met Val Asn Arg Ser Glu Met Val
545 550 555 560

His Gln His Gly Arg Pro Ala Pro His Gly Ser Ala Cys Arg Glu Ser
565 570 575

Ile Glu Val Pro Asp Lys Gln Phe Gly Leu Met Thr Glu Glu Leu Thr
580 585 590

Gln Leu Pro Ser Met Pro Asn Asn Pro Gln Arg Glu Lys Tyr Ile Pro
595 600 605

Gln Thr Gly Ser Cys Gln Leu Gln Ser Leu Glu His Asp Met Val Lys
610 615 620

Gly His Asn Leu Ala Gly Glu Leu His Lys Gln Val Thr Ser Pro Gln
625 630 635 640

Val Val Ile Gln Ser Asn Phe Cys Val Thr Pro Pro Asp Val Leu Gly
645 650 655

Arg Arg Thr Ser Gly Glu His Leu Arg Thr Leu Ile Ala Pro Thr His
660 665 670

Ala Ser Thr Cys Lys Asp Thr Leu Lys Ala Leu Ser Cys Gln Leu Glu
675 680 685

Ser Ser Arg Asp Ile Ile Arg Pro Pro Val Asn Pro Ile Gly Pro Ser
690 695 700

Ser Ala Asp Val Pro Arg Thr Asp Asn His Gln Val Lys Val Ser Glu
705 710 715 720

Glu Thr Val Thr Ala Lys Leu Pro Glu Lys Arg Lys Val Gly Arg Pro
725 730 735

Arg Lys Glu Leu Lys Pro Gly Glu Lys Pro Lys Pro Arg Gly Arg Pro
740 745 750

Arg Lys Gly Lys Val Val Gly Gly Glu Leu Ala Ser Lys Asp Ser His
755 760 765

Thr Asn Pro Leu Gln Asn Glu Ser Thr Ser Cys Ser Tyr Gly Pro Tyr
770 775 780

Ala Gly Glu Ala Ser Val Gly Arg Ala Val Lys Ala Asn Arg Val Gly
785 790 795 800

Glu Asn Ile Ser Gly Ala Met Val Ser Leu Leu Asp Ser Leu Asp Ile
805 810 815

-continued

```
Val Ile Gln Lys Ile Lys Val Leu Asp Ile Asn Lys Ser Glu Asp Pro
            820                 825                 830

Val Thr Ala Glu Pro His Gly Ala Leu Val Pro Tyr Asn Gly Glu Phe
        835                 840                 845

Gly Pro Ile Val Pro Phe Glu Gly Lys Val Lys Arg Lys Arg Ser Arg
    850                 855                 860

Ala Lys Val Asp Leu Asp Pro Val Thr Ala Leu Met Trp Lys Leu Leu
865                 870                 875                 880

Met Gly Pro Asp Met Ser Asp Cys Ala Glu Gly Met Asp Lys Asp Lys
                885                 890                 895

Glu Lys Trp Leu Asn Glu Glu Arg Lys Ile Phe Gln Gly Arg Val Asp
            900                 905                 910

Ser Phe Ile Ala Arg Met His Leu Val Gln Gly Asp Arg Arg Phe Ser
        915                 920                 925

Pro Trp Lys Gly Ser Val Val Asp Ser Val Val Gly Val Phe Leu Thr
    930                 935                 940

Gln Asn Val Ser Asp His Leu Ser Ser Ser Ala Phe Met Ala Leu Ala
945                 950                 955                 960

Ala Lys Phe Pro Val Lys Pro Glu Ala Ser Glu Lys Pro Ala Asn Val
                965                 970                 975

Met Phe His Thr Ile Ser Glu Asn Gly Asp Cys Ser Gly Leu Phe Gly
            980                 985                 990

Asn Ser Val Lys Leu Gln Gly Glu  Ile Leu Val Gln Glu  Ala Ser Asn
        995                 1000                 1005

Thr Ala  Ala Ser Phe Ile Thr  Thr Glu Asp Lys Glu  Gly Ser Asn
    1010                 1015                 1020

Ser Val  Glu Leu Leu Gly Ser  Ser Phe Gly Asp Gly  Val Asp Gly
    1025                 1030                 1035

Ala Ala  Gly Val Tyr Ser Asn  Ile Tyr Glu Asn Leu  Pro Ala Arg
    1040                 1045                 1050

Leu His  Ala Thr Arg Arg Pro  Val Val Gln Thr Gly  Asn Ala Val
    1055                 1060                 1065

Glu Ala  Glu Asp Gly Ser Leu  Glu Gly Val Val Ser  Ser Glu Asn
    1070                 1075                 1080

Ser Thr  Ile Ser Ser Gln Asn  Ser Ser Asp Tyr Leu  Phe His Met
    1085                 1090                 1095

Ser Asp  His Met Phe Ser Ser  Met Leu Leu Asn Phe  Thr Ala Glu
    1100                 1105                 1110

Asp Ile  Gly Ser Arg Asn Met  Pro Lys Ala Thr Arg  Thr Thr Tyr
    1115                 1120                 1125

Thr Glu  Leu Leu Arg Met Gln  Glu Leu Lys Asn Lys  Ser Asn Glu
    1130                 1135                 1140

Thr Ile  Glu Ser Ser Glu Tyr  His Gly Val Pro Val  Ser Cys Ser
    1145                 1150                 1155

Asn Asn  Ile Gln Val Leu Asn  Gly Ile Gln Asn Ile  Gly Ser Lys
    1160                 1165                 1170

His Gln  Pro Leu His Ser Ser  Ile Ser Tyr His Gln  Thr Gly Gln
    1175                 1180                 1185

Val His  Leu Pro Asp Ile Val  His Ala Ser Asp Leu  Glu Gln Ser
    1190                 1195                 1200

Val Tyr  Thr Gly Leu Asn Arg  Val Leu Asp Ser Asn  Val Thr Gln
    1205                 1210                 1215
```

```
Thr Ser  Tyr Tyr Pro Ser Pro  His Pro Gly Ile Ala  Cys Asn Asn
    1220                 1225                 1230

Glu Thr  Gln Lys Ala Asp Ser  Leu Ser Asn Met Leu  Tyr Gly Ile
    1235                 1240                 1245

Asp Arg  Ser Asp Lys Thr Thr  Ser Leu Ser Glu Pro  Thr Pro Arg
    1250                 1255                 1260

Ile Asp  Asn Cys Phe Gln Pro  Leu Ser Ser Glu Lys  Met Ser Phe
    1265                 1270                 1275

Ala Arg  Glu Gln Ser Ser Ser  Glu Asn Tyr Leu Ser  Arg Asn Glu
    1280                 1285                 1290

Ala Glu  Ala Ala Phe Val Lys  Gln His Gly Thr Ser  Asn Val Gln
    1295                 1300                 1305

Gly Asp  Asn Thr Val Arg Thr  Glu Gln Asn Gly Gly  Glu Asn Ser
    1310                 1315                 1320

Gln Ser  Gly Tyr Ser Gln Gln  Asp Asp Asn Val Gly  Phe Gln Thr
    1325                 1330                 1335

Ala Thr  Thr Ser Asn Leu Tyr  Ser Ser Asn Leu Cys  Gln Asn Gln
    1340                 1345                 1350

Lys Ala  Asn Ser Glu Val Leu  His Gly Val Ser Ser  Asn Leu Ile
    1355                 1360                 1365

Glu Asn  Ser Lys Asp Asp Lys  Lys Thr Ser Pro Lys  Val Pro Val
    1370                 1375                 1380

Asp Gly  Ser Lys Ala Lys Arg  Pro Arg Val Gly Ala  Gly Lys Lys
    1385                 1390                 1395

Lys Thr  Tyr Asp Trp Asp Met  Leu Arg Lys Glu Val  Leu Tyr Ser
    1400                 1405                 1410

His Gly  Asn Lys Glu Arg Ser  Gln Asn Ala Lys Asp  Ser Ile Asp
    1415                 1420                 1425

Trp Glu  Thr Ile Arg Gln Ala  Glu Val Lys Glu Ile  Ser Asp Thr
    1430                 1435                 1440

Ile Arg  Glu Arg Gly Met Asn  Asn Met Leu Ala Glu  Arg Ile Lys
    1445                 1450                 1455

Asp Phe  Leu Asn Arg Leu Val  Arg Asp His Gly Ser  Ile Asp Leu
    1460                 1465                 1470

Glu Trp  Leu Arg Tyr Val Asp  Ser Asp Lys Ala Lys  Asp Tyr Leu
    1475                 1480                 1485

Leu Ser  Ile Arg Gly Leu Gly  Leu Lys Ser Val Glu  Cys Val Arg
    1490                 1495                 1500

Leu Leu  Thr Leu His His Met  Ala Phe Pro Val Asp  Thr Asn Val
    1505                 1510                 1515

Gly Arg  Ile Cys Val Arg Leu  Gly Trp Val Pro Leu  Gln Pro Leu
    1520                 1525                 1530

Pro Glu  Ser Leu Gln Leu His  Leu Leu Glu Met Tyr  Pro Met Leu
    1535                 1540                 1545

Glu Asn  Ile Gln Lys Tyr Leu  Trp Pro Arg Leu Cys  Lys Leu Asp
    1550                 1555                 1560

Gln Arg  Thr Leu Tyr Glu Leu  His Tyr Gln Met Ile  Thr Phe Gly
    1565                 1570                 1575

Lys Val  Phe Cys Thr Lys Ser  Lys Pro Asn Cys Asn  Ala Cys Pro
    1580                 1585                 1590

Met Arg  Ala Glu Cys Lys His  Phe Ala Ser Ala Phe  Ala Ser Ala
    1595                 1600                 1605

Arg Leu  Ala Leu Pro Gly Pro  Glu Glu Lys Ser Leu  Val Thr Ser
```

```
    1610                1615                1620

Gly Thr  Pro Ile Ala Ala Glu  Thr Phe His Gln Thr  Tyr Ile Ser
    1625                1630                1635

Ser Arg  Pro Val Val Ser Gln  Leu Glu Trp Asn Ser  Asn Thr Cys
    1640                1645                1650

His His  Gly Met Asn Asn Arg  Gln Pro Ile Ile Glu  Glu Pro Ala
    1655                1660                1665

Ser Pro  Glu Pro Glu His Glu  Thr Glu Glu Met Lys  Glu Cys Ala
    1670                1675                1680

Ile Glu  Asp Ser Phe Val Asp  Asp Pro Glu Glu Ile  Pro Thr Ile
    1685                1690                1695

Lys Leu  Asn Phe Glu Glu Phe  Thr Gln Asn Leu Lys  Ser Tyr Met
    1700                1705                1710

Gln Ala  Asn Asn Ile Glu Ile  Glu Asp Ala Asp Met  Ser Lys Ala
    1715                1720                1725

Leu Val  Ala Ile Thr Pro Glu  Val Ala Ser Ile Pro  Thr Pro Lys
    1730                1735                1740

Leu Lys  Asn Val Ser Arg Leu  Arg Thr Glu His Gln  Val Tyr Glu
    1745                1750                1755

Leu Pro  Asp Ser His Pro Leu  Leu Glu Gly Phe Asn  Gln Arg Glu
    1760                1765                1770

Pro Asp  Asp Pro Cys Pro Tyr  Leu Leu Ser Ile Trp  Thr Pro Gly
    1775                1780                1785

Glu Thr  Ala Gln Ser Thr Asp  Ala Pro Lys Ser Val  Cys Asn Ser
    1790                1795                1800

Gln Glu  Asn Gly Glu Leu Cys  Ala Ser Asn Thr Cys  Phe Ser Cys
    1805                1810                1815

Asn Ser  Ile Arg Glu Ala Gln  Ala Gln Lys Val Arg  Gly Thr Leu
    1820                1825                1830

Leu Ile  Pro Cys Arg Thr Ala  Met Arg Gly Ser Phe  Pro Leu Asn
    1835                1840                1845

Gly Thr  Tyr Phe Gln Val Asn  Glu Val Phe Ala Asp  His Asp Ser
    1850                1855                1860

Ser Arg  Asn Pro Ile Asp Val  Pro Arg Ser Trp Ile  Trp Asn Leu
    1865                1870                1875

Pro Arg  Arg Thr Val Tyr Phe  Gly Thr Ser Ile Pro  Thr Ile Phe
    1880                1885                1890

Lys Gly  Leu Thr Thr Glu Glu  Ile Gln His Cys Phe  Trp Arg Gly
    1895                1900                1905

Phe Val  Cys Val Arg Gly Phe  Asp Arg Thr Ser Arg  Ala Pro Arg
    1910                1915                1920

Pro Leu  Tyr Ala Arg Leu His  Phe Pro Ala Ser Lys  Ile Thr Arg
    1925                1930                1935

Asn Lys  Lys Ser Ala Gly Ser  Ala Pro Gly Arg Asp  Asp Glu
    1940                1945                1950
```

<210> SEQ ID NO 3
<211> LENGTH: 1636
<212> TYPE: PRT
<213> ORGANISM: Oryza sativa

<400> SEQUENCE: 3

```
Met Glu Gly Gln Trp Leu His Glu Pro His Gly Ile Asn Leu Cys Phe
1               5                   10                  15
```

-continued

```
Ser Thr Ser Ser Thr Leu Pro Arg Met Asn Pro Ser Ile Glu Thr Gly
            20                  25                  30

Thr Arg Asn Val Thr His Val Pro Ser Lys Asn Val Ser Thr Ser Ser
        35                  40                  45

Ser Gln Ala Arg Lys Thr Thr Val Gln Lys Pro Lys Arg Lys Arg His
    50                  55                  60

Arg Pro Lys Val Ile Lys Glu Gly Lys Ala Thr Gln Ala His Lys Ser
65                  70                  75                  80

Thr Thr Ser Glu Pro Pro Lys Glu Lys Asp Lys Pro Ala Gly Lys Arg
                85                  90                  95

Lys Tyr Val Arg Arg Lys Glu Gln Asn Thr Thr Pro Thr Glu His His
            100                 105                 110

Pro Pro Ser Lys Asp Ala Val Ala His Thr Ile Val Val Pro Thr Leu
        115                 120                 125

Ala Lys Arg Cys Phe Asn Phe Asp Gly Arg Asp His His Glu Glu Asn
    130                 135                 140

Val Asp Leu Leu Ser Gln Thr Arg Val Glu Glu Thr Pro Thr Cys Tyr
145                 150                 155                 160

Gly Asp Ala Gln Leu Leu Thr Ser Ala Val Asp Gly Ser Asn Ile Gln
                165                 170                 175

Leu Val Gln Pro Trp Cys Gly Ile Gly Ser Pro Ile Phe Ala Ser Val
            180                 185                 190

Asp Pro Met Ala Asn Met Arg Gln Ile Trp Ala Glu Ser Ser Arg Ala
        195                 200                 205

Asn Arg Val Thr Phe Asp Leu Asn Asn Ser Ala Val Asn His Ile Pro
    210                 215                 220

Arg Arg Phe Ser Asn Pro Thr Asn Ser Tyr Gly Gln Asn Phe Gln Phe
225                 230                 235                 240

Gly Ser Arg Glu Gln Ile Asn Gln Tyr Gln His Phe Tyr Asp Asp Asp
                245                 250                 255

Ile Pro Asp Glu Ile Pro Glu Asn Leu Val Val Pro Ala Trp His Thr
            260                 265                 270

Gly Arg Thr Trp Met Val Gly Asn Phe Asn His Glu Ala Ser Thr Arg
        275                 280                 285

Val Val Asn Pro Met Pro Gln Gly Tyr Arg Val Pro Gln Ser Pro Ser
    290                 295                 300

Glu Pro Pro Thr Cys Ser Glu Arg Asn Thr Thr Asn Ile Asn Leu Ser
305                 310                 315                 320

Glu Phe Pro Ala Lys Asn Asp Gln Ser Lys Phe Ala Thr Asn Pro Asn
                325                 330                 335

Asp Gln Ile Gly Ala Ser Phe Gly Leu Cys Asp Ser His Phe Ser Asp
            340                 345                 350

Val His Ala Ile Gly Lys Lys Arg Gly Tyr Asp Thr Ile Thr Asp His
        355                 360                 365

Gln Val Ser Phe Asp Ala Tyr Leu Glu Gln Ser Asn Ser Arg Arg Gln
    370                 375                 380

Phe Tyr Ser Asp Pro Leu Ser Thr Ser Ser Glu Thr Tyr Leu Leu Thr
385                 390                 395                 400

Glu Thr Cys Lys Arg Met Arg Ser Glu Asn His Ser Ser Trp Leu Asp
                405                 410                 415

Gly Phe Ile Gly Asn Val Ser Ser Thr Ser Ala Asn Leu Ser Gly Asn
            420                 425                 430

Trp Asn Thr Asn Asn Val Leu Ala Ile Asn His Gly Val Cys Thr Thr
```

-continued

```
        435                 440                 445

Leu Ala Asp Val Gln Arg Ser Met Ala Leu Glu Glu Ser Arg Ser Ser
    450                 455                 460

Arg Gln Tyr Thr Asp Pro Thr Leu Pro Cys Thr Ser Asn Thr His Phe
465                 470                 475                 480

Ile Gly Ser Cys Ala Gln His Thr Asn Ser Pro Asp Ser Ala Met Asn
                485                 490                 495

Ser Leu Gly Glu Asn Ile Gly His Arg Asn Gly Asp His Gln Leu Glu
            500                 505                 510

Ser Leu Glu Ile Arg Pro Thr Gln His Tyr Thr Ser Glu Cys Leu Gly
        515                 520                 525

Leu Pro Asn Glu Trp Ser Gly His Leu Ser Ala Gly His Thr His Leu
    530                 535                 540

Pro Asn Glu Thr Met Ile Pro Ser Ile Asn Lys Asn Trp Ser Cys Ser
545                 550                 555                 560

Val Ala Trp Ala Ala Ser Ala Ala Gln Pro Thr Ala Thr Val Ser Gln
                565                 570                 575

Val Ala Ser Ala Ala Ala Ala Thr Ser Thr Ala Gln Pro Ser Glu Gln
            580                 585                 590

Arg Asp Tyr Ile Pro Ser Ser Gly Val His Gln Pro Gln Pro Leu Glu
        595                 600                 605

Asn Gln Met Val Lys Gly Gln Asp Leu Cys Gln Thr His Lys Thr Ser
    610                 615                 620

Thr Lys Tyr Val Ala Asp Gly Asn Pro Ser Ile Asn Thr Pro Val Glu
625                 630                 635                 640

His Ile Gln Arg Thr Pro Ile Glu Val Met Ser Ser Phe Gln Ser Val
                645                 650                 655

Asn Arg Pro Ala Thr Thr Lys Asn Cys His Leu Glu Ala Ser Arg Glu
            660                 665                 670

Thr Thr Ser Ala Asn Pro Thr Glu Lys Pro Lys Val Trp Ser Arg Pro
        675                 680                 685

Arg Lys Glu Val Glu Pro Val Gly Lys Pro Lys Ala Arg Gly His Pro
    690                 695                 700

Lys Lys Gln Ala Glu Pro Asp Glu Lys Pro Lys Ala Arg Gly Arg Val
705                 710                 715                 720

Arg Lys Thr Thr Glu Ala Asn Gly Lys Ala Glu Asp Arg Asp Pro Thr
                725                 730                 735

Met Lys Glu Asn Asp Glu Ala Ile Ile Glu Lys Leu Lys Leu Leu Ser
            740                 745                 750

Ile Asn Met Thr Ser Asn Asn Thr Val Glu Glu Thr Pro Lys Asp Leu
        755                 760                 765

Gly Ala Leu Val Pro Leu Glu Gly Lys Val Lys Lys Arg Gly Ser Arg
    770                 775                 780

Ala Glu Val Lys Ile Asp Pro Val Thr Asn Leu Met Trp Asn Leu Leu
785                 790                 795                 800

Met Ala Leu Asp Lys Cys Glu Gly Val Glu Gly Ile Asp Glu Asp Lys
                805                 810                 815

Glu Arg Leu Leu Glu Glu Glu Arg Arg Met Phe Arg Gly Arg Ile Asp
            820                 825                 830

Ser Phe Ile Ala His Met His Leu Val Gln Gly Asp Arg Arg Phe Ser
        835                 840                 845

Pro Trp Lys Gly Ser Ile Val Asp Ser Val Val Asp Val Phe Leu Thr
    850                 855                 860
```

-continued

```
Gln Asn Val Ser Asp His Leu Ser Ser Ser Ala Phe Met Ala Leu Ala
865                 870                 875                 880

Ala Arg Phe Pro Val Lys Ser Glu Gly Pro Glu Lys Pro Ala Ala Val
                885                 890                 895

Glu Lys Ser Thr Pro Thr Pro Pro Lys Gln Lys Asp Ser Cys Ser Gly
            900                 905                 910

Val Leu Gly Glu Ser Ala Lys Leu Gln Gly Asn Phe Phe Val Glu Glu
        915                 920                 925

Ile Gly Asp Leu Gly Ser Phe Asn Thr Val Asp Asp Gly Ser Leu Glu
    930                 935                 940

Gly Val Leu Ser Ser Gln Asn Ser Val Val Ser Pro Arg Asn Phe Ser
945                 950                 955                 960

Lys Tyr Leu Leu Asn Gly Thr Tyr Thr Met Gly Ser Ser Ser Ser Leu
                965                 970                 975

Val Lys Phe Thr Gln Glu Val Gly Ser Ser Gly Cys His Gln Val Ser
            980                 985                 990

Val Leu Pro Thr Ser Asp Leu Asn  Lys Ala Ala Pro Phe  Asp Leu Asp
        995                 1000                1005

Thr Thr  Tyr Gln Ile Cys Thr  Gly Leu Asp His Gly  Val Asn Ile
    1010                1015                1020

Ser Asp  Val Ala Gln Ser Glu  Val Ser Leu Tyr Gln  Gln His Pro
    1025                1030                1035

Ile Asp  Ala Ser Ile Asn Lys  Asn Lys Ala Lys Val  Thr Asp Tyr
    1040                1045                1050

Ser Ser  Gly Ser Phe Leu Tyr  Asp Asn Arg Asp Gly  Ser Leu Ser
    1055                1060                1065

Gln His  Met Tyr Ser Ser Phe  Pro Phe Gln Pro Ser  Gln Glu Ala
    1070                1075                1080

Glu Cys  Ser Ala Thr Val Lys  Gln Ser Phe Phe Gln  Gln Phe Ile
    1085                1090                1095

Ser Ser  Glu Glu Val Pro Ile  Ser Thr Gly His Ser  Phe Tyr Asp
    1100                1105                1110

Asn Ser  Phe Thr Ser Asn Arg  Thr Glu Asp Pro Tyr  Val Glu Gln
    1115                1120                1125

Gln Asp  Cys Phe Asn Asn Leu  Gln Glu Ala Tyr Thr  Thr Arg Thr
    1130                1135                1140

Ile Gln  Ile Asn Ser Glu Arg  Ser Gln Pro Glu Cys  Ser Gln Gln
    1145                1150                1155

Gln Asp  Asn Asp Ile Arg Val  Gln Ala Lys Thr Cys  Glu Lys His
    1160                1165                1170

Ser Ser  Ser Asn Leu Cys Gly  Asn Met Asn Ser His  Ser Asp Val
    1175                1180                1185

Pro Leu  Gly Ile Ala Ser Gly  Ser Ile Gly Lys Ser  Lys His Thr
    1190                1195                1200

Glu Lys  Arg Pro Lys Ala Arg  Asn Val Arg Gly Arg  Thr Lys Met
    1205                1210                1215

Lys His  Tyr Asp Trp Asp Asn  Leu Arg Lys Glu Val  Leu His Asn
    1220                1225                1230

His Gly  Asn Arg Gln Arg Ser  Asp Lys Ala Lys Asp  Thr Ile Asp
    1235                1240                1245

Trp Glu  Ala Asp Phe Leu Asn  Arg Leu Val Arg Asp  His Gly Ser
    1250                1255                1260
```

```
Ile Asp  Leu Glu Trp Leu Arg  Asp Ile Glu Pro Asp  Lys Ala Lys
    1265                 1270                 1275

Gly Phe  Leu Leu Ser Ile Arg  Gly Leu Gly Leu Lys  Ser Thr Glu
    1280                 1285                 1290

Cys Val  Arg Leu Leu Thr Leu  His Gln Met Ala Phe  Pro Val Asp
    1295                 1300                 1305

Thr Asn  Val Ala Arg Ile Cys  Val Arg Leu Gly Trp  Val Pro Leu
    1310                 1315                 1320

Gln Pro  Leu Pro Glu Ser Leu  Gln Leu His Leu Leu  Glu Leu Tyr
    1325                 1330                 1335

Pro Leu  Leu Glu His Ile Gln  Lys Tyr Ile Trp Pro  Arg Leu Cys
    1340                 1345                 1350

Lys Leu  Asp Gln Leu Ile Leu  Tyr Glu Leu His Tyr  Gln Met Ile
    1355                 1360                 1365

Thr Phe  Gly Lys Val Phe Cys  Ser Lys Ser Lys Pro  Asn Cys Asn
    1370                 1375                 1380

Ser Cys  Pro Met Arg Ala Glu  Cys Lys His Phe Ala  Ser Ala Phe
    1385                 1390                 1395

Ala Ser  Ala Arg Leu Ala Leu  Pro Gly Pro Ser Lys  Lys Thr Ser
    1400                 1405                 1410

Lys Pro  Glu Tyr Pro Asn Asp  Ala Glu Ser Ser His  Lys Lys Tyr
    1415                 1420                 1425

Thr His  Ser Arg Pro Met Gly  Gln Leu Ser Trp Asn  Thr Asn His
    1430                 1435                 1440

Pro Gly  His Val Tyr Glu Ala  Arg Glu Ala Glu Ile  Glu Asp Phe
    1445                 1450                 1455

Phe Ser  Glu Asp Pro Asp Glu  Ile Pro Ile Ile Asn  Leu Asn Val
    1460                 1465                 1470

Glu Glu  Phe Ala Gln Asn Leu  Lys Ser Tyr Ile His  Ala Asn Asn
    1475                 1480                 1485

Ile Glu  Ile Glu Asp Ala Asp  Met Ser Asn Ala Leu  Val Ala Ile
    1490                 1495                 1500

Ser Pro  Gln Ala Ala Ser Val  Pro Thr Ser Lys Leu  Lys Asn Val
    1505                 1510                 1515

Asn Arg  Leu Arg Thr Glu His  Gln Val Tyr Glu Leu  Pro Asp Ser
    1520                 1525                 1530

His Pro  Leu Leu Glu Gly Phe  Asp Gln Arg Glu Pro  Asp Asp Pro
    1535                 1540                 1545

Ser Pro  Tyr Leu Leu Ser Ile  Trp Thr Pro Gly Lys  Leu Met Cys
    1550                 1555                 1560

Ser His  Pro Thr Phe Thr Leu  Ile Gln Val Ile Leu  Met Ile Lys
    1565                 1570                 1575

Ile Ser  Thr Gly Glu Thr Ala  Gln Ser Thr Asp Ala  Pro Lys Thr
    1580                 1585                 1590

Phe Cys  Asn Ser Lys Glu Thr  Gly Lys Leu Cys Glu  Ser Ser Thr
    1595                 1600                 1605

Cys Phe  Ser Cys Asn Ser Thr  Arg Glu Met Gln Ser  Gln Lys Val
    1610                 1615                 1620

Arg Gly  Thr Leu Leu Ala Ser  Ser Leu Leu Arg Val  Pro
    1625                 1630                 1635
```

<210> SEQ ID NO 4
<211> LENGTH: 1847
<212> TYPE: PRT

```
<213> ORGANISM: Oryza sativa

<400> SEQUENCE: 4

Met Ala Lys Asp Glu Asn Pro Ser Tyr Leu His Leu Ile Phe Leu Ser
1               5                   10                  15

Ser Arg Ile Arg Val Phe Ile Leu Asp Pro Pro Leu Ser Leu Pro Leu
            20                  25                  30

Ser His Gly Gln Cys Glu Leu Gln Val Val Glu Glu Ala Ala Met Asp
        35                  40                  45

Pro Ser Gly Leu Asn Leu Gln Gly Asn Pro Ala Glu Asn Gln Glu Ser
    50                  55                  60

Trp Thr Ser Gly Val Ser Val Gly Arg Gly Thr Pro Asn Leu Gly Val
65                  70                  75                  80

Gly Thr Ala Val Ala Gly Arg Ser Cys Pro Ser Ser Thr Leu Phe Pro
                85                  90                  95

Gly Ser Ser Leu Ser Ser Thr Ala Leu Leu Asn Thr Met His Glu Gly
            100                 105                 110

Ser Phe Pro Gln Thr Ala Leu Val Ala Gly Ser Val Ser Ser Ala Asp
        115                 120                 125

Glu Gln His Gly Ala Pro Pro Val Arg Pro Ser Tyr Asn Leu Pro Ala
    130                 135                 140

Gly Cys Thr Gln Val Pro Ile Ser Ile Leu Val Phe His Arg Arg Leu
145                 150                 155                 160

Thr Gly Arg Gly Ser Arg Cys Arg Ser Pro Gln Ser Arg Ser Phe Met
                165                 170                 175

Pro Ala Pro Ala Leu Ser Gly Val Ser Glu Asp Gly Ala Tyr Gly Pro
            180                 185                 190

Ile Pro Gln Ser Asp Phe Leu Ser Leu Arg Gly Pro Ser Glu Val Phe
        195                 200                 205

Pro Gly Asp Met Ala Met Asn His Ser Glu Pro Ala Thr Ser Tyr Gly
    210                 215                 220

Tyr Asn Ser Glu Tyr Ala Pro Met His Leu Gln Pro Asn Gly Leu Tyr
225                 230                 235                 240

Thr Glu Ala Ser Asn Thr Glu Ser Glu Arg Glu Ala Ser Gln Leu Gln
                245                 250                 255

Gln Ser Ala Glu Ala Val Ile Cys Asp Ser Leu Ser Lys Leu Glu Ser
            260                 265                 270

Ala Met Glu Lys Ile Gln Gly Gln Asn Pro Gln Glu Ser Ser Gly Leu
        275                 280                 285

Val Ala Glu Gly Ser Ala Asp Asp Asn Ile His Lys Tyr His Gln Lys
    290                 295                 300

Ala Lys Arg Ala Arg Thr Gln Ile Thr His Ser Asp Lys Ile Asp Leu
305                 310                 315                 320

Pro Thr Gln Ala Val Ser Ala Cys Lys Glu Lys Thr Ile Thr Gln Ile
                325                 330                 335

Glu Met Gln Ile Ala Asp Ala Glu Arg Thr Glu Ala Leu Lys Gly Glu
            340                 345                 350

Asp Ala Pro Ala Gln Lys Leu Lys Thr Arg Arg Arg Lys His Arg Pro
        355                 360                 365

Lys Val Ile Arg Glu Asp Arg Pro Ala Lys Lys Gln Met Ala Thr Thr
    370                 375                 380

Ser Glu Glu Lys Pro Leu Asn Gln Lys Pro Lys Arg Lys Tyr Val Arg
385                 390                 395                 400
```

```
Lys Asn Arg Asn Pro Ser Ser Leu Glu Lys Cys Ala Glu Pro Phe Ser
                405                 410                 415

Asp His Ser Ile Ser Arg Glu Ser Arg Thr Thr Val Arg Ser Ser Ile
            420                 425                 430

Ala Ser Val Arg Arg Arg Leu Gln Phe Glu Phe Gly Glu His Gly Val
        435                 440                 445

Gln Arg Asp Gln Ser Ser Met Thr Asn Ser Trp Tyr Gln Asn Gln Glu
    450                 455                 460

Lys Pro Val Asn Ala Glu Ser Ser Leu Cys Ser Val Thr Lys Ser Ser
465                 470                 475                 480

Val Gln Val Glu His Gly Gln Glu Leu His Met Glu Asn Ser Pro Glu
                485                 490                 495

Gly Leu Phe Phe Gly Ile Asn Ser Lys Leu Asn Lys Ile Leu Asp Glu
            500                 505                 510

Tyr Ile His Leu Pro Glu Ala Ala Pro Lys Pro Ser Glu Gln Ile Pro
        515                 520                 525

Leu Ala Ala Ser Gly His Val Ser Glu Glu Leu Ala Arg Lys Gln Tyr
    530                 535                 540

Asp Val Arg His Thr His Asp Pro Asp Ser Thr Ser Tyr Asn Ile Glu
545                 550                 555                 560

Arg Ser Gly Leu Ile Thr Thr Lys Gly His Lys Lys Asp Leu Asp Leu
                565                 570                 575

Asn Tyr Ser Asn Thr Asn Gly Phe Gln Met Tyr Cys Ser Ala Ser Leu
            580                 585                 590

Leu Pro Glu Met Asp Ser Thr Lys Gly Ser Met Thr Lys Val Ser Lys
        595                 600                 605

Met Asp Lys Asn Lys Lys Arg His Tyr Gly Gly Glu Ser Ser Leu Ala
    610                 615                 620

Gly Thr Gln Ser Ser Ile Ile Met Arg Thr Ala Ala Glu Met Leu Ala
625                 630                 635                 640

Val Tyr Gln Ala Cys Gly Ile Lys Lys Lys Arg Ser Ala Arg Val Arg
                645                 650                 655

Arg Asn Ser Phe Leu Ser Val Met Asp Leu Glu Lys Asn Thr Ser Gln
            660                 665                 670

Glu Ser Thr Arg Leu Pro Arg Ser Cys Met Glu Ala Leu Tyr Glu Ser
        675                 680                 685

Ser Tyr Ile Lys Phe Met Thr Lys Lys Arg Ser Gln Lys Ala Arg Leu
    690                 695                 700

Asn Ser Pro Asn Ser Ile Gln Pro Asn Ile Asp Gln Lys Asn Arg Phe
705                 710                 715                 720

Ser Ser Glu Thr Val Phe Ser Gly Gly Phe Asn Gly Leu Lys Arg Ser
                725                 730                 735

Glu Glu Thr Phe Gln Lys Thr Leu Pro Gln Ile Pro Asp Asp Lys Arg
            740                 745                 750

Ile Asn Leu Asp Ile His Cys Lys Val Pro Val Glu Ser Ser Pro Asn
        755                 760                 765

Thr Ser Thr Pro Pro Tyr Met Asp Tyr Leu Gln Gly Val Thr Ser Lys
    770                 775                 780

Phe Arg Tyr Phe Asp Leu Asn Thr Glu Gln Val His Lys Thr Glu Met
785                 790                 795                 800

His Leu Ser Gln Thr Met Pro Ser Leu Ser Ser Leu Gly Ala Thr Asn
                805                 810                 815

Tyr Leu Pro Asn Ala Leu Val Pro Tyr Val Gly Gly Ala Val Val Pro
```

```
            820                 825                 830

Tyr Gln Thr Gln Phe His Leu Val Lys Lys Gln Arg Pro Arg Ala Lys
        835                 840                 845

Val Asp Leu Asp Phe Glu Thr Thr Arg Val Trp Asn Leu Leu Met Gly
    850                 855                 860

Lys Ala Ala Asp Pro Val Asp Gly Thr Asp Val Asp Lys Glu Arg Trp
865                 870                 875                 880

Trp Lys Gln Glu Arg Glu Val Phe Gln Gly Arg Ala Asn Ser Phe Ile
                885                 890                 895

Ala Arg Met Arg Leu Val Gln Gly Asp Arg Arg Phe Ser Pro Trp Lys
            900                 905                 910

Gly Ser Val Val Asp Ser Val Val Gly Val Phe Leu Thr Gln Asn Val
        915                 920                 925

Ala Asp His Leu Ser Ser Ser Ala Tyr Met Ala Leu Ala Ala Ser Phe
    930                 935                 940

Pro Thr Gly Ser His Gly Asn Cys Asn Asp Gly Ile Ala Gly Gln Asp
945                 950                 955                 960

Asn Glu Glu Ile Ile Ser Thr Ser Ala Val Gly Asp Arg Gly Thr Phe
                965                 970                 975

Glu Phe Phe Tyr Asn Gly Ser Arg Pro Asp Ile Gly Leu Asn Phe Glu
            980                 985                 990

Phe Ser Met Ala Cys Glu Lys Ile  His Met Glu Pro Lys  Asp Asn Thr
        995                 1000                1005

Thr Val  Asn Glu Leu Thr Lys  Gly Glu Asn Tyr Ser  Leu His Cys
    1010                 1015                 1020

Lys Glu  Ser Ala Gly Ser Leu  Cys Asp His Glu Thr  Glu Ile Asp
    1025                 1030                 1035

His Lys  Ala Lys Ser Ile Ser  Asp Phe Ser Ala Val  Glu Leu Thr
    1040                 1045                 1050

Ala Cys  Met Lys Asn Leu His  Ala Thr Gln Phe Gln  Lys Glu Ile
    1055                 1060                 1065

Ser Leu  Ser Gln Ser Val Val  Thr Ser Glu Ser Ile  Leu Gln Pro
    1070                 1075                 1080

Gly Leu  Pro Leu Ser Ser Gly  Met Asp His Ala Arg  Arg Asn Phe
    1085                 1090                 1095

Val Gly  Ser Ile Ser Asp Thr  Ala Ser Gln Gln Val  Gly Ser Asn
    1100                 1105                 1110

Phe Asp  Asp Gly Lys Ser Leu  Thr Gly Asn Asp Val  Thr Ala Asn
    1115                 1120                 1125

Glu Thr  Glu Tyr His Gly Ile  Lys Ala Ala Ala Thr  Asn Asn Tyr
    1130                 1135                 1140

Val Val  Asp Glu Pro Gly Ile  Pro Ser Gly Ser Ser  Leu Tyr Pro
    1145                 1150                 1155

Phe Phe  Ser Ala Ile Asp Cys  His Gln Leu Asp Gly  Arg Asn Asp
    1160                 1165                 1170

Thr His  Val Ser Ser Thr Ser  Pro Asn Cys Ser Ile  Cys Ser Ala
    1175                 1180                 1185

Ser Ser  Asn Phe Lys Ile Gly  Thr Ile Glu Glu Asn  Ser Ser Leu
    1190                 1195                 1200

Phe Met  Pro Phe Asp Ala His  Leu Ala Gln Arg Asn  Gly Asn Met
    1205                 1210                 1215

Ile Val  Asp Thr Asn Leu Ser  Ser Ala Leu Glu Ser  Thr Glu Leu
    1220                 1225                 1230
```

```
Pro Val  Lys Leu Leu His Cys  Gly Lys Arg Ser Cys  Tyr Glu Ala
    1235                 1240                 1245

Ser Glu  Phe Gln Asp His Glu  Ser Leu Tyr Ala Thr  Gly Gly Val
    1250                 1255                 1260

Ile Pro  Glu Thr Ala Thr Lys  Ala Asp Asp Ser Thr  Leu Lys Ser
    1265                 1270                 1275

Gly Phe  Ala Ser Phe Asn Gly  Leu Pro Asp Thr Ala  Ala Gln Ala
    1280                 1285                 1290

Ser Lys  Pro Lys Lys Ser Arg  Thr Thr Ser Lys Lys  Asn Ser Glu
    1295                 1300                 1305

Asn Phe  Asp Trp Asp Lys Leu  Arg Arg Gln Ala Cys  Gly Asn Tyr
    1310                 1315                 1320

Gln Met  Lys Glu Arg Ile Phe  Asp Arg Arg Asp Ser  Val Asp Trp
    1325                 1330                 1335

Glu Ala  Val Arg Cys Ala Asp  Val Gln Arg Ile Ser  His Ala Ile
    1340                 1345                 1350

Arg Glu  Arg Gly Met Asn Asn  Val Leu Ala Glu Arg  Ile Gln Lys
    1355                 1360                 1365

Phe Leu  Asn Arg Leu Val Thr  Asp His Gly Ser Ile  Asp Leu Glu
    1370                 1375                 1380

Trp Leu  Arg Asp Val Pro Pro  Asp Ser Ala Lys Asp  Tyr Leu Leu
    1385                 1390                 1395

Ser Ile  Arg Gly Leu Gly Leu  Lys Ser Val Glu Cys  Val Arg Leu
    1400                 1405                 1410

Leu Thr  Leu His His Leu Ala  Phe Pro Val Asp Thr  Asn Val Gly
    1415                 1420                 1425

Arg Ile  Cys Val Arg Leu Gly  Trp Val Pro Ile Gln  Pro Leu Pro
    1430                 1435                 1440

Glu Ser  Leu Gln Leu His Leu  Leu Glu Leu Tyr Pro  Val Leu Glu
    1445                 1450                 1455

Thr Ile  Gln Lys Tyr Leu Trp  Pro Arg Leu Cys Lys  Leu Asp Gln
    1460                 1465                 1470

Gln Thr  Leu Tyr Glu Leu His  Tyr Gln Met Ile Thr  Phe Gly Lys
    1475                 1480                 1485

Val Phe  Cys Thr Lys Ser Lys  Pro Asn Cys Asn Ala  Cys Pro Met
    1490                 1495                 1500

Arg Ser  Glu Cys Arg His Phe  Ala Ser Ala Phe Ala  Ser Ala Arg
    1505                 1510                 1515

Leu Ala  Leu Pro Ser Pro Gln  Asp Lys Arg Leu Val  Asn Leu Ser
    1520                 1525                 1530

Asn Gln  Phe Ala Phe His Asn  Gly Thr Met Pro Thr  Pro Asn Ser
    1535                 1540                 1545

Thr Pro  Leu Pro Gln Leu Glu  Gly Ser Ile His Ala  Arg Asp Val
    1550                 1555                 1560

His Ala  Asn Asn Thr Asn Pro  Ile Ile Glu Glu Pro  Ala Ser Pro
    1565                 1570                 1575

Arg Glu  Glu Glu Cys Arg Glu  Leu Leu Glu Asn Asp  Ile Glu Asp
    1580                 1585                 1590

Phe Asp  Glu Asp Thr Asp Glu  Ile Pro Ile Ile Lys  Leu Asn Met
    1595                 1600                 1605

Glu Ala  Phe Ser Gln Asn Leu  Glu Asn Cys Ile Lys  Glu Ser Asn
    1610                 1615                 1620
```

Lys Asp Phe Gln Ser Asp Asp Ile Thr Lys Ala Leu Val Ala Ile
1625 1630 1635

Ser Asn Glu Ala Ala Ser Ile Pro Val Pro Lys Leu Lys Asn Val
1640 1645 1650

His Arg Leu Arg Thr Glu His Tyr Val Tyr Glu Leu Pro Asp Ser
1655 1660 1665

His Pro Leu Met Gln Gln Leu Ala Leu Asp Gln Arg Glu Pro Asp
1670 1675 1680

Asp Pro Asn Glu Leu Lys Asp Thr Arg Glu Ala Pro Lys Pro Cys
1685 1690 1695

Cys Asn Pro Gln Thr Glu Gly Gly Leu Cys Ser Asn Glu Met Cys
1700 1705 1710

His Asn Cys Val Ser Glu Arg Glu Asn Gln Tyr Arg Tyr Val Arg
1715 1720 1725

Gly Thr Val Leu Val Pro Cys Arg Thr Ala Met Arg Gly Ser Phe
1730 1735 1740

Pro Leu Asn Gly Thr Tyr Phe Gln Val Asn Glu Val Phe Ala Asp
1745 1750 1755

His Ser Ser Ser His Asn Pro Ile Asn Ile Pro Arg Glu Gln Leu
1760 1765 1770

Trp Asn Leu His Arg Arg Met Val Tyr Phe Gly Thr Ser Val Pro
1775 1780 1785

Thr Ile Phe Lys Gly Leu Thr Thr Glu Glu Ile Gln His Cys Phe
1790 1795 1800

Trp Arg Gly Phe Val Cys Val Arg Gly Phe Asn Met Glu Thr Arg
1805 1810 1815

Ala Pro Arg Pro Leu Cys Pro His Phe His Leu Ala Ala Ser Lys
1820 1825 1830

Leu Arg Arg Ser Ser Lys Lys Ala Ala Thr Glu Gln Thr His
1835 1840 1845

<210> SEQ ID NO 5
<211> LENGTH: 1829
<212> TYPE: PRT
<213> ORGANISM: Oryza sativa

<400> SEQUENCE: 5

Met Ala Lys Asp Glu Asn Pro Ser Tyr Leu His Leu Ile Phe Leu Ser
1 5 10 15

Ser Arg Ile Arg Val Phe Ile Leu Asp Pro Pro His Ser Leu Ser Leu
20 25 30

Ser Asn Gly Gln Cys Glu Leu Gln Val Val Glu Glu Ala Ala Met Asp
35 40 45

Pro Ser Gly Leu Asn Leu Gln Gly Asn Pro Ala Glu Asn Gln Glu Ser
50 55 60

Trp Thr Ser Gly Val Ser Val Gly Arg Gly Thr Pro Asn Leu Gly Val
65 70 75 80

Gly Thr Ala Val Ala Gly Arg Ser Cys Pro Pro Leu Thr Leu Phe Pro
85 90 95

Gly Ser Ser Leu Ser Ser Thr Ala Leu Leu Asn Ala Met His Glu Gly
100 105 110

Ser Phe Pro Gln Ala Ala Leu Val Ala Gly Ser Gly Ser Ser Ala Asp
115 120 125

Glu Gln His Gly Gly Pro Pro Val Arg Pro Ser Tyr Asn Leu Pro Ala
130 135 140

```
Gly Cys Thr Gln Val Pro Ile Ser Ile Leu Val Phe His Arg Arg Leu
145                 150                 155                 160

Thr Gly Arg Gly Ser Arg Arg Arg Ser Phe Met Pro Ala Pro Ala Leu
                165                 170                 175

Ser Gly Val Ser Glu Asp Gly Ala Ser Gly Pro Ile Pro Gln Ser Asp
            180                 185                 190

Phe Leu Ser Leu Gly Gly Pro Ser Glu Val Phe Ala Glu His Ala Pro
        195                 200                 205

Met Leu Leu Gln Pro Asn Gly Leu Tyr Thr Glu Ala Ser Asn Thr Glu
    210                 215                 220

Ser Glu Arg Glu Ala Ser Gln Leu Gln Gln Ser Ala Glu Ala Val Ile
225                 230                 235                 240

Cys Asp Ser His Ser Lys Leu Glu Ser Val Met Glu Lys Ile Gln Gly
                245                 250                 255

Gln Asn Pro Gln Glu Ser Ile Gly Leu Val Ala Glu Gly Ser Thr Asp
            260                 265                 270

Asp Asn Ile His Lys Tyr His Gln Lys Ala Lys Arg Ala Arg Thr Gln
        275                 280                 285

Ile Thr His Ser Asp Lys Met Asp Leu Pro Thr Gln Ala Val Ser Ala
    290                 295                 300

Cys Lys Glu Lys Thr Leu Thr Gln Ile Glu Met Gln Ile Ala Asp Ala
305                 310                 315                 320

Glu Arg Thr Glu Ala Phe Lys Ser Glu Asp Ala Pro Ala Gln Lys Leu
                325                 330                 335

Lys Thr Arg Arg Arg Lys His Arg Pro Lys Val Ile Arg Glu Asp Arg
            340                 345                 350

Pro Ala Lys Lys Gln Met Ser Thr Thr Ser Lys Glu Lys Pro Leu Asn
        355                 360                 365

Gln Lys Pro Lys Arg Lys Tyr Val Trp Lys Asn Arg Asn Pro Ser Ser
    370                 375                 380

Leu Glu Lys Cys Ala Glu Pro Phe Ser Asp His Ser Ile Ser Arg Glu
385                 390                 395                 400

Ser Arg Thr Thr Val Arg Ser Ser Ile Ala Ser Val Arg Arg Arg Leu
                405                 410                 415

Gln Phe Glu Phe Gly Glu His Gly Val Gln Arg Asp Gln Ser Ser Arg
            420                 425                 430

Thr Asn Ser Trp Tyr Arg Asn Gln Glu Lys Pro Val Asn Ala Glu Ser
        435                 440                 445

Ser Leu Cys Ser Val Thr Lys Ser Ser Val Gln Val Glu His Gly Gln
    450                 455                 460

Glu Leu His Met Glu Asn Ser Pro Glu Gly Leu Phe Phe Gly Ile Asn
465                 470                 475                 480

Ser Lys Leu Asn Lys Ile Leu Asp Glu Tyr Ile His Leu Pro Glu Ala
                485                 490                 495

Ala Pro Lys Pro Ser Glu Glu Ile Pro Leu Ala Thr Ser Gly His Val
            500                 505                 510

Ser Glu Glu Leu Ala Arg Lys Gln Asp Asp Val Arg His Ile His Asp
        515                 520                 525

His Asn Glu Arg Ser Gly Leu Ile Thr Thr Lys Gln Asn Lys Lys Asp
    530                 535                 540

Leu Asp Leu Asn Tyr Ser Asn Thr Asn Gly Phe Gln Met Tyr Cys Ser
545                 550                 555                 560
```

-continued

```
Ala Ser Leu Leu Pro Glu Met Asp Ser Thr Lys Gly Arg Met Thr Lys
                565                 570                 575

Val Ser Lys Met Asp Lys Asn Gln Lys Arg His Tyr Gly Gly Glu Ser
            580                 585                 590

Ser Leu Ala Gly Thr Gln Ser Ser Ile Ile Met Arg Thr Ala Ala Glu
        595                 600                 605

Met Leu Ala Val Tyr Gln Ala Cys Gly Ile Lys Lys Lys Arg Ser Ala
    610                 615                 620

Arg Val Arg Arg Asn Ser Phe Leu Ser Val Met Asp Leu Glu Lys Asn
625                 630                 635                 640

Thr Ser Gln Glu Ser Thr Arg Leu Pro Arg Ser Cys Met Glu Ala Leu
                645                 650                 655

Tyr Glu Ser Ser Tyr Ile Lys Phe Met Thr Lys Lys Arg Ser Gln Lys
            660                 665                 670

Ala Arg Leu Asn Ser Pro Asn Ser Ile Gln Pro Asn Ile Asp Gln Lys
        675                 680                 685

Asn Arg Phe Ser Ser Glu Thr Ile Phe Ser Gly Gly Phe Asn Gly Leu
    690                 695                 700

Lys Arg Ser Glu Glu Thr Phe Gln Lys Thr Leu Pro Gln Ile Pro Asp
705                 710                 715                 720

Asp Lys Arg Ile Asn Leu Asp Ile His Cys Glu Val Pro Val Glu Asn
                725                 730                 735

Ser Pro Asn Thr Ser Thr Pro Pro Tyr Met Asp Tyr Leu Gln Gly Val
            740                 745                 750

Thr Ser Lys Phe Arg Tyr Phe Asp Leu Asn Thr Glu Gln Val His Lys
        755                 760                 765

Thr Glu Met His Leu Tyr Gln Thr Met Pro Ser Leu Ser Ser Leu Gly
    770                 775                 780

Ala Thr Asn Tyr Leu Pro Asn Ala Leu Val Pro Tyr Val Gly Gly Ala
785                 790                 795                 800

Val Val Pro Tyr Gln Thr Gln Phe His Leu Val Lys Lys Gln Arg Pro
                805                 810                 815

Arg Ala Lys Val Asp Leu Asp Phe Glu Thr Thr Arg Val Trp Asn Leu
            820                 825                 830

Leu Met Gly Lys Ala Ala Asp Pro Val Asp Gly Thr Asp Val Asp Lys
        835                 840                 845

Glu Arg Trp Trp Lys Gln Glu Arg Glu Val Phe Gln Gly Arg Ala Asn
    850                 855                 860

Ser Phe Ile Ala Arg Met Arg Leu Val Gln Gly Asp Arg Arg Phe Ser
865                 870                 875                 880

Pro Trp Lys Gly Ser Val Val Asp Ser Val Val Gly Val Phe Leu Thr
                885                 890                 895

Gln Asn Val Ala Asp His Leu Ser Ser Ser Ala Tyr Met Ala Leu Ala
            900                 905                 910

Ala Ser Phe Pro Pro Gly Ser Asp Gly Asn Cys Asn Asp Gly Ile Ala
        915                 920                 925

Gly Gln Asp Asn Glu Glu Ile Ile Ser Thr Ser Ala Val Arg Asp Arg
    930                 935                 940

Gly Thr Phe Glu Phe Phe Tyr Asp Gly Ser Arg Pro Asp Ile Gly Leu
945                 950                 955                 960

Asn Phe Glu Glu Leu Ser Met Ala Cys Glu Lys Ile His Met Glu Pro
                965                 970                 975

Lys Gly Asn Ala Thr Val Asn Glu Leu Thr Lys Gly Glu Asn Tyr Ser
```

-continued

```
            980                 985                 990

Leu His Cys Lys Glu Pro Ala Gly  Ser Leu Cys Asp His  Glu Thr Arg
        995                 1000                1005

Ile Asp  His Lys Ala Lys Ser  Ile Ser Asp Ile Ser  Leu Val Glu
    1010                 1015                 1020

Leu Thr  Ala Arg Met Lys Asn  Leu His Ala Thr Gln  Phe Gln Thr
    1025                 1030                 1035

Glu Ile  Ser Leu Ser Gln Ser  Val Val Thr Ser Glu  Ser Ile Leu
    1040                 1045                 1050

Gln Pro  Gly Leu Pro Leu Ser  Ser Gly Met Asp His  Ala Pro Arg
    1055                 1060                 1065

Asn Phe  Val Gly Gly Ile Ser  Asp Thr Ala Ser Gln  Gln Val Gly
    1070                 1075                 1080

Ser Asn  Phe Asp Asp Gly Lys  Ser Leu Thr Gly Asn  Asp Val Thr
    1085                 1090                 1095

Ala Asn  Glu Thr Glu Tyr His  Gly Ile Lys Ala Ala  Ala Thr Asn
    1100                 1105                 1110

Asn Tyr  Val Val Asp Glu Pro  Arg Ile Pro Ser Gly  Ser Asn Met
    1115                 1120                 1125

Tyr Pro  Phe Phe Ser Ala Thr  Asp Cys His Gln Leu  Asp Glu Arg
    1130                 1135                 1140

Asn Asp  Ile His Val Ser Ser  Thr Ser Pro Asn Ser  Ser Ile Gly
    1145                 1150                 1155

Ser Ala  Ser Ser Asn Phe Lys  Ile Gly Thr Ile Glu  Glu Asn Ser
    1160                 1165                 1170

Ser Phe  Phe Met Pro Phe Asp  Ala His Leu Ala Gln  Met Asn Gly
    1175                 1180                 1185

Asn Met  Ile Ala Gly Thr Asn  Val Ser Ser Ala Leu  Ala Ser Thr
    1190                 1195                 1200

Glu Leu  Pro Val Lys Leu Leu  His Cys Cys Lys Arg  Ser Cys Tyr
    1205                 1210                 1215

Glu Ala  Ser Glu Phe Gln Asp  His Glu Ser Leu Tyr  Ala Thr Gly
    1220                 1225                 1230

Gly Ala  Ile Pro Glu Thr Ala  Thr Lys Ala Asp Asp  Ser Thr Leu
    1235                 1240                 1245

Lys Ser  Gly Phe Ala Ser Phe  Asn Gly Leu Pro Asp  Thr Ala Ala
    1250                 1255                 1260

Gln Ala  Ser Lys Pro Lys Lys  Pro Arg Thr Thr Ser  Lys Lys Asn
    1265                 1270                 1275

Ser Glu  Asn Phe Asp Trp Asp  Lys Leu Arg Arg Gln  Ala Cys Gly
    1280                 1285                 1290

Asn Tyr  Gln Met Lys Glu Arg  Ile Phe Asp Arg Arg  Asp Ser Val
    1295                 1300                 1305

Asp Trp  Glu Ala Val Arg Cys  Ala Asp Val Gln Arg  Ile Ser His
    1310                 1315                 1320

Ala Ile  Arg Glu Arg Gly Met  Asn Asn Val Leu Ala  Glu Arg Ile
    1325                 1330                 1335

Gln Lys  Phe Leu Asn Arg Leu  Val Thr Asp His Gly  Ser Ile Asp
    1340                 1345                 1350

Leu Glu  Trp Leu Arg Asp Val  Pro Pro Asp Ser Ala  Lys Asp Tyr
    1355                 1360                 1365

Leu Leu  Ser Ile Arg Gly Leu  Gly Leu Lys Ser Val  Glu Cys Val
    1370                 1375                 1380
```

```
Arg Leu  Leu Thr Leu His His  Leu Ala Phe Pro Val  Asp Thr Asn
    1385                 1390                 1395

Val Gly  Arg Ile Cys Val Arg  Leu Gly Trp Val Pro  Ile Gln Pro
    1400                 1405                 1410

Leu Pro  Glu Ser Leu Gln Leu  His Leu Leu Glu Leu  Tyr Pro Val
    1415                 1420                 1425

Leu Glu  Thr Ile Gln Lys Tyr  Leu Trp Pro Arg Leu  Cys Lys Leu
    1430                 1435                 1440

Asp Gln  Gln Thr Leu Tyr Glu  Leu His Tyr Gln Met  Ile Thr Phe
    1445                 1450                 1455

Gly Lys  Val Phe Cys Thr Lys  Ser Lys Pro Asn Cys  Asn Ala Cys
    1460                 1465                 1470

Pro Met  Arg Ser Glu Cys Lys  His Phe Ala Ser Ala  Phe Ala Ser
    1475                 1480                 1485

Ala Arg  Leu Ala Leu Pro Ser  Pro Gln Asp Lys Arg  Leu Val Asn
    1490                 1495                 1500

Met Ser  Asn Gln Phe Asp Phe  Gln Asn Gly Thr Met  Pro Thr Pro
    1505                 1510                 1515

His Ser  Thr Pro Leu Leu Gln  Leu Glu Gly Ser Ile  His Ala Arg
    1520                 1525                 1530

Asp Val  His Ala Asn Asn Thr  Asn Pro Ile Ile Glu  Glu Pro Ala
    1535                 1540                 1545

Ser Pro  Arg Glu Glu Glu Cys  Arg Glu Leu Leu Glu  Asn Asp Ile
    1550                 1555                 1560

Glu Asp  Phe Asp Glu Asp Thr  Asp Glu Ile Pro Thr  Ile Lys Leu
    1565                 1570                 1575

Asn Met  Glu Ala Phe Ala Gln  Asn Leu Glu Asn Cys  Ile Lys Glu
    1580                 1585                 1590

Ser Asn  Lys Asp Phe Gln Ser  Asp Asp Ile Thr Lys  Ala Leu Val
    1595                 1600                 1605

Ala Ile  Ser Asn Glu Ala Ala  Ser Ile Pro Val Pro  Lys Leu Lys
    1610                 1615                 1620

Asn Val  His Arg Leu Arg Thr  Glu His Tyr Val Tyr  Glu Leu Pro
    1625                 1630                 1635

Asp Ser  His Pro Leu Met Gln  Gln Leu Ala Leu Asp  Gln Arg Glu
    1640                 1645                 1650

Pro Asp  Asp Pro Ser Pro Tyr  Leu Leu Ala Ile Trp  Thr Pro Asp
    1655                 1660                 1665

Glu Leu  Lys Asp Thr Arg Glu  Ala Pro Lys Pro Cys  Cys Asn Pro
    1670                 1675                 1680

Gln Thr  Glu Gly Gly Leu Cys  Ser Asn Glu Met Cys  His Asn Cys
    1685                 1690                 1695

Val Ser  Glu Arg Glu Asn Gln  Tyr Arg Tyr Val Arg  Gly Thr Val
    1700                 1705                 1710

Leu Val  Pro Cys Arg Thr Ala  Met Arg Gly Ser Phe  Pro Leu Asn
    1715                 1720                 1725

Gly Thr  Tyr Phe Gln Val Asn  Glu Val Phe Ala Asp  His Ser Ser
    1730                 1735                 1740

Ser His  Asn Pro Ile Asn Ile  Pro Arg Glu Gln Leu  Trp Asn Leu
    1745                 1750                 1755

His Arg  Arg Met Val Tyr Phe  Gly Thr Ser Val Pro  Thr Ile Phe
    1760                 1765                 1770
```

```
Lys Gly  Leu Thr Thr Glu Glu  Ile Gln His Cys Phe  Trp Arg Gly
    1775                 1780                 1785

Phe Val  Cys Val Arg Gly Phe  Asp Met Glu Thr Arg  Ala Pro Arg
    1790                 1795                 1800

Pro Leu  Cys Pro His Phe His  Leu Ala Ala Ser Lys  Leu Arg Arg
    1805                 1810                 1815

Ser Ser  Lys Thr Ala Ala Thr  Glu Gln Thr His
    1820                 1825


<210> SEQ ID NO 6
<211> LENGTH: 1987
<212> TYPE: PRT
<213> ORGANISM: Arabidopsis thaliana

<400> SEQUENCE: 6

Met Asn Ser Arg Ala Asp Pro Gly Asp Arg Tyr Phe Arg Val Pro Leu
1               5                   10                  15

Glu Asn Gln Thr Gln Gln Glu Phe Met Gly Ser Trp Ile Pro Phe Thr
            20                  25                  30

Pro Lys Lys Pro Arg Ser Ser Leu Met Val Asp Glu Arg Val Ile Asn
        35                  40                  45

Gln Asp Leu Asn Gly Phe Pro Gly Gly Glu Phe Val Asp Arg Gly Phe
    50                  55                  60

Cys Asn Thr Gly Val Asp His Asn Gly Val Phe Asp His Gly Ala His
65                  70                  75                  80

Gln Gly Val Thr Asn Leu Ser Met Met Ile Asn Ser Leu Ala Gly Ser
                85                  90                  95

His Ala Gln Ala Trp Ser Asn Ser Glu Arg Asp Leu Leu Gly Arg Ser
            100                 105                 110

Glu Val Thr Ser Pro Leu Ala Pro Val Ile Arg Asn Thr Thr Gly Asn
        115                 120                 125

Val Glu Pro Val Asn Gly Asn Phe Thr Ser Asp Val Gly Met Val Asn
    130                 135                 140

Gly Pro Phe Thr Gln Ser Gly Thr Ser Gln Ala Gly Tyr Asn Glu Phe
145                 150                 155                 160

Glu Leu Asp Asp Leu Leu Asn Pro Asp Gln Met Pro Phe Ser Phe Thr
                165                 170                 175

Ser Leu Leu Ser Gly Gly Asp Ser Leu Phe Lys Val Arg Gln Tyr Gly
            180                 185                 190

Pro Pro Ala Cys Asn Lys Pro Leu Tyr Asn Leu Asn Ser Pro Ile Arg
        195                 200                 205

Arg Glu Ala Val Gly Ser Val Cys Glu Ser Ser Phe Gln Tyr Val Pro
    210                 215                 220

Ser Thr Pro Ser Leu Phe Arg Thr Gly Glu Lys Thr Gly Phe Leu Glu
225                 230                 235                 240

Gln Ile Val Thr Thr Thr Gly His Glu Ile Pro Glu Pro Lys Ser Asp
                245                 250                 255

Lys Ser Met Gln Ser Ile Met Asp Ser Ser Ala Val Asn Ala Thr Glu
            260                 265                 270

Ala Thr Glu Gln Asn Asp Gly Ser Arg Gln Asp Val Leu Glu Phe Asp
        275                 280                 285

Leu Asn Lys Thr Pro Gln Gln Lys Pro Ser Lys Arg Lys Arg Lys Phe
    290                 295                 300

Met Pro Lys Val Val Val Glu Gly Lys Pro Lys Arg Lys Pro Arg Lys
305                 310                 315                 320
```

-continued

```
Pro Ala Glu Leu Pro Lys Val Val Val Glu Gly Lys Pro Lys Arg Lys
                325                 330                 335

Pro Arg Lys Ala Ala Thr Gln Glu Lys Val Lys Ser Lys Glu Thr Gly
            340                 345                 350

Ser Ala Lys Lys Lys Asn Leu Lys Glu Ser Ala Thr Lys Lys Pro Ala
        355                 360                 365

Asn Val Gly Asp Met Ser Asn Lys Ser Pro Glu Val Thr Leu Lys Ser
    370                 375                 380

Cys Arg Lys Ala Leu Asn Phe Asp Leu Glu Asn Pro Gly Asp Ala Arg
385                 390                 395                 400

Gln Gly Asp Ser Glu Ser Glu Ile Val Gln Asn Ser Ser Gly Ala Asn
                405                 410                 415

Ser Phe Ser Glu Ile Arg Asp Ala Ile Gly Gly Thr Asn Gly Ser Phe
            420                 425                 430

Leu Asp Ser Val Ser Gln Ile Asp Lys Thr Asn Gly Leu Gly Ala Met
        435                 440                 445

Asn Gln Pro Leu Glu Val Ser Met Gly Asn Gln Pro Asp Lys Leu Ser
    450                 455                 460

Thr Gly Ala Lys Leu Ala Arg Asp Gln Gln Pro Asp Leu Leu Thr Arg
465                 470                 475                 480

Asn Gln Gln Cys Gln Phe Pro Val Ala Thr Gln Asn Thr Gln Phe Pro
                485                 490                 495

Met Glu Asn Gln Gln Ala Trp Leu Gln Met Lys Asn Gln Leu Ile Gly
            500                 505                 510

Phe Pro Phe Gly Asn Gln Gln Pro Arg Met Thr Ile Arg Asn Gln Gln
        515                 520                 525

Pro Cys Leu Ala Met Gly Asn Gln Gln Pro Met Tyr Leu Ile Gly Thr
    530                 535                 540

Pro Arg Pro Ala Leu Val Ser Gly Asn Gln Gln Leu Gly Gly Pro Gln
545                 550                 555                 560

Gly Asn Lys Arg Pro Ile Phe Leu Asn His Gln Thr Cys Leu Pro Ala
                565                 570                 575

Gly Asn Gln Leu Tyr Gly Ser Pro Thr Asp Met His Gln Leu Val Met
            580                 585                 590

Ser Thr Gly Gly Gln Gln His Gly Leu Leu Ile Lys Asn Gln Gln Pro
        595                 600                 605

Gly Ser Leu Ile Arg Gly Gln Gln Pro Cys Val Pro Leu Ile Asp Gln
    610                 615                 620

Gln Pro Ala Thr Pro Lys Gly Phe Thr His Leu Asn Gln Met Val Ala
625                 630                 635                 640

Thr Ser Met Ser Ser Pro Gly Leu Arg Pro His Ser Gln Ser Gln Val
                645                 650                 655

Pro Thr Thr Tyr Leu His Val Glu Ser Val Ser Arg Ile Leu Asn Gly
            660                 665                 670

Thr Thr Gly Thr Cys Gln Arg Ser Arg Ala Pro Ala Tyr Asp Ser Leu
        675                 680                 685

Gln Gln Asp Ile His Gln Gly Asn Lys Tyr Ile Leu Ser His Glu Ile
    690                 695                 700

Ser Asn Gly Asn Gly Cys Lys Lys Ala Leu Pro Gln Asn Ser Ser Leu
705                 710                 715                 720

Pro Thr Pro Ile Met Ala Lys Leu Glu Glu Ala Arg Gly Ser Lys Arg
                725                 730                 735
```

```
Gln Tyr His Arg Ala Met Gly Gln Thr Glu Lys His Asp Leu Asn Leu
            740                 745                 750

Ala Gln Gln Ile Ala Gln Ser Gln Asp Val Glu Arg His Asn Ser Ser
        755                 760                 765

Thr Cys Val Glu Tyr Leu Asp Ala Ala Lys Lys Thr Lys Ile Gln Lys
    770                 775                 780

Val Val Gln Glu Asn Leu His Gly Met Pro Pro Glu Val Ile Glu Ile
785                 790                 795                 800

Glu Asp Asp Pro Thr Asp Gly Ala Arg Lys Gly Lys Asn Thr Ala Ser
                805                 810                 815

Ile Ser Lys Gly Ala Ser Lys Gly Asn Ser Ser Pro Val Lys Lys Thr
            820                 825                 830

Ala Glu Lys Glu Lys Cys Ile Val Pro Lys Thr Pro Ala Lys Lys Gly
        835                 840                 845

Arg Ala Gly Arg Lys Lys Ser Val Pro Pro Pro Ala His Ala Ser Glu
    850                 855                 860

Ile Gln Leu Trp Gln Pro Thr Pro Pro Lys Thr Pro Leu Ser Arg Ser
865                 870                 875                 880

Lys Pro Lys Gly Lys Gly Arg Lys Ser Ile Gln Asp Ser Gly Lys Ala
                885                 890                 895

Arg Gly Pro Ser Gly Glu Leu Leu Cys Gln Asp Ser Ile Ala Glu Ile
            900                 905                 910

Ile Tyr Arg Met Gln Asn Leu Tyr Leu Gly Asp Lys Glu Arg Glu Gln
        915                 920                 925

Glu Gln Asn Ala Met Val Leu Tyr Lys Gly Asp Gly Ala Leu Val Pro
    930                 935                 940

Tyr Glu Ser Lys Lys Arg Lys Pro Arg Pro Lys Val Asp Ile Asp Asp
945                 950                 955                 960

Glu Thr Thr Arg Ile Trp Asn Leu Leu Met Gly Lys Gly Asp Glu Lys
                965                 970                 975

Glu Gly Asp Glu Glu Lys Asp Lys Lys Lys Glu Lys Trp Trp Glu Glu
            980                 985                 990

Glu Arg Arg Val Phe Arg Gly Arg  Ala Asp Ser Phe Ile  Ala Arg Met
        995                 1000                1005

His Leu  Val Gln Gly Asp Arg  Arg Phe Ser Pro Trp  Lys Gly Ser
    1010                1015                1020

Val Val  Asp Ser Val Ile Gly  Val Phe Leu Thr Gln  Asn Val Ser
    1025                1030                1035

Asp His  Leu Ser Ser Ser Ala  Phe Met Ser Leu Ala  Ala Arg Phe
    1040                1045                1050

Pro Pro  Lys Leu Ser Ser Ser  Arg Glu Asp Glu Arg  Asn Val Arg
    1055                1060                1065

Ser Val  Val Val Glu Asp Pro  Glu Gly Cys Ile Leu  Asn Leu Asn
    1070                1075                1080

Glu Ile  Pro Ser Trp Gln Glu  Lys Val Gln His Pro  Ser Asp Met
    1085                1090                1095

Glu Val  Ser Gly Val Asp Ser  Gly Ser Lys Glu Gln  Leu Arg Asp
    1100                1105                1110

Cys Ser  Asn Ser Gly Ile Glu  Arg Phe Asn Phe Leu  Glu Lys Ser
    1115                1120                1125

Ile Gln  Asn Leu Glu Glu Glu  Val Leu Ser Ser Gln  Asp Ser Phe
    1130                1135                1140

Asp Pro  Ala Ile Phe Gln Ser  Cys Gly Arg Val Gly  Ser Cys Ser
```

-continued

```
    1145                1150                1155

Cys Ser  Lys Ser Asp Ala Glu  Phe Pro Thr Thr Arg  Cys Glu Thr
    1160                1165                1170

Lys Thr  Val Ser Gly Thr Ser  Gln Ser Val Gln Thr  Gly Ser Pro
    1175                1180                1185

Asn Leu  Ser Asp Glu Ile Cys  Leu Gln Gly Asn Glu  Arg Pro His
    1190                1195                1200

Leu Tyr  Glu Gly Ser Gly Asp  Val Gln Lys Gln Glu  Thr Thr Asn
    1205                1210                1215

Val Ala  Gln Lys Lys Pro Asp  Leu Glu Lys Thr Met  Asn Trp Lys
    1220                1225                1230

Asp Ser  Val Cys Phe Gly Gln  Pro Arg Asn Asp Thr  Asn Trp Gln
    1235                1240                1245

Thr Thr  Pro Ser Ser Ser Tyr  Glu Gln Cys Ala Thr  Arg Gln Pro
    1250                1255                1260

His Val  Leu Asp Ile Glu Asp  Phe Gly Met Gln Gly  Glu Gly Leu
    1265                1270                1275

Gly Tyr  Ser Trp Met Ser Ile  Ser Pro Arg Val Asp  Arg Val Lys
    1280                1285                1290

Asn Lys  Asn Val Pro Arg Arg  Phe Phe Arg Gln Gly  Gly Ser Val
    1295                1300                1305

Pro Arg  Glu Phe Thr Gly Gln  Ile Ile Pro Ser Thr  Pro His Glu
    1310                1315                1320

Leu Pro  Gly Met Gly Leu Ser  Gly Ser Ser Ser Ala  Val Gln Glu
    1325                1330                1335

His Gln  Asp Asp Thr Gln His  Asn Gln Gln Asp Glu  Met Asn Lys
    1340                1345                1350

Ala Ser  His Leu Gln Lys Thr  Phe Leu Asp Leu Leu  Asn Ser Ser
    1355                1360                1365

Glu Glu  Cys Leu Thr Arg Gln  Ser Ser Thr Lys Gln  Asn Ile Thr
    1370                1375                1380

Asp Gly  Cys Leu Pro Arg Asp  Arg Thr Ala Glu Asp  Val Val Asp
    1385                1390                1395

Pro Leu  Ser Asn Asn Ser Ser  Leu Gln Asn Ile Leu  Val Glu Ser
    1400                1405                1410

Asn Ser  Ser Asn Lys Glu Gln  Thr Ala Val Glu Tyr  Lys Glu Thr
    1415                1420                1425

Asn Ala  Thr Ile Leu Arg Glu  Met Lys Gly Thr Leu  Ala Asp Gly
    1430                1435                1440

Lys Lys  Pro Thr Ser Gln Trp  Asp Ser Leu Arg Lys  Asp Val Glu
    1445                1450                1455

Gly Asn  Glu Gly Arg Gln Glu  Arg Asn Lys Asn Asn  Met Asp Ser
    1460                1465                1470

Ile Asp  Tyr Glu Ala Ile Arg  Arg Ala Ser Ile Ser  Glu Ile Ser
    1475                1480                1485

Glu Ala  Ile Lys Glu Arg Gly  Met Asn Asn Met Leu  Ala Val Arg
    1490                1495                1500

Ile Lys  Asp Phe Leu Glu Arg  Ile Val Lys Asp His  Gly Gly Ile
    1505                1510                1515

Asp Leu  Glu Trp Leu Arg Glu  Ser Pro Pro Asp Lys  Ala Lys Asp
    1520                1525                1530

Tyr Leu  Leu Ser Ile Arg Gly  Leu Gly Leu Lys Ser  Val Glu Cys
    1535                1540                1545
```

```
Val Arg  Leu Leu Thr Leu His  Asn Leu Ala Phe Pro  Val Asp Thr
    1550                 1555                 1560

Asn Val  Gly Arg Ile Ala Val  Arg Met Gly Trp Val  Pro Leu Gln
    1565                 1570                 1575

Pro Leu  Pro Glu Ser Leu Gln  Leu His Leu Leu Glu  Leu Tyr Pro
    1580                 1585                 1590

Val Leu  Glu Ser Ile Gln Lys  Phe Leu Trp Pro Arg  Leu Cys Lys
    1595                 1600                 1605

Leu Asp  Gln Arg Thr Leu Tyr  Glu Leu His Tyr Gln  Leu Ile Thr
    1610                 1615                 1620

Phe Gly  Lys Val Phe Cys Thr  Lys Ser Arg Pro Asn  Cys Asn Ala
    1625                 1630                 1635

Cys Pro  Met Arg Gly Glu Cys  Arg His Phe Ala Ser  Ala Tyr Ala
    1640                 1645                 1650

Ser Ala  Arg Leu Ala Leu Pro  Ala Pro Glu Glu Arg  Ser Leu Thr
    1655                 1660                 1665

Ser Ala  Thr Ile Pro Val Pro  Pro Glu Ser Tyr Pro  Pro Val Ala
    1670                 1675                 1680

Ile Pro  Met Ile Glu Leu Pro  Leu Pro Leu Glu Lys  Ser Leu Ala
    1685                 1690                 1695

Ser Gly  Ala Pro Ser Asn Arg  Glu Asn Cys Glu Pro  Ile Ile Glu
    1700                 1705                 1710

Glu Pro  Ala Ser Pro Gly Gln  Glu Cys Thr Glu Ile  Thr Glu Ser
    1715                 1720                 1725

Asp Ile  Glu Asp Ala Tyr Tyr  Asn Glu Asp Pro Asp  Glu Ile Pro
    1730                 1735                 1740

Thr Ile  Lys Leu Asn Ile Glu  Gln Phe Gly Met Thr  Leu Arg Glu
    1745                 1750                 1755

His Met  Glu Arg Asn Met Glu  Leu Gln Glu Gly Asp  Met Ser Lys
    1760                 1765                 1770

Ala Leu  Val Ala Leu His Pro  Thr Thr Thr Ser Ile  Pro Thr Pro
    1775                 1780                 1785

Lys Leu  Lys Asn Ile Ser Arg  Leu Arg Thr Glu His  Gln Val Tyr
    1790                 1795                 1800

Glu Leu  Pro Asp Ser His Arg  Leu Leu Asp Gly Met  Asp Lys Arg
    1805                 1810                 1815

Glu Pro  Asp Asp Pro Ser Pro  Tyr Leu Leu Ala Ile  Trp Thr Pro
    1820                 1825                 1830

Gly Glu  Thr Ala Asn Ser Ala  Gln Pro Pro Glu Gln  Lys Cys Gly
    1835                 1840                 1845

Gly Lys  Ala Ser Gly Lys Met  Cys Phe Asp Glu Thr  Cys Ser Glu
    1850                 1855                 1860

Cys Asn  Ser Leu Arg Glu Ala  Asn Ser Gln Thr Val  Arg Gly Thr
    1865                 1870                 1875

Leu Leu  Ile Pro Cys Arg Thr  Ala Met Arg Gly Ser  Phe Pro Leu
    1880                 1885                 1890

Asn Gly  Thr Tyr Phe Gln Val  Asn Glu Leu Phe Ala  Asp His Glu
    1895                 1900                 1905

Ser Ser  Leu Lys Pro Ile Asp  Val Pro Arg Asp Trp  Ile Trp Asp
    1910                 1915                 1920

Leu Pro  Arg Arg Thr Val Tyr  Phe Gly Thr Ser Val  Thr Ser Ile
    1925                 1930                 1935
```

-continued

```
Phe Arg  Gly Leu Ser Thr Glu  Gln Ile Gln Phe Cys  Phe Trp Lys
    1940                 1945                 1950

Gly Phe  Val Cys Val Arg Gly  Phe Glu Gln Lys Thr  Arg Ala Pro
    1955                 1960                 1965

Arg Pro  Leu Met Ala Arg Leu  His Phe Pro Ala Ser  Lys Leu Lys
    1970                 1975                 1980

Asn Asn  Lys Thr
    1985
```

```
<210> SEQ ID NO 7
<211> LENGTH: 6835
<212> TYPE: DNA
<213> ORGANISM: Artificial Sequence
<220> FEATURE:
<223> OTHER INFORMATION: Full length cDNA encoding rice ROS1a mutant
      (Ta2) polypeptide

<400> SEQUENCE: 7

atgatagtgc atatgtatcc tttctttttc ttttcttttg ttttcataac tgtcttacag     60

aatttcatgt tggctggtga cacttgtctc actcattatt tggtatattt tgactaaatg    120

caacgtgttg gtgctcggta gtttatattt gtttttacgc attcttcatt gactgtatgt    180

atttgatgtt gataccctgg gctgtcttat tttataggtg gatgctggga ggccacatag    240

gaggcctgtg tgatccaagt gtgctgctcc tgagttgaaa ttgcatagcc atatagcaac    300

tactggtgta aacttgagag atgaagtagt gaaaggaaat atgcaggatt ttggacaatg    360

gctgcctcaa tctcagacca ctgccgatct atatttctcc agtattccaa taccatcaca    420

gttcgatact tccatagaga cgcagactag aacttctgca gttgtatcgt cagagaaaga    480

atctgctaat tcgttcgtcc ctcataatgg tactgggctt gttgaacgca ttagcaatga    540

tgctgggcta actgaagtag ttggaagtag tgctggacca actgaatgta ttgacttgaa    600

caagacacca gcacggaaac ccaagaagaa aaagcacagg ccaaaggtgc taaaggacga    660

taaaccatcg aagacaccta aatctgctac tccaatacct tcaacagaaa aggtagaaaa    720

accatctgga aagagaaaat atgtccgcaa gaagacatct ccaggccaac ctcctgcaga    780

acaggcagct agctcacact gcagatctga gctgaagtca gttaaacgaa gtttggactt    840

tggtggagaa gtactgcaag agagtacaca atctggatct caagttccgg tggcagaaat    900

atgtactggt cccaagcgtc aatcaatacc ttctaccatc caaagagatt cgcaaagcca    960

gttggcttgc cacgtggttt ctagcaccag ctcaattcac acttcagcta gtcagatggt   1020

taatgcacat ttgtttcctc ctgataacat gccaaatgga gtattgcttg acctcaataa   1080

ttctactagt cagttacaaa acgaacatgc taaatttgtg gacagtccgg cacgtctttt   1140

tggttccaga ataagacaga catcaggtaa aaattctttg ctagaaatct atgctggcat   1200

gtcagataga aatgtacctg atctcaacag ttcaatcagt cagacgcata gcatgtctac   1260

tgattttgct caatacttgc tttcatcctc acaagcttct gtaagggaaa cacaaatggc   1320

caatcagatg cttaatggtc ataggatgcc agaaaatcca attacaccta gtcattgtat   1380

tgaaagggct gcattgaagg aacatttgaa tcatgttcct cacgcaaaag ccgcagtgat   1440

gaatggccaa atgccccata gttacaggtt ggcgcaaaat cccatcctac ctccaaatca   1500

tattgaaggg tatcaagtga tggaaaattt gagtgaactt gtcacgacaa atgactatct   1560

aactgctagt cctttcagtc aaactggagc tgcaaatagg cagcataata ttggtgactc   1620

catgcatata catgcattgg atcctagaag agagagtaat gcttcaagtg gttcttggat   1680
```

-continued

```
atcattaggt gtgaacttta accaacaaaa taatggatgg gcatctgcag gtgctgccga   1740
tgctgcgagc tcacatgccc catatttttc agaacctcac aaaagaatga ggacagctta   1800
tcttaacaat tatccaaatg gagtcgtggg acatttttct acctcatcta cggatttgtc   1860
aaataatgag aatgaaaatg tggcctcagc aatcaactca aacgttttta cccttgctga   1920
tgcacaaaga ttgatagccc gtgagaaatc acgagcttcc caaagaatga tcagttttag   1980
atcatctaaa aatgatatgg ttaacagatc agaaatggtc catcaacatg gcagacctgc   2040
tccgcatggc tctgcatgca gggagtctat tgaagtacct gacaaacagt tcgggctcat   2100
gacagaagaa ctcacacaat tacctagtat gccaaataac ccacaaaggg aaaaatatat   2160
tccgcaaact ggaagttgcc aacttcagtc tttggaacat gacatggtta aagggcataa   2220
cttggcaggt gaattgcata agcaagtaac ttcacctcaa gttgttattc agagcaattt   2280
ctgtgttacc cctcctgatg tgctcggcag aagaaccagt ggggagcatt taagaaccct   2340
tatagctcca acacatgcat cgacatgtaa ggacactctg aaagctttaa gttgtcaact   2400
ggagagttct agagacatta ttaggcctcc tgtcaatcct atagggccat cctctgccga   2460
tgttccaaga actgataacc atcaagtcaa ggtttctgaa gaaaccgtta cagccaaact   2520
ccctgagaag cgaaaagtag gacgtcccag aaaagagtta aaacctggtg agaaaccaaa   2580
acctagaggc cgtccaagga agggaaaagt tgttggtgga gaacttgcat caaaggatag   2640
tcacactaat ccattgcaaa atgagagtac ttcatgttct tatggtcctt atgcagggga   2700
ggcttctgtt ggaagagcag ttaaagcaaa tagagttgga gaaaacattt ctggagctat   2760
ggtatcccta ctggattctt tagatattgt tattcaaaag ataaaggtct tggacataaa   2820
caaatcagaa gaccctgtga cagctgaacc tcatggtgct cttgtccctt acaatggaga   2880
atttggtcct attgttcctt ttgaggggaa agtgaaaaga aaacgctctc gagccaaagt   2940
ggatcttgac cctgtaactg ctttaatgtg gaagttacta atgggaccag atatgagtga   3000
ttgtgctgaa ggtatggata aggataaaga gaaatggcta aatgaagaaa gaaaaatatt   3060
ccaagggcgt gttgattcat ttattgctcg aatgcatcta gttcaaggag atcggcgttt   3120
ttctccttgg aaaggatcag ttgtagattc tgtagtggga gtatttctta cacagaatgt   3180
ttcggaccat ctttccagct ctgcatttat ggctcttgct gcaaaatttc ctgtaaagcc   3240
agaagcctct gaaaaacccg caaatgtgat gtttcataca atttcagaaa atggtgattg   3300
ttctgggttg tttggtaatt ctgtcaagct acagggtgag atccttgttc aggaggccag   3360
caacacagca gcctctttta tcacaaccga ggataaggaa ggaagtaaca gtgtggaatt   3420
gcttggaagt tcttttgggg atggagtgga tggtgcagca ggagtttatt ctaatattta   3480
tgagaatctg ccagctagac tgcatgctac taggcgtcca gtcgttcaaa ctggaaacgc   3540
tgtcgaagcg gaagatgggt cactggaggg tgttgtttca tcagaaaact ccactatttc   3600
atctcaaaat tcatcagatt atctatttca catgtctgat catatgtttt cgagcatgtt   3660
actaaatttc actgccgaag acattggcag cagaaatatg cccaaagcaa caagaaccac   3720
atatacagaa cttctacgaa tgcaggagct gaagaacaag tctaatgaaa ccattgaatc   3780
atcagagtat catggggttc cagtctcatg tagtaacaac attcaagtgc tcaatggaat   3840
acaaaatatc ggcagtaaac atcagccttt acattcctct atttcatatc accagactgg   3900
ccaagttcac ctcccagaca tagtacatgc gagtgatttg gagcaatcag tatacactgg   3960
ccttaataga gtgcttgatt ctaatgttac acaaaccagt tattatcctt cacctcatcc   4020
tggaattgcc tgtaacaatg aaacacaaaa ggctgactct ttaagcaaca tgttatatgg   4080
```

-continued

```
tatagataga tcagataaga ctacttccct gtctgagcct acaccaagaa tcgataactg   4140
ttttcaacca ttaagttcag agaaaatgtc atttgctagg gaacagtcct cttctgaaaa   4200
ttatctttca aggaatgaag ctgaagctgc atttgttaaa cagcatggaa catcaaatgt   4260
gcaaggtgat aatactgtca ggacagagca aaatggaggt gaaaattctc aatcaggata   4320
cagccaacag gatgataatg ttggatttca aacagcgaca accagtaatc tttattcttc   4380
aaacttatgc caaaaccaga aagcaaattc tgaagtacta cacggagttt cttccaactt   4440
gatagagaat tctaaagatg acaaaaagac ttcccccaaa gttccagtcg atggatcaaa   4500
agcaaagagg ccaagagttg gggctggtaa aaagaaaaca tatgattggg atatgttgag   4560
aaaagaagtt ctttacagtc atggtaataa agaaagatcc cagaatgcta aggactcaat   4620
tgattgggaa acaataagac aagcagaggt gaaggaaata tctgacacaa ttagagagcg   4680
aggaatgaat aacatgctgg cagaacggat aaaagacttc ctaaaccgat tggtgagaga   4740
ccatgggagc atcgatcttg agtggttgcg ctatgtcgat tcagataaag cgaaggacta   4800
tctcttaagc attagaggac ttggacttaa aagtgttgag tgtgtgcgtc ttttgacact   4860
ccatcacatg gcttttcctg tggatacaaa tgttggtaga atatgtgtga ggcttggatg   4920
ggtgccactt cagcccctac ccgagtctct tcagttgcac ctgttggaga tgtatccaat   4980
gctggagaac atacagaaat acctctggcc gaggttatgc aagcttgatc aacggacatt   5040
gtatgagctt cactatcaaa tgataacttt tggaaaggta ttttgtacaa aaagtaagcc   5100
caattgcaac gcatgcccaa tgagagctga gtgcaagcac tttgcaagtg catttgccag   5160
tgcaaggctc gctcttcctg gacctgaaga gaagagttta gttacatctg gaaccccaat   5220
agctgcagaa accttccacc agacatatat aagttctagg cctgtagtaa gtcagcttga   5280
gtggaattca aacacctgtc accatggtat gaacaatcgc cagccaatca ttgaggagcc   5340
agcaagccca gaacctgaac atgagacaga agagatgaaa gagtgtgcaa tagaggatag   5400
ttttgtcgat gatccagaag aaatccctac tatcaagctt aattttgagg agtttacaca   5460
gaacctgaag agttatatgc aagcaaataa cattgagatt gaagatgctg atatgtcaaa   5520
ggctttggtc gctataactc ctgaagttgc ttctatccca actcctaagc tcaagaatgt   5580
cagtcgccta aggacagagc accaagtcta tgaactgcca gattcacatc cacttcttga   5640
aggattcaac caaagagaac cagatgatcc ttgcccatac ctactctcta tatggacccc   5700
aggtgaaaca gctcaatcaa ctgatgcacc taagtcggtc tgcaattcac aagagaatgg   5760
tgaactatgt gcaagcaata catgctttag ttgcaacagt ataagagaag cgcaggccca   5820
aaaagttcga gggacactgc tgataccatg ccgaacagca atgagaggaa gctttccact   5880
taatgggaca tattttcaag tcaatgagtg ttcaaatgtt atgcggcagg tatttgctga   5940
tcatgactca agccggaacc cgattgatgt tccaaggagt tggatatgga atctccctag   6000
gagaactgtt tactttggaa cttcaattcc gacaatattt aaaggtttga caactgaaga   6060
aatacaacat tgcttttgga gaggatttgt gtgcgtgaga ggctttgata ggacatcaag   6120
agcacccaga ccactgtatg caagactcca ctttccagca agcaaaatta ccaggaataa   6180
aaaatctgca ggttctgctc caggaagaga tgatgaatag gccatctgga aaaccagaaa   6240
ggaaataaag aggaggtaca tatgatctgc cagaagatca ctgacctgaa atggatcgct   6300
gaccaataag ttgccgtagg caattcaatt atttctggcc atatacatct gctgaaagtt   6360
atgaactcca gccactgacg aattcgtggt gctggtattc ttcggcaaca tgatccatca   6420
```

-continued

```
tacagattct atgcttggtt gttgcaagca attcttatgc ggtgacagtt gctgctgata   6480
gggagaaaag gcatgtccgg cggctcagcg gctctaactg tactttcata tgagtggaac   6540
cgattgttgt acatgtgaaa agtttgccat tcaaaatggt cattcatgtt gttaggtcat   6600
tcatgtagtc gatgtcaaat taatcatcaa ttatttgatt tgattcattc acaagtttaa   6660
ttggctctag atacttgtga gctgcaggcc agcaatgtca taatgtatgt cgggaaaagg   6720
tagatataaa tcgtcagcat ttacctgaaa tacccttcct ctgtccataa atacaaggga   6780
ttttgggttg ttaagcgtat tttaagttcg atatgaaaat tactttgatg ttccg        6835
```

<210> SEQ ID NO 8
<211> LENGTH: 6814
<212> TYPE: DNA
<213> ORGANISM: Oryza sativa

<400> SEQUENCE: 8

```
atgatagtgc atatgtatcc tttctttttc ttttcttttg ttttcataac tgtcttacag     60
aatttcatgt tggctggtga cacttgtctc actcattatt tggtatattt tgactaaatg    120
caacgtgttg gtgctcggta gtttatattt gtttttacgc attcttcatt gactgtatgt    180
atttgatgtt gataccctgg gctgtcttat tttataggtg gatgctggga ggccacatag    240
gaggcctgtg tgatccaagt gtgctgctcc tgagttgaaa ttgcatagcc atatagcaac    300
tactggtgta aacttgagag atgaagtagt gaaaggaaat atgcaggatt ttggacaatg    360
gctgcctcaa tctcagacca ctgccgatct atatttctcc agtattccaa taccatcaca    420
gttcgatact tccatagaga cgcagactag aacttctgca gttgtatcgt cagagaaaga    480
atctgctaat tcgttcgtcc ctcataatgg tactgggctt gttgaacgca ttagcaatga    540
tgctgggcta actgaagtag ttggaagtag tgctggacca actgaatgta ttgacttgaa    600
caagacacca gcacggaaac ccaagaagaa aaagcacagg ccaaaggtgc taaaggacga    660
taaaccatcg aagacaccta aatctgctac tccaatacct tcaacagaaa aggtagaaaa    720
accatctgga aagagaaaat atgtccgcaa gaagacatct ccaggccaac ctcctgcaga    780
acaggcagct agctcacact gcagatctga gctgaagtca gttaaacgaa gtttggactt    840
tggtggagaa gtactgcaag agagtacaca atctggatct caagttccgg tggcagaaat    900
atgtactggt cccaagcgtc aatcaatacc ttctaccatc caaagagatt cgcaaagcca    960
gttggcttgc cacgtggttt ctagcaccag ctcaattcac acttcagcta gtcagatggt   1020
taatgcacat ttgtttcctc ctgataacat gccaaatgga gtattgcttg acctcaataa   1080
ttctactagt cagttacaaa acgaacatgc taaatttgtg gacagtccgg cacgtctttt   1140
tggttccaga ataagacaga catcaggtaa aaattctttg ctagaaatct atgctggcat   1200
gtcagataga aatgtacctg atctcaacag ttcaatcagt cagacgcata gcatgtctac   1260
tgattttgct caatacttgc tttcatcctc acaagcttct gtaagggaaa cacaaatggc   1320
caatcagatg cttaatggtc ataggatgcc agaaaatcca attacaccta gtcattgtat   1380
tgaaagggct gcattgaagg aacatttgaa tcatgttcct cacgcaaaag ccgcagtgat   1440
gaatggccaa atgccccata gttacaggtt ggcgcaaaat cccatcctac ctccaaatca   1500
tattgaaggg tatcaagtga tggaaaattt gagtgaactt gtcacgacaa atgactatct   1560
aactgctagt cctttcagtc aaactggagc tgcaaatagg cagcataata ttggtgactc   1620
catgcatata catgcattgg atcctagaag agagagtaat gcttcaagtg gttcttggat   1680
atcattaggt gtgaacttta accaacaaaa taatggatgg gcatctgcag gtgctgccga   1740
```

-continued

```
tgctgcgagc tcacatgccc catatttttc agaacctcac aaaagaatga ggacagctta   1800
tcttaacaat tatccaaatg gagtcgtggg acatttttct acctcatcta cggatttgtc   1860
aaataatgag aatgaaaatg tggcctcagc aatcaactca aacgttttta cccttgctga   1920
tgcacaaaga ttgatagccc gtgagaaatc acgagcttcc caaagaatga tcagttttag   1980
atcatctaaa aatgatatgg ttaacagatc agaaatggtc catcaacatg gcagacctgc   2040
tccgcatggc tctgcatgca gggagtctat tgaagtacct gacaaacagt tcgggctcat   2100
gacagaagaa ctcacacaat tacctagtat gccaaataac ccacaaaggg aaaaatatat   2160
tccgcaaact ggaagttgcc aacttcagtc tttggaacat gacatggtta aagggcataa   2220
cttggcaggt gaattgcata agcaagtaac ttcacctcaa gttgttattc agagcaattt   2280
ctgtgttacc cctcctgatg tgctcggcag aagaaccagt ggggagcatt taagaaccct   2340
tatagctcca acacatgcat cgacatgtaa ggacactctg aaagctttaa gttgtcaact   2400
ggagagttct agagacatta ttaggcctcc tgtcaatcct atagggccat cctctgccga   2460
tgttccaaga actgataacc atcaagtcaa ggtttctgaa gaaaccgtta cagccaaact   2520
ccctgagaag cgaaaagtag gacgtcccag aaaagagtta aaacctggtg agaaaccaaa   2580
acctagaggc cgtccaagga agggaaaagt tgttggtgga gaacttgcat caaaggatag   2640
tcacactaat ccattgcaaa atgagagtac ttcatgttct tatggtcctt atgcagggga   2700
ggcttctgtt ggaagagcag ttaaagcaaa tagagttgga gaaaacattt ctggagctat   2760
ggtatcccta ctggattctt tagatattgt tattcaaaag ataaaggtct tggacataaa   2820
caaatcagaa gaccctgtga cagctgaacc tcatggtgct cttgtccctt acaatggaga   2880
atttggtcct attgttcctt ttgaggggaa agtgaaaaga aaacgctctc gagccaaagt   2940
ggatcttgac cctgtaactg ctttaatgtg gaagttacta atgggaccag atatgagtga   3000
ttgtgctgaa ggtatggata aggataaaga gaaatggcta aatgaagaaa gaaaaatatt   3060
ccaagggcgt gttgattcat ttattgctcg aatgcatcta gttcaaggag atcggcgttt   3120
ttctccttgg aaaggatcag ttgtagattc tgtagtggga gtatttctta cacagaatgt   3180
ttcggaccat ctttccagct ctgcatttat ggctcttgct gcaaaatttc ctgtaaagcc   3240
agaagcctct gaaaaacccg caaatgtgat gtttcataca atttcagaaa atggtgattg   3300
ttctgggttg tttggtaatt ctgtcaagct acagggtgag atccttgttc aggaggccag   3360
caacacagca gcctctttta tcacaaccga ggataaggaa ggaagtaaca gtgtggaatt   3420
gcttggaagt tcttttgggg atggagtgga tggtgcagca ggagtttatt ctaatattta   3480
tgagaatctg ccagctagac tgcatgctac taggcgtcca gtcgttcaaa ctggaaacgc   3540
tgtcgaagcg gaagatgggt cactggaggg tgttgtttca tcagaaaact ccactatttc   3600
atctcaaaat tcatcagatt atctatttca catgtctgat catatgtttt cgagcatgtt   3660
actaaatttc actgccgaag acattggcag cagaaatatg cccaaagcaa caagaaccac   3720
atatacagaa cttctacgaa tgcaggagct gaagaacaag tctaatgaaa ccattgaatc   3780
atcagagtat catggggttc cagtctcatg tagtaacaac attcaagtgc tcaatggaat   3840
acaaaatatc ggcagtaaac atcagccttt acattcctct atttcatatc accagactgg   3900
ccaagttcac ctcccagaca tagtacatgc gagtgatttg gagcaatcag tatacactgg   3960
ccttaataga gtgcttgatt ctaatgttac acaaaccagt tattatcctt cacctcatcc   4020
tggaattgcc tgtaacaatg aaacacaaaa ggctgactct ttaagcaaca tgttatatgg   4080
```

-continued

```
tatagataga tcagataaga ctacttccct gtctgagcct acaccaagaa tcgataactg   4140
ttttcaacca ttaagttcag agaaaatgtc atttgctagg gaacagtcct cttctgaaaa   4200
ttatctttca aggaatgaag ctgaagctgc atttgttaaa cagcatggaa catcaaatgt   4260
gcaaggtgat aatactgtca ggacagagca aaatggaggt gaaaattctc aatcaggata   4320
cagccaacag gatgataatg ttggatttca aacagcgaca accagtaatc tttattcttc   4380
aaacttatgc caaaaccaga aagcaaattc tgaagtacta cacggagttt cttccaactt   4440
gatagagaat tctaaagatg acaaaaagac ttcccccaaa gttccagtcg atggatcaaa   4500
agcaaagagg ccaagagttg gggctggtaa aaagaaaaca tatgattggg atatgttgag   4560
aaaagaagtt ctttacagtc atggtaataa agaaagatcc cagaatgcta aggactcaat   4620
tgattgggaa acaataagac aagcagaggt gaaggaaata tctgacacaa ttagagagcg   4680
aggaatgaat aacatgctgg cagaacggat aaaagacttc ctaaaccgat tggtgagaga   4740
ccatgggagc atcgatcttg agtggttgcg ctatgtcgat tcagataaag cgaaggacta   4800
tctcttaagc attagaggac ttggacttaa aagtgttgag tgtgtgcgtc ttttgacact   4860
ccatcacatg gcttttcctg tggatacaaa tgttggtaga atatgtgtga ggcttggatg   4920
ggtgccactt cagcccctac ccgagtctct tcagttgcac ctgttggaga tgtatccaat   4980
gctggagaac atacagaaat acctctggcc gaggttatgc aagcttgatc aacggacatt   5040
gtatgagctt cactatcaaa tgataacttt tggaaaggta ttttgtacaa aaagtaagcc   5100
caattgcaac gcatgcccaa tgagagctga gtgcaagcac tttgcaagtg catttgccag   5160
tgcaaggctc gctcttcctg gacctgaaga gaagagttta gttacatctg gaaccccaat   5220
agctgcagaa accttccacc agacatatat aagttctagg cctgtagtaa gtcagcttga   5280
gtggaattca aacacctgtc accatggtat gaacaatcgc cagccaatca ttgaggagcc   5340
agcaagccca gaacctgaac atgagacaga agagatgaaa gagtgtgcaa tagaggatag   5400
ttttgtcgat gatccagaag aaatccctac tatcaagctt aattttgagg agtttacaca   5460
gaacctgaag agttatatgc aagcaaataa cattgagatt gaagatgctg atatgtcaaa   5520
ggctttggtc gctataactc ctgaagttgc ttctatccca actcctaagc tcaagaatgt   5580
cagtcgccta aggacagagc accaagtcta tgaactgcca gattcacatc cacttcttga   5640
aggattcaac caaagagaac cagatgatcc ttgcccatac ctactctcta tatggacccc   5700
aggtgaaaca gctcaatcaa ctgatgcacc taagtcggtc tgcaattcac aagagaatgg   5760
tgaactatgt gcaagcaata catgctttag ttgcaacagt ataagagaag cgcaggccca   5820
aaaagttcga gggacactgc tgataccatg ccgaacagca atgagaggaa gctttccact   5880
taatgggaca tattttcaag tcaatgaggt atttgctgat catgactcaa gccggaaccc   5940
gattgatgtt ccaaggagtt ggatatggaa tctccctagg agaactgttt actttggaac   6000
ttcaattccg acaatattta aaggtttgac aactgaagaa atacaacatt gcttttggag   6060
aggatttgtg tgcgtgagag gctttgatag gacatcaaga gcacccagac cactgtatgc   6120
aagactccac tttccagcaa gcaaaattac caggaataaa aaatctgcag gttctgctcc   6180
aggaagagat gatgaatagg ccatctggaa aaccagaaag gaaataaaga ggaggtacat   6240
atgatctgcc agaagatcac tgacctgaaa tggatcgctg accaataagt tgccgtaggc   6300
aattcaatta tttctggcca tatacatctg ctgaaagtta tgaactccag ccactgacga   6360
attcgtggtg ctggtattct tcggcaacat gatccatcat acagattcta tgcttggttg   6420
ttgcaagcaa ttcttatgcg gtgacagttg ctgctgatag ggagaaaagg catgtccggc   6480
```

-continued ggctcagcgg ctctaactgt actttcatat gagtggaacc gattgttgta catgtgaaaa 6540
gtttgccatt caaaatggtc attcatgttg ttaggtcatt catgtagtcg atgtcaaatt 6600
aatcatcaat tatttgattt gattcattca caagtttaat tggctctaga tacttgtgag 6660
ctgcaggcca gcaatgtcat aatgtatgtc gggaaaaggt agatataaat cgtcagcatt 6720
tacctgaaat acccttcctc tgtccataaa tacaagggat tttgggttgt taagcgtatt 6780
ttaagttcga tatgaaaatt actttgatgt tccg 6814

<210> SEQ ID NO 9
<211> LENGTH: 16885
<212> TYPE: DNA
<213> ORGANISM: Oryza sativa

<400> SEQUENCE: 9
agggcattgt agacattagc atttcaaacc cagtaatcca tgcctccaat aataataagc 60
taaaataaac aaggcctaag ttaatcatgc taactcgtgc tggctcaggc atgcgagtcc 120
tctagtcgga ctaggcacag ttcgagcaac atggttggtc atggggcatc ctatgcttgg 180
gccgctacca cggcacgtca caacccggtt gttatagcgg gcctgacaca aagcatgcaa 240
gcatgcatgt cccagtccaa cttccttttt ttttcatatt tttcatgtgg gaatcaattt 300
tcttatggtt tccctatatt tttatgattt ttctattttt tttatggacc agtcaggccg 360
atagatcgtc cttggtgcat gggcctactt atgcctgggc tatcacgaca tgccctgtag 420
cctccttgtg tcgtgcctag gttgaggcct cggcatgtgg gcccgcacat gtcatgcaac 480
tgtggtgctc atgccatgct gggctgggcc acccgtttcg acacaaatga acgaagcgta 540
acgttaatgc atgcacttct tacactcact ggagaggctc ctagtttgct tagctgccta 600
gcagcaaaag tcgcgttgtc ctccatgtcc ggatcgaagc ccatcatcaa tgtatttaga 660
tcagagccac acgttgagct gcgcttcacg acgggaccac cgccaaaaca cttgtttttc 720
ttccgtttaa tattctagtt tacaactttc tataataaaa tattaattca aggttttaac 780
attttagttg aaagttttaa aaattgtgtt gaaactttta aattttatac tggaagtttc 840
aaattttgtg ttgtaagttt caaactttgg attgactttt ttttagcaaa tgttttaaat 900
ttgagttaaa agtttcaaat atgggtagtg tttttagatt ttgtactgaa tgttttagaa 960
cttgagttga aacttttaga atttaagttg agaattttaa attttgagtt gaatgttttg 1020
aaattttggg ttgagttttt taaactgtcg ataaaaaaat aaatttgagc taaaagtttc 1080
aaattttgag tagagttttt caaatttgag ttgattgttt taaaccattg aaaaagctgg 1140
agcatgggaa ctcaagagtt acgattcttt tttttttcag ggaaggggtg aattctattg 1200
attaaacaga gtgattacaa tcccgtagga caatatcatg aatactagga ggagcatcaa 1260
gtctccacac tgcattattg ctagtccttt tggttaattg agctagttca tgagacactc 1320
tattacaccc tcttccaaca tgatttagat ggacttcagg aagtaaacca acaaaactcc 1380
tcgcttccac caacaaggca caccatcttg atttaggtcc tctttgttta ggcttaggtt 1440
tattggccta gacttttaag tcagcttatt agcttatatg atttataagc cggtggattt 1500
aatgtcctaa gtttagtggt tgagtcatac atctacctca cataagccaa aaaagcttct 1560
ccaacctagc ttttggctta atagtgttag agtggcttat ggcttcaaaa aagccaaacg 1620
gaaaagctgc ttgtttgttt aggcttagac ttttcgactt ataagttggc ttataagcct 1680
aaacaaagaa agccttattt tgcccaaggg ccatgagctt aatcacttct gagcaatcag 1740

-continued

```
tttcgaggat aatagacata ttgatccatt tagccgataa tgccaatcct tctttgcacg   1800
ccatgacttc aacttcttcg ggctgaggtg ctgtgaaaat gggtccgccg tgaggaaaga   1860
agtacttccc ctctacaatt cttgataacc actcccactc cgacgtctct tgtttaaatc   1920
tattcaaaat cacttcaaat atcgaattgc taaaaatgaa cttattgtgc tcatatttca   1980
ggtaggccca tccaaaccca tcaagcgagc tatagttatc gatgccacgc gtcaagcact   2040
cagctggcgt atgtgtgagg gagatatttg aaagttggca aaattacata aaccatccca   2100
tacccccatt ttgttataga agcccaccca ccgaacacta ccagaccgag attgctctct   2160
tcatggatag ttggttatgc ccatattctt caaatatgac accaaattta gtgttagggg   2220
caaaattgca taaacaaagt tgatatggta ctatgcgaat ctacgttgaa aaaaatggac   2280
cgaatcagct actcactttg tgttgggtgg gtagggtttt tattttaaca aaatggatta   2340
tcaagtggaa tttcaaaaca aaatgactat gcaactccat tccaatttat catattgttc   2400
atgtgcgcaa catcgatggt gggagtggag tcactcagtc tggactctgt agtggagtta   2460
cttggtcacg tactcacatg acatatcttc aaatggatag ctgattcggc ctgtttcttt   2520
aaatgtgata acaaataaag tgtcaaggca aaatagccta tgccaattca ctgtgaatcc   2580
acgtcgaaag aaataagcca aattagccac tcacatgtat tggttgggtg ggcttttaac   2640
aaaacaaacc tcaaaacaaa atgattgagt gactccactc cattttatca tattattcac   2700
gtgcaaggca gcggtggtga gagtgggggc cactcaatct ggactctaga gtagagttac   2760
tcagtcacat gagttattgt taaatgggta gttaatttgg cctatttctt caaatgcgac   2820
aacaaataaa gtgtcaaggc aaaaaaaaac ataaagcata tcttgctgca aatccacgtc   2880
aaaagaaaat aagccaaatt agctacgtat gcgcattgtt tgtgtggggg ttttcaacaa   2940
aatgggttat cgtgtggatc tcaaaacaaa atgactcaga gtaactccgc tctattttat   3000
cacattattc acgtgtaagg cagcgatgga gagagtgaac tatagtaaag ttactcagtc   3060
gcacactctt aaatgaatag ttgattccac ccatttctta aaatgtaaca acaaacaaag   3120
tgcccaggca aaaatacaca aacccaaatt agctacttat gtttattagt taggtgagtt   3180
ttacaacaaa ataatatatc atacgaaatc ccaaaacaaa atggctgagc gactccgttc   3240
tattttatca cattattcac gtgtcggaca gcgacggcgg ggcagtgaag tcactcagtc   3300
tggactctct gaagtggagt tactactcac gtgacgttac ttttttgggg aagtgtgtgc   3360
gctgcgatca gaagtagcca agcgtgcgcg aaatagcatt cccgacgctc acctcccctc   3420
ccccccctccc cccgcatcgt tttctctcac tctcctttcc tcacttttcc tctctctgac   3480
cgaatctctc ccactcctct ctactcctct caaccctagc tcgcctctac cctctctgct   3540
catcgggcgg cgcaggggaa ggaaggcggc gtccggctgc gcggagcccg gcgagggagg   3600
aggcggcgtc agggggggacc ggcgcgggag ggcggcgttc ggcgttcggc gcggggggcg   3660
gcggcgtccg gccgactgcg gcggcggcta gatccggcga aagaggctgc atcagcgccg   3720
attccccgac tccccaaccc tcaaacggta gcgaggtata ctcggttgtt ttcccctcag   3780
gtctcaggct gatcagacgc cgcactgccg atttccccct cgggcgagcc atcggagcgg   3840
gggccgttgg ctcccaaagc agacgcgaga attcactgaa attaccgcgc catcttatct   3900
ccgcaagttg aagaatataa ttcgggcgca gtaattttta gtgaattcat gtgtctacta   3960
ctacatatgt ctgcttggga gccaaccgcg tttcgatggc tcgcctgagg ggaaatcggc   4020
gggaggcgtt tggtcagctt tgctggtagt ggggggaatt tcacctaatg attgaatgat   4080
gggatatgct gggtaaagga aggtatggtt attttatatt atctagaaga gggtaaaaaa   4140
```

-continued

```
gggagatggt cctttggggg ctgtttgtct tgtttacatg ggtttaggaa atattgctta   4200
aatggatata aagttgaaaa atgtacttga gggaagttgt aggtgcacgt ggggtcccac   4260
aatttttctt cactagtgca cctttagtta tatatttttt gcgcaagagg acaaaggcgc   4320
tccgtgtaat tttgagtaag ggccggcggg atatttattt gtgtaaagga cctagccaag   4380
aaaagcatga tagtgcatat gtatcctttc tttttctttt cttttgtttt cataactgtc   4440
ttacagaatt tcatgttggc tggtgacact tgtctcactc attatttggt atattttgac   4500
taaatgcaac gtgttggtgc tcggtagttt atatttgttt ttacgcattc ttcattgact   4560
gtatgtattt gatgttgata ccctgggctg tcttatttta taggtggatg ctgggaggcc   4620
acataggagg cctgtgtgat ccaagtgtgc tgctcctgag ttgaaattgc atagccatat   4680
agcaactact ggtgtaaact tgagagatga agtagtgaaa ggaaatatgc aggattttgg   4740
acaatggctg cctcaatctc agaccactgc cgatctatat ttctccagta ttccaatacc   4800
atcacagttc gatacttcca tagagacgca gactagaact tctgcagttg tatcgtcaga   4860
gaaagaatct gctaattcgt tcgtccctca taatggtact gggcttgttg aacgcattag   4920
caatgatgct gggctaactg aagtagttgg aagtagtgct ggaccaactg aatgtattga   4980
cttgaacaag acaccagcac ggaaacccaa gaagaaaaag cacaggccaa aggtgctaaa   5040
ggacgataaa ccatcgaaga cacctaaatc tgctactcca ataccttcaa cagaaaaggt   5100
agaaaaacca tctggaaaga gaaaatatgt ccgcaagaag acatctccag gccaacctcc   5160
tgcagaacag gcagctagct cacactgcag atctgagctg aagtcagtta aacgaagttt   5220
ggactttggt ggagaagtac tgcaagagag tacacaatct ggatctcaag ttccggtggc   5280
agaaatatgt actggtccca agcgtcaatc aataccttct accatccaaa gagattcgca   5340
aagccagttg gcttgccacg tggtttctag caccagctca attcacactt cagctagtca   5400
gatggttaat gcacatttgt ttcctcctga taacatgcca aatggagtat tgcttgacct   5460
caataattct actagtcagt tacaaaacga acatgctaaa tttgtggaca gtccggcacg   5520
tctttttggt tccagaataa gacagacatc aggtaaaaat tctttgctag aaatctatgc   5580
tggcatgtca gatagaaatg tacctgatct caacagttca atcagtcaga cgcatagcat   5640
gtctactgat tttgctcaat acttgctttc atcctcacaa gcttctgtaa gggaaacaca   5700
aatggccaat cagatgctta atggtcatag gatgccagaa aatccaatta cacctagtca   5760
ttgtattgaa agggctgcat tgaaggaaca tttgaatcat gttcctcacg caaaagccgc   5820
agtgatgaat ggccaaatgc cccatagtta caggttggcg caaaatccca tcctacctcc   5880
aaatcatatt gaagggtatc aagtgatgga aaatttgagt gaacttgtca cgacaaatga   5940
ctatctaact gctagtcctt tcagtcaaac tggagctgca aataggcagc ataatattgg   6000
tgactccatg catatacatg cattggatcc tagaagagag agtaatgctt caagtggttc   6060
ttggatatca ttaggtgtga actttaacca acaaaataat ggatgggcat ctgcaggtgc   6120
tgccgatgct gcgagctcac atgccccata tttttcagaa cctcacaaaa gaatgaggac   6180
agcttatctt aacaattatc caaatggagt cgtgggacat ttttctacct catctacgga   6240
tttgtcaaat aatgagaatg aaaatgtggc ctcagcaatc aactcaaacg tttttaccct   6300
tgctgatgca caaagattga tagcccgtga gaaatcacga gcttcccaaa gaatgatcag   6360
ttttagatca tctaaaaatg atatggttaa cagatcagaa atggtccatc aacatggcag   6420
acctgctccg catggctctg catgcaggga gtctattgaa gtacctgaca aacagttcgg   6480
```

-continued

```
gctcatgaca gaagaactca cacaattacc tagtatgcca aataacccac aaagggaaaa   6540
atatattccg caaactggaa gttgccaact tcagtctttg gaacatgaca tggttaaagg   6600
gcataacttg gcaggtgaat tgcataagca agtaacttca cctcaagttg ttattcagag   6660
caatttctgt gttacccctc ctgatgtgct cggcagaaga accagtgggg agcatttaag   6720
aacccttata gctccaacac atgcatcgac atgtaaggac actctgaaag ctttaagttg   6780
tcaactggag agttctagag acattattag gcctcctgtc aatcctatag ggccatcctc   6840
tgccgatgtt ccaagaactg ataaccatca agtcaaggtt tctgaagaaa ccgttacagc   6900
caaactccct gagaagcgaa aagtaggacg tcccagaaaa gagttaaaac ctggtgagaa   6960
accaaaacct agaggccgtc caaggaaggg aaaagttgtt ggtggagaac ttgcatcaaa   7020
ggatagtcac actaatccat tgcaaaatga gagtacttca tgttcttatg gtccttatgc   7080
aggggaggct tctgttggaa gagcagttaa agcaaataga gttggagaaa acatttctgg   7140
agctatggta tccctactgg attctttaga tattgttatt caaaagataa aggtcttgga   7200
cataaacaaa tcagaagacc ctgtgacagc tgaacctcat ggtgctcttg tcccttacaa   7260
tggagaattt ggtcctattg ttccttttga ggggaaagtg aaaagaaaac gctctcgagc   7320
caaagtggat cttgaccctg taactgcttt aatgtggaag ttactaatgg gaccagatat   7380
gagtgattgt gctgaaggta tggataagga taaagagaaa tggctaaatg aagaaagaaa   7440
aatattccaa gggcgtgttg attcatttat tgctcgaatg catctagttc aaggtatttc   7500
tatcatttta aaattgtttt cctaacatga acatgatggc ttccatcttg tgattgctgc   7560
cctcacatta gtgaatggtc tcaaatcttc aatatttact gtgtacccaa atcctatttc   7620
ttcatcccaa tatattcatg tttgtactcg tactgtccca ttagacttgc attgtgctgt   7680
gaagatcaac acctttactt ttaggattac ctctatgttt gcaggagatc ggcgtttttc   7740
tccttggaaa ggatcagttg tagattctgt agtgggagta tttcttacac agaatgtttc   7800
ggaccatctt tccaggtgaa taatgcctag agcctatttg aaaactgtga cttgacttgc   7860
attgtgaggt tatgttgttt ttctgtctga ctatttcctt ttttttcagc tctgcattta   7920
tggctcttgc tgcaaaattt cctgtaaagc cagaagcctc tgaaaaaccc gcaaatgtga   7980
tgtttcatac aatttcagaa aatggtgatt gttctgggtt gtttggtaat tctgtcaagc   8040
tacagggtga gatccttgtt caggaggcca gcaacacagc agcctctttt atcacaaccg   8100
aggataagga aggaagtaac agtgtggaat tgcttggaag ttcttttggg gatggagtgg   8160
atggtgcagc aggagtttat tctaatattt atgagaatct gccagctaga ctgcatgcta   8220
ctaggcgtcc agtcgttcaa actggaaacg ctgtcgaagc ggaagatggg tcactggagg   8280
gtgttgtttc atcagaaaac tccactattt catctcaaaa ttcatcagat tatctatttc   8340
acatgtctga tcatatgttt tcgagcatgt tactaaattt cactgccgaa gacattggca   8400
gcagaaatat gcccaaagca acaagaacca catatacaga acttctacga atgcaggagc   8460
tgaagaacaa gtctaatgaa accattgaat catcagagta tcatggggtt ccagtctcat   8520
gtagtaacaa cattcaagtg ctcaatggaa tacaaaatat cggcagtaaa catcagcctt   8580
tacattcctc tatttcatat caccagactg gccaagttca cctcccagac atagtacatg   8640
cgagtgattt ggagcaatca gtatacactg gccttaatag agtgcttgat tctaatgtta   8700
cacaaaccag ttattatcct tcacctcatc ctggaattgc ctgtaacaat gaaacacaaa   8760
aggctgactc tttaagcaac atgttatatg gtatagatag atcagataag actacttccc   8820
tgtctgagcc tacaccaaga atcgataact gttttcaacc attaagttca gagaaaatgt   8880
```

-continued

```
catttgctag ggaacagtcc tcttctgaaa attatctttc aaggaatgaa gctgaagctg   8940
catttgttaa acagcatgga acatcaaatg tgcaaggtga taatactgtc aggacagagc   9000
aaaatggagg tgaaaattct caatcaggat acagccaaca ggatgataat gttggatttc   9060
aaacagcgac aaccagtaat ctttattctt caaacttatg ccaaaaccag aaagcaaatt   9120
ctgaagtact acacggagtt tcttccaact tgatagagaa ttctaaagat gacaaaaaga   9180
cttcccccaa agttccagtc gatggatcaa aagcaaagag gccaagagtt ggggctggta   9240
aaaagaaaac atatgattgg gatatgttga gaaaagaagt tctttacagt catggtaata   9300
aagaaagatc ccagaatgct aaggactcaa ttgattggga aacaataaga caagcagagg   9360
tgaaggaaat atctgacaca attagagagc gaggaatgaa taacatgctg gcagaacgga   9420
taaaagtaag tatggcataa aacagtttac attgaaagtt gacataactc tagtcatatg   9480
tgcatgcatg ctattccata tagatttgct tatttgttgg aattccaagt tttggatcaa   9540
ccatactcat ctttagcaat tcatgttgca ggacttccta aaccgattgg tgagagacca   9600
tgggagcatc gatcttgagt ggttgcgcta tgtcgattca gataaagcga agtaagctaa   9660
ctaaatttat tttgagcaaa cattcataat gcaattggcc cttgggcatt ctataatttg   9720
tcattttgac ctctgcattg cttagcaatg acaattggat gtagtgagca tgggtaataa   9780
tgtaagcaat gacaattgga tgtagtgggc atggttaata attgaacatg tctgtgtttg   9840
cgggataata atgcctatca cctgtgagcc tgtgacatgc aaaccttgaa cgttgaacct   9900
tgaacccccct acctcgcact gtgtgctctc aaccaactga gcaagtgagg gaccttgttg   9960
tatggaaaaa ataattttaa ataacccttg attcaaccaa agcttcataa aagaatatat  10020
tttctattat tcatttgaac cagcggttga accagtgaac cgatggtctt gctggtccgg  10080
atttaataat aactatggct agaacagatt agagcaccga atacttgcgc gatgctaaat  10140
atttcaatgg ggacacacct gctcgtgtgt tgcatcaact acctaagcca cacaggcatg  10200
gcaatcaaat cagcttgccc atgtaacatc aactatctga tcgcgagaag gccggagctc  10260
tcacttgatg tttgtcattc aaaaaatagt tattcaccaa tgcaatgtca agctcccgta  10320
aagaccatga atgtagttta tccttctttg atcaagtttt tatttatatt aaagtgttta  10380
ccaatgtaat cctacattat ttgtacctgg tttttacata taaatacatt gtaccttttg  10440
tgtttcttcc agggactatc tcttaagcat tagaggactt ggacttaaaa gtgttgagtg  10500
tgtgcgtctt ttgacactcc atcacatggc ttttcctgta tgtttccttt cacaaataat  10560
tttcaagaat cttcgtttct ttatttctgg agaagtggag attttatctg tatctgttga  10620
tgatgtaggt ggatacaaat gttggtagaa tatgtgtgag gcttggatgg gtgccacttc  10680
agcccctacc cgagtctctt cagttgcacc tgttggagat gtaagtatct taaatccact  10740
ggttggcttc actaatgctg gagagtgata ggagtttgat catctgctat tgaaggtatc  10800
caatgctgga gaacatacag aaatacctct ggccgaggtt atgcaagctt gatcaacgga  10860
cattgtgagt tttagaaatg cagttaaaaa ctatatatat aagagcatgt cattatctga  10920
gagtgtataa caggttcttg atgatatgta ggtatgagct tcactatcaa atgataactt  10980
ttggaaaggt atgagacaac aactttgata aagtgaattc aacccaatta ctgtgttttg  11040
atggaccatc tgtgttactt tccttctagg tattttgtac aaaaagtaag cccaattgca  11100
acgcatgccc aatgagagct gagtgcaagc actttgcaag tgcatttgcc aggtaattct  11160
caagatgtac atattttata tacattctgt gaaatcacgg tgatgattgt taggtatgaa  11220
```

-continued caattggctg agatcccccc cctcccccct cccatccttt tcctggtcct acaagttctc 11280
ctaggctaat ttaactggtg cataccacat ttatgttatt ttgatacatc aaagattatg 11340
tttgtggttg tgaggctata ttagtgtgtt gtatgtaact cagttttgca attgtagttt 11400
tagttagaac acgttgttct ctacatttta ataaatactt tttgactgga catcaatgac 11460
tggtgtattt ccgatataaa aaggttgatt gttgccgagg gatttcaatt cggtccgaat 11520
aggttcgaca aatgcagtgg gcctattagt ttaagagtga aagttctatc agctgtttga 11580
ctccactgtg acctttacac tttgtacttt tgaagaaaca gactaacctg ctcatattaa 11640
agtcttggaa tgactccatt gcgaccttta cgctttgtat tttagaagaa acagactaac 11700
ctgttcatat tagagtcttg gaactgtgtg tgtgtgtgtt ttttttttt ttgggggggg 11760 gggggcatgg agatttaatc caacattcct ggatgacctt atattggtaa tgatatggtt 11820
tttttatgat atagtgcaag gctcgctctt cctggacctg aagagaagag tttagttaca 11880
tctggaaccc caatagctgc agaaaccttc caccagacat atataagttc taggcctgta 11940
gtaagtcagc ttgagtggaa ttcaaacacc tgtcaccatg gtatgaacaa tcgccagcca 12000
atcattgagg agccagcaag cccagaacct gaacatgaga cagaagagat gaaagagtgt 12060
gcaatagagg atagttttgt cgatgatcca gaagaaatcc ctactatcaa gcttaatttt 12120
gaggagttta cacagaacct gaagagttat atgcaagcaa ataacattga gattgaagat 12180
gctgatatgt caaaggcttt ggtcgctata actcctgaag ttgcttctat cccaactcct 12240
aagctcaaga atgtcagtcg cctaaggaca gagcaccaag tgtatgatct tgtccctctt 12300
gcaaaaccaa tctcatgaat atttactatt gactatcatg tgttttgctg cattgcttac 12360
ttctctgttt tcaacatata tgtagctatg aactgccaga ttcacatcca cttcttgaag 12420
gagtaagttc ataaaacatt atagaattct gtactttcct tatcaccaac tgagaatata 12480
ttgatgctta ttttcttaca atacacagtt caaccaaaga gaaccagatg atccttgccc 12540
atacctactc tctatatgga ccccaggtaa gaagtgcata aacagaacac aatatcatgg 12600
gaaccaaact tttttcaatg gttacttata attgttgaaa tatgcaacag gtgaaacagc 12660
tcaatcaact gatgcaccta agtcggtctg caattcacaa gagaatggtg aactatgtgc 12720
aagcaataca tgctttagtt gcaacagtat aagagaagcg caggcccaaa aagttcgagg 12780
gacactgctg gtaagtagtt gtttctgtaa catatgctca gttgcccttg gttcaagatg 12840
tgctattcaa gtttatcatg ttcacgaata gtgataaagc tgctatctgt cctagctatt 12900
gtccaagcta taacagttct gattcactgg ttgggcacca gctagggaat aggatgtaaa 12960
aaacttatcc cgcagtttgt tgacaatctg tttttctttg ttgaaaatta aaaatagata 13020
ccatgccgaa cagcaatgag aggaagcttt ccacttaatg ggacatattt tcaagtcaat 13080
gaggtgaaaa cagaaagttc ttaaagttga tcttagttta attattataa taccattaaa 13140
atatatgcaa gtttctactt tctagtatct cttttattag tgttcaaatg ttatgcggca 13200
ggtatttgct gatcatgact caagccggaa cccgattgat gttccaagga gttggatatg 13260
gaatctccct aggagaactg tttactttgg aacttcaatt ccgacaatat ttaaaggtat 13320
ttcactaata aattttgacc aagaatagga tttttggcag cgccaaatgt gccactatct 13380
ttattgtgtg aagtccatta tgtgattgta ataatttgaa tcaccaagag gactaaggcc 13440
tgctttggga catattacga gcagcttttg cttgcaaaga aaccagattc tggtgccgca 13500
ccttctccgc tcttctgcca cccaagtccg tccaataccc ctcattgagc gcttggatcc 13560
taaccccatc tgccatcatg catcatcctg ctaacaactg cttccaccat tgcctgtttc 13620

-continued tgttgttggg aggcactcac gctgcttgct atagtttagg ttttctttgt gtcctgattt 13680
agatggaatt tccagctgct gtcttttaca taactagcta aatgtccgcg ctttgctatg 13740
gataatagaa aatatattat aatattgtca aataaattaa atatgtttta tacgaaatgt 13800
gttaacaatc cttttgctat agggaatatt gaccttaatt tgattttata tgtggctatc 13860
catttagatt tgtttgtttt tctaataata ataagttcaa gggctaatgt acaaaattga 13920
caatgggagt aggtggggtg gcagattcac tgccaccacc actaccttct tttaaagggg 13980
tatatagatt tgcagcagtg gttgcttgat ctgtgatttg aaatgtcaag tacacgctca 14040
tgcatcagca ccatatgtct acgctcctga cccaacatgc aaccaatgca attgagggtt 14100
ggctctgata caattactaa tgtcctatat ccaaaacaac tataggccta tgaccaaaca 14160
taattaataa cctcgcttgc gcttttgtcc tcacttgctc catgtaaaag ggttaacccg 14220
aggttactat gttaggaata gctgggttta tgaaacggtt caactctcaa ctcctcatat 14280
agcactaatt catgtattgc tgtcagcagt gatttgagtt ccagatcatg ctcataagat 14340
aggaccaaat tgtccttact atctactccc tccgtcccaa aatataaggt atttccggtc 14400
aaaatatctt atattttggg atggagggag tactatacta cggacccacc accaaatagt 14460
gccgcagaag agagagagag agagagaaga gggggtgggg gtgggggtgt atgggtgaaa 14520
taagaatagt gccaagtatt tgccaacaaa tgaggcggtc aaatgtgtca catcaattgg 14580
gaagtatgtc agatcaactg aaaatttgat tgggaaatta ttattcatgc aacaaagctg 14640
tacaactgat cccatgtttc tatcgcaggt ttgacaactg aagaaataca acattgcttt 14700
tggagaggta atcatttttt tttgtatgta cgttttggtt tccataacaa agagagatga 14760
agtgtatagg tactatgttt actgacaagg ataataatag tagcaagtat ataggcagag 14820
gagcatgtct ctattctacc agtattatta ctcataataa ctagtatatc cttttttttg 14880
ccatttcagc tgatagctac tctccagtca aaatatttgc catctctatt gaacttttca 14940
ttgtcttctg aatgtatctt actcttggat cattaatatt tcattttgtc acgatatagt 15000
ggtataggac aataaaatca tgggaagtat ttattttcat caccaatcta ctcatataat 15060
tttcaaatga caattataaa tatcttaaaa atatattgtt agttgtcctg tataaaataa 15120
ttgtcacacc ctagtccaca gcgacaagaa tttgtgtcta caggctagag tgagtactct 15180
agaagtatct tcataggaat cggaataaaa tgccaatgtg aatgaacaag gatatcaagt 15240
ataccctcaa aatctctaga gaggattgcg taaatatgta ggtgtaatta aacaattgtt 15300
tcatatggag ggttttctta aaggaggtac aagacttatc aatatgggta aagtagtttt 15360
tatccatagg cattgttggc agaaagctgc ttagggtaga atgctactcc ctccgtccca 15420
caatataaga gattttgagt ttttgcttgc aacgtttgac cactcggctt attcaaaaat 15480
ttttgaaatt attatttatt ttatttgtga cttactttat tattcacagt actttaagta 15540
caacttttcg ttttttatat ttgcaaaaaa aattgtataa gacgagtggt caaacgttgt 15600
acgcaaaaac tcaaaatccc ttatattgtg ggacggaggg agtacttatg gatgcctttt 15660
ttgtccaaga tgtcagtaac attttctttc agggatgtgg atttttactt ctttttttccc 15720
taactttttc aggatttgtg tgcgtgagag gctttgatag gacatcaaga gcacccagac 15780
cactgtatgc aagactccac tttccagcaa gcaaaattac caggaataaa aaatctgcag 15840
gttctgctcc aggaagagat gatgaatagg ccatctggaa aaccagaaag gaaataaaga 15900
ggaggtacat atgatctgcc agaagatcac tgacctgaaa tggatcgctg accaataagt 15960

```
tgccgtaggc aattcaatta tttctggcca tatacatctg ctgaaagtta tgaactccag  16020

ccactgacga attcgtggtg ctggtattct tcggcaacat gatccatcat acagattcta  16080

tgcttggttg ttgcaagcaa ttcttatgcg gtgacagttg ctgctgatag ggagaaaagg  16140

catgtccggc ggctcagcgg ctctaactgt actttcatat gagtggaacc gattgttgta  16200

catgtgaaaa gtttgccatt caaaatggtc attcatgttg ttaggtcatt catgtagtcg  16260

atgtcaaatt aatcatcaat tatttgattt gattcattca caagtttaat tggctctaga  16320

tacttgtgag ctgcaggcca gcaatgtcat aatgtatgtc gggaaaaggt agatataaat  16380

cgtcagcatt tacctgaaat acccttcctc tgtccataaa tacaagggat tttgggttgt  16440

taagcgtatt ttaagttcga tatgaaaatt actttgatgt tccgaagggc ttattttgtc  16500

ttgggttgtt tagcatgtca taaggttgat attaaattac tttcatgccc ttaggagttt  16560

tggaaagttg acgcttaaca gatgcgacta gcagtaagca ataaatgtct agatggattg  16620

agaaagtagt atttcttccg tctcaaaata ttgctataag ctctgtttgt tagggttcta  16680

acttctaaat tactttagaa gttaggtata tagtgaagtt gtggaactat ttaaatatag  16740

ttatatctct ctagtttatt ttttatttta tgagagcact tcaattcatt ccactctttt  16800

tttttttgga attgaaatca tttggttgtg cttcagttct agaaaatgtg gagctagagt  16860

tgaagacgtg ttaaacgggt cctta                                        16885


<210> SEQ ID NO 10
<211> LENGTH: 35
<212> TYPE: DNA
<213> ORGANISM: Oryza sativa

<400> SEQUENCE: 10

caatgaggta tttgctgatc atgactcaag ccgga                                35


<210> SEQ ID NO 11
<211> LENGTH: 56
<212> TYPE: DNA
<213> ORGANISM: Oryza sativa

<400> SEQUENCE: 11

caatgagtgt tcaaatgtta tgcggcaggt atttgctgat catgactcaa gccgga         56


<210> SEQ ID NO 12
<211> LENGTH: 152
<212> TYPE: PRT
<213> ORGANISM: Oryza sativa

<400> SEQUENCE: 12

Cys Asn Ser Gln Glu Asn Gly Glu Leu Cys Ala Ser Asn Thr Cys Phe
1               5                   10                  15

Ser Cys Asn Ser Ile Arg Glu Ala Gln Ala Gln Lys Val Arg Gly Thr
            20                  25                  30

Leu Leu Ile Pro Cys Arg Thr Ala Met Arg Gly Ser Phe Pro Leu Asn
        35                  40                  45

Gly Thr Tyr Phe Gln Val Asn Glu Val Phe Ala Asp His Asp Ser Ser
    50                  55                  60

Arg Asn Pro Ile Asp Val Pro Arg Ser Trp Ile Trp Asn Leu Pro Arg
65                  70                  75                  80

Arg Thr Val Tyr Phe Gly Thr Ser Ile Pro Thr Ile Phe Lys Gly Leu
                85                  90                  95

Thr Thr Glu Glu Ile Gln His Cys Phe Trp Arg Gly Phe Val Cys Val
```

```
            100                 105                 110

Arg Gly Phe Asp Arg Thr Ser Arg Ala Pro Arg Pro Leu Tyr Ala Arg
        115                 120                 125

Leu His Phe Pro Ala Ser Lys Ile Thr Arg Asn Lys Lys Ser Ala Gly
    130                 135                 140

Ser Ala Pro Gly Arg Asp Asp Glu
145                 150


<210> SEQ ID NO 13
<211> LENGTH: 159
<212> TYPE: PRT
<213> ORGANISM: Oryza sativa

<400> SEQUENCE: 13

Cys Asn Ser Gln Glu Asn Gly Glu Leu Cys Ala Ser Asn Thr Cys Phe
1               5                   10                  15

Ser Cys Asn Ser Ile Arg Glu Ala Gln Ala Gln Lys Val Arg Gly Thr
            20                  25                  30

Leu Leu Ile Pro Cys Arg Thr Ala Met Arg Gly Ser Phe Pro Leu Asn
        35                  40                  45

Gly Thr Tyr Phe Gln Val Asn Glu Cys Ser Asn Val Met Arg Gln Val
    50                  55                  60

Phe Ala Asp His Asp Ser Ser Arg Asn Pro Ile Asp Val Pro Arg Ser
65                  70                  75                  80

Trp Ile Trp Asn Leu Pro Arg Arg Thr Val Tyr Phe Gly Thr Ser Ile
                85                  90                  95

Pro Thr Ile Phe Lys Gly Leu Thr Thr Glu Glu Ile Gln His Cys Phe
            100                 105                 110

Trp Arg Gly Phe Val Cys Val Arg Gly Phe Asp Arg Thr Ser Arg Ala
        115                 120                 125

Pro Arg Pro Leu Tyr Ala Arg Leu His Phe Pro Ala Ser Lys Ile Thr
    130                 135                 140

Arg Asn Lys Lys Ser Ala Gly Ser Ala Pro Gly Arg Asp Asp Glu
145                 150                 155


<210> SEQ ID NO 14
<211> LENGTH: 7
<212> TYPE: PRT
<213> ORGANISM: Oryza sativa

<400> SEQUENCE: 14

Cys Ser Asn Val Met Arg Gln
1               5


<210> SEQ ID NO 15
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 15

tgagtagttg cgttgttct                                                19


<210> SEQ ID NO 16
<211> LENGTH: 18
<212> TYPE: DNA
<213> ORGANISM: Artificial Sequence
<220> FEATURE:
<223> OTHER INFORMATION: oligonucleotide primer
```

<400> SEQUENCE: 16
tcttagtgag ccgtttct 18

<210> SEQ ID NO 17
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 17
ccttctgtgc tatgggtt 18

<210> SEQ ID NO 18
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 18
catgccaaga caccactt 18

<210> SEQ ID NO 19
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 19
tggctttgga aacggtag 18

<210> SEQ ID NO 20
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 20
tttagaggga tgtgcgtca 19

<210> SEQ ID NO 21
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 21
aaacaacgat ccagcaaa 18

<210> SEQ ID NO 22
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 22
ttggcaccgt attactttc 19

<210> SEQ ID NO 23

<211> LENGTH: 24
<212> TYPE: DNA
<213> ORGANISM: Artificial Sequence
<220> FEATURE:
<223> OTHER INFORMATION: oligonucleotide primer

<400> SEQUENCE: 23
acgcattctt cattgactgt atgt 24

<210> SEQ ID NO 24
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 24
gccctttcaa tacaatgact aggt 24

<210> SEQ ID NO 25
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 25
gaacatttga atcatgttcc tcac 24

<210> SEQ ID NO 26
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 26
actatccttt gatgcaagtt ctcc 24

<210> SEQ ID NO 27
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 27
gttggaagag cagttaaagc aaat 24

<210> SEQ ID NO 28
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 28
cttcggcagt gaaatttagt aaca 24

<210> SEQ ID NO 29
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 29
tacagaactt ctacgaatgc agga 24

<210> SEQ ID NO 30
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 30
gcaacatgaa ttgctaaaga tgag 24

<210> SEQ ID NO 31
<211> LENGTH: 35
<212> TYPE: DNA
<213> ORGANISM: Artificial Sequence
<220> FEATURE:
<223> OTHER INFORMATION: oligonucleotide primer

<400> SEQUENCE: 31
ctatacctcc tcaactccgg tcaccgtctc cggcg 35

<210> SEQ ID NO 32
<211> LENGTH: 35
<212> TYPE: DNA
<213> ORGANISM: Artificial Sequence
<220> FEATURE:
<223> OTHER INFORMATION: oligonucleotide primer
<220> FEATURE:
<221> NAME/KEY: C
<222> LOCATION: (18)..(18)
<223> OTHER INFORMATION: 5-methylcytosine

<400> SEQUENCE: 32
ctatacctcc tcaactccgg tcaccgtctc cggcg 35

<210> SEQ ID NO 33
<211> LENGTH: 35
<212> TYPE: DNA
<213> ORGANISM: Artificial Sequence
<220> FEATURE:
<223> OTHER INFORMATION: oligonucleotide primer
<220> FEATURE:
<221> NAME/KEY: C
<222> LOCATION: (17)..(17)
<223> OTHER INFORMATION: 5-methylcytosine

<400> SEQUENCE: 33
ctatacctcc tcaactccgg tcaccgtctc cggcg 35

<210> SEQ ID NO 34
<211> LENGTH: 35
<212> TYPE: DNA
<213> ORGANISM: Artificial Sequence
<220> FEATURE:
<223> OTHER INFORMATION: oligonucleotide primer
<220> FEATURE:
<221> NAME/KEY: C
<222> LOCATION: (22)..(22)
<223> OTHER INFORMATION: 5-methylcytosine

<400> SEQUENCE: 34
ctatacctcc tcaactccgg tcaccgtctc cggcg 35

<210> SEQ ID NO 35
<211> LENGTH: 34
<212> TYPE: DNA

<213> ORGANISM: Artificial Sequence
<220> FEATURE:
<223> OTHER INFORMATION: oligonucleotide primer
<220> FEATURE:
<221> NAME/KEY: g
<222> LOCATION: (18)..(18)
<223> OTHER INFORMATION: abasic site

<400> SEQUENCE: 35
ctatacctcc tcaactcggt caccgtctcc ggcg 34

<210> SEQ ID NO 36
<211> LENGTH: 34
<212> TYPE: DNA
<213> ORGANISM: Artificial Sequence
<220> FEATURE:
<223> OTHER INFORMATION: oligonucleotide primer
<220> FEATURE:
<221> NAME/KEY: C
<222> LOCATION: (17)..(17)
<223> OTHER INFORMATION: abasic site

<400> SEQUENCE: 36
ctatacctcc tcaactcggt caccgtctcc ggcg 34

<210> SEQ ID NO 37
<211> LENGTH: 34
<212> TYPE: DNA
<213> ORGANISM: Artificial Sequence
<220> FEATURE:
<223> OTHER INFORMATION: oligonucleotide primer
<220> FEATURE:
<221> NAME/KEY: T
<222> LOCATION: (15)..(15)
<223> OTHER INFORMATION: abasic site

<400> SEQUENCE: 37
ctatacctcc tcaatccggt caccgtctcc ggcg 34

<210> SEQ ID NO 38
<211> LENGTH: 34
<212> TYPE: DNA
<213> ORGANISM: Artificial Sequence
<220> FEATURE:
<223> OTHER INFORMATION: oligonucleotide primer
<220> FEATURE:
<221> NAME/KEY: A
<222> LOCATION: (12)..(12)
<223> OTHER INFORMATION: abasic site

<400> SEQUENCE: 38
ctatacctcc taactccggt caccgtctcc ggcg 34

<210> SEQ ID NO 39
<211> LENGTH: 35
<212> TYPE: DNA
<213> ORGANISM: Artificial Sequence
<220> FEATURE:
<223> OTHER INFORMATION: oligonucleotide primer

<400> SEQUENCE: 39
ctatacctcc tcaactctgg tcaccgtctc cggcg 35

<210> SEQ ID NO 40
<211> LENGTH: 35
<212> TYPE: DNA
<213> ORGANISM: Artificial Sequence
<220> FEATURE:
<223> OTHER INFORMATION: oligonucleotide primer

<400> SEQUENCE: 40
cgccggagac ggtgaccgga gttgaggagg tatag 35

<210> SEQ ID NO 41
<211> LENGTH: 35
<212> TYPE: DNA
<213> ORGANISM: Artificial Sequence
<220> FEATURE:
<223> OTHER INFORMATION: oligonucleotide primer
<220> FEATURE:
<221> NAME/KEY: C
<222> LOCATION: (17)..(17)
<223> OTHER INFORMATION: 5-methylcytosine

<400> SEQUENCE: 41
cgccggagac ggtgaccgga gttgaggagg tatag 35

<210> SEQ ID NO 42
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 42
ttaatctaga atgcagagca ttatggactc g 31

<210> SEQ ID NO 43
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 43
cggtcgactt aggttttgtt gttcttcaat ttgc 34

<210> SEQ ID NO 44
<211> LENGTH: 22
<212> TYPE: PRT
<213> ORGANISM: Artificial Sequence
<220> FEATURE:
<223> OTHER INFORMATION: Motif

<400> SEQUENCE: 44

Asp His Gly Ser Ile Asp Leu Glu Trp Leu Arg Asp His Gly Ser Ile
1 5 10 15

Asp Leu Glu Trp Leu Arg
20

<210> SEQ ID NO 45
<211> LENGTH: 17
<212> TYPE: PRT
<213> ORGANISM: Artificial Sequence
<220> FEATURE:
<223> OTHER INFORMATION: Motif

<400> SEQUENCE: 45

Gly Leu Gly Leu Lys Ser Val Glu Cys Val Arg Leu Leu Thr Leu His
1 5 10 15

His

<210> SEQ ID NO 46
<211> LENGTH: 11

```
<212> TYPE: PRT
<213> ORGANISM: Artificial Sequence
<220> FEATURE:
<223> OTHER INFORMATION: Motif

<400> SEQUENCE: 46

Ala Phe Pro Val Asp Thr Asn Val Gly Arg Ile
1               5                   10


<210> SEQ ID NO 47
<211> LENGTH: 21
<212> TYPE: PRT
<213> ORGANISM: Artificial Sequence
<220> FEATURE:
<223> OTHER INFORMATION: Motif

<400> SEQUENCE: 47

Val Arg Leu Gly Trp Val Pro Leu Gln Pro Leu Pro Glu Ser Leu Gln
1               5                   10                  15

Leu His Leu Leu Glu
            20


<210> SEQ ID NO 48
<211> LENGTH: 22
<212> TYPE: PRT
<213> ORGANISM: Artificial Sequence
<220> FEATURE:
<223> OTHER INFORMATION: Motif

<400> SEQUENCE: 48

Glu Leu His Tyr Gln Met Ile Thr Phe Gly Lys Val Phe Cys Thr Lys
1               5                   10                  15

Ser Lys Pro Asn Cys Asn
            20


<210> SEQ ID NO 49
<211> LENGTH: 14
<212> TYPE: PRT
<213> ORGANISM: Artificial Sequence
<220> FEATURE:
<223> OTHER INFORMATION: Motif

<400> SEQUENCE: 49

His Phe Ala Ser Ala Phe Ala Ser Ala Arg Leu Ala Leu Pro
1               5                   10


<210> SEQ ID NO 50
<211> LENGTH: 1393
<212> TYPE: PRT
<213> ORGANISM: Arabidopsis thaliana

<400> SEQUENCE: 50

Met Glu Lys Gln Arg Arg Glu Glu Ser Ser Phe Gln Gln Pro Pro Trp
1               5                   10                  15

Ile Pro Gln Thr Pro Met Lys Pro Phe Ser Pro Ile Cys Pro Tyr Thr
            20                  25                  30

Val Glu Asp Gln Tyr His Ser Ser Gln Leu Glu Glu Arg Arg Phe Val
        35                  40                  45

Gly Asn Lys Asp Met Ser Gly Leu Asp His Leu Ser Phe Gly Asp Leu
    50                  55                  60

Leu Ala Leu Ala Asn Thr Ala Ser Leu Ile Phe Ser Gly Gln Thr Pro
65                  70                  75                  80

Ile Pro Thr Arg Asn Thr Glu Val Met Gln Lys Gly Thr Glu Glu Val
```

-continued

```
                85                  90                  95

Glu Ser Leu Ser Ser Val Ser Asn Asn Val Ala Glu Gln Ile Leu Lys
            100                 105                 110

Thr Pro Glu Lys Pro Lys Arg Lys Lys His Arg Pro Lys Val Arg Arg
        115                 120                 125

Glu Ala Lys Pro Lys Arg Glu Pro Lys Pro Arg Ala Pro Arg Lys Ser
    130                 135                 140

Val Val Thr Asp Gly Gln Glu Ser Lys Thr Pro Lys Arg Lys Tyr Val
145                 150                 155                 160

Arg Lys Lys Val Glu Val Ser Lys Asp Gln Asp Ala Thr Pro Val Glu
                165                 170                 175

Ser Ser Ala Ala Val Glu Thr Ser Thr Arg Pro Lys Arg Leu Cys Arg
            180                 185                 190

Arg Val Leu Asp Phe Glu Ala Glu Asn Gly Glu Asn Gln Thr Asn Gly
        195                 200                 205

Asp Ile Arg Glu Ala Gly Glu Met Glu Ser Ala Leu Gln Glu Lys Gln
    210                 215                 220

Leu Asp Ser Gly Asn Gln Glu Leu Lys Asp Cys Leu Leu Ser Ala Pro
225                 230                 235                 240

Ser Thr Pro Lys Arg Lys Arg Ser Gln Gly Lys Arg Lys Gly Val Gln
                245                 250                 255

Pro Lys Lys Asn Gly Ser Asn Leu Glu Glu Val Asp Ile Ser Met Ala
            260                 265                 270

Gln Ala Ala Lys Arg Arg Gln Gly Pro Thr Cys Cys Asp Met Asn Leu
        275                 280                 285

Ser Gly Ile Gln Tyr Asp Glu Gln Cys Asp Tyr Gln Lys Met His Trp
    290                 295                 300

Leu Tyr Ser Pro Asn Leu Gln Gln Gly Gly Met Arg Tyr Asp Ala Ile
305                 310                 315                 320

Cys Ser Lys Val Phe Ser Gly Gln Gln His Asn Tyr Val Ser Ala Phe
                325                 330                 335

His Ala Thr Cys Tyr Ser Ser Thr Ser Gln Leu Ser Ala Asn Arg Val
            340                 345                 350

Leu Thr Val Glu Glu Arg Arg Glu Gly Ile Phe Gln Gly Arg Gln Glu
        355                 360                 365

Ser Glu Leu Asn Val Leu Ser Asp Lys Ile Asp Thr Pro Ile Lys Lys
    370                 375                 380

Lys Thr Thr Gly His Ala Arg Phe Arg Asn Leu Ser Ser Met Asn Lys
385                 390                 395                 400

Leu Val Glu Val Pro Glu His Leu Thr Ser Gly Tyr Cys Ser Lys Pro
                405                 410                 415

Gln Gln Asn Asn Lys Ile Leu Val Asp Thr Arg Val Thr Val Ser Lys
            420                 425                 430

Lys Lys Pro Thr Lys Ser Glu Lys Ser Gln Thr Lys Gln Lys Asn Leu
        435                 440                 445

Leu Pro Asn Leu Cys Arg Phe Pro Pro Ser Phe Thr Gly Leu Ser Pro
    450                 455                 460

Asp Glu Leu Trp Lys Arg Arg Asn Ser Ile Glu Thr Ile Ser Glu Leu
465                 470                 475                 480

Leu Arg Leu Leu Asp Ile Asn Arg Glu His Ser Glu Thr Ala Leu Val
                485                 490                 495

Pro Tyr Thr Met Asn Ser Gln Ile Val Leu Phe Gly Gly Gly Ala Gly
            500                 505                 510
```

-continued

Ala Ile Val Pro Val Thr Pro Val Lys Lys Pro Arg Pro Arg Pro Lys
515 520 525

Val Asp Leu Asp Asp Glu Thr Asp Arg Val Trp Lys Leu Leu Leu Glu
530 535 540

Asn Ile Asn Ser Glu Gly Val Asp Gly Ser Asp Glu Gln Lys Ala Lys
545 550 555 560

Trp Trp Glu Glu Glu Arg Asn Val Phe Arg Gly Arg Ala Asp Ser Phe
565 570 575

Ile Ala Arg Met His Leu Val Gln Gly Asp Arg Arg Phe Thr Pro Trp
580 585 590

Lys Gly Ser Val Val Asp Ser Val Val Gly Val Phe Leu Thr Gln Asn
595 600 605

Val Ser Asp His Leu Ser Ser Ser Ala Phe Met Ser Leu Ala Ser Gln
610 615 620

Phe Pro Val Pro Phe Val Pro Ser Ser Asn Phe Asp Ala Gly Thr Ser
625 630 635 640

Ser Met Pro Ser Ile Gln Ile Thr Tyr Leu Asp Ser Glu Glu Thr Met
645 650 655

Ser Ser Pro Pro Asp His Asn His Ser Ser Val Thr Leu Lys Asn Thr
660 665 670

Gln Pro Asp Glu Glu Lys Asp Tyr Val Pro Ser Asn Glu Thr Ser Arg
675 680 685

Ser Ser Ser Glu Ile Ala Ile Ser Ala His Glu Ser Val Asp Lys Thr
690 695 700

Thr Asp Ser Lys Glu Tyr Val Asp Ser Asp Arg Lys Gly Ser Ser Val
705 710 715 720

Glu Val Asp Lys Thr Asp Glu Lys Cys Arg Val Leu Asn Leu Phe Pro
725 730 735

Ser Glu Asp Ser Ala Leu Thr Cys Gln His Ser Met Val Ser Asp Ala
740 745 750

Pro Gln Asn Thr Glu Arg Ala Gly Ser Ser Ser Glu Ile Asp Leu Glu
755 760 765

Gly Glu Tyr Arg Thr Ser Phe Met Lys Leu Leu Gln Gly Val Gln Val
770 775 780

Ser Leu Glu Asp Ser Asn Gln Val Ser Pro Asn Met Ser Pro Gly Asp
785 790 795 800

Cys Ser Ser Glu Ile Lys Gly Phe Gln Ser Met Lys Glu Pro Thr Lys
805 810 815

Ser Ser Val Asp Ser Ser Glu Pro Gly Cys Cys Ser Gln Gln Asp Gly
820 825 830

Asp Val Leu Ser Cys Gln Lys Pro Thr Leu Lys Glu Lys Gly Lys Lys
835 840 845

Val Leu Lys Glu Glu Lys Lys Ala Phe Asp Trp Asp Cys Leu Arg Arg
850 855 860

Glu Ala Gln Ala Arg Ala Gly Ile Arg Glu Lys Thr Arg Ser Thr Met
865 870 875 880

Asp Thr Val Asp Trp Lys Ala Ile Arg Ala Ala Asp Val Lys Glu Val
885 890 895

Ala Glu Thr Ile Lys Ser Arg Gly Met Asn His Lys Leu Ala Glu Arg
900 905 910

Ile Gln Gly Phe Leu Asp Arg Leu Val Asn Asp His Gly Ser Ile Asp
915 920 925

-continued

```
Leu Glu Trp Leu Arg Asp Val Pro Pro Asp Lys Ala Lys Glu Tyr Leu
    930                 935                 940

Leu Ser Phe Asn Gly Leu Gly Leu Lys Ser Val Glu Cys Val Arg Leu
945                 950                 955                 960

Leu Thr Leu His His Leu Ala Phe Pro Val Asp Thr Asn Val Gly Arg
                965                 970                 975

Ile Ala Val Arg Leu Gly Trp Val Pro Leu Gln Pro Leu Pro Glu Ser
            980                 985                 990

Leu Gln Leu His Leu Leu Glu Met  Tyr Pro Met Leu Glu  Ser Ile Gln
        995                 1000                1005

Lys Tyr  Leu Trp Pro Arg Leu  Cys Lys Leu Asp Gln  Lys Thr Leu
    1010                 1015                1020

Tyr Glu  Leu His Tyr Gln Met  Ile Thr Phe Gly Lys  Val Phe Cys
    1025                 1030                1035

Thr Lys  Ser Lys Pro Asn Cys  Asn Ala Cys Pro Met  Lys Gly Glu
    1040                 1045                1050

Cys Arg  His Phe Ala Ser Ala  Phe Ala Ser Ala Arg  Leu Ala Leu
    1055                 1060                1065

Pro Ser  Thr Glu Lys Gly Met  Gly Thr Pro Asp Lys  Asn Pro Leu
    1070                 1075                1080

Pro Leu  His Leu Pro Glu Pro  Phe Gln Arg Glu Gln  Gly Ser Glu
    1085                 1090                1095

Val Val  Gln His Ser Glu Pro  Ala Lys Lys Val Thr  Cys Cys Glu
    1100                 1105                1110

Pro Ile  Ile Glu Glu Pro Ala  Ser Pro Glu Pro Glu  Thr Ala Glu
    1115                 1120                1125

Val Ser  Ile Ala Asp Ile Glu  Glu Ala Phe Phe Glu  Asp Pro Glu
    1130                 1135                1140

Glu Ile  Pro Thr Ile Arg Leu  Asn Met Asp Ala Phe  Thr Ser Asn
    1145                 1150                1155

Leu Lys  Lys Ile Met Glu His  Asn Lys Glu Leu Gln  Asp Gly Asn
    1160                 1165                1170

Met Ser  Ser Ala Leu Val Ala  Leu Thr Ala Glu Thr  Ala Ser Leu
    1175                 1180                1185

Pro Met  Pro Lys Leu Lys Asn  Ile Ser Gln Leu Arg  Thr Glu His
    1190                 1195                1200

Arg Val  Tyr Glu Leu Pro Asp  Glu His Pro Leu Leu  Ala Gln Leu
    1205                 1210                1215

Glu Lys  Arg Glu Pro Asp Asp  Pro Cys Ser Tyr Leu  Leu Ala Ile
    1220                 1225                1230

Trp Thr  Pro Gly Glu Thr Ala  Asp Ser Ile Gln Pro  Ser Val Ser
    1235                 1240                1245

Thr Cys  Ile Phe Gln Ala Asn  Gly Met Leu Cys Asp  Glu Glu Thr
    1250                 1255                1260

Cys Phe  Ser Cys Asn Ser Ile  Lys Glu Thr Arg Ser  Gln Ile Val
    1265                 1270                1275

Arg Gly  Thr Ile Leu Ile Pro  Cys Arg Thr Ala Met  Arg Gly Ser
    1280                 1285                1290

Phe Pro  Leu Asn Gly Thr Tyr  Phe Gln Val Asn Glu  Val Phe Ala
    1295                 1300                1305

Asp His  Ala Ser Ser Leu Asn  Pro Ile Asn Val Pro  Arg Glu Leu
    1310                 1315                1320

Ile Trp  Glu Leu Pro Arg Arg  Thr Val Tyr Phe Gly  Thr Ser Val
```

-continued

```
    1325                1330                1335

Pro Thr  Ile Phe Lys Gly Leu  Ser Thr Glu Lys Ile  Gln Ala Cys
    1340                1345                1350

Phe Trp  Lys Gly Tyr Val Cys  Val Arg Gly Phe Asp  Arg Lys Thr
    1355                1360                1365

Arg Gly  Pro Lys Pro Leu Ile  Ala Arg Leu His Phe  Pro Ala Ser
    1370                1375                1380

Lys Leu  Lys Gly Gln Gln Ala  Asn Leu Ala
    1385                1390
```

RICE GRAIN WITH REDUCED ROS1a ACTIVITY

CROSS-REFERENCE TO RELATED APPLICATIONS

This application is a divisional of U.S. application Ser. No. 15/777,059, filed May 17, 2018, now allowed, which is a § 371 national stage of PCT International Application No. PCT/AU2016/051106, filed Nov. 17, 2016, claiming priority of Australian Patent Application No. 2015904754, filed Nov. 18, 2015, the contents of each of which are hereby incorporated by reference into the subject application.

REFERENCE TO SEQUENCE LISTING

This application incorporates-by-reference nucleotide and/or amino acid sequences which are present in the file named "220617_90508-Z_Sub_Seq_Listing_JMP.txt," which is 158 kilobytes in size, and which was created Jun. 14, 2022—in the IBM-PC machine format, an having operating system compatibility with MS-Windows, which is contained in the text file filed Jun. 17, 2022 as part of this application.

FIELD OF THE INVENTION

The present invention relates to rice grain with thickened aleurone. Also provided is a rice plant comprising at least one genetic variation which reduces the activity of at least one ROS1a gene in the plant. Grain of the invention, or aleurone therefrom, has improved nutritional properties, and hence is particularly useful for human and animal feed products.

BACKGROUND OF THE INVENTION

Worldwide, cereal grains such as wheat, rice, maize and to a lesser extent barley, oats and rye are the major source of human caloric intake from the starch content of the grain. Cereal grain is also important in supplying other nutritional components such as protein, vitamins, minerals and dietary fibre. Different parts of the grains contribute differently for these nutritional components. Starch is stored in the starchy endosperm of cereal grains, whereas the other nutritional components are more concentrated in the embryo and bran (Buri et al., 2004). However, the bran is often removed before use in food, particularly in rice which is then eaten as white rice.

Cereal grain develops from double fertilisation events between maternal and paternal gametophytes. One of two sperm cells from the pollen tube fuses with an egg to produce a zygote that develops into an embryo, and the other sperm cell fuses with the diploid central cell of the megagametophyte to produce a primary endosperm nucleus, from which the genetically triploid endosperm develops. Thus, the endosperm including the aleurone is triploid, having two copies of the maternal haploid genome and one copy of the paternal haploid genome. In dicotyledonous seeds, the endosperm is consumed by the developing embryo whereas in monocotyledons such as rice the endosperm persists to make up the bulk of the mature grain.

The mature endosperm of cereals has four cell types with distinct characteristics, namely the starchy endosperm which is characterised by its abundant contents of starch granules and storage proteins, the epidermal-like aleurone which is most often one cell layer in thickness surrounding most of the starchy endosperm, transfer cells at the base of the seed over the main maternal vasculature, and a layer of embryo-surrounding cells which form a lining for the embryo early in grain development but later may only surround the suspensor which connects the embryo and starchy endosperm (Becraft et al., 2001a). The embryo forms within a cavity within the starchy endosperm. Cereal aleurone tissue therefore comprises the outermost layer(s) of the endosperm in cereal grains, and surrounds the starchy endosperm and part of the embryo.

Aleurone cells are distinguished from starchy endosperm cells by their morphology, biochemical composition and gene expression profiles (Becraft and Yi, 2011). Aleurone cells are generally oil and protein-rich and secrete enzymes allowing the mobilization of endosperm reserves during seed germination. Each aleurone cell is enclosed within a fibrous cell wall that is thicker than endosperm cell walls and that is composed mainly of arabinoxylans and beta glucans in various ratios and are highly autofluorescent. The aleurone layer is the only layer of the endosperm that in cereals is sometimes pigmented with anthocyanins.

Cereal aleurone is only one cell layer in thickness in wheat and wild-type maize (Buttrose 1963; Walbot, 1994), mostly one but up to three cell layers in the dorsal region of the endosperm in rice (Hoshikawa, 1993), and three cell layers in wild-type barley (Jones, 1969). In normal endosperm, the aleurone is extremely regular and the patterns of cell division are highly organised. Wild-type mature aleurone cells are nearly cuboid in section with a dense cytoplasm including granules, small vacuoles and inclusion bodies made of protein, lipid and phytin or of protein plus carbohydrate. In mature cereal grains, the aleurone is the only endosperm tissue that remains alive, although in a dormant, desiccated form. Upon imbibition, the embryo produces gibberellins which induce synthesis of amylases and other hydrolases by the aleurone which are released into the starchy endosperm to break down storage compounds to form sugars and amino acids for early growth of the embryo into a seedling.

The regulation of aleurone development in cereal grains has been reviewed by Becraft and Yi (2011). Multiple levels of genetic regulation control aleurone cell fate, differentiation and organisation, and many genes are involved in the processes, only some of which have been identified. For example, maize defective kernal1 (dek1) loss-of-function mutants have no aleurone layer indicating that the wild-type Dek1 polypeptide is required for specifying the outer cell layer as aleurone (Becraft et al., 2002). The Dek1 polypeptide is a large integral membrane protein with 21 membrane-spanning domains and a cytoplasmic domain containing an active calpain protease. Another gene in maize, CRINKLY4 (CR4) encodes a receptor kinase that functions as a positive regulator of aleurone fate, and cr4 mutants have reduced aleurone (Becraft et al., 2001b).

Several instances of thickened aleurones in cereal grain mutants have been reported in the literature, but none have proven useful because of pleiotrophic effects, or agronomic and production problems.

Shen et al. (2003) reported the identification of maize mutants in the supernumary aleurone layers1 (sal1) gene which in different mutants had 2-3 or up to seven layers of aleurone cells instead of the normal single layer. The SAL1 polypetide was identified as a class E vacuolar sorting protein. Homozygous sal1-1 mutant grain had defective embryos that failed to germinate and had much reduced starchy endosperm. A less complete mutant that was homozygous for the sal1-2 allele exhibited a 2 cell-layer aleurone. However, the mutant plants grew to a height of only 30% of the wild-type, had a reduced root mass and were poor in seed setting (Shen et al. 2003). These plants were not agronomically useful.

Yi et al. (2011) reported the identification of a thick aleurone1 (thk1) mutant in maize. The mutant kernals showed a multilayer aleurone. However, the mutant kernals lacked well-developed embryos and did not germinate when sown. The wild-type Thk1 gene encoded a Thk1 polypetide which acted downstream of the Dek1 polypeptide which was required for aleurone development in maize (Becraft et al., 2002).

A maize extra cell layer (Xcl) gene mutant was identified by its effect on leaf morphology. It produced a double aleurone layer as well as multilayered leaf epidermis (Kessler et al., 2002). The Xcl mutation was a semi-dominant mutation that disrupted cell division and differentiation patterns in maize, producing thick and narrow leaves with an abnormal shiny appearance.

Maize mutants in the disorgal1 and disorgal2 (dil1 and dil2) genes exhibited aleurones having a variable number of layers with cells of irregular shapes and sizes (Lid et al., 2004). However, homozygous dil1 and dil2 mutant grains were shrunken due to reduced accumulation of starch, and the mature mutant grains germinated at low rates and did not develop into viable plants.

In barley, elo2 mutants showed similarly disorganised cells and irregularities of the aleurone layers, resulting from aberrant periclinal cell division (Lewis et al., 2009). The plants also showed increased cell layers in the leaf epidermis, with bulging and distorted cells on the epidermis. Importantly, the homozygous mutant plants were dwarfed, producing grain weight of less than 60% of wild-type, and were not useful for grain production.

In rice, two transcription factors that control the expression of seed storage proteins also influence aleurone cell fate (Kawakatsu et al., 2009). Reduction in expression by co-suppression constructs of a gene encoding a rice prolamin box binding factor (RPBF) polypeptide, which is in the DOF zinc finger transcription factor class, resulted in a sporadic multilayered aleurone consisting of large, disordered cells. There was also a significant reduction in seed storage protein expression and accumulation, and starch and lipids were accumulated at substantially reduced levels. Expression of the rice homologs of the maize Dek1, CR4 and SAL1 genes was also reduced, showing that the RPBF and RISBZ1 factors operated in the same regulatory pathway as those genes.

Demethylation of DNA

In a completely different area of plant science, demethylation of DNA is now summarised. Plants methylate some cytosine nucleotides in nuclear DNA at carbon 5 of the pyrimidine ring, forming 5-methylcytosine (5-meC). The methylated cytosine may occur in any of three contexts, namely CG, CHG (where H=A, C or T) and CHH methylation, each catalysed by a different methyltransferase. At least in *Arabidopsis thaliana* and probably in most plants including rice (Zemach et al., 2010), CG methylation is catalysed by enzymes in the Methyltransferase 1 (Met1) family, CHG methylation is catalysed by methylases in the Chromomethylase family, and CHH methylation occurs through an RNA-mediated reaction catalysed by Domains Rearranged Methylases (DRM) using small RNAs as guide sequences (Law and Jacobsen, 2010). Cytosine methylation, which occurs in only a small proportion of all cytosines, most often occurs in heterochromatic DNA and in regions rich in repetitive DNA and transposons, suppressing their activity. It also occurs in transcribed regions of the nuclear DNA, including in promoter regions of genes, and is thereby involved in the control of expression of many genes.

Cytosine methylation of DNA is reversible through demethylation, which may happen passively through DNA replication or actively through the activity of demethylation enzymes. One pathway for active demethylation of DNA in plants is through a base excision repair (BER) pathway which uses DNA glycosylase enzymes. These enzymes remove 5-meC from the double-stranded DNA backbone and then cleave the DNA backbone (lyase activity) at the abasic site by successive β- and δ-elimination reactions. The repair is completed by insertion of an unmethylated cytosine nucleotide by a DNA polymerase activity.

There are four 5-meC DNA glycosylase/lyases in the *Arabidopsis* genome, designated Demeter (DME), Demeter-like 2 (DML2), Demeter-like 3 (DML3) and Repressor of Silencing (ROS1). Genetic and biochemical analyses showed that all four function as DNA demethylases (Gong et al., 2002; Agius et al., 2006; Morales-Ruiz et al., 2006), with DME functioning primarily in the egg cell and endosperm and the others functioning in other tissues. Other plants similarly show a multiplicity of demethylases (Zemach et al., 2010).

There is a need for rice grain having thickened aleurone from plants, particularly rice plants that are also phenotypically normal and agronomically useful.

SUMMARY OF THE INVENTION

In one aspect, the present invention provides grain of a rice plant, the grain comprising an aleurone, a starchy endosperm, a ROS1a gene encoding a ROS1a polypeptide and (i) one or more genetic variations which each reduce the activity of at least one ROS1a gene in the plant when compared to a corresponding wild-type rice plant, and/or (ii) said aleurone is thickened compared to aleurone from a corresponding wild-type grain.

In an embodiment, the ROS1a polypeptide has DNA glycosylase activity. In an embodiment, the ROS1a polypeptide has a level of DNA glycosylase activity which is between 2% and about 60% of the level of DNA glycosylase activity of a corresponding wild-type ROS1a polypeptide and/or of ROS1a polypeptide whose amino acids have a sequence set forth in SEQ ID NO: 2.

In another embodiment, the ROS1a polypeptide is a variant of a corresponding wild-type ROS1a polypeptide in that their amino acid sequences are different. In a preferred embodiment, the rice grain comprises a ROS1a (Ta2) variant polypeptide which has an amino acid sequence provided as SEQ ID NO:1, the polypeptide being a variant of the wild-type ROS1a polypeptide whose amino acid sequence is provided as SEQ ID NO:2.

In an embodiment, the grain has a level of ROS1a polypeptide between 2% and about 60% of that present in the grain compared to the level of ROS1a polypeptide in the corresponding wild-type grain.

In an embodiment, the thickened aleurone comprises at least two, at least three, at least four or at least five layers of cells, about 3, about 4, about 5 or about 6 layers of cells, or 2-8, 2-7, 2-6 or 2-5 layers of cells. In an embodiment, the grain is from a rice plant and the thickened aleurone comprises 5-8, 5-7, 5-6 or 2-5 layers of cells. In an embodiment, the aleurone layer is increased in thickness compared to the aleurone of a wild-type rice grain by about 100%, or about 150% or about 200%, or about 250%.

The genetic variation, preferably an introduced genetic variation, which reduces the activity of at least one ROS1a gene in the plant can be any type of genetic manipulation which reduces or impairs the production of wild-type levels of ROS1a polypeptide in the rice grain. Examples of such genetic variations include, but are not necessarily limited to, (a) a ROS1a gene encoding a mutant ROS1a polypeptide with reduced DNA glycosylase activity relative to the wild-type ROS1a polypeptide (SEQ ID NO:2);

(b) a ROS1a gene which when expressed produces a reduced level of a wild-type ROS1a polypeptide, for example which comprises a splice-site mutation that results in a reduced level of expression of the ROS1a gene, relative to the wild-type ROS1a gene whose cDNA sequence is provided as SEQ ID NO:8, or which ROS1a gene comprises a mutation in its promoter which results in reduced expression of the ROS1a gene relative to the wild-type ROS1a gene;

(c) an exogenous nucleic acid construct which encodes a polynucleotide which reduces expression of a ROS1a gene in the rice plant, preferably wherein the nucleic acid construct comprises a DNA region encoding the polynucleotide operably linked to a promoter which is expressed in developing grain of the rice plant at least at a time point between the time of anthesis and 7 days post-anthesis, and (d) a ROS1a gene comprising a premature translational stop codon in its protein coding region such that the gene encodes, but may or may not produce, a truncated polypeptide relative to a wild-type ROS1a polypeptide.

In a preferred embodiment, the rice grain comprises (i) an aleurone, (ii) a starchy endosperm, (iii) a ROS1a gene which comprises a genetic variation which reduces the activity of the ROS1a gene in a rice plant compared to a wild-type ROS1a gene, wherein said ROS1a gene which comprises the genetic variation encodes a variant ROS1a polypeptide relative to SEQ ID NO:2, and wherein the aleurone is thickened compared to aleurone from a corresponding wild-type rice grain. In an embodiment, the genetic variation in the ROS1a gene is an introduced genetic modification. In a preferred embodiment, the variant ROS1a polypeptide is different in amino acid sequence to the sequence provided as SEQ ID NO:2 at least by an insertion or deletion of one or more amino acids or an amino acid substitution relative to SEQ ID NO:2. In an even more preferred embodiment, the variant ROS1a polypeptide is different in amino acid sequence to the sequence provided as SEQ ID NO:2 by an insertion of one or more amino acids or by a single amino acid substitution relative to SEQ ID NO:2, such as, for example, one of the amino acid substitutions as listed in Table 3. The rice grain may have been treated so that it is no longer able to germinate such as, for example, having been cooked, or it may not have been so treated such that it is able to germinate and grow and thereby provide a rice plant of the invention. In a most preferred embodiment, the aleurone of the rice grain is pigmented such as, for example, the rice grain is black rice as defined herein.

In another preferred embodiment, the rice grain comprises (i) an aleurone, (ii) a starchy endosperm, (iii) a ROS1a gene which comprises a genetic variation which reduces the activity of the ROS1a gene in a rice plant compared to a wild-type ROS1a gene, wherein said ROS1a gene which comprises the genetic variation encodes a ROS1a polypeptide whose amino acid sequence is the same as a wild-type ROS1a polypeptide such as, for example, SEQ ID NO:2, wherein said ROS1a gene is expressed in a rice plant at a reduced level relative to a wild-type ROS1a gene, wherein the aleurone is thickened compared to aleurone from a corresponding wild-type rice grain. In an embodiment, the genetic variation in the ROS1a gene is an introduced genetic modification which results in the ROS1a gene being expressed at the reduced level. In an embodiment, the genetic variation is selected from the group consisting of (i) a splice-site mutation that results in a reduced level of expression of the ROS1a gene, relative to the wild-type ROS1a gene whose cDNA sequence is provided as SEQ ID NO:8, (ii) a ROS1a gene promoter mutation which results in reduced expression of the ROS1a gene relative to the wild-type ROS1a gene, and (iii) an exogenous nucleic acid molecule, preferably integrated into the nuclear genome of the rice plant, which encodes an RNA polynucleotide which reduces expression of a ROS1a gene in the rice plant. The rice grain may have been treated so that it is no longer able to germinate such as, for example, having been cooked, or it may not have been so treated such that it is able to germinate and grow and thereby give rise to a rice plant of the invention. In a most preferred embodiment, the aleurone of the rice grain is pigmented such as, for example, the rice grain is black rice as defined herein.

In an embodiment, the rice plant has a level of DNA glycosylase activity in its developing grain which is between 2% and about 60% of the level of DNA glycosylase activity in a corresponding wild-type developing grain. In a preferred embodiment, the rice plant has a level of DNA glycosylase activity in its developing grain which is between 2% and 50%, or between 2% and 40%, or between 2% and 30%, or between 2% and 20% of the level of DNA glycosylase activity in a corresponding wild-type developing grain.

In an embodiment, the activity of at least one ROS1a gene in the rice plant is reduced in one or more or all of aleurone, pericarp, nucellar projection, ovary, testa and starchy endosperm of the developing grain.

In an embodiment, the activity of a ROS1a gene is reduced at least at a time point between the time of anthesis and 7 days post-anthesis and/or in the egg cell prior to anthesis. In an embodiment, the exogenous nucleic acid molecule may be operably linked to a promoter which is expressed at least at a time point between the time of anthesis and 7 days post-anthesis, such that the encoded RNA polynucleotide reduces expression of the ROS1a gene in the rice plant during that time.

In an embodiment, the rice plant is male and female fertile.

In an embodiment, the rice plant exhibits delayed grain maturation. In an embodiment, the grain maturation is delayed by 2-10 days or 2-15 days relative to a wild-type rice plant.

In an embodiment, the grain comprises, when compared to a corresponding wild-type grain, one or more or all of the following, each on a weight basis, i) a higher mineral content, preferably the mineral content is the content of one or more or all of zinc, iron potassium, magnesium, phosphorus and sulphur, ii) a higher antioxidant content, iii) a higher phytate content, iv) a higher content of one or more or all of vitamins B3, B6 and B9, v) a higher dietary fibre content and/or insoluble fibre content, vi) a starch content which is between about 90% and about 100% by weight relative to the starch content of the corresponding wild-type grain;

vii) a higher sucrose content, viii) a higher monosaccharide content, and ix) a lipid content of at least 90% or at least 100% relative to the lipid content of the corresponding wild-type grain. In an embodiment, the content of the component is increased by 10-50% or preferably 10-100% relative to the corresponding content in a wild-type rice grain.

In an embodiment, the grain comprises an embryo.

In an embodiment, the grain is whole grain or cracked grain.

In an embodiment, the grain has been processed so that it is no longer able to germinate, preferably by heat treatment. For example, the grain has been cooked with water at 100° C. for at least 5 minutes. In an embodiment, the grain is cracked grain or milled grain.

In an alternative embodiment, the grain has a germination rate which is between about 70% and about 100% relative to the germination rate of a corresponding wild-type grain. That is, a collection of at least 100 grains has an average germination rate of 70-100% relative to wild-type. When the grains germinate and grow, rice plants of the invention are produced.

In an embodiment, the grain comprises a ROS1a gene which encodes a ROS1a polypeptide which has DNA glycosylase activity, preferably in one or more of aleurone, testa and starchy endosperm of the grain, wherein the ROS1a polypeptide which has DNA glycosylase activity is preferably a mutant ROS1a polypeptide.

In another embodiment, the grain comprises a mutant ROS1a polypeptide having decreased DNA glycosylase activity when expressed in the rice plant compared to a corresponding wild-type ROS1a polypeptide, preferably wherein the mutant ROS1a polypeptide comprises one or more amino acid substitutions, deletions or insertions which reduces DNA glycosylase activity compared to the corresponding wild-type ROS1a polypeptide. The mutant ROS1a polypeptide may have no DNA glycosylase activity, provided the grain comprises another ROS1a polypeptide which has DNA glycosylase activity. For example, the ROS1a gene may encode two ROS1a polypeptides through alternative splicing, one of which has DNA glycosylase activity whereas the other does not. In a preferred embodiment, the mutant ROS1a polypeptide has an insertion of seven amino acids relative to the wild-type ROS1a polypeptide, such as for example the mutant ROS1a polypeptide whose amino acid sequence is provided as SEQ ID NO:1.

In a further embodiment, the grain has a reduced total amount of ROS1a polypeptide compared to a corresponding wild-type grain, preferably reduced in one or more of aleurone, testa and starchy endosperm of the grain, provided that the grain comprises a ROS1a gene which encodes a ROS1a polypeptide which has DNA glycosylase activity. The total amount of ROS1a polypeptide may also be decreased in the pollen of the rice plant.

In another embodiment, the genetic variation, preferably introduced genetic variation, is an exogenous nucleic acid construct which encodes a polynucleotide which reduces expression of a ROS1a gene in the rice plant, preferably reduced in the rice plant at least at a time point between the time of anthesis and 7 days post-anthesis, provided that the grain comprises at least one ROS1a gene which encodes a ROS1a polypeptide which has DNA glycosylase activity.

In an embodiment, the grain is pigmented in its outer layer(s), for example the grain is brown grain or black grain of the rice plant, the grain comprising (i) an aleurone having a thickness of at least 2 cell layers, or 2-7 cell layers, and (ii) a mutant ROS1a gene which encodes a ROS1a polypeptide which comprises one or more amino acid substitutions, insertions or deletions which reduces DNA glycosylase activity when compared to a corresponding wild-type rice ROS1a polypeptide, the reduced DNA glycosylase activity occurring in the rice plant at least at a time point between the time of anthesis and 7 days post-anthesis, provided that at least at a time point between the time of anthesis and 7 days post-anthesis the rice plant has between 2% and about 60% of the level of DNA glycosylase activity in developing grain compared to the wild-type rice plant.

In an embodiment, the grain is pigmented in its outer layer(s), for example the grain is brown grain or black grain of a rice plant, the grain comprising (i) an aleurone having a thickness of at least 2 cell layers, or 2-7 cell layers, and (ii) an exogenous nucleic acid construct which encodes a polynucleotide which reduces expression of a ROS1a gene in the rice plant, wherein the exogenous nucleic acid construct comprises a DNA region encoding the polynucleotide operably linked to a promoter which is expressed in developing grain of the rice plant at least at a time point between the time of anthesis and 7 days post-anthesis, such that at least at a time point between the time of anthesis and 7 days post-anthesis the rice plant has between 2% and about 60% of the level of DNA glycosylase activity in the developing grain compared to the wild-type rice plant. In a preferred embodiment, the promoter is a promoter other than a constitutive promoter, such as, for example, a promoter which is expressed in the endosperm of developing seed. In a most preferred embodiment, the promoter is an LTP promoter.

In another embodiment, the ROS1a polypeptide comprises amino acids whose sequence is at least 95% identical to SEQ ID NO: 2, or the ROS1a polypeptide(s) comprises amino acids whose sequence is at least 95% identical, at least 97.5% identical, or at least 99% identical, to SEQ ID NO: 2 and which sequence is different to the amino acid sequence of the corresponding wild-type ROS1a polypeptide.

In an embodiment, the ROS1a polypeptide comprises one or more or all of the following motifs; DHGSIDLEWLR (SEQ ID NO: 44), GLGLKSVECVRLLTLHH (SEQ ID NO: 45), AFPVDTNVGRI (SEQ ID NO: 46), VRLGWVPLQPLPESLQLHLLE (SEQ ID NO: 47), ELHYQMITFGKVFCTKSKPNCN (SEQ ID NO: 48) and HFASAFASARLALP (SEQ ID NO: 49).

The present invention also provides a population of rice grains, each of which comprises the same genetic variation(s), the same ROS1a gene, the same ROS1a polypeptide and/or has the same characteristics as described in the above embodiments. That is, the population is genetically and/or phenotypically uniform. The population of such rice grains may be obtained or derived from a single progenitor rice plant or grain, for example may be derived at least 2, at least 3 or at least 4 progeny generations from a progenitor plant or grain.

The present inventors have identified variant ROS1a polypeptides with reduced DNA glycosylase activity. Thus, in another aspect the present invention provides a purified and/or recombinant ROS1a polypeptide whose amino acid sequence is different to the amino acid sequence of a corresponding wild-type ROS1a polypeptide and which has reduced, preferably no, DNA glycosylase activity when compared to the corresponding wild-type ROS1a polypeptide.

In an embodiment, the purified and/or recombinant ROS1a polypeptide comprises amino acids having a sequence which is at least 95% identical, at least 97.5% identical, or at least 99% identical, to SEQ ID NO: 2.

In another aspect, the present invention provides an isolated and/or exogenous polynucleotide encoding a ROS1a polypeptide of the invention.

In a further aspect, the present invention provides an isolated and/or exogenous polynucleotide which, when present in a rice plant, reduces the expression of a ROS1a gene.

The skilled person is well aware of different types of polynucleotides that can be used to reduce the expression of a target gene, and how these polynucleotides can be designed. Examples include, but are not limited to, an antisense polynucleotide, a sense polynucleotide, a catalytic polynucleotide, a microRNA, a double stranded RNA (dsRNA) molecule or a processed RNA product thereof.

In an embodiment, the polynucleotide is a dsRNA molecule, or a processed RNA product thereof, comprising at least 19 consecutive nucleotides which is at least 95% identical to the complement of SEQ ID NO: 7 or 8 (where thymine (T) is uracil (U)), or at least 95% identical to the complement an mRNA encoding a ROS1a polypeptide whose amino acid sequence is provided as SEQ ID NO: 1 or 2.

In another embodiment, the dsRNA molecule is a microRNA (miRNA) precursor and/or wherein the processed RNA product thereof is a miRNA.

In an embodiment, the polynucleotide is used for reducing the expression of a ROS1a gene in developing grain of a rice plant at least at a time point between the time of anthesis and 7 days post-anthesis.

In a further aspect, the present invention provides nucleic acid construct and/or vector encoding a polynucleotide of the invention, wherein the nucleic acid construct or vector comprises a DNA region encoding the polynucleotide operably linked to a promoter which is expressed in developing grain of a rice plant at least at a time point between the time of anthesis and 7 days post-anthesis.

In a further aspect, the present invention provides a recombinant cell comprising an exogenous polynucleotide of the invention, or a nucleic acid construct and/or vector of the invention.

In an embodiment, the cell is a rice plant cell such as a cell of rice grain, preferably a rice aleurone.

In an embodiment, the exogenous polynucleotide, nucleic acid construct or vector is integrated into the genome of the cell, preferably into the nuclear genome.

Also provided is a cell of a rice plant comprising a ROS1a gene encoding a ROS1a polypeptide and a genetic variation, preferably an introduced genetic variation, which reduces the activity of at least one ROS1a gene in the cell when compared to a corresponding wild-type cell.

In an embodiment, the cell is an aleurone, pericarp, nucellar projection, ovary, testa or starchy endosperm cell.

In another aspect, the present invention provides a rice plant, or a population of rice plants, which produces grain of the invention, a polypeptide of the invention, a polynucleotide of the invention, a nucleic acid construct and/or vector of the invention and/or which comprises a cell of the invention. In an embodiment, each of the rice plants Also provided is a population of at least 100, or at least 1,000, rice plants of the invention growing in a field. In a preferred embodiment, the rice plants in the field are mostly (>50%), preferably all, rice plants of the invention. In a most preferred embodiment, the at least 100, or at least 1,000, rice plants are genetically and/or phenotypically the same, for example comprising the same genetic variation.

In another aspect, the present invention provides a method of producing a cell of the invention, the method comprising a step of introducing an exogenous polynucleotide of the invention, or a nucleic acid construct and/or vector of the invention, into a cell, preferably a rice cell.

In a further aspect, the present invention provides a method of producing a rice plant of the invention or transgenic grain therefrom, the method comprising the steps of i) introducing into a rice cell, an exogenous polynucleotide of the invention, or a nucleic acid construct and/or vector of the invention,
ii) obtaining a transgenic rice plant from a cell obtained from step i), the transgenic rice plant being transgenic for the exogenous polynucleotide, nucleic acid construct or vector or part thereof, and
iii) optionally harvesting grain from the plant of step ii), the grain being transgenic for the exogenous polynucleotide, nucleic acid construct or vector, and
iv) optionally producing one or more generations of transgenic progeny plants from the transgenic grain, the progeny plants being transgenic for the exogenous polynucleotide, nucleic acid construct or vector, thereby producing the rice plant or transgenic grain.

In another aspect, the present invention provides a method of producing a rice plant of the invention or grain therefrom, the method comprising the steps of i) introducing into a rice cell, a mutation of an endogenous ROS1a gene such that the mutated ROS1a gene encodes a ROS1a polypeptide of the invention, or does not encode a ROS1a polypeptide,
ii) obtaining a rice plant from a cell obtained from step i), the rice plant comprising the mutation of the endogenous ROS1a gene, and
iii) optionally harvesting grain from the plant of step ii), the grain comprising the mutation of the endogenous ROS1a gene, and
iv) optionally producing one or more generations of progeny plants from the grain, the progeny plants comprising the mutation of the endogenous ROS1a gene, thereby producing the rice plant or grain.

In an embodiment, the rice plant or grain comprises at least one ROS1a gene which encodes a ROS1a polypeptide which has DNA glycosylase activity.

In a further aspect, the present invention provides a method of selecting a rice plant or rice grain of the invention, the method comprising the steps of i) screening a population of rice plants or grain each of which were obtained from a mutagenic treatment of progenitor rice cells, grain or plants, for the production of grain of the invention or for the presence of a mutation in a ROS1a gene, or the presence of rice grain of the invention, and
ii) selecting from the population of step (i) a rice plant which produces grain of the invention or which comprises a mutant ROS1a gene, or rice grain of step (i) which is rice grain of the invention, thereby selecting the rice plant or grain.

The method may comprise a step of producing one or more progeny plants or grain from the selected rice plant, or at least two generations of progeny plants, and/or harvesting grain from progeny plants. Preferably, the progeny plants are homozygous for the genetic variation.

In a further aspect, the present invention provides a method of selecting a rice plant of the invention, the method comprising the steps of i) producing one or more progeny plants from rice grain, the rice grain having been derived from a cross of two parental rice plants,
ii) screening the one or more progeny plants of step i) for the production of grain of the invention, and
iii) selecting a progeny plant which produces the grain, thereby selecting the rice plant. In a preferred embodiment, the rice grain is black rice grain.

In an embodiment, screening step i) or step ii) comprises one or more or all of:
i) analysing a sample comprising DNA from a progeny plant for the genetic variation,
ii) analysing the thickness of aleurone of grain obtained from a progeny plant, and
iii) analysing the nutritional content of the grain or a part thereof.

Preferably, the genetic variation is an introduced genetic variation.

In an embodiment, step iii) comprises one or more or all of:
i) selecting a progeny plant which is homozygous for the genetic variation, wherein the genetic variation reduces DNA glycosylase activity in the rice plant when compared to a corresponding wild-type rice plant,
ii) selecting a progeny plant whose grain has an increased aleurone thickness compared to a corresponding wild-type grain,
iii) selecting a progeny plant whose grain or a part thereof has an altered nutritional content compared to a corresponding wild-type grain or part thereof.

In a further embodiment, the method further comprises
i) crossing two parental rice plants, preferably wherein one of the parental rice plants produces grain of the invention, or
ii) backcrossing one or more progeny plants from step i) with plants of the same genotype as a first parental rice plant which does not produce grain of the invention for a sufficient number of times to produce a plant with a majority of the genotype of the first parental rice plant but which produces grain of the invention, and
iii) selecting a progeny plant which produces grain of the invention.

Also provided is a rice plant and rice grain, and products therefrom, produced using a method of the invention.

Further provided is the use of an exogenous polynucleotide of the invention, or a nucleic acid construct and/or vector of the invention, to produce a recombinant cell, a transgenic rice plant or transgenic grain.

In an embodiment, the use is to produce rice grain of the invention.

In a further aspect, the present invention provides a method for identifying a rice plant which produces grain of the invention, the method comprising the steps of
i) obtaining a nucleic acid sample from a rice plant, and
ii) screening the sample for the presence or absence of a genetic variation which reduces the activity of a ROS1a gene in the plant when compared to a corresponding wild-type rice plant.

In an embodiment, the genetic variation is one or both of
a) a nucleic acid construct expressing a polynucleotide, or the polynucleotide encoded thereby, which when present in a rice plant reduces the expression of a ROS1a gene, and
b) a gene, or mRNA encoded thereby, which expresses a mutant ROS1a polypeptide with reduced ROS1a polypeptide activity.

In an embodiment, the presence of the genetic variation indicates that grain of the plant has a thickened aleurone when compared to a corresponding plant lacking the genetic variation(s).

In yet another aspect, the present invention provides a method for identifying a rice plant which produces grain of the invention, the method comprising the steps of
i) obtaining grain from a rice plant, and
ii) screening the grain or a portion thereof for one or more of
 a) a thickened aleurone,
 b) the amount of ROS1a polypeptide and/or activity in the grain, and
 c) the amount of mRNA encoded by ROS1a genes in the grain.

In an embodiment, the method identifies a rice plant of the invention.

In another aspect, the present invention provides a method of producing a rice plant part, preferably grain, the method comprising,
a) growing a rice plant, or at least 100 such rice plants in a field, of the invention, and
b) harvesting the rice plant part from the rice plant or rice plants.

In a further aspect, the present invention provides a method of producing rice flour, bran, wholemeal, malt, starch or oil obtained from grain, the method comprising;
a) obtaining grain of the invention, and
b) processing the grain to produce the flour, bran, wholemeal, malt, starch or oil.

In another aspect, the present invention provides a product produced from grain of the invention, or a rice plant of the invention, or from a part of said grain or rice plant.

In an embodiment, the product comprises one or more or all of the ROS1a gene, the genetic variation (preferably introduced genetic variation), the exogenous nucleic acid construct and the thickened aleurone.

In an embodiment, the part is rice bran.

In an embodiment, the product is a food ingredient, beverage ingredient, food product or beverage product. Examples include, but are not limited to,
i) the food ingredient or beverage ingredient is selected from the group consisting of wholemeal, flour, bran, starch, malt and oil,
ii) the food product is selected from the group consisting of: leavened or unleavened breads, pasta, noodles, animal fodder, breakfast cereals, snack foods, cakes, pastries and foods containing a flour-based sauce, or
iii) the beverage product is a packaged beverage or a beverage comprising ethanol.

In a further aspect, the present invention provides a method of preparing a food or beverage ingredient of the invention, the method comprising processing grain of the invention, or bran, flour, wholemeal, malt, starch or oil from the grain, to produce the food or beverage ingredient.

In another aspect, the present invention provides a method of preparing a food or beverage product of the invention, the method comprising mixing grain of the invention, or bran, flour, wholemeal, malt, starch or oil from the grain, with another food or beverage ingredient. Preferably, the weight of the grain, bran, flour, wholemeal, malt, starch or oil that is used in the method is at least 10% on a weight basis relative to the food product.

Also provided is the use of grain of the invention or part thereof, or a rice plant of the invention or part thereof, as animal feed or food, or to produce feed for animal consumption or food for human consumption.

In a further aspect, the present invention provides a composition comprising one or more of a polypeptide of the invention, a polynucleotide of the invention, a nucleic acid construct and/or vector of the invention, or a cell of the invention, and one or more acceptable carriers.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Schematic diagram of the map-based cloning of the ta2 gene. Numbers below each line show the number of recombinants in the mapping population which displayed recombination between the marker and the ta2 gene. The solid bars on the third line show the extent of the coding regions on the rice chromosome. The solid bars on the fourth line show the protein coding regions in the gene; the intervening lines represent the introns (intron 1 is in the 5'UTR and not shown here). The asterisk shows the position of the ta2 mutation in intron 14 at position Chr1: 6451738 with reference to the rice genome sequence.

Figure 2:
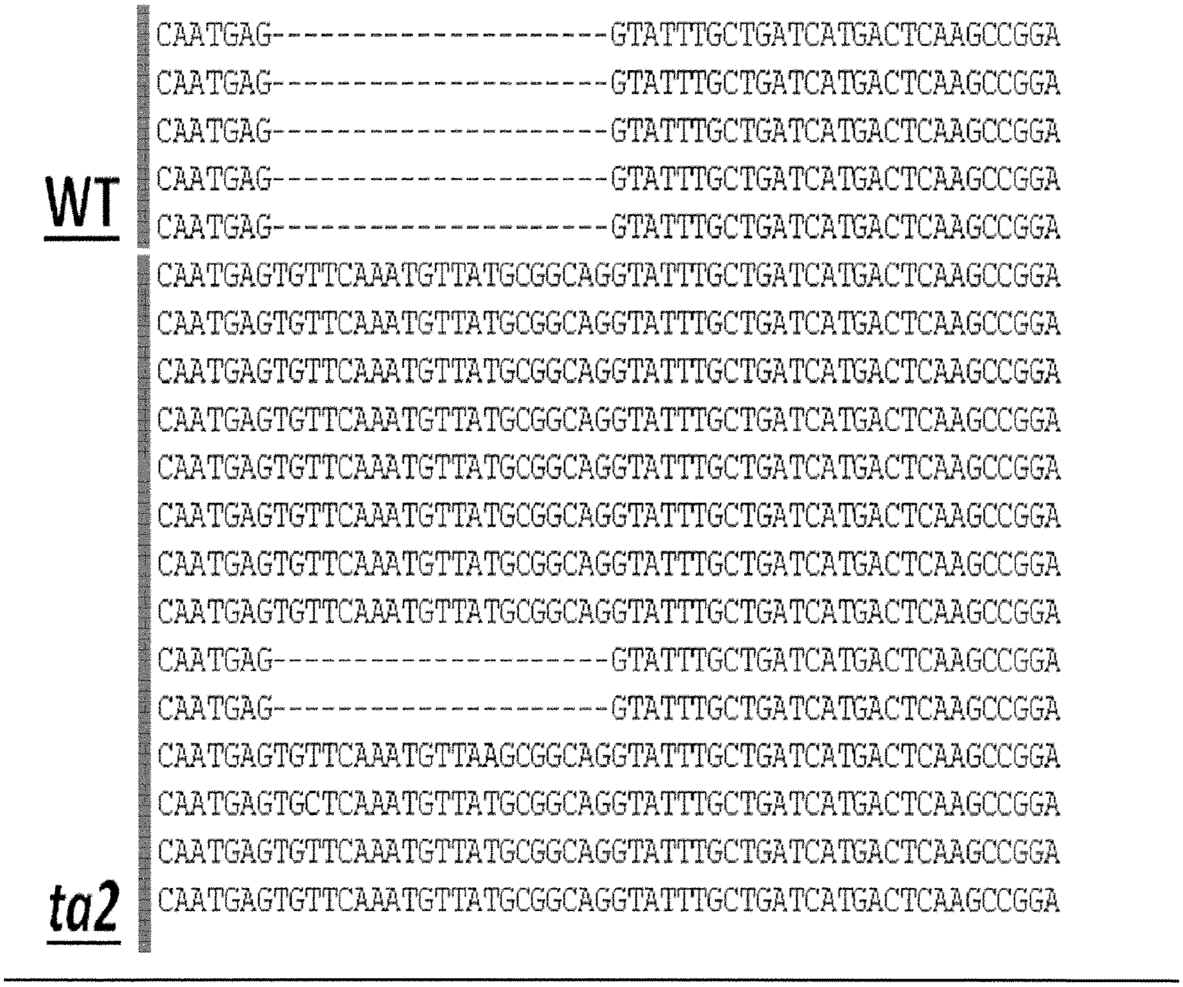

FIG. 2. Nucleotide sequences of cDNAs corresponding to mRNAs obtained from developing grains of wild-type (WT) and ta2 genotypes. Dashes in the WT and two of the ta2 sequences indicate absence of nucleotides. Most of the ta2 mRNAs had 21 nucleotide insertions. The wild-type sequence is SEQ ID NO: 10, the mutant sequence is SEQ ID NO: 11.

FIG. 3. Predicted amino acid sequences from cDNAs corresponding to mRNAs obtained from developing grains of wild-type (upper amino acid sequence, SEQ ID NO: 12) and ta2 (lower sequence, SEQ ID NO: 13). Dashes in the WT sequence indicate absence of amino acids opposite the seven amino acid insertion (CSNVMRQ; SEQ ID NO: 14) in the ta2 polypeptide. Stars below the sequences indicate that the same amino acids were present in the wild-type and mutant polypeptides at those positions.

FIG. 4. Amino acid sequence alignment of *Arabidopsis* DME (NM001085058.1) (SEQ ID NO:6), *Arabidopsis* ROS1a (NM129207.4) (SEQ ID NO:50) and rice ROS1a homologs (SEQ ID NO:2). Asterisks below the alignment represent amino acid positions which are conserved in all three polypeptides. Semi-colons represent fully conservative amino acid changes, whereas single dots represent partially conservative amino acid changes.

FIG. 5. Amino acid sequence alignment *Arabidopsis* ROS1a (NM129207.4) (SEQ ID NO:50) and rice ROS1a homologs (SEQ ID NO:2). Asterisks below the alignment represent amino acid positions which are conserved in all three polypeptides. Semi-colons represent fully conservative amino acid changes, whereas single dots represent partially conservative amino acid changes.

Figure 6:
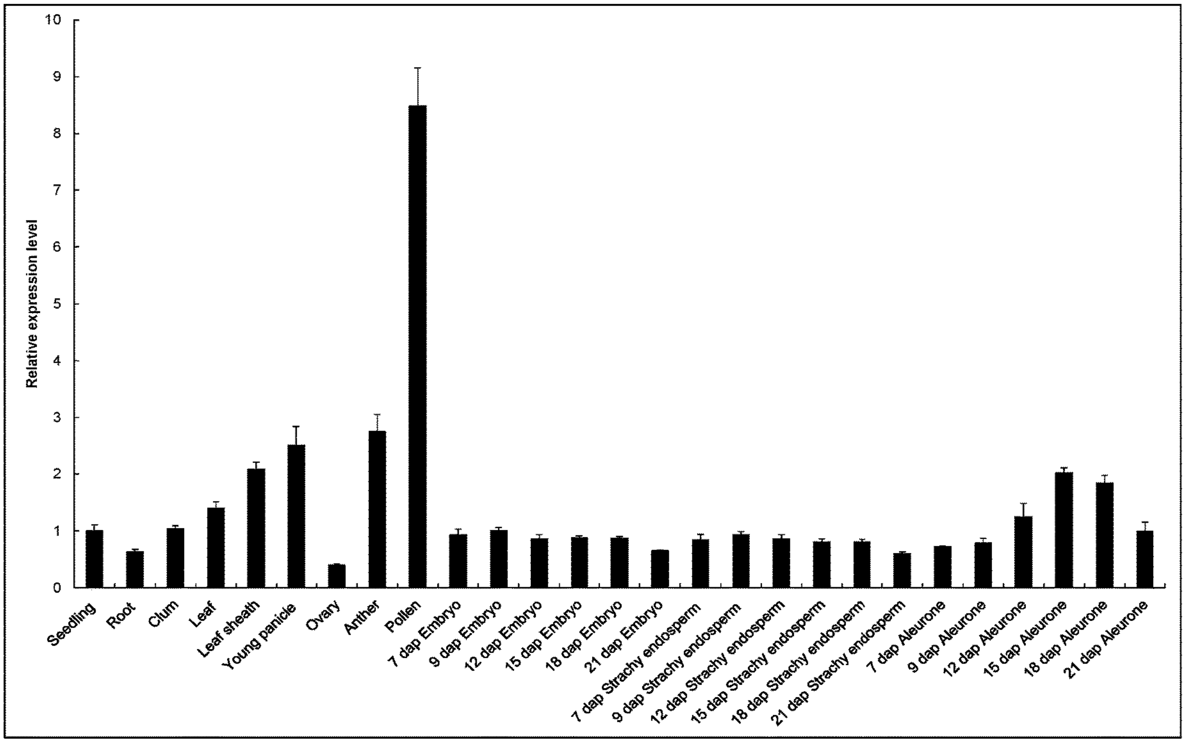

FIG. 6. Real-time RT-PCR results showing relative expression of the rice TA2 gene in multiple tissues.

KEY TO THE SEQUENCE LISTING

SEQ ID NO: 1—Rice ROS1a mutant (Ta2) polypeptide.

SEQ ID NO: 2—Wild-type rice ROS1a polypeptide.

SEQ ID NO: 3—Wild-type rice ROS1b polypeptide.

SEQ ID NO: 4—Wild-type rice ROS1c polypeptide.

SEQ ID NO: 5—Wild-type rice ROS1d polypeptide.

SEQ ID NO: 6—*Arabidopsis* DEMETER polypeptide.

SEQ ID NO: 7—Full length cDNA encoding rice ROS1a mutant (Ta2) polypeptide. Open reading frame spans nucleotides 341 to 6220.

SEQ ID NO: 8—Full length cDNA encoding rice ROS1a polypeptide. Open reading frame spans nucleotides 341 to 6199.

SEQ ID NO: 9—Rice ROS1a gene. Promoter and 5'UTR: nucleotides 1-4726, translation start codon ATG 4727-4729; translation stop codon TAG 15867-15869; 3'-UTR from 15870-16484, downstream of the gene from 16485-16885. Nucleotide positions of introns are: intron 1, 7494-7724; 2, 7816-7909; 3, 9426-9571; 4, 9652-10452; 5, 10538-10628; 6, 10721-10795; 7, 10865-10951; 8, 10989-11069; 9, 11153-11834; 10, 12282-12385; 11, 12423-12508; 12, 12567-12650; 13, 12791-13017; 14, 13084-13201; 15, 13317-14668; 16, 14708-15732.-11006. The sequence includes 401 nucleotides at the 3' end which does not form part of the gene.

SEQ ID NO: 10— Partial wild type rice ROS1a cDNA sequence provided in FIG. 2.

SEQ ID NO: 11— Partial mutant (Ta2) rice ROS1a cDNA sequence provided in FIG. 2.

SEQ ID NO: 12— Partial wild type rice ROS1a protein sequence provided in FIG. 3.

SEQ ID NO: 13— Partial mutant (Ta2) rice ROS1a protein sequence provided in FIG. 3.

SEQ ID NO: 14— Additional amino acids in ROS1a mutant (Ta2) polypeptide when compared to wild type (SEQ ID NO:2).

SEQ ID NOs 15 to 43— Oligonucleotide primers.

SEQ ID NO's 44 to 49—Highly conserved amino acid motifs within the glycosylase domain of the wild-type rice ROS1a polypeptide.

SEQ ID NO: 50—*Arabidopsis* ROS1a polypeptide.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, plant molecular biology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology:

A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−10%, more preferably +/−5%, more preferably +/−2.5%, even more preferably +/−1%, of the designated value. The term "about" includes the exact designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Selected Definitions

The terms "aleurone" and "aleurone layer" are used interchangeably herein. The aleurone layer is the outermost layer of the endosperm of rice grain, distinct from the inner starchy endosperm, and surrounds the starchy endosperm and part of the embryo. The cells that make up the aleurone layer are therefore the outermost cells of the endosperm, the starchy component of the grain. While it is technically part of the endosperm, sometimes referred to as the peripheral endosperm, the aleurone is considered part of the bran from a practical standpoint as it is removed with the pericarp and testa layers of the bran. Unlike cells of the starchy endosperm, aleurone cells remain alive at grain maturity. The aleurone layer is an important part of the nutritional value of rice grain comprising minerals, vitamins such as vitamin A and B group vitamins, phytochemicals, and fiber.

Embodiments of the invention relate to a range of number of "layers of cells", at least in part because at any one cross sectional point of grain of the invention, the layers of cells observed at any single point within the cross section, or between cross sections, may vary to some extent. More specifically, an aleurone with, for example, seven layers of cells may not have the seven layers surrounding the entire inner starchy endosperm but has seven layers surrounding at least half of the inner starchy endosperm.

The term "thickened" when used in relation to aleurone of grain of the invention is a relative term used when comparing grain of the invention to a corresponding wild-type grain. Aleurone of grain of the invention has an increased number of cells and/or increased number of layers of cells when compared to aleurone of corresponding wild-type grain. The aleurone is thereby increased in thickness as measured in μm. In an embodiment, the thickness is increased by at least 50%, preferably by at least 100%, and may be increased by as much as 500% or 600%, each percentage being relative to the thickness of the aleurone of a corresponding wild-type grain, and understanding each percentage to be the average increase over the ventral side of the grain and preferably over the whole grain. In an embodiment, the thickness of the aleurone layer is determined across an entire cross section of the grain. In an embodiment, the thickness of the aleurone is determined by at least analysis on the ventral side of the grain. In another embodiment, thickened aleurone of grain of the invention comprises cells of varying size and irregular orientation compared to that of corresponding wild-type grain where the aleurone generally has regularly oriented rectangular cells.

Polypeptides

As used herein, the term "ROS1 polypeptide" refers to a member of a protein family of DNA glycosylase related molecules which are related in amino acid sequence to SEQ ID NOs: 1 to 5 in that they are at least 95% identity to one or more of the amino acid sequences set forth in SEQ ID NOs: 1 to 5. ROS1 polypeptides include the ROS1a, ROS1b, ROS1c and ROS1d polypeptides of wild-type rice, including naturally occurring variants and mutant forms thereof. ROS1 polypeptides include such polypeptides found in wild-type rice plants as well as variants thereof produced either artificially or found in nature, such as found in either Indica and *Japonica* rice plants, and either have or do not have DNA glycosylase activity, including ROS1 polypeptides which have some DNA glycosylase activity but at a reduced level compared to a corresponding wild-type ROS1 polypeptide. Examples of ROS1 polypeptides of wild-type rice plants include those which have the amino acid sequence set forth in one of SEQ ID NOs: 2 to 5, as well as variant polypeptides which have an amino acid sequence which is at least 95%, at least 97%, or preferably at least 99% identical to one or more of the amino acid sequences set forth in SEQ ID NOs: 2 to 5 and which are found in nature. As used herein, ROS1 polypeptides do not include Demeter (DME) polypeptides which are a related DNA glycosylase family which are much less than 95% identical in amino acid sequence to SEQ ID NOs:1 to 5.

As used herein, the term "ROS1a polypeptide" means a DNA glycosylase related molecule whose amino acid sequence is at least 95% identical to SEQ ID NO: 2, preferably at least 97% or more preferably at least 99% identical to SEQ ID NO:2. ROS1a polypeptides include the polypeptides found in wild-type rice plants as well as variants thereof produced either artificially or found in nature, and either have or do not have DNA glycosylase activity, provided they have the required level of amino acid sequence identity to SEQ ID NO:2. For example, the ROS1a polypeptide whose sequence is provided as SEQ ID NO:1 is thought to have no DNA glycosylase activity, yet it is a ROS1a polypeptide as defined herein. In a preferred embodiment, the ROS1a polypeptide has some DNA glycosylase activity but at a reduced level compared to the wild-type ROS1a polypeptide whose amino acid sequence is provided as SEQ ID NO:2. For example, Table 3 lists ROS1a mutant polypeptides which are thought to have reduced DNA glycosylase activity.

The skilled person can readily use known techniques to distinguish a ROS1a polypeptide from other structurally related proteins such as other ROS1 polypeptides, specifically from ROS1b, ROS1c and ROS1d polypeptides, for example, using in silica phylogenetic analysis or protein alignments. A ROS1a polypeptide can therefore be identified as a ROS1a polypeptide based on structural features alone. For example, see FIGS. 4 and 5 herein. A ROS1a polypeptide of the invention may or may not have DNA glycosylase activity, or may have reduced DNA glycosylase activity when compared to a wild-type ROS1a polypeptide such as one with the amino acid sequence set forth in SEQ ID NO: 2.

As used herein, the term "which sequence is different to the amino acid sequence of the corresponding wild-type ROS1a polypeptide", or similar phrases, are comparative terms where the amino acid sequence of a ROS1a polypeptide of the invention is different to the amino acid sequence of the protein from which it is derived and/or most closely related that exists in nature. In an embodiment, the amino acid sequence of the ROS1a polypeptide has one or more insertions, deletions or amino acid substitutions (or a combination of these) relative to the corresponding wild-type amino acid sequence. The ROS1a polypeptide may have 2, 3, 4, 5 or 6-10 amino acid substitutions relative to the corresponding wild-type ROS1a polypeptide. In a preferred embodiment, the ROS1a polypeptide has only a single insertion, single deletion or single amino acid substitution relative to the corresponding wild-type polypeptide. In this context, the "single insertion" and "single deletion" includes where multiple (e.g., 2, 3, 4, 5, 6, 7, 8, 9, 10 or more), contiguous amino acids are inserted or deleted, respectively and the "corresponding wild-type polypeptide" means the wild-type polypeptide from which the variant is derived and/or the natural polypeptide to which the variant is most closely related. The ROS1a polypeptide may be a truncated ROS1a polypeptide which may be encoded by, for example, a ROS1a gene which comprises a premature translational stop codon in the protein open reading frame relative to the wild-type ROS1a gene from which it is derived, or the ROS1a polypeptide may be full-length i.e. having the same number of amino acid residues as the corresponding wild-type ROS1a polypeptide. An example of a naturally occurring (wild-type) ROS1a polypeptide is one whose amino acid sequence is set forth as SEQ ID NO: 2, and examples of variant ROS1a polypeptides which have only a single insertion, deletion or amino acid substitution are given in SEQ ID NO:1 and Table 3.

As used herein, the term "DNA glycosylase activity" refers to an enzyme involved in base excision repair (classified under EC number EC 3.2.2). The enzyme typically also has DNA lyase activity, in which the DNA base is excised and the backbone DNA strand is cleaved. In an embodiment, "DNA glycosylase activity" as used in the context of the present invention relates to active demethylation where 5-methylcytosine residues are excised and replaced with unmethylated cytosines. In a preferred embodiment, a ROS1a polypeptide of the invention with DNA glycosylase activity has at least five identifiable motifs. One is a helix-hairpin-helix (HhH) motif (for example, amino acids 1491-1515 in SEQ ID NO:2 or a homologous amino acid sequence). Another is a glycine/proline-rich motif followed by a conserved aspartic acid (GPD), and four conserved cysteine residues (in the region of amino acids 1582-1598 of SEQ ID NO:2) to hold a [4Fe-4S] cluster in place. There is also a lysine-rich domain (for example, amino acids 87-139 in SEQ ID NO:2 or a homologous amino acid sequence). Unlike other members of the HhH DNA glycosylase superfamily members, ROS1a polypeptide-family members contain two additional conserved domains (domains A and B) flanking the central glycosylase domain. In the rice ROS1a polypeptide (SEQ ID NO:2), domain A occurs at amino acids 859 to 965, the glycosylase domain occurs at amino acids 1403 to 1616, and domain B occurs at amino acids 1659 to 1933. Domain A contains a repetitive mixed-charge cluster at amino acids 882-892. DNA glycosylase activity can be measured using standard techniques known in the art, such as described in Example 8.

Highly conserved amino acid motifs within the glycosylase domain of the wild-type rice ROS1a polypeptide include DHGSIDLEWLR (SEQ ID NO: 44, amino acids 1467-1477 in SEQ ID NO:2), GLGLKSVECVRLLTLHH (SEQ ID NO: 45, amino acids 1493-1509 in SEQ ID NO:2), AFPVDTNVGRI (SEQ ID NO: 46, amino acids 1511-1521 in SEQ ID NO:2), VRLGWVPLQPLPESLQLHLLE (SEQ ID NO: 47, amino acids 1523-1543 in SEQ ID NO:2), ELHYQMITFGKVFCTKSKPNCN (SEQ ID NO: 48, amino acids 1569-1590 in SEQ ID NO:2) and HFASAFASARLALP (SEQ ID NO: 49, amino acids 1600-1613 in SEQ ID NO:2). One or two amino acid substitutions may occur in these motifs, or not. Other conserved amino acids can be readily identified by aligning the amino acid sequences for wild-type rice ROS1a (SEQ ID NO:2) with the DME polypeptide from *Arabidopsis thaliana* (SEQ ID NO:6) and/or the *A. thaliana* ROS1a polypeptide (see FIGS. 4 and 5). Further guidance regarding the identification of conserved amino acids can be obtained from Kapazoglou et al. (2012).

As used herein, the terms "which reduces DNA glycosylase activity compared to the corresponding wild-type ROS1a polypeptide", "which has reduced, preferably no, DNA glycosylase activity when compared to the corresponding wild-type ROS1a polypeptide", or similar phrases, are relative terms where the DNA glycosylase activity of a variant/mutant ROS1a polypeptide is lower than the protein from which it is derived and/or most closely related that exists in nature. For instance, as the skilled person would appreciate, the rice Tat mutant described herein (SEQ ID NO:1) has reduced DNA glycosylase activity when compared to the corresponding wild-type rice ROS1a polypeptide (SEQ ID NO:2). Other examples of ROS1a polypeptides with reduced DNA glycosylase activity comprise mutations/variations corresponding to the amino acids described in Table 3 which confer a thickened aleurons phenotype such as substituting the serine at an amino acid position corresponding to amino acid number 156 of SEQ ID NO:2 with another amino acid such as a phenylalanine, substituting the serine at an amino acid position corresponding to amino acid number 214 of SEQ ID NO:2 with another amino acid such as a phenylalanine, substituting the serine at an amino acid position corresponding to amino acid number 1413 of SEQ ID NO:2 with another amino acid such as an asparagine, substituting the alanine at an amino acid position corresponding to amino acid number 441 of SEQ ID NO:2 with another amino acid such as a valine, substituting the serine at an amino acid position corresponding to amino acid number 1357 of SEQ ID NO:2 with another amino acid such as a phenylalanine, substituting the lysine at an amino acid position corresponding to amino acid number 501 of SEQ ID NO:2 with another amino acid such as a serine, and substituting the arginine at an amino acid position corresponding to amino acid number 482 of SEQ ID NO:2 with another amino acid such as a lysine. In a particularly preferred embodiment, the grain has at least some DNA glycosylase activity, preferably some ROS1a DNA glycosylase activity, because evidence suggests that the absence of DNA glycosylase activity in the egg cell and early in seed development is lethal to rice plants. In an embodiment, the grain has between about 30% and 98%, or between about 40% and 98%, or between about 40% and 90%, or between about 40% and 85%, or between about 40% and 80%, less DNA glycosylase activity when compared to grain from a corresponding isogenic plant lacking an genetic variation (preferably introduced genetic variation) which reduces DNA glycosylase activity in the grain.

By "substantially purified polypeptide" or "purified polypeptide" we mean a polypeptide that has generally been separated from the lipids, nucleic acids, other peptides, and other contaminating molecules with which it is associated in its native state. Preferably, the substantially purified polypeptide is at least 90% free from other components with which it is naturally associated. In an embodiment, the polypeptide of the invention has an amino acid sequence which is different to a naturally occurring ROS1a polypeptide i.e. is an amino acid sequence variant, as defined above.

Grain, plants and host cells of the invention may comprise an exogenous polynucleotide encoding a polypeptide of the invention. In these instances, the grain, plants and cells produce a recombinant polypeptide. The term "recombinant" in the context of a polypeptide refers to the polypeptide encoded by an exogenous polynucleotide when produced by a cell, which polynucleotide has been introduced into the cell or a progenitor cell by recombinant DNA or RNA techniques such as, for example, transformation. Typically, the cell comprises a non-endogenous gene that causes an altered amount of the polypeptide to be produced. In an embodiment, a "recombinant polypeptide" is a polypeptide made by the expression of an exogenous (recombinant) polynucleotide in a plant cell.

The terms "polypeptide" and "protein" are generally used interchangeably.

The % identity of a polypeptide is determined by GAP (Needleman, and Wunsch, 1970) analysis (GCG program) with a gap creation penalty=5, and a gap extension penalty=0.3. The query sequence is at least 1,000 amino acids in length, and the GAP analysis aligns the two sequences over a region of at least 1,000 amino acids. More preferably, the query sequence is at least 1,250 amino acids in length and the GAP analysis aligns the two sequences over a region of at least 1,250 amino acids. More preferably, the query sequence is at least 1,500 amino acids in length and the GAP analysis aligns the two sequences over a region of at least 1,500 amino acids. Even more preferably, the GAP analysis aligns two sequences over their entire length, which for a ROS1a polypeptide is about 1,800 to 2,100 amino acid residues.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

As used herein, the phrase "at a position corresponding to amino acid number" or variations thereof refers to the relative position of the amino acid compared to surrounding amino acids. In this regard, in some embodiments a polypeptide of the invention may have deletional or substitutional mutation which alters the relative positioning of the amino acid when aligned against, for instance, SEQ ID NO: 2. Determining a corresponding amino acid position between two closely related proteins is well within the capability of the skilled person.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics. Preferred amino acid sequence mutants have only one, two, three, four or less than 10 amino acid changes relative to the reference wildtype polypeptide. Mutant polypeptides of the invention have reduced "ROS1a polypeptide activity" when compared to a corresponding wild-type naturally occurring ROS1a polypeptide such as a polypeptide which comprises amino acids having a sequence set forth as SEQ ID NO: 2.

Mutant (altered) polypeptides can be prepared using any technique known in the art, for example, using directed evolution or rational design strategies (see below). Products derived from mutated/altered DNA can readily be screened using techniques described herein to determine if they have reduced ROS1a polypeptide activity, such as reduced DNA glycosylase activity, when compared to one or more or all of a ROS1a polypeptide which comprises amino acids having a sequence provided as SEQ ID NO: 2. For instance, the method may comprise producing a transgenic plant expressing the mutated/altered DNA and determining i) the effect of the mutated/altered DNA on aleurone thickness and ii) whether a ROS1a gene has been mutated/altered.

In designing amino acid sequence mutants, the location of the mutation site and the nature of the mutation will depend on characteristic(s) to be modified. The sites for mutation can be modified individually or in series, e.g., by (1) substituting with non-conservative amino acid choices, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. Where it is not desirable to maintain a certain activity, or to reduce a certain activity, it is preferable to make non-conservative substitutions, particularly at amino acid positions which are highly conserved in the relevant protein family. Examples of conservative substitutions are shown in Table 1, and hence non-conservative substitutions will be those not shown in Table 1.

In an embodiment a mutant/variant polypeptide has one or two or three or four amino acid changes when compared to a naturally occurring polypeptide. In a preferred embodiment, the changes are in one or more of the motifs which are highly conserved between the different ROS1a polypeptides provided herewith, particularly in known conserved structural domains. As the skilled person would be aware, such changes can reasonably be predicted to alter the activity of the polypeptide when expressed in a cell.

The primary amino acid sequence of a polypeptide of the invention can be used to design variants/mutants thereof based on comparisons with closely related enzymes, particularly DNA glycosylases. As the skilled addressee will appreciate, residues highly conserved amongst closely related proteins are more likely to be able to be altered, especially with non-conservative substitutions, and activity reduced than less conserved residues (see above).

TABLE 1

| Conservative substitutions. | |
|---|---|
| Original Residue | Conservative Substitutions |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Also included within the scope of the invention are polypeptides of the present invention which are differentially modified after synthesis, e.g., by post-translational modification in a cell, for example by phosphorylation, which may modulate its activity.

Polynucleotides and Genes

The present invention refers to various polynucleotides. As used herein, a "polynucleotide" or "nucleic acid" or "nucleic acid molecule" means a polymer of nucleotides, which may be DNA or RNA, and includes genomic DNA, mRNA, cRNA, dsRNA, and cDNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein, or comprise one or more modified nucleotides not found in nature, well known to those skilled in the art. The polymer may be single-stranded, essentially double-stranded or partly double-stranded. Basepairing as used herein refers to standard basepairing between nucleotides, including G:U basepairs. "Complementary" means two polynucleotides are capable of basepairing (hybridizing) along part of their lengths, or along the full length of one or both. A "hybridized polynucleotide" means the polynucleotide is actually basepaired to its complement. The term "polynucleotide" is used interchangeably herein with the term "nucleic acid". Preferred polynucleotides of the invention encode a polypeptide of the invention.

By "isolated polynucleotide" we mean a polynucleotide which has generally been separated from the polynucleotide sequences with which it is associated or linked in its native state, if the polynucleotide is found in nature. Preferably, the isolated polynucleotide is at least 90% free from other components with which it is naturally associated, if it is found in nature. Preferably the polynucleotide is not naturally occurring, for example by covalently joining two shorter polynucleotide sequences in a manner not found in nature (chimeric polynucleotide).

The present invention involves reduction of gene activity and the construction and use of chimeric genes. As used herein, the term "gene" includes any deoxyribonucleotide sequence which includes a protein coding region or which is transcribed in a cell but not translated, as well as associated non-coding and regulatory regions. Such associated regions are typically located adjacent to the coding region or the transcribed region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

An "allele" refers to one specific form of a genetic sequence (such as a gene) within a cell, an individual plant or within a population, the specific form differing from other forms of the same gene in the sequence of at least one, and frequently more than one, variant sites within the sequence of the gene. The sequences at these variant sites that differ between different alleles are termed "variances", or "polymorphisms". A "polymorphism" as used herein denotes a variation in the nucleotide sequence between alleles at a genetic locus of the invention, of different species, cultivars, strains or individuals of a plant. A "polymorphic position" is a preselected nucleotide position within the sequence of the gene at which the sequence difference occurs. In some cases, genetic polymorphisms cause an amino acid sequence variation within a polypeptide encoded by the gene, and thus a polymorphic position can result in the location of a polymorphism in the amino acid sequence at a predetermined position in the sequence of the polypeptide. In other instances, the polymorphic region may be in a non-polypeptide encoding region of the gene, for example in the promoter region and may thereby influence expression levels of the gene. Typical polymorphisms are deletions, insertions or substitutions. These can involve a single nucleotide (single nucleotide polymorphism or SNP) or two or more nucleotides.

As used herein, a "mutation" is a polymorphism which produces a phenotypic change in the plant or a part thereof. As known in the art, some polymorphisms are silent, for example a single nucleotide change in a protein coding region which does not change the amino acid sequence of the encoded polypeptide due to the redundancy of the genetic code. A diploid plant will typically have one or two different alleles of a single gene, but only one if both copies of the gene are identical i.e. the plant is homozygous for the allele. Polyploid plants generally have more than one homoeolog of any particular gene. For instance, hexaploid wheat has three subgenomes (often referred to as "genomes") designated the A, B and D genomes, and therefore has three homoeologs of most of its genes, one in each of the A, B and D genomes.

The term "ROS1a gene encoding a ROS1a polypeptide" or "ROS1a gene" as used herein refers to a nucleotide sequence which encodes a ROS1a polypeptide as defined herein. The ROS1a gene may be an endogenous naturally occurring gene, or comprise a genetic variation (preferably an introduced genetic variation) as defined herein. A ROS1a gene encoding a ROS1a polypeptide in grain of the invention may or may not have introns. In one example, the grain of the invention is from rice and at least one allele of an ROS1a gene encodes a ROS1a polypeptide with reduced DNA glycosylase activity when compared to a ROS1a polypeptide from a corresponding a wild type rice plant (such as which comprises a sequence of amino acids as provided in 1.0 SEQ ID NO: 2). An example of such a ROS1a polypeptide with reduced DNA glycosylase activity is the rice Ta2 mutant (SEQ ID NO:1).

As used herein, the phrase "or inactivation of a ROS1a gene" or "reduction of expression of a ROS1a gene" or variations thereof refers to any genetic variation which reduces (partially), or completely prevents, the expression of the gene encoding a functional ROS1a polypeptide. Such genetic variations include mutations in the promoter region of the gene which reduce transcription of the gene being transcribed, for example by using gene editing to delete or substitute nucleotides from the promoter of the ROS1a gene, or intron splicing mutations which alter the amount or position of splicing to form mRNA.

A genomic form or clone of a gene containing the transcribed region may be interrupted with non-coding sequences termed "introns" or "intervening regions" or "intervening sequences", which may be either homologous or heterologous with respect to the "exons" of the gene. An "intron" as used herein is a segment of a gene which is transcribed as part of a primary RNA transcript but is not present in the mature mRNA molecule. Introns are removed or "spliced out" fro'm the nuclear or primary transcript; introns therefore are absent in the messenger RNA (mRNA). "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or, preferably, for integration into the host genome.

As used herein, a "chimeric gene" refers to any gene that comprises covalently joined sequences that are not found joined in nature. Typically, a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. In an embodiment, the protein coding region of an ROS1a gene is operably linked to a promoter or polyadenylation/terminator region which is heterologous to the ROS1a gene, thereby forming a chimeric gene. In an alternate embodiment, a gene encoding a polynucleotide which, when present in grain of a rice plant, down regulates the production and/or activity of a ROS1a polypeptide in the grain is operably linked to a promoter or polyadenylation/terminator region which is heterologous to the polynucleotide, thereby forming a chimeric gene.

The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule", "recombinant polynucleotide" or variations thereof refer to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations.

Foreign or exogenous genes may be genes that are inserted into a non-native organism, native genes introduced into a new location within the native host, or chimeric genes. A "transgene" is a gene that has been introduced into the genome by a transformation procedure. The term "genetically modified" includes introducing genes into cells by transformation or transduction, mutating genes in cells and altering or modulating the regulation of a gene in a cell or organisms to which these acts have been done or their progeny.

Furthermore, the term "exogenous" in the context of a polynucleotide (nucleic acid) refers to the polynucleotide when present in a cell that does not naturally comprise the polynucleotide. The cell may be a cell which comprises a non-endogenous polynucleotide resulting in an altered amount of production of the encoded polypeptide, for example an exogenous polynucleotide which increases the expression of an endogenous polypeptide, or a cell which in its native state does not produce the polypeptide. Increased production of a polypeptide of the invention is also referred to herein as "over-expression". An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide of the invention operably linked to a promoter suitable of driving transcription of the open reading frame in a cell of interest.

The % identity of a polynucleotide is determined by GAP (Needleman and Wunsch, 1970) analysis (GCG program) with a gap creation penalty=5, and a gap extension penalty=0.3. The query sequence is at least 3,000 nucleotides in length, and the GAP analysis aligns the two sequences over a region of at least 3,000 nucleotides. Even more preferably, the query sequence is at least 3,750 nucleotides in length and the GAP analysis aligns the two sequences over a region of at least 3,750 nucleotides. Even more preferably, the query sequence is at least 4,500 nucleotides in length and the GAP analysis aligns the two sequences over a region of at least 4,500 nucleotides. Even more preferably, the GAP analysis aligns two sequences over their entire length.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

The present invention also relates to the use of oligonucleotides, for instance in methods of screening for a polynucleotide of, or encoding a polypeptide of, the invention. As used herein, "oligonucleotides" are polynucleotides up to 50 nucleotides in length. The minimum size of such oligonucleotides is the size required for the formation of a stable hybrid between an oligonucleotide and a complementary sequence on a nucleic acid molecule of the present invention. They can be RNA, DNA, or combinations or derivatives of either. Oligonucleotides are typically relatively short single stranded molecules of 10 to 30 nucleotides, commonly 15-25 nucleotides in length. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least nucleotides, even more preferably at least 25 nucleotides in length. Oligonucleotides of the present invention used as a probe are typically conjugated with a label such as a radioisotope, an enzyme, biotin, a fluorescent molecule or a chemiluminescent molecule.

The present invention includes oligonucleotides that can be used as, for example, probes to identify nucleic acid molecules, or primers to produce nucleic acid molecules. Probes and/or primers can be used to clone homologues of the polynucleotides of the invention from other species. Furthermore, hybridization techniques known in the art can also be used to screen genomic or cDNA libraries for such homologues.

Polynucleotides and oligonucleotides of the present invention include those which hybridize under stringent conditions to one or more of the sequences provided as SEQ ID NO: 1 or 2. As used herein, stringent conditions are those that (1) employ low ionic strength and high temperature for washing, for example, 0.015 M NaCl/0.0015 M sodium citrate/0.1% $NaDodSO_4$ at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid). A variant of a polynucleotide or an oligonucleotide of the invention includes molecules of varying sizes of, and/or are capable of hybridising to, the rice genome close to that of the reference polynucleotide or oligonucleotide molecules defined herein, preferably the endogenous ROS1a gene. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise to the target region. In addition, variants may readily be designed which hybridise close to, for example to within 50 nucleotides, the region of the plant genome where the specific oligonucleotides defined herein hybridise. In particular, this includes polynucleotides which encode the same polypeptide or amino acid sequence but which vary in nucleotide sequence by redundancy of the genetic code. The terms "polynucleotide variant" and "variant" also include naturally occurring allelic variants.

Genetic Variations

As used herein, the term "genetic variation" refers to one or more cells of the grain, preferably cells in at least one or more or all of aleurone, pericarp, nucellar projection, ovary, testa and starchy endosperm of the developing grain, or of a plant or part thereof of the invention which have a genetic modification which may be introduced by man, or may be naturally occurring in rice plant (for example, crossed to produce a plant of the invention).

As used herein, the term "one or more introduced genetic variations" refers to one or more cells of the grain, preferably cells in at least one or more or all of aleurone, pericarp, nucellar projection, ovary, testa and starchy endosperm of the developing grain, or of a plant or part thereof of the invention which have a genetic modification introduced by man. In a preferred embodiment, every cell in the grain or the plant or part thereof comprises the introduced genetic variation. As the skilled person would understand, there are many different types of genetic modifications which can be made such as, but not limited to, a nucleic construct encoding an exogenous polynucleotide which reduces the expression of a ROS1a gene (such as a dsRNA molecule or microRNA), a nucleic construct encoding an exogenous polynucleotide which encodes a ROS1a polypeptide whose amino acid sequence is different to the amino acid sequence of a corresponding wild-type ROS1a polypeptide and which has reduced (preferably some but can be no) DNA glycosylase activity when compared to the corresponding wild-type ROS1a polypeptide, the genome manipulated by gene editing to reduce the activity of an endogenous ROS1a gene, and using TILLING to introduce mutations and select for plants producing grain with reduced ROS1a polypeptide DNA glycolyase activity.

As used herein, the term "reduce the activity of at least one ROS1a gene" as it relates to the "one or more genetic variations" or "one or more introduced genetic variations" refers to the genetic variation resulting in a reduction in the amount or activity of a ROS1a polypeptide expressed by the gene when compared to a corresponding wild-type rice plant. In an embodiment, the grain comprises a ROS1a polypeptide with at least some DNA glycolyase activity.

In an embodiment, the genetic variation does not down-regulate the DNA glycolyase activity of a non-ROS1a polypeptide. For example, the genetic variation does not reduce the DNA glycosylase activity of each of the ROS1b, ROS1c and ROS1d polypeptides by more than 10% or 30% in the rice plant of the invention. Alternatively, the genetic variation reduces the DNA glycosylase activity of at least one of the ROS1b, ROS1c and ROS1d polypeptides by at least 30%.

RNA Interference

RNA interference (RNAi) is particularly useful for specifically reducing the expression of a gene, which results in reduced production of a particular protein if the gene encodes a protein. Although not wishing to be limited by theory, Waterhouse et al. (1998) have provided a model for the mechanism by which dsRNA (duplex RNA) can be used to reduce protein production. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules is well within the capacity of a person skilled in the art, particularly considering Waterhouse et al. (1998), Smith et al. (2000), WO 99/32619, WO 99/53050, WO 99/49029 and WO 01/34815.

In one example, a DNA is introduced that directs the synthesis of an at least partly double stranded RNA product (s) with homology to a ROS1a gene. The DNA therefore comprises both sense and antisense sequences that, when transcribed into RNA, can hybridize to form the double stranded RNA region. In one embodiment of the invention, the sense and antisense sequences are separated by a spacer region that comprises an intron which, when transcribed into RNA, is spliced out. This arrangement has been shown to result in a higher efficiency of gene silencing (Smith et al., 2000). The double stranded region may comprise one or two RNA molecules, transcribed from either one DNA region or two. The presence of the double stranded molecule is thought to trigger a response from an endogenous system that destroys both the double stranded RNA and also the homologous RNA transcript from the target gene, efficiently reducing or eliminating the activity of the target gene.

The length of the sense and antisense sequences that hybridize should each be at least 19 contiguous nucleotides, preferably at least 30 or at least 50 contiguous nucleotides, more preferably at least 100 or at least 200 contiguous nucleotides. Generally, a sequence of 100-1000 nucleotides corresponding to a region of the target gene mRNA is used. The full-length sequence corresponding to the entire gene transcript may be used. The degree of identity of the sense sequence to the targeted transcript (and therefore also the identity of the antisense sequence to the complement of the target transcript) should be at least 85%, at least 90%, or 95-100%, preferably is identical to the targeted sequence. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ("siRNA") molecules comprise a nucleotide sequence that is identical to about 19-25 contiguous nucleotides of the target mRNA. Preferably, the siRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the organism in which it is to be introduced, for example, as determined by standard BLAST search.

DsRNA's useful for the invention could readily be produced using routine procedures.

MicroRNA

MicroRNAs (abbreviated miRNAs) are non-coding RNA molecules having a length generally 19-25 nucleotides (commonly about 20-24 nucleotides in plants) that are derived from larger precursors that form imperfect stem-loop structures. The miRNA is typically fully complementary to a region of a target mRNA whose expression is to be reduced, but need not be fully complementary.

miRNAs bind to complementary sequences on target messenger RNA transcripts (mRNAs), usually resulting in translational repression or target degradation and gene silencing. Artificial miRNAs (amiRNAs) can be designed based on natural miRNAs for reducing the expression of any gene of interest, as well known in the art.

In plant cells, miRNA precursor molecules are believed to be largely processed in the nucleus. The pri-miRNA (containing one or more local double-stranded or "hairpin" regions as well as the usual 5' "cap" and polyadenylated tail of an mRNA) is processed to a shorter miRNA precursor molecule that also includes a stem-loop or fold-back structure and is termed the "pre-miRNA". In plants, the pre-miRNAs are cleaved by distinct DICER-like (DCL) enzymes, yielding miRNA:miRNA* duplexes. Prior to transport out of the nucleus, these duplexes are methylated.

In the cytoplasm, the miRNA strand from the miRNA:miRNA duplex is selectively incorporated into an active RNA-induced silencing complex (RISC) for target recognition. The RISC-complexes contain a particular subset of Argonaute proteins that exert sequence-specific gene repression (see, for example, Millar and Waterhouse, 2005; Pasquinelli et al., 2005; Almeida and Allshire, 2005).

MicroRNA's useful for the invention could readily be produced using routine procedures. For example, the design of a ROS1a amiRNA (artificial microRNA) construct may be based on the general method described by Fahim et al. (2012). WMD3 software (www.wmd3.weigelworld.org/) can be used to identify suitable amiRNA targets in a ROS1a gene. The amiRNA targets are selected according to four criteria: 1) relative 5' instability by using sequences which are AT rich at the 5'-end and GC rich at the 3'-end; 2) U at position 1 and A at the cleavage site (between positions 10 and 11); 3) maximum of 1 and 4 mismatches at positions 1 to 9, and 13 to 21, respectively; and 4) having a predicted free energy ($\Delta G$) of less than $-30$ kcal $mol^{-1}$ when the amiRNA would hybridise to the target RNA (Ossowski et. al., 2008). For gene-specific reduction of expression, candidate amiRNA sequences are chosen in a region which shows the lowest homology upon the alignment of all the homologs of OsROS1$\alpha$, thus reducing the potential for off-target reduction of the expression of ROS1 homologs and homoeologs. The precursor of rice miR395 (Guddeti et al., 2005; Jones-Rhoades and Bartel, 2004; Kawashima et al., 2009) may be chosen as the amiRNA backbone for insertion of the amiRNA sequences. To design and make the construct, five endogenous miRNA targets in the miR395 were replaced by five amiRNA targets for TA2 knock down.

Cosuppression

Genes can suppress the expression of related endogenous genes and/or transgenes already present in the genome, a phenomenon termed homology-dependent gene silencing. Most of the instances of homology dependent gene silencing fall into two classes—those that function at the level of transcription of the transgene, and those that operate post-transcriptionally.

Post-transcriptional homology-dependent gene silencing (i.e., cosuppression) describes the loss of expression of a transgene and related endogenous or viral genes in transgenic plants. Cosuppression often, but not always, occurs when transgene transcripts are abundant, and it is generally thought to be triggered at the level of mRNA processing, localization, and/or degradation. Several models exist to explain how cosuppression works (see in Taylor, 1997).

Cosuppression involves introducing an extra copy of a gene or a fragment thereof into a plant in the sense orientation with respect to a promoter for its expression. The size of the sense fragment, its correspondence to target gene regions, and its degree of sequence identity to the target gene can be determined by those skilled in the art. In some instances, the additional, copy of the gene sequence interferes with the expression of the target plant gene. Reference is made to WO 97/20936 and EP 0465572 for methods of implementing co-suppression approaches.

Antisense Polynucleotides

The term "antisense polynucleotide" shall be taken to mean a DNA or RNA molecule that is complementary to at least a portion of a specific mRNA molecule encoding an endogenous polypeptide and capable of interfering with a post-transcriptional event such as mRNA translation. The use of antisense methods is well known in the art (see for example, G. Hartmann and S. Endres, Manual of Antisense Methodology, Kluwer (1999)). The use of antisense techniques in plants has been reviewed by Bourque (1995) and Senior (1998). Bourque (1995) lists a large number of examples of how antisense sequences have been utilized in plant systems as a method of gene inactivation. Bourque also states that attaining 100% inhibition of any enzyme activity may not be necessary as partial inhibition will more than likely result in measurable change in the system. Senior (1998) states that antisense methods are now a very well established technique for manipulating gene expression.

In one embodiment, the antisense polynucleotide hybridises under physiological conditions, that is, the antisense polynucleotide (which is fully or partially single stranded) is at least capable of forming a double stranded polynucleotide with mRNA encoding an endogenous ROS1a polypeptide under normal conditions in a cell.

Antisense molecules may include sequences that correspond to the structural genes or for sequences that effect control over the gene expression or splicing event. For example, the antisense sequence may correspond to the targeted coding region of endogenous gene, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 30 or at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%, typically 100% identical. The antisense RNA molecule may of course comprise unrelated sequences which may function to stabilize the molecule.

Genome Editing Using Site-Specific Nucleases

Genome editing uses engineered nucleases composed of sequence specific DNA binding domains fused to a non-specific DNA cleavage module. These chimeric nucleases enable efficient and precise genetic modifications by inducing targeted DNA double stranded breaks that stimulate the cell's endogenous cellular DNA repair mechanisms to repair the induced break. Such mechanisms include, for example, error prone non-homologous end joining (NHEJ) and homology directed repair (HDR).

In the presence of donor plasmid with extended homology arms, HDR can lead to the introduction of single or multiple transgenes to correct or replace existing genes. In the absence of donor plasmid, NHEJ-mediated repair yields small insertion or deletion mutations of the target that cause gene disruption.

Engineered nucleases useful in the methods of the present invention include zinc finger nucleases (ZFNs), transcription activator-like (TAL) effector nucleases (TALEN) and CRISPR-Cas9 type site-specific nucleases.

Typically nuclease encoded genes are delivered into cells by plasmid DNA, viral vectors or in vitro transcribed mRNA. The use of fluorescent surrogate reporter vectors also allows for enrichment of ZFN-, TALEN- or CRISPR-modified cells.

Complex genomes often contain multiple copies of sequences that are identical or highly homologous to the intended DNA target, potentially leading to off-target activity and cellular toxicity. To address this, structure (Miller et al., 2007; Szczepek et al., 2007) and selection based (Doyon et al., 2011; Guo et al., 2010) approaches can be used to generate improved ZFN and TALEN heterodimers with optimized cleavage specificity and reduced toxicity.

In order to target genetic recombination or mutation by ZFN according to a preferred embodiment of the present invention, two 9 bp zinc finger DNA recognition sequences must be identified in the host DNA. These recognition sites will be in an inverted orientation with respect to one another and separated by about 6 bp of DNA. ZFNs are then generated by designing and producing zinc finger combinations that bind DNA specifically at the target locus, and then linking the zinc fingers to a DNA cleavage domain.

A transcription activator-like (TAL) effector nuclease (TALEN) comprises a TAL effector DNA binding domain and an endonuclease domain.

TAL effectors are proteins of plant pathogenic bacteria that are injected by the pathogen into the plant cell, where they travel to the nucleus and function as transcription factors to turn on specific plant genes. The primary amino acid sequence of a TAL effector dictates the nucleotide sequence to which it binds. Thus, target sites can be predicted for TAL effectors, and TAL effectors can be engineered and generated for the purpose of binding to particular nucleotide sequences.

Fused to the TAL effector-encoding nucleic acid sequences are sequences encoding a nuclease or a portion of a nuclease, typically a nonspecific cleavage domain from a type II restriction endonuclease such as Fold (Kim et al., 1996). Other useful endonucleases may include, for example, HhaI, HindIII, Nod, BbvCI, EcoRI, BglI, and AlwI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

A sequence-specific TALEN can recognize a particular sequence within a preselected target nucleotide sequence present in a cell. Thus, in some embodiments, a target nucleotide sequence can be scanned for nuclease recognition sites, and a particular nuclease can be selected based on the target sequence. In other cases, a TALEN can be engineered to target a particular cellular sequence.

Nucleic Acid Constructs

The present invention includes nucleic acid constructs comprising the polynucleotides of or useful for the invention, and vectors and host cells containing these, methods of their production and use, and uses thereof.

The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In preferred embodiments of the present invention, the cis-acting sequence is an activator sequence that enhances or stimulates the expression of an expressible genetic sequence.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the genes from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, such as a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of an organism such as a plant. The term constitutive as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of, for example, the plant, such as, for example, endosperm, embryo, leaves, fruit, tubers or root. In a preferred embodiment, a promoter is expressed selectively or preferentially in grain of a plant, preferably a rice plant. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the plastid, cytosol, vacuole, or apoplastic space may be achieved by the inclusion in the structure of the gene product of appropriate signals, eg. a signal peptide, for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in, for example, a plant. Typically, the promoter is expressed at a level 10-fold higher in the specific tissue or organ than in other tissues or organs.

Seed specific promoters for the invention which are suitable are the oilseed rape napin gene promoter (U.S. Pat. No. 5,608,152), the *Vicia faba* USP promoter (Baumlein et al., 1991), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumin B4 promoter (Baumlein et al., 1992), and promoters which lead to the seed-specific expression in rice and the like. Notable promoters which are suitable are the barley LPT2 or LPT1 gene promoters (WO 95/15389 and WO 95/23230) or the promoters described in WO 99/16890 (promoters from the barley hordein gene). Other promoters include those described by Broun et al. (1998), Potenza et al. (2004), US 20070192902 and US 20030159173. In an embodiment, the seed specific promoter is preferentially expressed in defined parts of the seed such as the endosperm, preferably the developing aleurone. In a further embodiment, the seed specific promoter is not expressed, or is only expressed at a low level, after the seed germinates.

In an embodiment, the promoter is at least active at a time point between the time of anthesis and 7 days post-anthesis, or active entirely during this period. An example of such a promoter is a ROS1a gene promoter.

In an embodiment, the promoter operably linked to an exogenous polynucleotide which reduces the expression of a ROS1a gene is not a high MW glutenin promoter.

The promoters contemplated by the present invention may be native to the host plant to be transformed or may be derived from an alternative source, where the region is functional in the host plant. Other sources include the *Agrobacterium* T-DNA genes, such as the promoters of genes for the biosynthesis of nopaline, octapine, mannopine, or other opine promoters, tissue specific promoters (see, e.g., U.S. Pat. No. 5,459,252 and WO 91/13992); promoters from viruses (including host specific viruses), or partially or wholly synthetic promoters. Numerous promoters that are functional in mono- and dicotyledonous plants are well known in the art (see, for example, Greve, 1983; Salomon et al., 1984; Garfinkel et al., 1983; Barker et al., 1983); including various promoters isolated from plants and viruses such as the cauliflower mosaic virus promoter (CaMV 35S, 19S). Non-limiting methods for assessing promoter activity are disclosed by Medberry et al. (1992 and 1993), Sambrook et al. (1989, supra) and U.S. Pat. No. 5,164,316.

Alternatively or additionally, the promoter may be an inducible promoter or a developmentally regulated promoter which is capable of driving expression of the introduced polynucleotide at an appropriate developmental stage of the, for example, plant. Other cis-acting sequences which may be employed include transcriptional and/or translational enhancers. Enhancer regions are well known to persons skilled in the art, and can include an ATG translational initiation codon and adjacent sequences. When included, the initiation codon should be in phase with the reading frame of the coding sequence relating to the foreign or exogenous polynucleotide to ensure translation of the entire sequence if it is to be translated. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

The nucleic acid construct of the present invention may comprise a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal functions for addition of polyadenylic acid tracts to the 3' end of a mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from an octopine synthase (ocs) gene or nopaline synthase (nos) gene of *Agrobacterium tumefaciens* (Bevan et al., 1983). Suitable 3' non-translated sequences may also be derived from plant genes such as the ribulose-1,5-bisphosphate carboxylase (ssRUBISCO) gene, although other 3' elements known to those of skill in the art can also be employed.

As the DNA sequence inserted between the transcription initiation site and the start of the coding sequence, i.e., the untranslated 5' leader sequence (5'UTR), can influence gene expression if it is translated as well as transcribed, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi (1987).

Vectors

The present invention includes use of vectors for manipulation or transfer of genetic constructs. By "chimeric vector" is meant a nucleic acid molecule, preferably a DNA molecule derived, for example, from a plasmid, bacteriophage, or plant virus, into which a nucleic acid sequence may be inserted or cloned. A vector preferably is double-stranded DNA and contains one or more unique restriction sites and may be capable of autonomous replication in a defined host cell including a target cell or tissue or a progenitor cell or tissue thereof, or capable of integration into the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, pBS-derived vectors, or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP 275957, a gene encoding a 5-enolpyruvylshikimate-3-phosphate synthase (EPSPS) conferring tolerance to N-phosphonomethylglycine as, for example, described by Hinchee et al. (1988), a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., 1985), which may be employed in calcium-sensitive bioluminescence detection; a green fluorescent protein gene (Niedz et al., 1995) or derivatives thereof; a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Preferably, the nucleic acid construct is stably incorporated into the genome of, for example, the plant or cell of the invention. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which includes at least one polynucleotide molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

The level of a ROS1s polypeptide may be modulated by decreasing the level of expression of a gene encoding the protein in the rice plant, leading to increased aleurone thickness. The level of expression of a gene may be modulated by altering the copy number per cell, for example by introducing a synthetic genetic construct comprising the coding sequence and a transcriptional control element that is operably connected thereto and that is functional in the cell. A plurality of transformants may be selected and screened for those with a favourable level and/or specificity of transgene expression arising from influences of endogenous sequences in the vicinity of the transgene integration site. A favourable level and pattern of transgene expression is one which results in increased aleurone thickness. Alternatively, a population of mutagenized seed or a population of plants from a breeding program may be screened for individual lines with increased aleurone thickness.

Recombinant Cells

Another embodiment of the present invention includes a recombinant cell comprising a host cell transformed with one or more recombinant molecules of the present invention, or progeny cells thereof. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred host cells are plant cells, more preferably a rice cell.

Plants with Genetic Variations

The term "plant" as used herein as a noun refers to whole plants and refers to any member of the Kingdom Plantae, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, cotyledons, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are cotyledon, embryo and embryo axis. The invention accordingly includes plants and plant parts and products comprising these.

The terms "grain" and "seed" are used interchangeably herein. "Grain" can refer to mature grain in the plant, developing grain in the plant, harvested grain or to grain after processing such as, for example, milling or polishing, where most of the grain stays intact, or after imbibition or germination, according to the context. Mature grain commonly has a moisture content of less than about 18-20%. In an embodiment, developing grain of the invention is at least about 10 days after pollination (DAP). In an embodiment, developing grain of the invention is at least includes grain between anthesis and 7 days post-anthesis.

A "transgenic plant" as used herein refers to a plant with one or more genetic variations as defined herein such contains a nucleic acid construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants".

A "non-transgenic plant" is one which has not been genetically modified by the introduction of genetic material by recombinant DNA techniques.

"Wild-type", as used herein, refers to a cell, tissue, grain or plant that has not been modified according to the invention. Wild-type cells, tissue or plants may be used as controls to compare levels of expression of an exogenous nucleic acid or the extent and nature of trait modification with cells, tissue, grain or plants modified as described herein.

As used herein, the term "corresponding wild-type" rice plant or grain, or similar phrases, refers to a rice plant or grain which comprises at least 50%, more preferably at least 75%, more preferably at least 95%, more preferably at least 97%, more preferably at least 99%, and even more preferably 99.5% of the genotype of a rice plant or grain of the invention, but does not comprise the one or more genetic variations (such as introduced genetic variations) which each reduce the activity of a ROS1a gene in the plant or grain, and/or a thickened aleurone. In an embodiment, a rice grain or plant of the invention is isogenic relative a wild-type rice grain or plant apart from the one or more genetic variations (such as introduced genetic variations). Preferably, the corresponding wild-type plant or grain is of/from the same cultivar or variety as the progenitor of the plant/grain of the invention, or a sibling plant line which lacks the one or more genetic modifications and/or does not have a thickened aleurone, often termed a "segregant". In an embodiment, the rice plant or grain of the invention has a genotype that is less than 50% identical to the genotype of rice cultivar Zhonghua 11 (ZH11). ZH11 has been commercially available since 1986.

Transgenic plants, as defined in the context of the present invention include progeny of the rice plants which have been genetically modified using recombinant techniques, wherein the progeny comprise the transgene of interest. Such progeny may be obtained by self-fertilization of the primary transgenic plant or by crossing such plants with another rice plant. This would generally be to modulate the production of at least one protein defined herein in the desired plant or plant organ. Transgenic plant parts include all parts and cells of said plants comprising the transgene such as, for example, cultured tissues, callus and protoplasts.

As used herein, the term "rice" refers to any species of the Genus *Oryza*, including progenitors thereof, as well as progeny thereof produced by crosses with other species. It is preferred that the plant is of a *Oryza* species which is commercially cultivated such as, for example, a strain or cultivar or variety of *Oryza sativa* or suitable for commercial production of grain.

As used herein, "brown rice" means the whole grain of rice including the bran layer and embryo (germ) but not the hull which has been removed, usually during harvesting. That is, brown rice has not been polished to remove the aleurone and embryo. The "brown" refers to the presence of brown or yellow-brown pigments in the bran layer. Brown rice is considered a wholegrain. As used herein "white rice" (milled rice) means rice grain from which the bran and germ have been removed i.e. essentially the starchy endosperm of the whole rice grain. Both of these classes of rice grain may come in short, medium or long grain forms. Compared with white rice, brown rice has a higher content of protein, minerals and vitamins and a higher lysine content in its protein content.

As used herein, "pigmented rice" includes black rice and red rice, each of which contain pigments in the aleurone layer, such as proanthocyanidins (tannins). Pigmented rice has a higher riboflavin content than non-pigmented rice, but similar thimine content. "Black rice" has a black or almost black coloured bran layer due to anthocyanins, and may turn a deep purple colour upon cooking. "Purple rice" (also known as "forbidden rice") is a short grain variant of black rice and is included in black rice as defined here. It is purple in colour in the uncooked state and deep purple when cooked. "Red rice" contains a variety of anthocyanins that gives the bran a red/maroon colour, including cyanidin-3-glucoside (chrysanthemin) and peonidin-3-glucoside (oxy-coccicy-anin).

Each of these types of rice grain may be treated so as prevent germination, for example by cooking (boiling) or by dry heating. Brown and pigmented rice is typically cooked for 20-40 min, depending on the desired texture, whereas white rice is typically cooked for 12-18 min. Cooking or heating reduces the levels of antinutritional factors in rice grain such as trypsin inhibitor, oryzacystatin and haemagglutinins (lectins) by denaturation of these proteins, but not of the phytate content. Rice grain may also be soaked in water before cooking, or slow-cooked for longer times, as known in the art. Rice grain may also be cracked, parboiled, or heat-stabilised. Rice bran may be steam treated to stabilise it, for example for about 6 min at 100° C.

In an embodiment, grain of the invention has delayed grain maturation when compared to corresponding wild-type grain. Delayed maturation can be determined by using the seed setting rate (%) which entails calculating the percentage of florets in the plant that were filled by a seed by the mature grain stage.

In an embodiment, grain of the invention has a decreased germination capacity when compared corresponding wild-type grain. For example, the grain has about 70% to about 80%, or about 75%, preferably 70% to 100%, of the germination capacity of corresponding wild-type grain when cultured at 28° C. under 12 h light/12 h dark cycles without humidity control in a growth chamber. The term "germination" as used herein is defined as when the radicle had visibly emerged through the seed coat.

In an embodiment, plants of the invention have one or more or all of normal plant height, fertility (male and female), grain size and 1000 grain weight relative to the wild-type parental variety (such as an isogenic plant comprising a ROS1a polypeptide with a sequence of amino acids provided as SEQ ID NO: 2). In an embodiment, grain of the invention is capable of producing a rice plant which has one or more or all of: normal plant height, fertility (male and female), grain size and 1000 grain weight relative to the wild-type parental variety. As used herein, the term "normal" can be determined by measuring the same trait in the wild-type parental variety grown under the same conditions as a plant of the invention. In an embodiment, to be normal a plant of the invention has +/−10%, more preferably +/−5%, more preferably +/−2.5%, even more preferably +/−1%, of the level/number etc of the defined feature when compared to the wild-type parental variety.

Transgenic plants, as defined in the context of the present invention include plants (as well as parts and cells of said plants) and their progeny which have been genetically modified using recombinant techniques to cause production of at least one polypeptide of the present invention in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

In a preferred embodiment, the transgenic plants are homozygous for each and every gene or nucleic acid construct that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

In an embodiment, a method of selecting a rice plant of the invention further comprises analysing a DNA sample from the plant for at least one "other genetic marker". As used herein, the "other genetic marker" may be any molecules which are linked to a desired trait of a plant. Such markers are well known to those skilled in the art and include molecular markers linked to genes determining traits such disease resistance, yield, plant morphology, grain quality, dormancy traits, grain colour, gibberellic acid content in the seed, plant height, flour colour and the like. Examples of such genes are the Rht genes that determine a semi-dwarf growth habit and therefore lodging resistance.

Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. Nos. 4,945,050 and 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. A particle delivery system suitable for use with the present invention is the helium acceleration PDS-1000/He gun is available from Bio-Rad Laboratories. For the bombardment, immature embryos or derived target cells such as scutella or calli from immature embryos may be arranged on solid culture medium.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. Nos. 5,177,010, 5,104,310, 5,004,863, 5,159,135). Further, the integration of the T-DNA is a relatively precise process resulting in few rearrangements. The region of DNA to be transferred is defined by the border sequences, and intervening DNA is usually inserted into the plant genome.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., Methods for Plant Molecular Biology, Academic Press, San Diego, (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Marker Assisted Selection

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity. This process, termed "embryo rescue", used in combination with DNA extraction at the three leaf stage and analysis of at least one genetic variation that alters ROS1a activity and that confers upon the plant increased aleurone thickness, allows rapid selection of plants carrying the desired trait, which may be nurtured to maturity in the greenhouse or field for subsequent further backcrossing to the recurrent parent.

Any molecular biological technique known in the art can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000; Langridge et al., 2001). The invention also includes the use of molecular marker techniques to detect polymorphisms linked to alleles of the (for example) ROS1a gene which alters ROS1a activity and that confers upon the plant increased aleurone thickness. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al. (2001).

In an embodiment, a linked loci for marker assisted selection is at least within 1 cM, or 0.5 cM, or 0.1 cM, or 0.01 cM from a gene encoding a polypeptide of the invention.

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (M. J. McPherson and S. G Moller (editors), BIOS Scientific Publishers Ltd, Oxford, (2000)). PCR can be performed on cDNA obtained from reverse transcribing mRNA isolated from plant cells expressing a ROS1a gene or allele which upon the plant increased aleurone thickness. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al., (supra) and Sambrook et al., (supra). Sequencing can be carried out by any suitable method, for example, dideoxy sequencing, chemical sequencing or variations thereof. Direct sequencing has the advantage of determining variation in any base pair of a particular sequence.

Tilling

Plants of the invention can be produced using the process known as TILLING (Targeting Induced Local Lesions IN Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to early the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique.

TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Grain Processing

Due to the thickened aleurone, rice grain of the invention, and flour and bran therefrom, has an improved nutritional content. Isolated aleurone tissue should contain low levels of starch and pericarp, and represents a major portion of the grain's physiologically beneficial substances for human nutrition. For instance, grain of the invention and/or flour produced therefrom comprises, when compared to a corresponding wild-type grain and/or flour produced therefrom, one or more or all of the following, each on a weight basis, i) a higher mineral content such as about at least 20% or at least about 25% higher, preferably the mineral content is the content one or more or all of zinc (such as at least about 10% or at least about 15% higher), iron (such as at least about 10% or at least about 15% higher), potassium (such as at least about 20% or at least about 25% higher), magnesium (such as at least about 18% or at least about 22% higher), phosphorus (such as at least about 17% or at least about 21% higher) and sulphur (such as at least about 5% or at least about 8% higher), ii) a higher antioxidant content such as at least about 25%, or at least about 35%, more total phenolic compounds, and/or at least about 60%, or at least about 70%, more hydrophilic antioxidants, iii) a higher phytate content such as at least about 10% or at least about 15% higher, iv) a higher content of one or more or all of vitamins B3, B6 and B9, v) a higher dietary fibre content and/or insoluble fibre content (such as at least about 150%, or at least about 180%, higher total fibre), vi) a starch content which is between about 90% and about 100% by weight relative to the starch content of the corresponding wild-type grain, vii) a higher sucrose content, viii) a higher monosaccharide content (for example arabinose, xylose, galactose, glucose content) such as at least about 1.5 or at least about 2 fold higher, ix) higher fat content such as at least about 20%, at least about 30% or at least about 50%, or about 50%, higher, and x) similar nitrogen levels.

Each of these nutritional components of grain can be determined using routine techniques such as outlined in Examples 1 and 5.

In one embodiment, rice grain of the invention and/or flour produced therefrom, comprises one or more or all of the following, each on a weight basis, i) at least about 20%, at least about 30% or at least about 50%, or about 50% more fat when compared to corresponding wild-type grain/flour,
ii) at least about 11 mg/g or at least about 12 mg/g total phytate,
iii) at least about 20% or at least about 25% more mineral content in flour obtained from the grain when compared to flour from a corresponding wild-type grain,
iv) at least about 14 mg/kg or at least about 15 mg/kg total zinc,
v) at least about 13 mg/kg or at least about 13.5 mg/kg total iron,
vi) at least about 150%, or at least about 180% more total fibre when compared to corresponding wild-type grain/flour,
vii) a starch content which is between about 90% and about 100% by weight relative to the starch content of the corresponding wild-type grain/flour,
viii) at least about 1.5 or at least about 2 fold higher monosaccharide content (for example arabinose, xylose, galactose, glucose content) when compared to corresponding wild-type grain/flour, and
ix) at least about 25%, or at least about 35%, more total phenolic compounds, and/or at least about 60%, or at least about 70%, more hydrophilic antioxidants, when compared to corresponding wild-type grain/flour.

In an embodiment, the grain comprises an increased proportion of amylose in its total starch content compared to the corresponding wild-type grain. Methods of producing such grain are described in, for example, WO 2002/037955, WO 2003/094600, WO 2005/040381, WO 2005/001098, WO 2011/011833 and WO 2012/103594.

In an embodiment, grain of the invention comprises an increased proportion of oleic acid and/or a decreased proportion of palmitic acid in its total fatty acid content compared to the corresponding wild-type grain. Methods of producing such grain are described in, for example, WO 2008/006171 and WO 2013/159149.

Grain/seed of the invention, or other plant parts of the invention, can be processed to produce a food ingredient, food or non-food product using any technique known in the art.

As used herein, the term “other food or beverage ingredient” refers to any substance suitable for consumption by an animal, preferably any substance suitable for consumption by a human, when provided as part of a food or beverage. Examples include, but are not limited to, grain from other plant species, sugar, etc, but excluding water.

In one embodiment, the product is whole grain flour such as, for example, an ultrafine-milled whole grain flour, or a flour made from about 100% of the grain. The whole grain flour includes a refined flour constituent (refined flour or refined flour) and a coarse fraction (an ultrafine-milled coarse fraction).

Refined flour may be flour which is prepared, for example, by grinding and bolting cleaned grain. The particle size of refined flour is described as flour in which not less than 98% passes through a cloth having openings not larger than those of woven wire cloth designated “212 micrometers (U.S. Wire 70)”. The coarse fraction includes at least one of: bran and germ. For instance, the germ is an embryonic plant found within the grain kernel. The germ includes lipids, fiber, vitamins, protein, minerals and phytonutrients, such as flavonoids. The bran includes several cell layers and has a significant amount of lipids, fiber, vitamins, protein, minerals and phytonutrients, such as flavonoids. Further, the coarse fraction may include an aleurone layer which also includes lipids, fiber, vitamins, protein, minerals and phytonutrients, such as flavonoids. The aleurone layer, while technically considered part of the endosperm, exhibits many of the same characteristics as the bran and therefore is typically removed with the bran and germ during the milling process. The aleurone layer contains proteins, vitamins and phytonutrients, such as ferulic acid.

Further, the coarse fraction may be blended with the refined flour constituent. The coarse fraction may be mixed with the refined flour constituent to form the whole grain flour, thus providing a whole grain flour with increased nutritional value, fiber content, and antioxidant capacity as compared to refined flour. For example, the coarse fraction or whole grain flour may be used in various amounts to replace refined or whole grain flour in baked goods, snack products, and food products. The whole grain flour of the present invention (i.e.-ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In further embodiments, enzymes found within the bran and germ of the whole grain flour and/or coarse fraction are inactivated in order to stabilize the whole grain flour and/or coarse fraction. Stabilization is a process that uses steam, heat, radiation, or other treatments to inactivate the enzymes found in the bran and germ layer. Flour that has been stabilized retains its cooking characteristics and has a longer shelf life.

In additional embodiments, the whole grain flour, the coarse fraction, or the refined flour may be a component (ingredient) of a food product and may be used to product a food product. For example, the food product may be a bagel, a biscuit, a bread, a bun, a croissant, a dumpling, an English muffin, a muffin, a pita bread, a quickbread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In alternative embodiments, the whole grain flour, refined flour, or coarse fraction may be a component of a nutritional supplement. For instance, the nutritional supplement may be a product that is added to the diet containing one or more additional ingredients, typically including: vitamins, minerals, herbs, amino acids, enzymes, antioxidants, herbs, spices, probiotics, extracts, prebiotics and fiber. The whole grain flour, refined flour or coarse fraction of the present invention includes vitamins, minerals, amino acids, enzymes, and fiber. For instance, the coarse fraction contains a concentrated amount of dietary fiber as well as other essential nutrients, such as B-vitamins, selenium, chromium, manganese, magnesium, and antioxidants, which are essential for a healthy diet. For example 22 grams of the coarse fraction of the present invention delivers 33% of an individual's daily recommend consumption of fiber. The nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients. The supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage, this embodiment may be particularly attractive as a fiber supplement for children.

In an additional embodiment, a milling process may be used to make a multi-grain flour or a multi-grain coarse fraction. For example, bran and germ from one type of grain may be ground and blended with ground endosperm or whole grain cereal flour of another type of cereal. Alternatively bran and germ of one type of grain may be ground and blended with ground endosperm or whole grain flour of another type of grain. It is contemplated that the present invention encompasses mixing any combination of one or more of bran, germ, endosperm, and whole grain flour of one or more grains. This multi-grain approach may be used to make custom flour and capitalize on the qualities and nutritional contents of multiple types of cereal grains to make one flour.

It is contemplated that the whole grain flour, coarse fraction and/or grain products of the present invention may be produced by any milling process known in the art. An exemplary embodiment involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like. After grinding, the grain is discharged and conveyed to a sifter. Further, it is contemplated that the whole grain flour, coarse fraction and/or grain products of the present invention may be modified or enhanced by way of numerous other processes such as: fermentation, instantizing, extrusion, encapsulation, toasting, roasting, or the like.

EXAMPLES

Example 1. General Materials and Methods

Observation of Aleurone by Staining with Sudan Red Solution

Stain solution was prepared by adding 1 g of Sudan red IV to 50 ml of polyethylene glycol solution (average molecular weight 400, Sigma, Cat. No. 202398), incubated at 90° C. for one hour, and mixed with equal volume of 90% glycerol. After removing the fruit coat (palea and lemma) of each grain, mature rice grains were incubated in distilled water for five hours and then sectioned transversely or longitudinally using a razor blade. Sections were stained in Sudan red solution at room temperature for 24 to 72 hours. The sections were then counter-stained with Lugol staining solution at room temperature for 20 min (Sigma, 32922) and observed under dissecting microscope (Sreenivasulu, 2010).

Staining of Aleurone with Evans Blue

Evans Blue stain solution was prepared by dissolving 0.1 g of Evans blue (Sigma, E2129) in 100 ml distilled water. After removing the fruit coat (palea and lemma) of each grain, mature rice grains were sectioned transversely using a razor blade. Sections were incubated in distilled water at room temperature for 30 min, the stain added and left at room temperature for 2 min. The stain solution was then discarded, the sections washed twice with distilled water and observed under a dissecting microscope.

Light Microscopic Observation of Rice Endosperm

Rice grains were fixed in formalin-acetic acid-alcohol (FAA) solution (60% ethanol, 5% glacial acetic acid and 2% formaldehyde), degassed for one hour, dehydrated in a series of alcohol solutions containing 70%, 80%, 95% and then 100% ethanol, infiltrated by LR white resin (Electron Microscopy Sciences, 14380) and polymerized for 24 hours at 60° C. Microtome sectioning was done using a Leica UC7 microtome. Sections were stained in 0.1% toluidine blue solution (Sigma, T3260) at room temperature for 2 min, then washed twice with distilled water and examined by light microscopy. Alternatively, sections were stained in 0.01% Calcofluor white solution (Sigma, 18909) at room temperature for 2 min and examined by light microscopy.

Staining with PAS and Commassie Blue

The fixed sections on slides were incubated in preheated 0.4% periodic acid (Sigma, 375810) at 57° C. for 30 min, then rinsed three times in distilled water. Schiff reagent (Sigma, 3952016) was applied and the slides incubated at room temperature for 15 min, then rinsed three times in distilled water. The sections were then incubated in 1% Coomassie blue (R-250), ThermoScientific, 20278) at room temperature for 2 min, and rinsed three times in distilled water. Dehydration of the sections was achieved using a series of alcohol solutions having 30%, 50%, 60%, 75%, 85%, 95% to 100% ethanol for 2 min each, followed by clearing of each slide in 50% xylene and 100% xylene solution (Sigma, 534056) for 2 min each. Coverslips were then mounted with Eukitt® quick hardening mounting medium (Fluka, 03989) and the sections observed under a light microscope.

DNA Extraction and PCR Conditions

Two methods were used for DNA extraction from plant leaf samples—a rapid DNA extraction method to provide less pure DNA samples and a more extensive DNA extraction method for purer DNA, modified from Huang (2009). In the first method, four glass beads with diameter of 2 mm (Sigma, 273627), 1 to 2 mg of rice leaf tissue and 150 μl of extraction buffer (10 mM Tris, pH9.5, 0.5 mM EDTA, 100 mM KCl) were added to each well of a 96-well PCR plate. The plate was sealed and mixtures homogenised using a Mini-Beadbeater-96 mixer (GlenMills, 1001) for 1 min. After centrifugation at 3000 rpm for 5 min, the extracted supernatants containing DNA were used in PCR reactions.

In the second method, two glass beads with diameter of 2 mm and 0.2 g leaf were in 1.5 ml Eppendorf tubes were cooled in liquid nitrogen for 10 min. Samples were then homogenised in the Mini-Beadbeater-96 for 1 min, then 600 μl DNA extraction buffer (2% SDS, 0.4M NaCl, 2 mM EDTA, 10 mM Tris-HCl, pH8.0) was added to each tube and the mixtures incubated at 65° C. for one hour. After cooling the mixtures, 450 μl of 6M NaCl was added, mixed and centrifuged at 12000 rpm for 20 min. Each supernatant was transferred to a new tube and the DNA precipitated using an equal volume of 2-propanol at −20° C. for one hour. DNA was recovered by centrifugation at 2400 rpm at 4° C. for 20 min and the pellets washed twice with 75% ethanol. The pellets were air-dried at room temperature and each resuspended in 600 μl distilled water containing 10 ng/ulRNAse (ThermoScientific, EN0201)) and used in PCR reactions.

The PCR reactions used 5 μl of 2×PCR buffer containing Taq Polymerase (ThermoScientific, K0171), 5' and 3' oligonucleotide primers and 1 μl of DNA sample in a total volume of 10 μl. Amplification was performed using 35 cycles of 94° C. for sec, 55° C. for 30 sec and 72° C. for 30 sec. Amplification products were analysed by gel electrophoresis using 3% agarose gels. Control PCR reactions used DNA preparations from homozygous Zhonghua11 (ZH11) (wild-type japonica rice), homozygous NJ6 (wild type indica rice), and the mixture of ZH11 and NJ6.

For genetic mapping of the ta2 allele, PCR amplifications for the genetic markers used the following primer pairs (5' to 3' sequences): INDEL 127 (position 6,343,260 on Chromosome 1), forward primer TGAGTAGTTGCGTTGTTCT (SEQ ID NO: 15), reverse primer TCTTAGTGAGCCGTTTCT (SEQ ID NO: 16); INDEL 129 (position 6,560,681 on Chromosome 1), forward primer CCTTCTGTGCTATGGGTT (SEQ ID NO: 17), reverse primer CATGCCAAGACACCACTT (SEQ ID NO: 18); INDEL 128 (position 6,470,027 on Chromosome 1), forward primer TGGCTTTGGAAACGGTAG (SEQ ID NO: 19), reverse primer TTTAGAGGGATGTGCGTCA (SEQ ID NO: 20); INDEL 149 (position 6,427,144 on Chromosome 1), forward primer AAACAACGATCCAGCAAA (SEQ ID NO: 21), reverse primer TTGGCACCGTATTACTTTC (SEQ ID NO: 22).

TILLING Assays

The primers that were used in the TILLING assays had the nucleotide sequences:

```
TA2-1F:
                                (SEQ ID NO: 23)
ACGCATTCTTCATTGACTGTATGT

TA2-1R:
                                (SEQ ID NO: 24)
GCCCTTTCAATACAATGACTAGGT

TA2-2F:
                                (SEQ ID NO: 25)
GAACATTTGAATCATGTTCCTCAC

TA2-2R:
                                (SEQ ID NO: 26)
ACTATCCTTTGATGCAAGTTCTCC

TA2-3F:
                                (SEQ ID NO: 27)
GTTGGAAGAGCAGTTAAAGCAAAT

TA2-3R:
                                (SEQ ID NO: 28)
CTTCGGCAGTGAAATTTAGTAACA

TA2-4F:
                                (SEQ ID NO: 29)
TACAGAACTTCTACGAATGCAGGA

TA2-4R:
                                (SEQ ID NO: 30)
GCAACATGAATTGCTAAAGATGAG.
```

The PCR amplifications with ExTaq were performed with the following reaction conditions: 95° C. for 2 min; 8 cycles of 94° C. for 20 s, 68° C. for 30 s (1° C. decrease per cycle), and 72° C. for 60 s for every 1 kb of amplicon length, followed by 35 cycles of 94° C. for 20 s, 60° C. for 30 s, and 72° C. for 60 s for each 1 kb of amplicon length, and a final extension at 72° C. for 5 min. PCR products from the wild-type and test samples were mixed and subjected to a complete denaturation-slow annealing program to form heteroduplexes under the following conditions: 99° C. for 10 mM for denaturation, followed by 70 cycles of decrements, starting at 70° C., 20 s each, with a 0.3° C. decrease per cycle, and then holding at 15° C. to reanneal the denatured PCR products to form heteroduplexes. CelI digestions of annealed PCR products were performed in 15 μL reaction mixtures containing CelI buffer (10 mM HEPES, pH 7.5, 10 mM KCl, 10 mM $MgSO_4$, 0.002% Triton X-100, and 0.2 ng/mL bovine serum albumin (BSA), 4 μL of PCR product, and 1 unit CelI (10 units/μL) if PCR products were polymerized by Ex Taq, or 20 units CelI if the PCR products were polymerized by KOD), at 45° C. for 15 min, followed by adding 3 μL of 0.5 M EDTA (pH 8.0) to stop the reaction. Alternatively, the digestions were performed in 15-μL reaction mixtures containing 4 μL of PCR products and 2 units of mung bean nuclease (MBN, 10 units/μL, Cat. No. M02505; New England Biolabs, USA) in MBN buffer (20 mM Bis-Tris, pH 6.5, 10 mM $MgSO_4$, 0.2 mM $ZnSO_4$, 0.002% Triton X-100, and 0.2 μg/mL BSA) at 60° C. for 30 min, followed by adding 2 μL of 0.2% SDS to stop the reaction.

CelI-digested PCR products in 96-well PCR plates were diluted to 100 μL with deionized water, and capillary electrophoresis was performed at 9 kV, 30 s for pre-run, 15 s for injection of 1 ng/μL molecular weight marker 75 and 15 kb or 50 and 3 kb dsDNA (Fermentas, Canada), 45 s for sample injection, and 40 min for sample separations in an AdvanCE™ FS96 apparatus (Advanced Analytical Technologies, USA). Gel pictures were acquired and analysed using PROSize software (Advanced Analytical Technologies, USA) for capillary electrophoresis.

DNA Glycosylase (DME) Enzyme Assays

Demeter (DME) is a bifunctional DNA glycosylase/lyase with activity on 5-methylcytosine substrates. Plants have 5-methylcytosine in the three sequence contexts: CpG, CpNpG, and CpNpN and DME has activity on 5-methylcytosine in each of these sequence contexts. In the enzyme assay which is performed in vitro, the cleavage of the phosphodiester linkage on the 5' side of a methylated cytosine was detected, yielding δ elimination products. Treatment of the DNA reaction products with strong base (NaOH) prior to gel electrophoresis confirmed the δ elimination process at the predicted position.

Synthetic oligonucleotides which were to be used as substrates in the enzyme assays were synthesized as follows with nucleotide modifications denoted within parentheses as shown below:

```
MEA-1.6F,
                                (SEQ ID NO: 31)
5'-CTATACCTCCTCAACTCCGGTCACCGTCTCCGGCG

MEA-1.6F18meC,
                                (SEQ ID NO: 32)
5'-CTATACCTCCTCAACTC(5-meC)GGTCACCGTCTCCGGCG

MEA-1.6F17meC,
                                (SEQ ID NO: 33)
5'-CTATACCTCCTCAACT(5-meC)CGGTCACCGTCTCCGGCG
```

-continued

MEA-1.6F22meC,
(SEQ ID NO: 34)
5'-CTATACCTCCTCAACTCCGGT(5-meC)ACCGTCTCCGGCG

MEA-1.6F18AP,
(SEQ ID NO: 35)
5'-CTATACCTCCTCAACTC(abasic)GGTCACCGTCTCCGGCG

MEA-1.6F17AP,
(SEQ ID NO: 36)
5'-CTATACCTCCTCAACT(abasic)CGGTCACCGTCTCCGGCG

MEA-1.6F15AP,
(SEQ ID NO: 37)
5'-CTATACCTCCTCAA(abasic)TCCGGTCACCGTCTCCGGCG

MEA-1; 6F12AP,
(SEQ ID NO: 38)
5'-CTATACCTCCT(abasic)AACTCCGGTCACCGTCTCCGGCG

MEA-1.6F18T,
(SEQ ID NO: 39)
5'-CTATACCTCCTCAACTCTGGTCACCGTCTCCGGCG

MEA-1.6R,
(SEQ ID NO: 40)
5'-CGCCGGAGACGGTGACCGGAGTTGAGGAGGTATAG

MEA-1.6R17meC,
(SEQ ID NO: 41)
5'-CGCCGGAGACGGTGAC(5-meC)GGAGTTGAGGAGGTATAG.

Twenty pmol of each oligonucleotide was end-labelled in a 50 µL reaction using units of T4 polynucleotide kinase in the presence of 30 µCi of (γ-32P)-ATP (6000 Ci/mmol, Perkin Elmer Life Sciences) at 37° C. for 1 hr. Each labelled oligonucleotide was purified using a Qiaquick Nucleotide Removal Kit (Qiagen) as described by the manufacturer. Labelled oligonucleotides were annealed to the appropriate complementary oligonucleotides in 10 mMTris-HCl (pH 8.0), 1 mM EDTA and 0.1 M NaCl. Each mixture was heated to 100° C. for 10 min and then slowly cooled to room temperature overnight. MspI or HpaII restriction endonuclease digestion followed by gel electrophoresis was used to determine the efficiency of annealing. Only substrates that were greater than 90% double-stranded were used in glycosylase activity assays.

5'-labeled oligonucleotide substrates (13.3 nM) were incubated with DME protein (250 nM) in a 15 ml reaction with 40 mM HEPES-KOH (pH 8.0), 0.1M KCl, 0.1 mM EDTA, 0.5 mM dithiothreitol, and 200 mg/ml BSA at 37° for 1 hr. The reaction was terminated with 15 ml of 95% formamide, 20 mM EDTA, 0.05% bromophenol blue, 0.05% xylene cyanol FF and boiled for 5 mM. To induce elimination, NaOH was added at a final concentration of 0.1 M and the reaction was boiled for 7 min. Products were fractionated on a 15% polyacrylamide gel containing 7.5 M urea and 1×TBE. Electrophoresis was done at 1000V for 4 hr with a Hoefer SQ3 gel apparatus. The gel was exposed to Kodak BioMax MR film at −80° C.

Analytical Methods

Proximates and other major constituents in grain, food ingredients and food samples were determined using standard methods, for example as described below.

Grain moisture content was measured according to (Association of Official Analytical Chemists) AOAC Method 925.10. Briefly, grain samples (~2 g) were dried to constant weight in an oven at 130° C. for about 1 h.

Ash content was measured according to AOAC Method 923.03. Samples used for moisture determination were ashed in a muffle furnace at 520° C. for 15 h.

Protein Content of Grain, Food Ingredients and Food Samples

Protein content was measured according to AOAC Method 992.23. Briefly, total nitrogen was analysed by the Dumas combustion method using an automated nitrogen analyser (Elementar Rapid N cube, Elementar Analysensysteme GmbH, Hanau, Germany). The protein content of grain or food samples (g/100 g) was estimated by multiplying nitrogen content by 6.25.

Sugars, Starch and Other Polysaccharides

Total starch content was measured according to AOAC Method 996.11 which uses the enzymatic method of McCleary et al. (1997).

The amount of sugars was measured according to AOAC Method 982.14. Briefly, simple sugars were extracted with aqueous ethanol (80% ethanol) and then quantified by HPLC using a polyamine-bonded polymeric gel column, using acetonitrile:water (75:25 v/v) as the mobile phase and an evaporative light scattering detector.

Total neutral non-starch polysaccharides (NNSP) were measured by the gas chromatographic procedure of Theander et al. (1995) with a slight modification which involved a 2 h hydrolysis with 1 M sulfuric acid followed by centrifugation.

Fructans (fructo-oligosaccharides) were analysed by the method detailed by AOAC Method 999.03. Briefly, the fructo-oligosaccharides were extracted into water followed by digestion with a sucrase/maltase/invertase mixture. The resultant free sugars were then reduced with sodium borohydride and digested to fructose/glucose with fructanose. The released fructose/glucose was measured using p-hydroxybenzioc acid hydrazine (PAFIBAH).

Fibre Content

Total Dietary Fibre (TDF) was measured according to AOAC Method 985.29 and Soluble and Insoluble Fibre (SIF) according to AOAC Method 991.43. Briefly, TDF was determined by the gravimetric technique of Prosky et al. (1985), as detailed in the AOAC Method 985.29, and SIF was determined by a gravimetric technique as described in AOAC 991.43.

Total Lipid

Samples of 5 g flour were incubated with 1% Clarase 40000 (Southern Biological, MC23.31) at 45° C. for one hour. Lipids were extracted from the samples into chloroform/methanol by multiple extractions. After centrifugation to separate phases, the chloroform/methanol fraction was removed and dried at 101° C. for 30 min to recover the lipid. The mass of residue left represents the total lipid in the sample (AOAC Method 983.23).

Fatty Acid Profile of Lipids

Lipid was extracted from milled flours into chloroform according to AOAC Method 983.23. A portion of the chloroform fraction containing the lipid was evaporated under a stream of nitrogen after addition of an aliquot of heptadecanoic acid as an internal standard. The residue was suspended in 1% sulfuric acid in dry methanol and the mixture heated at 50° C. for 16 h. The mixture was diluted with water and extracted twice with hexane. The combined hexane solution was loaded onto a small column of Florisil and the column washed with hexane and the fatty acid methyl esters then eluted with 10% ether in hexane. The eluent was evaporated to dryness and the residue dissolved in iso-octane for injection onto the GC. Fatty acid methyl esters were quantified against a mixture of standard fatty acids. GC conditions: Column SGE BPX70 30 m×0.32 mm×0.25 um; Injection 0.5 μL; Injector 250° C.; 15:1 split; Flow 1.723 ml/min constant flow; Oven 150° C. for 0.5 min, 10° C./min to 180° C., 1.5° C./min to 220° C., 30° C./min to 260° C. (total run-time 33 mins); Detector FID at 280° C.

Antioxidant Activity (ORAC-H)

The hydrophilic antioxidant activity (ORAC-H) was determined following the method of Huang (2002a and 2002b) with modification as described by Wolbang et al. (2010). The samples were extracted for lipophilic antioxidants followed by hydrophilic antioxidants as follows: 100 mg of sample weighed in triplicate into 2 mL microtubes. 1 mL hexane:dichloromethane (50:50) was then added and mixed vigorously for 2 min and centrifuged at 13,000 rpm for 2 min at 10° C. The supernatant was transferred to a glass vial and the pellet re-extracted with a further 2 mL of hexane:dichloromethane mix. The mixing and centrifuge steps were then repeated, and the supernatant transferred to the same glass vial. Residual solvent from the pellet was evaporated under a gentle stream of nitrogen. 1 mL of acetone: water: acetic acid mix (70:29.5:0.5) then added and mixed vigorously for 2 min. The mixture was then centrifuged as before and the supernatant used in the ORAC-H plate assay. Samples were diluted as required with phosphate buffer. The area under the curve (AUC) was calculated and compared against AUC values for Trolox standards. The ORAC value is reported as uMTrolox equivalents/g of sample.

Phenolics

Total phenolics content as well as phenolics in the free, conjugated and bound states were determined following extraction according to the method described by Li et al. (2008) with minor modifications. Briefly, the free phenolics were determined in 100 mg samples following extraction into 2 mL 80% methanol by sonication for 10 mins in a glass vial (8 ml capacity). The supernatant was transferred to a second glass vial and the extraction of the residue repeated. The combined supernatants were evaporated to dryness under nitrogen. 2 mL of acetic acid (2%) was added to adjust the pH to about 2 and then 3 mL ethyl acetate added to extract the phenolics with shaking for 2 mins. The vials were centrifuged at 2000×g for 5 mins at 10° C. Supernatants were transferred to a clean glass vial and the extraction repeated twice more. Combined supernatants were evaporated under nitrogen at 37° C. Residues were dissolved in 2 mL 80% methanol and refrigerated.

Samples for the conjugated phenolics were treated as for the free phenolic assay for the initial 80% methanol extraction. At this point 2.5 mL (2M) sodium hydroxide and a magnetic bar were added to the evaporated supernatants in the glass vial which was then filled with nitrogen and capped tightly. The vials were mixed and heated at 110° C. for 1 h with stirring. Samples were cooled on ice before extraction with 3 mL ethyl acetate by shaking for 2 min. The vials were centrifuged at 2000×g for 5 min at 10° C. Supernatants were discarded and pH adjusted to about 2 with 12 M HCl. Phenolics were extracted using 3×3 mL aliquots of ethyl acetate as described for the free phenolics. The supernatants were combined and evaporated to dryness under nitrogen at 37° C. and the residue was taken up in 2 mL 80% methanol and refrigerated.

Bound phenolics were measured from the residues following methanolic extraction of the free phenolics. 2.5 mL (2M) sodium hydroxide and a magnetic bar were added to the residue before filling the vial with nitrogen and capping it tightly. The vials were mixed and heated at 110° C. for 1 h with stirring. Samples were cooled on ice before extraction with 3 mL ethyl acetate by shaking for 2 mins. The vials were centrifuged at 2000×g for 5 mins at 10° C. The supernatant was discarded and pH adjusted to about 2 with 12 M HCl. Phenolics were extracted with 3×3 mL aliquots of ethyl acetate as described for the free phenolics. The supernatants were combined and evaporated to dryness under nitrogen at 37° C. and the residue was taken up in 2 mL 80% methanol and refrigerated.

Total phenolics were determined using 100 mg of samples by adding 200 uL 80% methanol to wet the samples prior to hydrolysis. 2.5 mL (2M) sodium hydroxide and a magnetic bar were added before filling the vial with nitrogen and capping tightly. The vials were mixed and heated at 110° C. for 1 hr with stirring. Samples were cooled on ice before extraction with 3 mL ethyl acetate by shaking for 2 mins. The vials were centrifuged at 2000×g for 5 mins at 10° C. The supernatant was discarded and pH adjusted to about 2 with 12 M HCl. Phenolics were extracted with 3×3 mL aliquots of ethyl acetate as described for the free phenolics. The supernatants were combined and evaporated to dryness under nitrogen at 37° C. and the residue was taken up in 4 mL 80% methanol and refrigerated.

The amount of phenolics in the treated/extracted samples was measured using Folin Ciocalteu's assay for determination of phenolics. Gallic acid standards at 0, 1.56, 3.13, 6.25, 12.5, and 25 μg/mL were used to prepare a standard curve. 1 mL of standards were added to 4 mL glass tubes. For test samples, 100 μL aliquots of thoroughly mixed samples were added to 900 μL water in 4 mL glass tubes. 100 mL of Folin Ciocalteu's reagent was then added to each tube which was vortexed immediately. 700 sodium bicarbonate solution (1 M) was added after 2 min and then mixed by vortexing. Each solution was incubated at room temperature in the dark for 1 h and then absorbance read at 765 nm. Results were expressed in μg gallic acid equivalents/g sample.

Phytate

Determination of the phytate content of the flour samples was based on the method of Harland and Oberleas, as described in AOAC Official Methods of Analysis (1990). Briefly, a 0.5 g flour sample was weighed and extracted with 2.4% HCl using a rotating wheel (30 rpm) for 1 hour at room temperature. The mixture was then centrifuged at 2000×g for 10 minutes and the supernatant extracted and diluted 20-fold with milli-Q water. An anion exchange column (500 mg Agilent Technologies) was placed on a vacuum manifold and conditioned for use following the manufacturer's instructions. The diluted supernatant was then loaded onto a column and non-phytate species removed by washing with 0.05 M HCl. Phytate was then eluted with 2 M HCl. The collected eluate was digested using a heating block. The sample was cooled and the volume made up to 10 mL with milli-Q water. Phosphorous levels were determined by spectrophotometer using the molybdate, sulphonic acid colouring method with absorbance readings at 640 nm. Phytate was calculated using the following formula:

$$\text{Phytate (mg/g)} = P\text{conc} * V1 * V2 / (1000 * \text{sample weight} * 0.282)$$

where P conc is the concentration of phosphorous (μg/mL), as determined by spectrophotometry, V1 is the volume of the final solution, V2 is the volume of the extracted phytate solution, and 0.282 is the phosphorus to phytate conversion factor.

Total Mineral Content Estimation

Total mineral content of samples was measured by ash assay using AOAC Methods 923.03 and 930.22. About 2 g of flour was heated at 540° C. for 15 hours and the mass of ash residue was then weighed. Wholemeal flour samples of 0.5 g were digested using tube block digestion with 8M nitric acid at 140° C. for eight hours. Zinc, iron, potassium, magnesium, phosphorus and sulphur contents were then analysed using inductively coupled plasma atomic emission spectrometry (TCP-AES) according to Zarcinas (1983a and 1983b).

Minerals were analysed at CSIRO, Urrbrae, Adelaide South Australia, at Waite Analytical Service (University of Adelaide, Waite, South Australia) and at Dairy Technical Services (DTS, North Melbourne, Victoria). Elements were determined by Inductively Coupled Plasma-Optical Emission Spectroscopy (ICP-OES) after digestion with nitric acid solution (CSIRO) or dilute nitric acid and hydrogen peroxide (DTS) or by Inductively Coupled Plasma Atomic Emission Spectroscopy (ICP-AES) after digestion with nitric/perchloric acid solution.

Vitamins

Vitamins B1 (Niacin), B3 (Pyridoxine) and total folate analyses were performed by DTS as well as National Measurement Institute (NMI). Niacin was measured by AOAC Methods 13th Ed (1980) 43.045, according to Lahey, et al. (1999). Pyridoxine was measured according to Mann et al. (2001). The method incorporated a pre-column transformation of phosphorylated and free vitamin B6 forms into pyridoxine (pyridoxol). Acid phosphatase hydrolysis was used for dephosphorylation followed by de-amination with glyoxylic acid in the presence of $Fe^{2+}$ to convert pyridoxamine to pyridoxal. Pyridoxal was then reduced by sodium borohydride to pyridoxine.

Folic acid was measured either according to VitaFast Folic acid kit using the manufacturer's instructions, or according to AOAC method 2004.05.

Example 2. Isolation and Characterisation of Thick-Aleurone (Ta) Mutants

Establishment and Cultivation of a Mutagenized Rice Population

About 8000 grains (designated $M_0$ grains) from wild-type rice cultivar Zhonghua11 (ZH11) were mutagenized by treatment with 60 mM ethyl methane sulfonate (EMS) using standard conditions. Mutagenised grains were sown in the field and the resultant plants cultivated to produce $M_1$ grains. $M_1$ grains were harvested and then sown in the field to produce $M_1$ plants. 8925 panicles were harvested from 1327 individual $M_1$ plants. From these plants 36,420 $M_2$ grains were screened, including at least 4 grains from each panicle.

Mutant Screening by Staining of Half Grains

The fruit coat (palea and lemma) of $M_2$ rice grains were removed. Each of the 36,420 grains was transverse bisected. The halves containing an embryo were saved in 96-well plates for subsequent germination, while each half grain without an embryo was stained with Evans Blue and observed under a dissecting microscope to detect mutant grains having thickened aleurones relative to the wild-type. The staining was based on the principle that Evans Blue could only penetrate and stain non-viable cells such as the cells of the starchy endosperm while no colour change was observed in the viable aleurone layer. From initial Evans Blue staining and histological analyses, individual grains exhibiting significant increases in aleurone thickness as well as grains showing a significant thickening in the ventral side aleurone of the seed were observed. Other grains showed an increase in aleurone thickness but to a lesser extent. The unstained region of the ventral side of each seed was especially examined for thickness of the aleurone layer. Variants with increases in thickness of the aleurone layer on the dorsal side of the grains were also observed. Only variants with significant increases in the thickness of the aleurone layer across the entire cross-section were chosen for further analysis.

Compared with wild-type half-grains, the half-grains having a thicker unstained region with Evans Blue were selected. Amongst the 36,420 grains examined, 219 grains (0.60%) having differences in aleurone thickness were identified and selected. These had been obtained from 162 panicles from 140 individual $M_1$ plants, and therefore most represented independent mutants. One mutant grain in particular was identified and characterised further as described below, having a mutation designated thick-aleurone 2 (ta2). The corresponding wild-type gene was therefore designated Ta2; that designation is used herein.

To maintain the putative mutant lines, each corresponding embryonated half grain was germinated on medium containing half-strength MS salts medium (Murashige and Skoog, 1962) solidified with 1% Bacto agar (Bacto, 214030) and cultured at 25° C. under light of intensity 1500-2000 Lux with 16 h light/8 h dark cycles. The plantlets were transferred to soil at the two to three leaflet stage and the resultant plants grown to maturity. Upon the germination and cultivation of the corresponding embryonated half grains, 115 seeds (52.5% survival) were grown up to produce mature and fertile plants.

Candidate mutant plants which exhibited little or no defects in general agronomical traits such as those that were of normal plant height, fertility (male and female fertility), grain size and 1000 grain weight relative to the wild-type parental variety as well as showing stable inheritance of the thickened aleurone trait were identified, selected and further analysed. Among them, a mutant designated ta2 which showed a more extreme multi-aleurone phenotype of six to seven cell layers was selected and analysed in detail. The wild-type grains exhibited an aleurone of one cell layer, as expected.

Histological Analyses of the Ta2 Mutant Grains

Developing grain from wild-type ZH11 and ta2 mutant plants were studied and compared for morphological changes from 1 to 30 days after pollination (DAP). The ripening phase of rice grain can be said to have three stages: a milk grain stage, a dough grain stage and a mature grain stage. In the dough grain stage, the grains in wild-type panicles began to change in colour from green to yellow, following by a gradual destruction of vesicular tissue connecting the stalk and caryopsis. Grains in the ta2 panicles were delayed in the colour change. Microscopic examination of the transverse sections of the rice grains also showed an increase in the degree of chalkiness (opaqueness) in ta2 mutant grains. Scanning electron microscopy (SEM) was then used to study the structure of the starch granule organization in the middle part of the starchy endosperm. In wild-type grains, starch granules were tightly packed and showed a smooth surface and regular shape, while in ta2 grains, a looser packing of irregular-shaped starch granules was observed. In summary, at least three changes were observed in the plants and grain having the ta2 mutation: a delay in grain maturation, an increase in the degree of chalkiness of the grain and in starch granule structure.

Developing mutant and wild-type grains at 6, 7, 8, 9, 10, 12, 15, 18, 21, 24, 27 and 30 DAP were stained with Evans Blue and the aleurone layers examined by light microscopy. No significant difference was observed in the thickness of the developing aleurone layers between wild-type and ta2 mutant grains up until 10 DAP. After 10 DAP, the aleurone layers of ta2 mutants were thicker than in the wild-type grains, and the difference reached a maximum at around 20 DAP. These results were consistent with those from Sudan red staining.

The wild-type and ta2 mutant grains (30 DAP) were further examined for histological differences by sectioning (1 μm), staining and light microscopy. After staining with 0.1% toluidine blue which stains nucleic acid blue and polysaccharide purple, a single layer of large, regularly oriented, rectangular cells was observed in wild-type aleurones. In contrast, sections of ta2 mutant grains had aleurone layers of six to eight cell layers, the cells also being of varying sizes and irregular orientation. These observations indicated that the thickened aleurones in the ta2 grains were mainly caused by the increase in the number of cell layers rather than the enlargement of individual aleurone cells.

Further staining with 0.01% Calcoflour White, a fluorescent cell wall stain, showed no difference in cell wall thickness between wild-type and ta2 mutant grains. The cell walls of aleurone cells were thicker than cell walls in the starchy endosperm for both wild-type and ta2 grains.

Analysis of the Agronomical Characteristics of Ta2 Mutant Plants and Grains

After backcrossed to wild-type (ZH11) plants for three generations in the field to yield the BC3F3 generation, thereby removing additional, unlinked mutations that might have arisen from the mutagenic treatment, ta2 mutant plants were analysed for some agronomical traits. The ta2 mutant plants and grain were not significantly different, compared to wild-type plants and grain, in plant height, 1000 grain-weight, grain size (length, width and thickness) and caly-opsis morphology (Table 2). In contrast, wild-type plants showed a seed setting rate of 98.9% whereas ta2 mutant plants showed a decrease in seed setting rate at 73.4%. The seed setting rate was calculated as the percentage of florets in the plant that were filled by a seed by the mature grain stage. Moreover, the ta2 mutant grains showed a decrease in germination capacity of 75.1% in comparison with wild-type grain of 97.3% when cultured at 28° C. under 12 h light/12 h dark cycles without humidity control in a growth chamber. Germination was defined as when the radicle had visibly emerged through the seed coat.

Example 3. Genetic Analysis of the Ta2 Mutant

Based on the maternal origin of aleurone and endosperm tissues in a growing plant, two genetic experiments were performed to determine whether the thick aleurone phenotype was maternally determined. Firstly, a test cross was performed between a maternal ta2 (mutant) plant and a paternal wild-type plant, and F2 progeny grains obtained. Of the F2 grains, 49.4% (n=634) showed the thickened aleurone phenotype, which deviated significantly from the 3:1 (wild-type:mutant) ratio predicted for Mendelian inheritance of a dominant gene in an F2 population. Secondly, a reciprocal cross was performed between a 02 plant and a wild-type plant. All F1 seeds (100%; n=589) showed the thickened aleurone phenotype, while in the reciprocal cross using the wild-type as the maternal plant, all F1 seeds (n=197) resulted in the wild-type phenotype. These crosses showed that the aleurone phenotype was determined by the maternal plant genotype.

TABLE 2

Comparison of wild-type (ZH11) and ta2 mutant plants for agronomical traits.

| | ZH11 | ta2 |
|---|---|---|
| Plant Height (cm) | 103.7 (±3.24) | 112.2 (±6.05) |
| Seed setting rate (%) | 98.9 (±3.41) | 73.41 (±3.41) |
| 1000 seeds weight (g) | 22.73 (±0.17) | 22.07 (±0.33) |
| Seed length (mm) | 7.46 (±0.26) | 7.55 (±0.27) |
| Seed width (mm) | 3.27 (±0.12) | 3.15 (±0.10) |
| Seed thickness (mm) | 2.35 (±0.10) | 2.27 (±0.11) |

In order to establish whether the maternal effect was determined by the gametophytic or sporophytic genotype, F1 plants which were heterozygous Tat/tat, obtained from a cross between homozygous Ta2/Ta2 and homozygous ta2/ta2 plants, were used in reciprocal crosses with either ta2 homozygous (ta2/ta2) or wild-type plants. In the reciprocal crosses between a maternal heterozygote and a paternal wild-type, 47.3% (n=188) of F1 grains showed the ta2 mutant phenotype, while in the reciprocal cross between a maternal ta2 plant and a paternal heterozygote, 99.3% (n=425) of F1 individuals showed the ta2 mutant phenotype. From these results, it was concluded that the TA2 gene conferred the phenotype by a gametophytic, maternal mode of inheritance.

According to the above genetic analyses, a model of ta2 inheritance can be proposed, according to a gametophytic maternal mode of inheritance. When the genotype of the maternal gametophyte is ta2, the endosperm phenotype is the mutant ta2 (thickened aleurone) and is independent of the paternal genotype. Therefore, the thick aleurone phenotype was determined solely by the genotype of the maternal gametophyte during the development of the triploid starchy endosperm and aleurone, such that a maternal heterozygote resulted in 50% of progeny having a thick aleurone phenotype, independent of the paternal genotype, and a maternal ta2/ta2 homozygote resulted in 100% of progeny having a thick aleurone phenotype. Further experiments are needed to test whether the gametophytic maternal effect of TA2 is caused by the presence of the additional copy of the maternal gene in the triploid endosperm or by the effect of gene imprinting by the maternal gametophyte to suppress the expression of a paternal TA2 gene.

Example 4. Identification of the Ta2 Gene by Genetic Mapping and Sequence Analysis

Identification and Use of SSR and INDEL Markers for Gene Mapping

For gene mapping, an F2 population of plants was produced from the genetic cross between a plant containing the ta2 mutation in the genetic background of ZH11 (a Japonica variety) and a plant of the Indica variety NJ6. To identify genetic markers which were polymorphic between ZH11 and NJ6 and which could then be used in the gene mapping, a set of PCR experiments was performed on leaf DNA samples from homozygous ZH11 plants, homozygous NJ6 plants and a 1:1 mixture of the DNAs. Analysis of the PCR products by gel electrophoresis allowed comparison of the products from ZH11, NJ6 and the mixtures to identify polymorphic markers. Primer pairs were selected for the gene mapping only if the amplifications with separate ZH11 and NJ6 DNAs showed discrete and different amplified products and the mixed DNA showed the combination of both products. A total of 124 primer pairs were thereby selected including 54 insertion-deletion polymorphisms (INDEL) and 70 short sequence repeats (SSR) polymorphisms. These genetic markers were distributed at approximately 3-4 Mbp intervals along the rice genome and gave good coverage for gene mapping.

For genetic mapping of the ta2 allele, 143 plants from the F2 population were scored with the 124 polymorphic markers. Homozygosity of the individual F2 plants in the mapping population for the aleurone phenotype was assessed carefully by phenotyping of F3 progeny grains obtained from each F2 plant. Leaf DNA was extracted as described in Example 1. PCR amplifications were done as described in Example 1 and the products separated by gel electrophoresis through 3% agarose. It was concluded from the results that the ta2 locus was located between markers INDEL 127 and INDEL 129 on Chromosome 1 (FIG. 1, uppermost line), which from the genome sequence of rice corresponding to a physical distance of approximately 217 kb.

Another 5000 F2 plants were screened with this pair of markers. 362 individuals were identified and selected which exhibited a recombination between INDEL 127 and INDEL 129. When these recombinant plants were phenotyped, the ta2 locus was thereby mapped to a 42.8 kb region which lay between the INDEL 149 and INDEL 128 markers (FIG. 1, second line).

To obtain the nucleotide sequence of this region in the ta2 mutant plants and compare it to the wild-type sequence and thereby identify a mutation corresponding to ta2, primers flanking the genomic region were designed and DNA sequencing was carried out. The comparison of the genomic DNA sequences identified two single-nucleotide polymorphisms (SNPs) in the sequenced region, both in the gene annotated as LOC_01 g11900. The first was a single nucleotide G (wild-type) to A (ta2) polymorphism at nucleotide position Chr1: 6451738, with reference to the rice genome sequence of the Japonica variety, located in intron 14 between exon 14 and exon 15 of the gene LOC_01 g11900 in chromosome 1 (asterisk in FIG. 1). The second polymorphism was a G (wild-type) to A (ta2) substitution at position Chr1: 6452308, which was located in the intronic region (intron 15) between exons 15 and 16 of the gene LOC_01 g11900 in chromosome 1.

Upon RNA extraction, reverse transcription and sequencing of the cDNA corresponding to the ta2 allele, it was observed that the first G to A polymorphism at Chr1: 6451738 was associated with an insertion of 21 bp (FIG. 2) between exon 14 and exon 15, corresponding to an in-frame insertion of seven amino acids in the predicted amino acid sequence (FIG. 3). In contrast, there was no change in the cDNA sequence for the mutation between exons 15 and 16, corresponding to the second polymorphism at position locus Chr1: 6452308. It was concluded from these data that the first polymorphism in intron 14 was the causative change, i.e. the ta2 mutation in that grain. This conclusion was confirmed in the Examples below. It was also concluded that the mutation led to a change in the splicing pattern of the RNA transcript of the ta2 gene relative to the wild-type Tat gene, thereby causing the ta2 phenotype. From the ratio of the number of cDNAs having the 21 nucleotide insertion to the number of the cDNAs lacking the insertion, it was estimated that about 80% of the RNA transcripts from the ta2 (mutant) gene were spliced at the newly created splice site. Presuming that the mutant polypeptide having the 7 amino acid insertion was inactive, it was concluded that the mutant ta2 gene retained about 20% of the activity relative to the wild-type.

The gene at position LOC_01 g11900 in chromosome 1 of the rice genome has been annotated as the rice ROS1a gene (OsROS1α), a homolog of the *Arabidopsis thaliana* Demeter gene (AtDME) which encodes a bifunctional DNA glycosylase/lyase. The *Arabidopsis* DME enzyme acts as a DNA demethylase, reducing methylation of C residues in DNA. Therefore the Tat gene is synonymous with OsROS1a gene and a homolog of the *Arabidopsis* DME gene.

The nucleotide sequence of the rice ROS1a gene is shown in SEQ ID NO:9, including a promoter and 5-UTR (untranslated region) of 4726 nucleotides, a protein coding region from nucleotides 4727-15869 including 16 introns, and a 3'UTR of 615 nucleotides. The nucleotide positions of the 16 introns are provided in the legend to SEQ ID NO:9. SEQ ID NO:9 also includes at its 3' end a downstream region of 401 nucleotides which is not considered to be part of the OcROS1 gene. The nucleotide sequence of the cDNA corresponding to wild-type OsROS1 gene is provided in SEQ ID NO:8, and the encoded polypeptide of 1952 amino acids is provided as SEQ ID NO:2.

Rice has four ROS1 genes which encode polypeptides designated OsROS1a, OsROS1b (LOC_Os02 g29230), OsROS1c (LOC_Os05 g3735) and OsROS1d (LOC_Os05 g37410). Rice also has two other Demeter homologs which are thought to encode DNA glycosylases, namely Demeter-like-2 (DML2) and Demeter-like-3 (DML3).

Description of the Structural Features in the Wild-Type Rice TA2 Polypeptide After finding that the rice TA2 gene was the same as OsROS1α, the OsTA2 (OsROS1) polypeptide amino acid sequence was examined. Several typical DNA glycosylase structural features were identified. The glycosylase domain of ROS1 proteins has at least three identified motifs which are sufficiently conserved to be recognisable: the helix-hairpin-helix (HhH) motif (represented by, for example, amino acids 1491-1515 in OsTA2), a glycine/proline-rich motif followed by a conserved aspartic acid (GPD), and four conserved cysteine residues (for example in the region of amino acids 1582-1598) to hold a [4Fe-4S] cluster in place. There was also a lysine-rich domain (represented by, for example, amino acids 87-139 in OsTA2). Unlike other members of the HhH DNA glycosylase superfamily, ROS1-family members contain two additional conserved domains (domains A and B) flanking the central glycosylase domain (Mok et al., 2010). In the rice TA2 polypeptide (SEQ ID NO:2), domain A occurs at amino acids 859 to 965, the glycosylase domain occurs at amino acids 1403 to 1616, and domain B occurs at amino acids 1659 to 1933. Domain A contains a repetitive mixed-charge cluster at amino acids 882-892. It has been reported that the conserved DNA glycosylase domain of AtDME and the flanking domains A and B are necessary and sufficient for DNA glycosylase/lyase enzymatic activity, as shown by mutagenesis analysis (Mok et al., 2010).

Example 5. Analysis of Nutritional Components in Ta2 Mutant Grain

To measure the composition of mutant grain, particularly for nutritionally important components, ZH11 and ta2 plants were grown at the same time and under the same conditions in the field. Whole grain flour samples were prepared from grain harvested from the plants and used for the compositional analysis. The results (means of duplicate measurements) of the proximate analyses of the flours are given in Table 2.

TABLE 2

Compositional analysis office grain (in g/100 g of grain)

| | Moisture | Ash | Protein | Total Fat | Total Starch | Total Sugars | Total Fibre | Soluble Fibre | Insoluble Fibre |
|---|---|---|---|---|---|---|---|---|---|
| ZH 11 | 9.54 | 1.79 | 15.3 | 3.30 | 66.0 | 1.02 | 1.6 | 0.7 | 2.9 |
| ta2 | 8.99 | 2.27 | 15.6 | 4.96 | 60.3 | 2.58 | 4.9 | 0.4 | 3.9 |

The proximate analyses indicated an increase of about 50% in the total fat content in the ta2 mutant flour. Total nitrogen analyses showed no significant change in the protein levels between the ta2 mutant and wild-type grains. Ash assays, which measured the amount of materials left behind after combustion of dehumidified flour samples, demonstrated an increase of 26% in ta2 grain relative to wild-type. The total fibre level increased by about 200% in ta2 grain. The starch content decreased by 8.6% in ta2 grain relative to wild-type. These data demonstrated that the increase in thickness of the aleurone layer in the ta2 mutant caused an increase in the level of aleurone-rich nutrients such as lipid, minerals and fibres without changing the size of the seed. In order to understand these and other changes in greater detail, more extensive analyses were done as follows.

Minerals

To measure mineral contents, ICP-AES was used which combines inductively coupled plasma (ICP) with atomic emission spectrometry (AES) techniques. This is a standard method for measuring mineral content, providing a sensitive and high throughput quantitation of a large number of elements in a single analysis. The data obtained from the analysis showed that the mutant grain had levels of zinc and iron which were increased by about 15% on a weight basis relative to the wild-type grain. Zinc levels increased from 13.9 mg/kg to 16.0 mg/kg, while iron increased from 12.4 mg/kg to 14.2 mg/kg.

Increases in potassium, magnesium, phosphorus and sulphur were also observed, being increased by about 28%, 23%, 22% and 9%, respectively. These results were consistent with the increase in ash content in ta2 grain, which measures mostly minerals.

Antioxidants

Antioxidants are biomolecules capable of counteracting the negative effects of oxidation in animal tissues, thus protecting against oxidative stress-related diseases such as inflammation, cardiovascular disease, cancer and aging-related disorders (Huang, 2005).

The antioxidant capacity in flours obtained from the to mutant and wild-type rice grain was measured by an oxygen radical absorbance capacity (ORAC) assay as described in Example 1. In the ORAC assay, the antioxidant capacity is represented by the competition kinetics between endogenous radical scavenging biomolecules and the oxidisable molecular fluorescent probe fluorescein, against the synthetic free radicals generated by AAPH (2,2'-azobis(2-amidino-propane) dihydrochloride). The capacity was calculated by comparison of the area under the kinetic curve (AUC), representing the fluorescence degradation kinetics of the molecular probe fluorescein for the grains with the AUC generated by Trolox standards (Prior, 2005). An alternative approach to quantifying antioxidant capacity is through the use of the Folin-Ciocalteau reagent (FCR); this represents the antioxidant capacity by measuring the reducing capacity of the total phenolic compounds in the food sample. The FCR assay is relatively simple, convenient and reproducible. However, the more time-consuming ORAC assay measures more biologically relevant activity. Since antioxidants include a wide range of polyphenols, reducing agents and nucleophiles, measurement by both FCR and ORAC can provide a better coverage and more comprehensive representation of the total antioxidant capacity. As reported by Prior (2005), the results of FCR assay and ORAC measurement are usually consistent.

Both of the FCR and ORAC assays showed increased antioxidant capacity of flour from the ta2 mutant whole grain flour relative to wild-type, ZH11 whole grain flour. FCR demonstrated an increase of about 35% in total phenolic compounds in the ta2 mutant. There was also an 83% increase in hydrophilic antioxidant content in the flour from the ta2 mutant.

Phytate

When grown under conditions with adequate phosphorus, about 70% of total phosphorus content in rice grain is in the form of phytate or phytic acid (myo-inostitol-1,2,3,4,5,6-hexakisphosphate). Dietary phytate may also have beneficial roles for health as a strong antioxidant (Schlemmer, 2009). Total phytate analyses showed an increase in phytate content about 19% in ta2 as compared to the wild-type, increasing from about 10.8 mg/g to about 12.7 mg/g.

B Vitamins

Levels of the vitamins B3, B6 and B9 in the ta2 flour were higher than those in wild-type flour by about 19%, 63% and 58%, respectively. When the assay was repeated with four replicates, the mean increases were about 20%, 33% and 38%, respectively. Aleurone was known to be richer in vitamins B3, B6 and B9 than endosperm (Calhoun, 1960), so the increase in aleurone thickness in the to mutant grains was concluded to be responsible for the increase in vitamin B3, B6 and B9 contents.

Dietary Fibre

Total dietary fibre measured as described in Example 1 as was observed to increase by about 70%. Insoluble fibre increased by about 55%.

Carbohydrates

There was a 9% decrease in the starch content of the ta2 grain on a weight basis. In contrast, sucrose levels increased by 2.5-fold in the mutant grain, and monosaccharides (arabinose, xylose, galactose, glucose) were increased from 31% to 118% relative to the wild-type.

Conclusions

The nutritional analyses showed that wholegrain flour produced from field-grown ta2 grain was significantly increased relative to wild-type in most of the aleurone-rich nutrients including the macro-nutrients such as lipid and fibre, micronutrients such as minerals (iron, zinc, potassium, magnesium, phosphorus, sulphur), B vitamins such as B3, B6 and B9, antioxidants, and aleurone-associated biomolecules such as phenolic compounds and phytate. There was also a substantial increase in free sucrose and monosaccharides. Concomitant with the increase in these nutrients and micronutrients was a small decrease in starch content in the ta2 mutant, as a relative percentage.

Example 6. Screening for Additional Mutant Alleles in the Ta2 Gene

The mutagenised population of rice plants in the ZH11 genetic background (Example 2) were screened by TILLING assays as described in Example 1 to identify further polymorphisms in the Ta2 gene, so that they could be tested for a thickened aleurone phenotype. The method used heteroduplexing of labelled wild-type RNA and candidate mutant RNA with digestion by endonuclease CelI essentially as described by Jiang et al. (2013). The 5' region of the TA2 gene was chosen for screening first of all, but any region of the gene could have been chosen.

Numerous single nucleotide polymorphisms were identified in the 5' region of the Ta2 gene by the TILLING assays. Grains from the plants having the polymorphisms were examined for thickened aleurones and other grain phenotypes as for the first ta2 mutant. Some grains exhibited thickened aleurones. Those grains that exhibited mutant phenotypes were selected and progeny plants obtained from them. The nucleotide sequence of the Ta2 gene in each was determined, confirming the presence of the mutations. The altered nucleotide(s) in the Ta2 gene in each mutant was identified. Another three thick aleurone mutants are also being sequenced. Other grains which contained polymorphisms but which did not exhibit thickened aleurones were also identified and maintained for comparison. The mutants and the other polymorphic lines, and their aleurone phenotype, that were identified are summarised in Table 3. The mutants having thickened aleurone are shown as: ++, greatly thickened aleurone; +, weakly thickened aleurone; –, unaltered aleurone phenotype. It was clear that a variety of mutations and resultant phenotypes was obtained.

The aleurone in wild-type ZH11 grain showed one cell layer in thickness. In contrast in the specific mutants, the aleurones in the mutant grains comprising the V441A mutation were thickened in the dorsal side, comprising about 5-6 cell layers. The aleurones in mutant S1357F grains were about 4-5 cell layers in thickness and the grains were shrunken, whereas the aleurones of mutant R482K grains were 2-3 cell layers thick and the grains were not shrunken. The aleurones in mutant S214F grains contained 2-4 cell layers and the grains were shrunken, as were the grain from mutants S156F and S1413N. In contrast, the aleurones of K501S grains had 2-3 cell layers and its grains were not shrunken. Therefore, a variety of mutants and phenotypes were readily obtained in the Ta2 gene.

TABLE 3

Mutations identified in rice Ta2 gene.

| Mutation designation | Gene region | Mutation | Thick aleurone | Seed phenotype |
|---|---|---|---|---|
| A1810 | Exon | S156F | ++ | shrunken |
| B19 | Exon | S214F | ++ | shrunken |
| A155 | Exon | S1413N | ++ | shrunken |
| A1774 | Exon | A441V | ++ | normal |
| A2918 | Exon | S1357F | ++ | shrunken |
| D11253 | Exon | K501S | + | normal |
| A775 | Exon | R482K | + | normal |
| A1711 | Exon | To be determined | ++ | |
| D11190 | Exon | To be determined | ++ | |
| B857 | Exon | To be determined | + | |
| D11080 | Exon | D3V | – | |
| A654 | Exon | T221I | – | |
| D113281 | Exon | P883S | – | |
| D10394 | Exon | P843C | – | |
| A3033 | Exon | A78V | – | |
| B1193 | Exon | E123K | – | |
| D11321 | Exon | R487K | – | |
| A790 | Exon | R530K | – | |
| D11029 | Exon | D1425N | – | |
| A2004 | Exon | S1272N | – | |
| A1152 | Exon | P1225L | – | |
| A2435 | Exon | R1390N | – | |
| B696 | Exon | synonymous | – | |
| D11283 | Exon | synonymous | – | |
| D11184 | Exon | synonymous | – | |
| D11253 | Exon | synonymous | – | |
| A1687 | Exon | synonymous | – | |
| B1339 | Exon | synonymous | – | |
| B1979 | Exon | synonymous | – | |
| B2089 | Exon | synonymous | – | |
| A3033 | Exon | A78V | – | |

Of the 60 newly identified lines having polymorphisms in the TA2 gene, 19 had amino acid changes (substitutions) in the predicted polypeptide products. Of those, at least 7 exhibited thickened aleurone phenotypes. The S1413N and D1425N mutations lay within the glycosylase domain; the other identified mutations lay outside of the glycosylase domain. Apart from the initial splice-site variant mutant, all of the identified mutations were amino acid substitutions. None were deletions or stop codons, leading the inventors to conclude that null mutations in OsROS1 might be lethal. It has been reported that in *Arabidopsis*, maternal dme mutations resulted in aborted seeds (Choi et al., 2002 and 2004). In rice, the presence of a ros1a maternal null allele resulted in early stage endosperm developmental failure regardless of the paternal genotype (Ono et al., 2012).

The recovery of ten new, independent mutant alleles in the TA2 (OsROS1α) gene, each of which had a thickened aleurone layer in the grain, indicated conclusively that the mutations in this gene had caused the thick aleurone phenotype. Furthermore these new mutations were all in a different region of the gene to the first ta2 mutation indicating that the gene could be altered in various positions along the full-length gene to achieve the thick aleurone phenotype.

Several of the ta2 genes from the mutants showing thick aleurones are cloned and the encoded polypeptides are expressed and tested for DNA glycosylase/lyase activity. This confirms that the polypeptides have reduced DNA glycosylase/lyase activity compared to the wild-type polypeptide.

Example 7. Complementation Analysis of the Ta2 Mutant

In order to strengthen the conclusion that mutations in the Ta2 (OsROS1a) gene were responsible for the thickened aleurone and associated phenotypes, complementation experiments were performed by introducing a wild-type copy of the gene into the mutant line by transformation. To construct the transformation plasmid for the complementation experiment, a 16,882 nucleotide DNA fragment (nucleotide sequence provided as SEQ ID NO:9) including the Ta2 gene was isolated from the wild-type rice genome. This fragment contained, in order, a 4726-bp upstream sequence which was considered to contain the promoter of the gene, the entire OsTA2 protein coding region including all of the introns, a 615 nucleotide 3'-UTR and a 401-bp downstream region. It was amplified from ZH11 genomic DNA using a series of oligonucleotide primers, assembled, and then digested with KpnI and SalI and ligated to the binary vector pCAMBIA1300. That vector also contained a hygromycin resistance gene as a selectable marker gene. The plasmid for transformation and a control plasmid (empty vector) were each introduced into *Agrobacterium tumefaciens* strain EHA105 and used to transform rice recipient cells using the method as described by Nishimura et al. (2006). A total of 32 To transgenic plants were regenerated from the transformation with the wild-type Ta2 gene. These plants were transferred to soil and grown to maturity in a growth chamber. When PCR was used to test for the presence of the hygromycin resistance gene, 20 transformant lines were identified and selected which carried the hygromycin gene. These were grown to maturity and grain (T1 seed) harvested from each plant. Each of these plants contained the T-DNA from the vector containing the wild-type Ta2 gene as demonstrated by PCR assays.

Grains harvested from these plants were examined for their aleurone phenotype by staining with Evans blue. At least three of the transformed plants produced grains with normal aleurones like the wild-type, indicating positive expression of the introduced gene and therefore complementation of the ta2 mutation. This conclusively proved that the mutations in the Ta2 gene caused the mutant phenotypes.

The Ta2 gene is referred to hereinafter as the ROS1a gene; these terms are interchangeable.

Example 8. In Vitro Enzyme Activity Assays of Recombinantly Expressed TA2 and Ta2 Proteins As described in Example 4 above, the Ta2 gene in rice was the same as the OsROS1a gene, which is homologous to the *Arabidopsis thaliana* DNA demethylase/glycosylase named as Demeter (DME; Gehring et al., 2006). DME breaks the phosphodiester linkage on the 3' side of a 5-methylcytosine residue in a hemi-methylated DNA substrate.

The enzyme activity from recombinantly expressed rice Ta2 and ta2 proteins is therefore tested by measuring their activity on a hemi-methylated DNA substrate which has been labelled, to generate end-labelled DNAs that migrate on denaturing polyacrylamide gels at the predicted position for β elimination products, as described by Gehring et al. (2006).

In order to recombinantly express and purify the Ta2 and ta2 polypeptides, full-length ROS1a cDNAs from the wild-type and mutant ta2 plants are used as templates in a PCR reaction with oligonucleotides JH021 (5'-TTAATCTAGAATGCAGAGCATTATGGACTCG-3'; SEQ ID NO:42) and JH017 (5'-CGGTCGACTTAGGTTTTGTTGTTCTTCAATTTGC-3'; SEQ ID NO:43), which add XbaI and SalI restriction sites, respectively, to the ends of the amplified DNA fragment. The PCR products are digested with XbaI and SalI and cloned into the pMAL-c2x vector (NEB) to create c2x-ROS1a genetic constructs. The genetic constructs are transformed into *E. coli* Rosetta cells (Novagen). To produce the polypeptides, transformed cells are grown at 28° C. in LB supplemented with 0.2% glucose, 100 μg/mL of ampicillin and 50 μg/mL of chloramphenicol until an OD600 of 0.4 is reached. ROS1a-Mal fusion protein expression is induced with 10 μM of IPTG at 18° C. for 1 hr. The cultures are centrifuged at 6,500 rpm for 15 min at 4° C. and the pellet is resuspended in 30 mL of 4° C. column buffer (20 mM Tris-HCl, pH 7.4, 200 mM NaCl, 1 mM EDTA). Cells are sonicated for 2 min on ice using a Branson Sonifier 250 at output power setting of 4. The lysates are centrifuged at 9,000 rpm for 25 min at 4° C. and the supernatants collected and subjected to gravity column purification. The ROS1a-Mal fusion proteins are purified through amylose resin following the manufacturer's protocol (New England Biolabs). Eluted proteins are dialyzed in the Slide-A-Lyzer dialysis cassette (10,000 MWCO; Pierce) against 50% glycerol at 4° C. overnight. Protein concentrations are determined by the Bradford method using the Protein Assay kit (Bio-Rad Laboratories) and the proteins stored at −20° C. until further use.

The ROS1a-Mal fusion proteins are assayed for DNA glycosylase activity against hemi-methylated double-stranded DNA substrates as described in Example 1 (Gehring et al., 2006).

As controls, no lyase activity or covalent trapping is detected when ROS1a is incubated with non-methylated DNA oligonucleotides or when hemi-methylated DNA substrate is incubated in the absence of enzyme.

Example 9. Homologues of the ROS1a Gene in Rice

The plant genes that encode DNA glycosylases which mediate DNA demethylation have been characterised mainly in *Arabidopsis thaliana* (Chan et al., 2005; Law and Jacobsen, 2010; Zhu, 2009). They include the Demeter (DME, Choi et al., 2002; Gehring et al., 2006), ROS1 (Gong et al., 2002; Agius et al., 2006), Demeter-like 2 (DML2) and Demeter-like 3 genes (DML3, Choi et al., 2002; Ortega-Galisteo et al., 2008). The largest of these genes (and encoded polypeptides), DME, is expressed most strongly in the homodiploid central cell of the female gametophyte before fertilisation where it promotes maternal allele-specific global hypomethylation and expression of imprinted genes including in the endosperm. In contrast, ROS1, DML2 and DML3 are expressed in vegetative tissues (Gong et al., 2002; Penterman et al., 2007). Compared with ROS1, the level of expression of the DML2 and DML3 genes was low (Mathieu et al., 2007). Moreover, homozygous mutations in ros1, dml2 and dml3 yielded no obvious morphological phenotypes whereas a maternal dme mutation resulted in aborted seeds, i.e. embryo lethal, and was not transmitted to progeny (Choi et al., 2002 and 2004). Despite their low expression levels, the ROS1, DML2 and DML3 polypeptides still function as DNA glycosylases/lyases (Gong et al., 2002; Morales-Ruiz et al., 2006; Penterman et al., 2007). From this data, one would not have expected a ROS1 mutation to have caused a thickened aleurone phenotype.

Phylogenetic analysis revealed that the rice genome encodes 6 putative DNA glycosylases for cytosine demethylation, including four that appear to be ROS1 orthologs (OsROS1a, OsROS1b, OsROS1c, OsROS1d) and two apparent DML3 orthologs (Zemach et al., 2010). A null mutation in OsROS1a was identified but was not transmitted from either male or female plants containing the mutation to progeny, presumably because ROS1a wild-type DNA glycosylase is indispensible in both male and female gametophytic development (Ono et al., 2012). The inventors are not aware of any published reports of partial mutations in OsROS1a.

The three identified motifs in the DNA glycosylase domain, namely the helix-hairpin-helix (HhH) motif, a glycine/proline-rich motif followed by a conserved aspartic acid (GPD), and the four conserved cysteine residues (Example 4) were present in each member of the Demeter family. The glycosylase domain structure was also found in human 8-oxoguanine DNA glycosylase (hOGG1), *E. coli* adenine DNA glycosylase (MutY), and endonuclease III (Endo III) (Bruner et al. 2000; Guan et al. 1998; Mok et al., 2010). Unlike other members of the HhH DNA glycosylase superfamily, DME-family members contained two additional conserved domains (domain A and domain B) flanking the central glycosylase domain (Mok et al., 2010).

The nucleotide sequences of the protein coding regions for the homologous genes were aligned by ClustalW (www.ebi.ac.uk/Tools/msa/clustalw2/). The extent of sequence identity of the rice ROS1a protein coding region to the corresponding region of the homologous genes in other species is shown in Table 4.

The inventors concluded from these analyses that rice has multiple ROS1 gene homologs but no DME genes. In rice, as for *Arabidopsis*, ROS1 was clearly distinguishable from its homologs DML2 and DML3 in the same species in terms of the extent of sequence identity.

TABLE 4

Nucleotide sequence identity to coding region of rice OsROS1a or TaROS1a-5B.

| Gene | Accession Number | Identity to OsROS1a |
|---|---|---|
| OsROS1a | LOC_Os01g11900 | 100% |
| OsROS1b | LOC_Os02g29230 | 41.7% |
| OsROS1c | LOC_Os05g37350 | 42.0% |
| OsROS1d | LOC_Os05g37410 | 41.9% |
| OsDML3a | LOC_Os02g29380 | 34.9% |
| OsDML3b | LOC_Os04g28860 | 33.2% |
| AtDME | NM001085058.1 | 40.6% |
| AtROS1 | NM129207.4 | 41.5% |
| AtDML2 | NM111836.5 | 39.2% |
| AtDML3 | NM119567.3 | 40.4% |

Example 10. Expression of ROS1a Gene in Rice

Experiments were carried out to analyse expression of the TA2 gene in different rice tissues, including in parts of the developing grain. In a first experiment, TA2 mRNA was detected in rice tissue sections by in situ hybridisation as described by Brewer et al. (2006). Briefly, various rice tissues were fixed in FAA fixative for 8 h at 4° C. after vacuum infiltration, dehydrated using a graded ethanol series followed by a xylene series, and embedded in Paraplast Plus (Sigma-Aldrich). Microtome sections (8 μm) were mounted on Probe-On Plus microscope slides (Fisher).

From the hybridisation signals, it was concluded that TA2 was expressed in the pericarp, testa and aleurone tissues and in the starchy endosperm of rice, but not in the vascular bundle.

Realtime reverse transcription polymerase chain reaction (RT-PCR) was used to assay relative expression levels in different plant tissues. Surprisingly, the results indicated highest relative expression in pollen, followed by anthers, young panicles and aleurone tissue (FIG. 6). It was considered that the specific expression of OsROS1a in anthers might be involved in the suppression of transposons in the male gametophyte. In *Arabidopsis* tricellular pollen, active DNA demethylation is important in maintaining a basal expression of transposons in vegetative cell nuclei so as to produce siRNA for reinforcing RNA dependent DNA methylation (RdDM) of the transposons in male gametes, i.e. the two sperm cells (Zhu, 2009; Zhu et al., 2007).

Expression of ROS1a in the developing seed increased to 10 days post anthesis and then declined thereafter. Strong expression was observed in both the starchy endosperm and aleurone tissues. The expression pattern early in seed development was consistent with the formation of thickened aleurone, prior to cellularisation of the endosperm during seed development. The inventors concluded that reduced expression of ROS1a in the period from the day of anthesis to 7 days post anthesis (pollination) (0-7 DAP) was critical to formation of the thick alerone.

Example 11. Patterns of Gene Methylation in Rice

To determine the patterns of methylation of all rice genes, collectively, in the ta2 mutant plants relative to the wild-type TA2 plants, DNA was isolated from endosperms and embryos and treated with bisulfite which reacts with unmethylated cytosines, followed by Illumina sequencing. Endosperms were isolated at 10 DAP from the developing rice grains of the ta2 and wild-type (ZH11) plants, and embryos from the wild-type plants at the same stage of grain development. For sequencing following bisulfite treatment, custom Illumina adapters were synthesized in which cytosines were replaced by 5-methylcytosines, so that the adapters would survive the bisulfite conversion. Paired end (PE) adapters were synthesized which allowed each molecule to be sequenced from both ends, thus facilitating subsequent alignment to the genomic scaffold sequence. About 0.5-1 μg of genomic DNA was isolated from endosperms dissected from each of the wild-type and ta2 plants as well as from wild-type embryos. The isolated DNA preparations were sheared by sonication to fragments of 100-500 bp. The adapters were ligated to the sheared fragments following the Illumina protocol. The DNAs were then treated twice with sodium bisulfite, which converts unmethylated cytosines (C) to uridines (U), using the Qiagen EpiTect kit and amplified by 18 cycles of PCR using PfuTurboCx DNA polymerase (Stratagene), a proofreading enzyme that tolerates uridines in the template strand. This PCR amplification resulted in a library of DNA fragments with distinct adapters at each end, so that the 'forward' Illumina sequencing primer yielded a nucleotide sequence from the 'original' genomic DNA-derived strand (where a C corresponded to a methylated C, and a T corresponded to a non-methylated C where a C occurred in the genomic sequence), and the 'reverse' Illumina sequencing primer produced a nucleotide sequence from the complementary strand (where a G corresponded to a methylated C on the opposite strand, and an A corresponded to a non-methylated C where a C occurred in the genomic sequence).

The extent of CG and CHG methylation in the DNA obtained from the ta2 endosperms was greater than that in the DNA obtained from the control ZH11 endosperms, indicating that the mutation of TA2 (OsROS1a) reduced the demethylation process in rice endosperm, whereas the extent of CHH methylation in the ta2 endosperm was not significantly different to that in wild-type ZH11 endosperm.

Example 12. Further Analysis of Nutritional Components in Ta2 Mutant Grain

Further analyses were carried out to measure the nutritional components of mutant grain compared to the corresponding wild-type grain (ZH11), grown at the same time and under the same conditions in the field. Whole grain flour samples were prepared from the grain harvested from the plants and used for compositional analysis as described in Example 5. The results of the proximate analyses of the flours for grain grown in Australia are given in Table 5. The results for grain grown in China are given in Table 6.

The proximate analyses indicated an increase of about 50% in the total lipid content in the ta2 mutant flour. Total nitrogen analyses showed a significant change in the protein levels between the ta2 mutant and wild-type grains in China but not in Australia, which may have due to different nitrogen fertiliser regimes. The total fibre level increased by about 66% or 91% in ta2 grain. The starch content decreased by 9% in ta2 grain relative to wild-type. These data confirmed that the increase in thickness of the aleurone layer in the ta2 mutant caused an significant increase in the levels of aleurone-rich nutrients such as lipid, minerals and fibres without changing the size of the seed. Even though the absolute numbers differed in the two growth environments, the relative increases in ta2 grain were reasonably consistent.

TABLE 5

Composition of ros1a mutant rice grain (Australia) compared to wild-type

| Component | | Units | ZH11 | ta2 | % change |
|---|---|---|---|---|---|
| Total Starch | | g/100 g | 67.9 | 61.8 | −9% |
| Fibre | Total Dietary fibre | g/100 g | 3.45 | 5.73 | 66% |
| | Soluble Dietary Fibre | g/100 g | 0.54 | 0.56 | 4% |
| | Insoluble Dietary Fibre | g/100 g | 2.74 | 4.26 | 55% |
| B Vitamins | Niacin (Vitamin B3) | mg/100 g | 6.53 | 7.90 | 21% |
| | Pyridoxine (Vitamin B6) | mg/100 g | 0.10 | 0.13 | 33% |
| | Folate (Vitamin B9) | µg/100 g | 19.4 | 25.6 | 32% |
| Mineral | Total Ash | g/100 g | 1.79 | 2.39 | 33% |
| | Iron | mg/kg | 12.4 | 14.2 | 14% |
| | Zinc | mg/kg | 13.7 | 16.0 | 17% |
| | Potassium | mg/kg | 3,930 | 4,780 | 22% |
| | Magnesium | mg/kg | 1,270 | 1,560 | 23% |
| | Sulphur | mg/kg | 1,240 | 1,350 | 9% |
| Simple sugar | Sucrose | g/100 g | 0.95 | 2.54 | 169% |
| NNSP | Total | mg/100 mg | 1.54 | 2.48 | 61% |
| NNSP components | Arabinose | mg/100 mg | 0.28 | 0.62 | 61% |
| | Xylose | mg/100 mg | 0.26 | 0.50 | 89% |
| | Mannose | mg/100 mg | 0.11 | 0.16 | 59% |
| | Galactose | mg/100 mg | 0.10 | 0.20 | 53% |
| | Glucose | mg/100 mg | 0.77 | 1.01 | 47% |

TABLE 5-continued

Composition of ros1a mutant rice grain (Australia) compared to wild-type

| Component | | Units | ZH11 | ta2 | % change |
|---|---|---|---|---|---|
| Protein | | g/100 g | 15.18 | 15.26 | 1% |
| Phytate | | mg/g | 10.79 | 12.69 | 18% |
| Phenolics | Total Phenolics | µg/g | 3,180 | 4,570 | 43% |
| | Free Phenolics | µg/g | 529 | 665 | 26% |
| | Conjugated Phenolics | µg/g | 348 | 692 | 99% |
| | Bound Phenolics | µg/g | 2,250 | 2,950 | 31% |
| Antioxidants | ORAC | µmol/g | 12.3 | 22.6 | 84% |
| Moisture | | | 9.5 | 8.9 | −6% |
| Lipid | Total lipid | g/100 g | 3.29 | 4.95 | 50% |
| Lipid composition | Fatty acid 18:0 | | 5.1% | 4.5% | −13% |
| | Fatty acid 18:1n9t | | 3.3% | 2.6% | −22% |
| | Fatty acid 18:1n9c | | 32.7% | 43.2% | 32% |
| | Fatty acid 18:1n7 | | 1.7% | 1.4% | −19% |
| | Fatty acid 18:2n6 | | 36.0% | 27.9% | −22% |

TABLE 6

Composition of ros1a mutant rice grain (China) compared to wild-type

| Component | Specific component | ZH11 | ta2 | % change |
|---|---|---|---|---|
| Protein | total protein | 12.38 | 14.12 | 14.05 |
| Amino acids | Asparagine | 1.16 | 1.53 | 31.90 |
| | Threonine | 0.45 | 0.54 | 20.00 |
| | Serine | 0.64 | 0.73 | 14.06 |
| | Glutamine | 2.29 | 2.40 | 4.80 |
| | Glycine | 0.59 | 0.76 | 28.81 |
| | Alanine | 0.71 | 0.84 | 18.31 |
| | Cysteine | 0.26 | 0.30 | 15.38 |
| | Valine | 0.72 | 0.79 | 9.72 |
| | Methionine | 0.22 | 0.22 | 0.00 |
| | Isoleucine | 0.50 | 0.53 | 6.00 |
| | Leucine | 1.02 | 1.05 | 2.94 |
| | Tyrosine | 0.59 | 0.58 | −1.69 |
| | Phenylalanine | 0.66 | 0.69 | 4.55 |
| | Histidine | 0.43 | 0.54 | 25.58 |
| | Lysine | 0.43 | 0.60 | 39.53 |
| | Arginine | 1.14 | 1.39 | 21.93 |
| | Proline | 0.52 | 0.59 | 13.46 |
| Starch | amylose | 9.80 | 5.14 | −47.55 |
| Minerals | Selenium (Se) | 0.03 | 0.03 | 8.78 |
| | Calcium | 167.89 | 231.39 | 37.82 |
| | Fe | 15.24 | 17.76 | 16.54 |
| | Zn | 28.68 | 41.37 | 44.25 |
| Antioxidants | total flavonoids | 0.06 | 0.08 | 33.33 |
| Fibre | Total dietary fibre | 3.26 | 6.23 | 91.10 |
| Vitamins | Vitamin A | 1.53 | 5.52 | 260.78 |
| | Vitamin E | 0.47 | 1.00 | 112.77 |
| | Vitamin B1 | 0.50 | 0.57 | 12.97 |
| | Vitamin B2 | 0.04 | 0.08 | 116.67 |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

This application claims priority from AU 2015904754 filed 18 Nov. 2015, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Agius et al. (2006) Proc. Natl. Acad. Sci. U.S.A. 103:11796-11801.
Almeida and Allshire (2005) TRENDS Cell Biol 15: 251-258.
Barker et al. (1983) Plant Mol. Biol. 2: 235-350.
Baumlein et al. (1991) Mol. Gen. Genet. 225:459-467.
Becraft et al. (2001a) In Bhojwani and Soh (eds). Current Trends in the Embryology of Angiosperms, Kluwer Academic Publishers, pp 353-374.
Becraft et al. (2001b) Plant Physiol. 127:4039-4048.
Becraft et al. (2002) Development 129:5217-5225.
Becraft and Yi (2011) J. Exp. Botany 62:1669-1675.
Bevan et al. (1983) Nucl. Acid Res. 11: 369-385.
Bourque (1995) Plant Sci. 105: 125-149.
Brewer et al. (2006) Nature Protocols. 1:1462-1467.
Broun et al. (1998) Plant J. 13:201-210.
Bruner et al. (2000) Nature 403:859-866.
Buri et al. (2004) Cereal Foods World 49:274-282.
Buttrose et al. (1963) Aust. J. Biol. Sci. 16:768-774.
Calhoun (1960) Cereal Chemistry. 37:755.
Capecchi (1980) Cell 22:479-488.
Chan et al. (2005) Nature Rev. Genet. 6:351-360.
Choi et al. (2002) Cell 110:33-42.
Choi et al. (2004) Proc. Natl. Acad. Sci. U.S.A. 101:7481-7486.
Clapp (1993) Clin. Perinatol. 20:155-168.
Curiel et al. (1992) Hum. Gen. Ther. 3:147-154.
Comai et al. (2004) Plant J 37: 778-786.
Doyon et al. (2011) Nat. Methods 8:74-79.
Eglitis et al. (1988) Biotechniques 6:608-614.
Fahim (2012) Plant Biotechnology Journal. 10:150-163.
Garfinkel et al. (1983) Cell 27: 143-153.
Gehring (2006) Cell 124:495-506.
Gong et al. (2002) Cell 111:803-814.
Graham et al. (1973) Virology 54:536-539.
Greve (1983) J. Mol. Appl. Genet. 1: 499-511.
Guan et al. (1998) Nature Structural Biology 5:1058-1064.
Guddeti (2005) Cell Research. 15:631-638.
Guo et al. (2010) J. Mol. Biol. 400:96-107.
Harland and Oberleadls (1990) Newer methods for the analysis of phytate and its hydrolysis products. In: Spiller G A, ed. CRC handbook of dietary fiber in human nutrition. 2nd ed. Boca Raton, Florida: CRC Press; pages 101-104.
Henikoff et al. (2004) Plant Physiol 135: 630-636.
Hinchee et al. (1988) Biotech. 6:915.
Hoshikawa (1993) in Matsuo and Hoshikawa (eds), Science of the Rice Plant: Morphology. Nobunkyo, Tokyo, pp 339-376.
Huang (2002a) Journal of Agricultural and Food Chemistry. 50:1815-1821.
Huang (2002b) Journal of Agricultural and Food Chemistry. 50:4437-4444.
Huang (2005) Journal of Agricultural and Food Chemistry. 53:1841-1856.
Jiang et al (2013) Molecular Cell. 14:787-799.
Jones (1969) Planta 85:359-375.
Jones-Rhoades and Bartel (2004) Mol. Cell 14:787-799.
Joshi (1987) Nucl. Acids Res. 15:6643-6653.
Kapazoglou et al. (2012) BMC Plant Biology 13:172.
Kawakatsu et al. (2009) The Plant J. 59:908-920.
Kawashima (2009) The Plant Journal. 57:313-321.
Kessler et al. (2002) Development 129:1859-1869.
Kim et al. (1996) Proc. Natl. Acad. Sci. USA 93:1156-1160.
Lahey et al. (1999) Food Chemistry 65:129-133.
Langridge et al. (2001) Aust. J. Agric. Res. 52: 1043-1077.
Law and Jacobsen (2010) Nature Rev. Genet. 11:204-220.
Lemieux (2000) Current Genomics 1: 301-311.
Lewis et al. (2009) Plant and Cell Physiol. 50:554-571.
Li et al. (2008) J. Agric. Food Chem. 56:9732-9739.
Lid et al. (2004) Planta 218:370-378.
Lu et al. (1993) J. Exp. Med. 178:2089-2096.
Mann et al. (2001) J. AOAC Int. 84:1593.
Mathieu et al. (2007) Cell 130:851-862.
McCleary et al. (1997) J AOAC Int. 80:571-580.
Medberry et al. (1992) Plant Cell 4: 185-192.
Medberry et al. (1993) Plant J. 3: 619-626.
Miller et al. (2007) Nat. Biotechnol. 25:778-785.
Millar and Waterhouse (2005) Funct Integr Genomics 5:129-135.
Mok et al. (2010) Proc. Natl. Acad. Sci. U.S.A. 107:19225-19230.
Morales-Ruiz et al. (2006) Proc. Natl. Acad. Sci. U.S.A. 103:6853-6858.
Murashige and Skoog (1962) Physiologia Plantarum 15:473-497.
Needleman and Wunsch (1970) J. Mol Biol. 45:443-453.
Niedz et al. (1995) Plant Cell Reports 14: 403-406.
Nishimura et al. (2006) Nature Protocols. 1:2796-2802.
Ono et al. (2012) Plant J. 71:564-574.
Ortega-Galisteo et al. (2008) Plant Mol. Biol. 67:671-681.
Ossowski (2008) The Plant Journal. 53:674-690.
Ow et al. (1986) Science 234:856-859.
Pasquinelli et al. (2005) Curr Opin Genet Develop 15: 200-205.
Penterman et al. (2007) Proc. Natl. Acad. Sci. U.S.A. 104:6752-6757.
Potenza et al. (2004) In Vitro Cell Dev. Biol. Plant 40:1-22.
Prasher et al. (1985) Biochem. Biophys. Res. Comm. 126: 1259-68.
Prior (2005) Journal of Agricultural and Food Chemistry. 53:4290-4302.
Prosky et al. (1985) AOAC Official method 991.
Salomon et al. (1984) EMBO J. 3: 141-146.
Schlemmer (2009) Molecular Nutrition and Food Research. 55 (Supplement 2):S330-S375.
Senior (1998) Biotech. Genet. Engin. Revs. 15: 79-119.
Shen et al. (2003) Proc. Natl. Acad. Sci. USA 100:6552-6557.
Slade and Knauf (2005) Transgenic Res. 14: 109-115.
Smith et al. (2000) Nature 407: 319-320.
Sreenivasulu (2010) The Plant Journal. 64:589-603.
Stalker et al. (1988) Science 242:419-423.
Szczepek et al. (2007) Nat. Biotechnol. 25:786-793.
Taylor (1997) The Plant Cell 9:1245-1249.
Theander et al. (1995) J AOAC Int. 78:1030-1044.
Thillet et al. (1988) J. Biol. Chem. 263:12500.
Wagner et al. (1992) Proc. Natl. Acad. Sci. USA 89:6099-6103.
Walbot (1994) p78-80 in Freeling and Walbot (eds), The Maize Handbook, Springer Verlag, New York.
Waterhouse et al. (1998) Proc. Natl. Acad. Sci. USA 95: 13959-13964.
Wolbang (2010) J. Agric Food Chem. 58, 1732-1740.
Zarcinas (1983a) CSIRO Division of Soils Technical Paper. 1-36.
Zarcinas (1983b) Communications in Soil Science and Plant Analysis. 18:131-146.
Zemach et al. (2010) Proc. Natl. Acad. Sci. U.S.A. 107: 18729-18734.
Zhu (2009) Annual Review of Genetics 43:143-166.
Zhu et al. (2007) Current Biology 17:54-59.

The invention claimed is:

1. A method of producing a rice plant which produces grain comprising an aleurone that is thickened compared to aleurone from a corresponding wild-type grain, the method comprising the steps of
   i) introducing into one or more rice cells a mutation of an endogenous ROS1a gene such that the mutated ROS1a gene encodes a ROS1a polypeptide whose amino acid sequence is different compared to the amino acid sequence of the corresponding wild-type ROS1a polypeptide,
   ii) obtaining one or more rice plants from the one or more cells obtained from step i), the one or more rice plants comprising the mutations of the endogenous ROS1a gene introduced in step i), and
   iii) detecting the mutation of the endogenous ROS1a gene and measuring the aleurone of the one or more plants of step ii), and selecting a plant of step ii) which produces grain comprising the mutation of the endogenous ROS1a gene and an aleurone that is thickened compared to aleurone from a corresponding wild-type grain thereby producing the rice plant.

2. A method of selecting a rice plant which produces a rice grain comprising an aleurone that is thickened compared to aleurone from a corresponding wild-type grain, the method comprising the steps of
   i) screening a population of rice plants or grain, each of which were obtained from a mutagenic treatment of progenitor rice cells, grain or plants for grain with aleruone that is thickened compared to aleurone from a corresponding wild-type grain and the presence of a mutation in a ROS1a gene, and
   ii) selecting from the population of step (i) a rice plant which comprises said mutation and which produces grain with an aleurone that is thickened compared to aleurone from a corresponding wild-type grain, thereby selecting the rice plant.

3. The method of claim 1, further comprising harvesting grain from the plant selected in step iii).

4. The method of claim 3, further comprising producing one or more generations of progeny plants from the harvested grain.

5. The method of claim 4, further comprising harvesting grain from the one or more generations of progeny plants.

6. The method of claim 4, wherein the one or more generations of progeny plants are homozygous for the mutation of the endogenous ROS1a gene.

7. The method of claim 5, wherein the grain harvested from the one or more generations of progeny plants are homozygous for the mutation of the endogenous ROS1a gene.

8. The method of claim 5, further comprising processing the grain to produce flour, bran, wholemeal, malt starch, or oil.

9. The method of claim 5, further comprising processing the grain or bran, flour, wholemeal, malt, starch or oil from the grain, to produce a food or beverage ingredient.

10. The method of claim 5, further comprising mixing the grain or bran, flour, wholemeal, malt, starch or oil from the grain, with a food or beverage ingredient.

11. The method of claim 4, wherein producing one or more generations of progeny plants from the harvested grain comprises backcrossing with a recurrent parent plant.

12. The method of claim 2, further comprising harvesting grain from the plant selected in step ii).

13. The method of claim 12, further comprising producing one or more generations of progeny plants from the harvested grain.

14. The method of claim 13, further comprising harvesting grain from the one or more generations of progeny plants.

15. The method of claim 13, wherein the one or more generations of progeny plants are homozygous for the mutation of the endogenous ROS1a gene.

16. The method of claim 14, wherein the grain harvested from the one or more generations of progeny plants are homozygous for the mutation of the endogenous ROS1a gene.

17. The method of claim 14, further comprising processing the grain to produce flour, bran, wholemeal, malt starch, or oil.

18. The method of claim 14, further comprising processing the grain or bran, flour, wholemeal, malt, starch or oil from the grain, to produce a food or beverage ingredient.

19. The method of claim 14, further comprising mixing the grain or bran, flour, wholemeal, malt, starch or oil from the grain, with a food or beverage ingredient.

20. The method of claim 13, wherein producing one or more generations of progeny plants from the harvested grain comprises backcrossing with a recurrent parent plant.

* * * * *